(12) United States Patent
Furuta et al.

(10) Patent No.: US 9,540,366 B2
(45) Date of Patent: Jan. 10, 2017

(54) RING-FUSED HETEROCYCLIC COMPOUND

(71) Applicant: Kyowa Hakko Kirin Co., Ltd., Tokyo (JP)

(72) Inventors: Takayuki Furuta, Tokyo (JP); Takashi Sawada, Tokyo (JP); Tomohiro Danjo, Tokyo (JP); Takahiro Nakajima, Tokyo (JP); Noriaki Uesaka, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 0 days.

(21) Appl. No.: 14/418,253

(22) PCT Filed: Jul. 31, 2013

(86) PCT No.: PCT/JP2013/070755
§ 371 (c)(1),
(2) Date: Jan. 29, 2015

(87) PCT Pub. No.: WO2014/021383
PCT Pub. Date: Feb. 6, 2014

(65) Prior Publication Data
US 2015/0284384 A1    Oct. 8, 2015

(30) Foreign Application Priority Data

Jul. 31, 2012 (JP) ................................ 2012-169480

(51) Int. Cl.
| C07D 471/02 | (2006.01) |
| C07D 491/02 | (2006.01) |
| C07D 498/02 | (2006.01) |
| C07D 513/02 | (2006.01) |
| C07D 515/02 | (2006.01) |

(Continued)

(52) U.S. Cl.
CPC ........... C07D 471/04 (2013.01); A61K 31/437 (2013.01); A61K 31/444 (2013.01); A61K 31/4545 (2013.01); A61K 31/5377 (2013.01)

(58) Field of Classification Search
None
See application file for complete search history.

(56) References Cited

U.S. PATENT DOCUMENTS 4,450,164 A    5/1984  Bristol et al.
5,047,411 A  *  9/1991  Takasugi .............. C07D 263/58
                                                 514/300

(Continued)

FOREIGN PATENT DOCUMENTS

DE   19644934 A1   4/1998
EP    1277754 A1   1/2003

(Continued)

OTHER PUBLICATIONS

Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Cornelison, TL. Human papillomavirus genotype 16 vaccines for cervical cancer prophylaxis and treatment. Curr. Opin. Oncol. 2000, vol. 12(5), p. 466.*
Patani, KV. et al. Bioisosterism: A Rational Approach in Drug Design. Chem. Rev. 1996, vol. 96, p. 3172.*
Anderson et al. "Thalamic Cav3.1 T-Type Ca2+ Channel Plays a Crucial Role in Stabilizing Sleep." *PNAS.* 102.5(2005):1743-1748.
Baylis et al. "Comparison of L-Type and Mixed L- and T-Type Calcium Channel Blockers on Kidney Injury Caused by Deoxycorticosterone-Salt Hypertension in Rats." *Am. J. Kidney Dis.* 38.6(2001):1292-1297.

(Continued)

*Primary Examiner* — Rita Desai
*Assistant Examiner* — Ben S Michelson
(74) *Attorney, Agent, or Firm* — Mintz Levin Cohn Ferris Glovsky and Popeo, P.C.; David G. Conlin; Joohee Lee

(57) ABSTRACT

The ring-fused heterocyclic compound or a pharmaceutically acceptable salt thereof according to the present invention has a T-type calcium channel regulatory effect, and is useful, for example, as a medicament for treating and/or preventing pruritus. The present invention provides a ring-fused heterocyclic compound represented by the following general formula (I) or a pharmaceutically acceptable salt thereof and the like which has a T-type calcium channel regulatory effect and is useful as a therapeutic and/or preventive agent for pruritus, and the like.

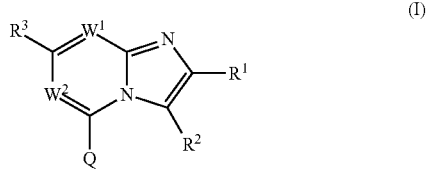

[wherein, $R^1$ represents optionally substituted lower alkyl and the like, $R^2$ represents optionally substituted lower alkyl and the like, $R^3$ represents the formula (II):

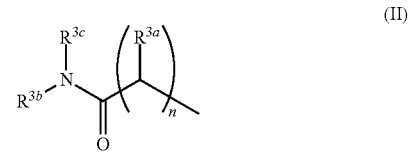

(wherein, n represents 0 or 1, $R^{3a}$ represents a hydrogen atom and the like, $R^{3b}$ represents a hydrogen atom and the like, and $R^{3c}$ represents a hydrogen atom and the like) and the like, Q represents a hydrogen atom and the like, and $W^1$ represents a nitrogen atom and the like, $W^2$ represents a nitrogen atom and the like].

25 Claims, No Drawings

(51) Int. Cl.
| | |
|---|---|
| A61K 31/44 | (2006.01) |
| C07D 471/04 | (2006.01) |
| A61K 31/437 | (2006.01) |
| A61K 31/444 | (2006.01) |
| A61K 31/4545 | (2006.01) |
| A61K 31/5377 | (2006.01) |

(56) References Cited

U.S. PATENT DOCUMENTS

| | | |
|---|---|---|
| 5,498,774 A | 3/1996 | Mitsudera et al. |
| 5,633,237 A | 5/1997 | Hansen, Jr. et al. |
| 6,414,008 B1* | 7/2002 | Hauel .................. C07D 235/06 514/394 |
| 6,469,039 B1 | 10/2002 | Hauel et al. |
| 6,586,452 B1 | 7/2003 | Shih et al. |
| 9,000,186 B2* | 4/2015 | Sawada ............... A61K 31/4184 548/302.7 |
| 2002/0099212 A1 | 7/2002 | Kayakiri et al. |
| 2003/0004181 A1 | 1/2003 | Hauel et al. |
| 2003/0236264 A1 | 12/2003 | Rogers et al. |
| 2004/0023972 A1 | 2/2004 | Sundermann et al. |
| 2004/0142961 A1 | 7/2004 | Sundermann et al. |
| 2005/0197351 A1 | 9/2005 | Lee et al. |
| 2005/0239822 A1 | 10/2005 | Hennies et al. |
| 2006/0003985 A1 | 1/2006 | Renger et al. |
| 2006/0030610 A1 | 2/2006 | Koch et al. |
| 2006/0148801 A1 | 7/2006 | Hsieh et al. |
| 2007/0049604 A1 | 3/2007 | Nam et al. |
| 2007/0099896 A1 | 5/2007 | Sundermann et al. |
| 2007/0173504 A1 | 7/2007 | Pacofsky et al. |
| 2008/0070888 A1 | 3/2008 | McKittrick et al. |
| 2008/0085896 A1 | 4/2008 | Lee et al. |
| 2009/0029345 A1 | 1/2009 | Russell et al. |
| 2009/0076070 A1 | 3/2009 | Harada et al. |
| 2009/0143376 A1 | 6/2009 | Milburn et al. |
| 2009/0234019 A1 | 9/2009 | Gray et al. |
| 2009/0239853 A1* | 9/2009 | Sawada ................ C07D 487/04 514/228.2 |
| 2010/0029637 A1 | 2/2010 | De Lombaert et al. |
| 2010/0168084 A1 | 7/2010 | Huber et al. |
| 2010/0222387 A1 | 9/2010 | Barrow et al. |
| 2011/0112064 A1 | 5/2011 | Barrow et al. |
| 2011/0207711 A1 | 8/2011 | Katz et al. |
| 2012/0220457 A1 | 8/2012 | Miller et al. |
| 2013/0005721 A1 | 1/2013 | Stearns et al. |
| 2013/0065884 A1 | 3/2013 | No et al. |
| 2013/0085133 A1 | 4/2013 | Severson et al. |
| 2014/0038941 A1 | 2/2014 | Sawada et al. |
| 2014/0163008 A1 | 6/2014 | Yamamoto et al. |

FOREIGN PATENT DOCUMENTS

| | | |
|---|---|---|
| JP | 2002148801 A | 5/2002 |
| WO | WO-02066477 A2 | 8/2002 |
| WO | WO-02066478 A1 | 8/2002 |
| WO | WO-08068392 A1 | 6/2008 |
| WO | WO-09027077 A2 | 3/2009 |
| WO | WO-11050245 A1 | 4/2011 |

OTHER PUBLICATIONS

Bertolesi et al. "The Ca2+ Channel Antagonists Mibefradil and Pimozide Inhibit Cell Growth via Different Cytotoxic Mechanisms." *Mol. Pharmacol.* 62.2(2002):210-219.

Bezprozvanny et al. "Voltage-Dependent Blockage of Diverse Types of Voltage-Gated Ca2+ Channels Expressed in *Xenopus* Oocytes by the Ca2+ Channel Antagonist Mibefradil (Ro 40-5967)." *Mol. Pharmacol.* 48(1995):540-549.

Bilici et al. "Protective Effect of T-Type Calcium Channel Blocker in Histamine-Induced Paw Inflammation in Rat." *Pharmacol. Res.* 44.6(2001):527-531.

Bourinet et al. "Silencing of the Cav3.2 T-Type Calcium Channel Gene in Sensory Neurons Demonstrates Its Major Role in Nociception." *EMBO J.* 24(2005):315-324.

Cataldi et al. "Zn2+ Slows Down Cav3.3 Gating Kinetics: Implications for Thalamocortical Activity." *J. Neurophysiol.* 98(2007):2274-2284.

Chen et al. "Association Between Genetic Variation of *CACNA1 H* and Childhood Absence Epilepsy." *Ann. Neurol.* 54(2003):239-243.

Choi et al. "Attenuated Pain Responses in Mice Lacking Cav3.2 T-Type Channels." *Genes Brain Behavior*. 6(2007):425-431.

Dogrul et al. "Reversal of Experimental Neuropathic Pain by T-Type Calcium Channel Blockers." *Pain.* 105(2003):159-168.

Farghaly. "Synthesis and Reactions of 3-[3-(dimethylamino)propenoyl]-1,7- diphenyl[1,2,4]triazolo [4,3-*a* ]pyrimidin-5(1*H* )-one." *J. Chem. Res.* 3(2008):152-156.

Flatters et al. "Ethosuximide Reverses Paclitaxel- and Vincristine-Induced Painful Peripheral Neuropathy." *Pain.* 109(2004):150-161.

Gray et al. "The Role of Voltage Gated T-Type Ca2+ Channel Isoforms in Mediating "Capacitative" Ca2+ Entry in Cancer Cells." *Cell Calcium.* 36(2004):489-497.

Harada et al. "Clinical Efficacy of Efonidipine Hydrochlorida, a T-Type Calcium Channel Inhibitor, on Sympathetic Activities: Examination Using Spectral Analysis of Heart Rate/Blood Pressure Variabilities and 123I-Metaiodobenzylguanidine Myocardial Scintigraphy." *Circ. J.* 67(2003):139-145.

Hayashi et al. "Ca2+ Channel Subtypes and Pharmacology in the Kidney." *Circ. Res.* 100(2007):342-353.

Hayashi et al. "Pathophysiological Significance of T-Type Ca2+ Channels: Role of T-Type Ca2+ Channels in Renal Microcirculation." *J. Pharmacol. Sci.* 99(2005):221-227.

Iftinca et al. "Regulation of Neuronal T-Type Calcium Channels." *Trends Pharmacol. Sci.* 30.1(2009):32-40.

Ishimitsu et al. "Efonidipine Reduces Proteinuria and Plasma Aldosterone in Patients with Chronic Glomerulonephritis." *Hypertens. Res.* 30(2007):621-626.

Jagodic et al. "Cell-Specific Alterations of T-Type Calcium Current in Painful Diabetic Neuropathy Enhance Excitability of Sensory Neurons." *J. Neurosci.* 27.12(2007):3305-3316.

Kaminski et al. "Antiulcer Agents. 4. Conformational Considerations and the Antiulcer Activity of Substituted Imidazo [1,2-*a* ]pyridines and Related Analogues." *J. Med. Chem.* 32(1989):1686-1700.

Katsura et al. "Studies on Antiulcer Drugs. III. Synthesis and Antiulcer Activities of Imidazo[1,2-*a* ]pyridinylethyl-benzoxazols and Related Compounds. A Novel Class of Histamine H2-Receptor Antagonists." *Chem. Pharm. Bull.* 40.6(1992):1424-1438.

Kim et al. "Lack of the Burst Firing of Thalamocortical Relay Neurons and Resistance to Absence Seizures in Mice Lacking α1G T-Type Ca2+ Channels." *Neuron* . 31(2001):35-45.

Kuwahara et al. "Pathophysiological Significance of T-Type Ca2+ Channels: Transcriptional Regulation of T-Type Ca2+ Channel—Regulation of CACNA1H by Neuron-Restrictive Silencer Factor." *J. Pharmacol. Sci.* 99(2003):211-213.

Lee et al. "Lack of Delta Waves and Sleep Disturbances During Non-Rapid Eye Movement Sleep in Mice Lacking α1G-Subunit of T-Type Calcium Channels." *PNAS.* 101.52(2004):18195-18199.

Levine et al. "Effect of Mibefradil, a T-Type Calcium Channel Blocker, on Morbidity and Mortality in Moderation to Severe Congestive Heart Failure: The MACH-1 Study." *Circulation.* 101(2000):758-764.

Masurier et al. "New Opportunities with the Duff Reaction." *J. Org. Chem.* 73(2008):5989-5992.

Messinger et al. "In vivo Silencing of the Cav3.2 T-Type Calcium Channels in Sensory Neurons Alleviates Hyperalgesia in Rats with Streptozocin-Induced Diabetic Neuropathy." *Pain.* 145(2009):184-195.

Na et al. "Attenuated Neuropathic Pain in Cav3.1 Null Mice." *Mol. Cells.* 25.2(2008):242-246.

Noll. "Comparative Pharmacological Properties among Calcium Channel Blockers: T-Channel versus L-Channel Blockade." *Cardiol.* 89(1998):10-15.

Ono et al. "Pathophysiological Significance of T-Type Ca2+ Channels: Properties and Functional Roles of T-Type Ca2+ Channels in Cardiac Pacemaking." *J. Pharmacol. Sci.* 99(2005):197-204.

(56) References Cited

OTHER PUBLICATIONS

Perez-Reyes et al. "Molecular Physiology of Low-Voltage-Activated T-Type Calcium Channels." *Physiol. Rev.* 83(2003):117-161.
Rossier et al. "Inhibitory Action of Mibefradil on Calcium Signaling and Aldosterone Synthesis in Bovine Adrenal Glomerulose Cells." *J. Pharmacol. Exp. Ther.* 287.3(1998):824-831.
Shen et al. "Prophylactic and Therapeutic Functions of T-Type Calcium Blockers Against Noise-Induced Hearing Loss." *Hearing Res.* 226(2007):52-60.
Shin et al. "T-Type Ca2+ Channels as Therapeutic Targets in the Nervous System." *Curr. Opin. Pharmacol.* 8(2008):33-41.
Tanaka et al. "Pathophysiological Significance of T-Type Ca2+ Channels: T-Type Ca2+ Channels and Drug Development." *J. Pharmacol. Sci.* 99(2005):214-220.
Todorovic et al. "Regulation of T-Type Calcium Channels in the Peripheral Pain Pathway." *Channels.* 1.4(2007):238-245.
Wen et al. "Intrathecal Administration of Cav3.2 and Cav3.3 Antisense Oligonucleotide Reverses Tactile Allodynia and Thermal Hyperalgesi in Rats Following Chronic Compression of Dorsal Root of Ganglion." *Acta. Pharmacol. Sin.* 27.12(2006):1547-1552.
Written Opinion of the International Searching Authority issued in International Application No. PCT/JP2013/070755 dated Jan. 31, 2015. (English translation).
Yasui et al. "Pathophysiological Significance of T-Type Ca2+ Channels: Expression of T-Type Ca2+ Channels in Fetal and Diseased Heart." *J. Pharmacol. Sci.* 99(2005):205-210.

\* cited by examiner

RING-FUSED HETEROCYCLIC COMPOUND

CROSS REFERENCE TO RELATED APPLICATION

The present application claims priority to International Patent Application No. PCT/JP2013/070755 filed Jul. 31, 2013, which also claims priority to Japanese Patent Application No 2012-169480, filed Jul. 31, 2012, the entire contents of both applications are incorporated herein for all purposes by this reference.

TECHNICAL FIELD

The present invention relates to a novel ring-fused heterocyclic compound or a pharmaceutically acceptable salt thereof having a T-type calcium channel regulatory activity and useful as a therapeutic and/or preventive agent for pruritus, and the like, and a T-type calcium channel inhibitor and the like which comprise, as an active ingredient, the ring-fused heterocyclic compound or a pharmaceutically acceptable salt thereof.

BACKGROUND ART

Voltage-dependent calcium channels are ion channels that cause influx of calcium ions into cells under the potential difference between the interior and the exterior of a cell, and are known to have important biological functions, including neuronal excitation, synaptic transmission, muscle contraction, cardiac automaticity, secretion of neurotransmitters and hormones, cell proliferation and differentiation, and the like. Voltage-dependent calcium channels have been classified into any of the five categories T, L, P/Q, N, and R by their electrophysiological and pharmacological properties [Physiological Review, Vol. 83, p. 117 (2003)]. Among these five channels, only the T-type channels are activated by high membrane potentials, and are called low-voltage-activated channels. The other four channels are called high-voltage-activated (hereinafter, "HVA") channels, because of their activation at low membrane potentials. As the name suggests, the T (transient)-type calcium channels are characterized by transient activation and quick inactivation. On the other hand, the HVA channels require a long time for inactivation.

It is known that the HVA channels basically act as a heterotetramer having $\alpha 1$, $\alpha 2/\delta$, $\beta$, and $\gamma$ subunits. It is known that, among these subunits, the $\alpha 1$ subunit is the subunit that forms a channel pore, whereas the other subunits act as regulatory or accessory subunits. On the other hand, it is believed that the T-type calcium channels act as the $\alpha 1$ subunit alone. Currently, ten kinds of $\alpha 1$ subunits are known in voltage-dependent calcium channels, and three of these $\alpha 1$ subunits, $\alpha 1G$ (Cav3.1), $\alpha 1H$ (Cav3.2), and $\alpha 1I$ (Cav3.3) are known to form the T-type calcium channels.

The expression of T-type calcium channels has been confirmed in the peripheral and central nervous systems, heart, kidneys, smooth muscle, skeletal muscle, endocrine cells, bone, sperm, and the like. As physiological functions of the T-type calcium channels, neuronal firing, sleeping, pain transmission, heart's pacemaker function, renovascular tonus, hormone secretion, fertilization, and the like, are reported [Physiological Review, Vol. 83, p. 117 (2003); Trends in Pharmacological Science, Vol. 30, p. 32 (2008); Proceedings of the National Academy of Science of the United States of America, Vol. 102, p. 1743 (2005); Proceedings of the National Academy of Science of the United States of America, Vol. 101, p. 18195 (2004)].

As a disease associated with enhancement of the T-type calcium channels, epilepsy [Neuron, Vol. 31, p. 35 (2001); Annals of Neurology, Vol. 54, p. 239 (2003); Journal of Neurophysiology, Vol. 98, p. 2274 (2007)], pain [Channels, Vol. 1, p. 238 (2007); EMBO Journal, Vol. 24, p. 315 (2005); Journal of Neuroscience, Vol. 27, p. 3305 (2007); Molecular Cells, Vol. 25, p. 242 (2008); Acta Pharamacologica Sinica, Vol. 27, p. 1547 (2006); Genes, Brain and Behavior, Vol. 6, p. 425 (2007); Pain, Vol. 105, p. 159 (2003); Pain, Vol. 109, p. 150 (2004); Pain, Vol. 145, p. 184 (2009)], heart disease [Journal of Pharmacological Sciences, Vol. 99, p. 197 (2005); Journal of Pharmacological Sciences, Vol. 99, p. 205 (2005); Journal of Pharmacological Sciences, Vol. 99, p. 211 (2005); Journal of Pharmacological Sciences, Vol. 99, p. 214 (2005)], kidney disease [American Journal of Kidney Disease, Vol. 38, p. 1241 (2001); Journal of Pharmacological Science, Vol. 99, p. 221 (2005); Circulation Research, Vol. 100, p. 342 (2007)], inflammation and edema [Pharmacological Research, Vol. 44, p. 527 (2001)], arteriosclerosis [Cardiology, Vol. 89, p. 10 (1998)], aldosteronism [The Journal of Pharmacology and Experimental Therapeutics, Vol. 287, p. 824 (1998)], cancer [Cell Calcium, Vol. 36, p. 489 (2004); Molecular Pharmacology, Vol. 62, p. 210 (2002)], hearing impairment [Hearing Research, Vol. 226, p. 52 (2007)], and the like, have been reported. T-type calcium channel antagonists are thus considered effective for the treatment or prevention of these diseases. In fact, the cardioprotective effect [Circulation Journal, Vol. 67, p. 139-145 (2003); Circulation, Vol. 101, p. 758 (2000)] and the renoprotective effect [Hypertension Research, Vol. 30, p. 621 (2007)] of T-type calcium channel antagonists are reported in the clinic. Further, it was reported that T-type calcium channels are involved in sleeping [Proceedings of the National Academy of Science of the United States of America, Vol. 102, p. 1743 (2005); Proceedings of the National Academy of Science of the United States of America, Vol. 101, p. 18195 (2004)], and their antagonists may be effective for the treatment and/or prevention of sleep disorder [Current Opinion in Pharmacology, Vol. 8, p. 33 (2008)]. Further, in recent years, it was reported that T-type calcium channel antagonists may be effective for the treatment and/or prevention of pruritus (WO2010/110428).

Among the compounds that act on the T-type calcium channels, many compounds are known as a T-type calcium channel inhibitor. Examples include efonidipine (see, Non-Patent Documents 1 and 2, and the like), mibefradil (see, Non-Patent Document 3, and the like), diphenylmethane derivatives (see, Patent Document 1, and the like), dihydroquinazoline derivatives (see, Patent Documents 2 and 3, and the like), piperidine derivatives (see, Patent Document 4, and the like), piperazine derivatives (see, Patent Document 5, and the like), azetidine and azetidone derivatives (see, Patent Document 6, and the like), thiazole derivatives (see, Patent Document 7, and the like), pyridine derivatives (see, Patent Document 8, and the like), and the like.

On the other hand, as a imidazopyridine derivative, compounds described in Patent Documents 9 to 38 and the like are known.

Furthermore, as a T-type calcium channel inhibitor, imidazopyridine derivatives and the like (see, Non-Patent Document 39) are known.

PRIOR ART

Patent Document

Patent Document 1: WO2006/023883
Patent Document 2: WO2004/035000

Patent Document 3: Publication of European Patent Application 01568695
Patent Document 4: WO2007/002361
Patent Document 5: Publication of European Patent Application 01757590
Patent Document 6: WO2008/033447
Patent Document 7: WO2007/075852
Patent Document 8: WO2007/120729
Patent Document 9: Publication of US Patent Application 2006/030610
Patent Document 10: Publication of US Patent Application 2005/0239822
Patent Document 11: Publication of US Patent Application 2006/0148801
Patent Document 12: WO2008/032764
Patent Document 13: U.S. Pat. No. 4,450,164
Patent Document 14: WO2011/057145
Patent Document 15: WO2011/038086
Patent Document 16: WO2010/017047
Patent Document 17: WO2009/027077
Patent Document 18: WO2008/068392
Patent Document 19: WO2008/045688
Patent Document 20: WO2008/016648
Patent Document 21: WO2006/101455
Patent Document 22: WO2005/105798
Patent Document 23: Publication of US Patent Application 2004/0142961
Patent Document 24: WO2002/066478
Patent Document 25: WO2002/030428
Patent Document 26: WO2001/083481
Patent Document 27: Publication of German Patent Application 19644934
Patent Document 28: WO1991/008211
Patent Document 29: Publication of European Patent Application 404190
Patent Document 30: WO2006/094235
Patent Document 31: WO2002/066477
Patent Document 32: WO1999/000372
Patent Document 33: WO2003/070732
Patent Document 34: Publication of US Patent Application 2010/0168084
Patent Document 35: WO2011/097607
Patent Document 36: Publication of US Patent Application 2010/0184800
Patent Document 37: WO1998/037075
Patent Document 38: Publication of European Patent Application 356234
Patent Document 39: WO2012/105594

Non-Patent Document

Non-Patent Document 1: Circulation Journal, Vol. 67, p. 139-145 (2003)
Non-Patent Document 2: Hypertension Research, Vol. 30, p. 621-626 (2007)
Non-Patent Document 3: Molecular Pharmacology, Vol. 48, p. 540-549 (1995)

DISCLOSURE OF THE INVENTION

Problem that the Invention is to Solve

It is an object of the present invention to provide a novel ring-fused heterocyclic compound or a pharmaceutically acceptable salt thereof and the like, having a T-type calcium channel regulatory activity and useful as, for example, a T-type calcium channel inhibitor, a therapeutic and/or preventive agent for pruritus, and the like. Another object is to provide a T-type calcium channel inhibitor and the like, which comprise, as an active ingredient, the ring-fused heterocyclic compound or a pharmaceutically acceptable salt thereof.

Means for Solving the Problem

The present invention relates to the following (1) to (39).
(1) A ring-fused heterocyclic compound represented by the general formula (I) or a pharmaceutically acceptable salt thereof.

[Chemical Formula 1]

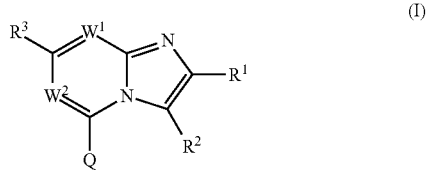

{wherein, $R^1$ represents optionally substituted lower alkyl, optionally substituted cycloalkyl, or optionally substituted lower alkanoyl,
$R^2$ represents optionally substituted lower alkyl, $-SO_2NR^{2a}R^{2b}$ (wherein, $R^{2a}$ and $R^{2b}$ are combined together with the adjacent nitrogen atom thereto to form an optionally substituted nitrogen-containing heterocyclic group), $-C(=O)C(=O)R^{2c}$ (wherein, $R^{2c}$ represents optionally substituted lower alkoxy, optionally substituted mono-lower alkylamino, or an optionally substituted aliphatic heterocyclic group), or $-NR^{2d}R^{2e}$ (wherein, $R^{2d}$ and $R^{2e}$ may be the same or different, and each represents a hydrogen atom, optionally substituted lower alkyl, optionally substituted cycloalkyl, or optionally substituted lower alkanoyl),
$R^3$ represents

[Chemical Formula 2]

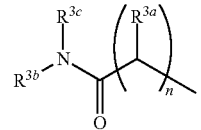

[wherein, n represents 0 or 1,
$R^{3a}$ represents a hydrogen atom or optionally substituted lower alkyl,
$R^{3b}$ and $R^{3c}$ may be the same or different, and each represents a hydrogen atom, optionally substituted lower alkyl, optionally substituted cycloalkyl, optionally substituted aralkyl, optionally substituted aryl, an optionally substituted aromatic heterocyclic group, an optionally substituted aliphatic heterocyclic group, $-OR^{3d}$ (wherein, $R^{3d}$ represents an optionally substituted aliphatic heterocyclic group), $-NHC(=O)R^{3e}$ (wherein, $R^{3e}$ represents optionally substituted aryl, optionally substituted cycloalkyl, or optionally substituted lower alkyl), or $-C(=O)R^{3f}$ (wherein, $R^{3f}$ represents optionally substituted lower alkyl, optionally substituted cycloalkyl, or an optionally substituted aliphatic heterocyclic group), or $R^{3b}$ and $R^{3c}$ are combined together with an adjacent nitrogen atom thereto to form an optionally substituted nitrogen-containing heterocyclic group],
-L¹-R³ᶠ [wherein, L¹ represents —CH=CH—, —CH(OH)—CH(OH)—, —C(=O)—CH(OH)—, or —CH(OH)—C(=O)—, R³ᶠ represents optionally substituted aryl, an optionally substituted aromatic heterocyclic group, an optionally substituted aliphatic heterocyclic group, —C(=O)NHR³ᵍ (wherein, R³ᵍ represents optionally substituted lower alkyl or an optionally substituted aliphatic heterocyclic group), or —C(=O)NH—OR³ʰ (wherein, R³ʰ represent optionally substituted lower alkyl or an optionally substituted aliphatic heterocyclic group)],

[Chemical Formula 3]

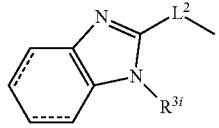

(wherein, L² represents a bond, —CH₂—, —CH(OH)—, or —C(=O)—, --- may be the same or different, and each represents a single bond or a double bond,
R³ⁱ represents a hydrogen atom or optionally substituted lower alkyl), or
an optionally substituted aromatic heterocyclic group,
Q represents a hydrogen atom, halogen, hydroxy, cyano, formyl, optionally substituted lower alkyl, optionally substituted lower alkenyl, optionally substituted lower alkynyl, optionally substituted lower alkoxy, optionally substituted lower alkanoyl, or optionally substituted lower alkylsulfonyl,
W¹ represents a nitrogen atom or C—R⁴ (wherein, R⁴ represents a hydrogen atom or optionally substituted lower alkoxy), and
W² represents a nitrogen atom or C—R⁵ (wherein, R⁵ represents a hydrogen atom, halogen, or optionally substituted lower alkyl)}
(2) The ring-fused heterocyclic compound or a pharmaceutically acceptable salt thereof according to the above (1), wherein R³ is

[Chemical Formula 4]

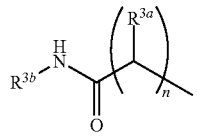

(wherein, n, R³ᵃ, and R³ᵇ have the same meanings as described above, respectively),
-L¹-R³ᶠ (wherein, L¹ and R³ᶠ have the same meanings as described above, respectively),

[Chemical Formula 5]

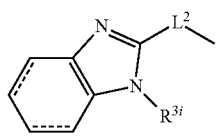

(wherein, L², R³ⁱ, and --- have the same meanings as described above, respectively), or
an optionally substituted aromatic heterocyclic group.
(3) The ring-fused heterocyclic compound or a pharmaceutically acceptable salt thereof according to the above (1), wherein R³ is

[Chemical Formula 6]

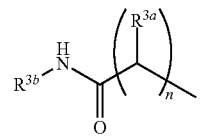

(wherein, n, R³ᵃ, and R³ᵇ have the same meanings as described above, respectively).
(4) The ring-fused heterocyclic compound or a pharmaceutically acceptable salt thereof according to the above (3), wherein n is 0.
(5) The ring-fused heterocyclic compound or a pharmaceutically acceptable salt thereof according to the above (4), wherein R³ᵇ is optionally substituted lower alkyl or an optionally substituted aliphatic heterocyclic group.
(6) The ring-fused heterocyclic compound or a pharmaceutically acceptable salt thereof according to any one of the above (1) to (5), wherein R¹ is optionally substituted lower alkyl.
(7) The ring-fused heterocyclic compound or a pharmaceutically acceptable salt thereof according to any one of the above (1) to (5), wherein R¹ is lower alkyl substituted with halogen.
(8) The ring-fused heterocyclic compound or a pharmaceutically acceptable salt thereof according to any one of the above (1) to (7), wherein R² is optionally substituted lower alkyl, —SO₂NR²ᵃR²ᵇ (wherein, R²ᵃ and R²ᵇ have the same meanings as described above, respectively), or —C(=O)C(=O)R²ᶜ (wherein, R²ᶜ has the same meanings as described above).
(9) The ring-fused heterocyclic compound or a pharmaceutically acceptable salt thereof according to any one of the above (1) to (7), wherein R² is optionally substituted lower alkyl.
(10) The ring-fused heterocyclic compound or a pharmaceutically acceptable salt thereof according to any one of the above (1) to (7), wherein R² is cyclohexylmethyl which may have substituent(s) selected from the group consisting of halogen, hydroxy, cyano, or hydroxymethyl.
(11) The ring-fused heterocyclic compound or a pharmaceutically acceptable salt thereof according to any one of the above (1) to (7), wherein R² is difluorocyclohexylmethyl.
(12) The ring-fused heterocyclic compound or a pharmaceutically acceptable salt thereof according to any one of the above (1) to (11), wherein Q is halogen, cyano, or optionally substituted lower alkyl.
(13) The ring-fused heterocyclic compound or a pharmaceutically acceptable salt thereof according to any one of the above (1) to (11), wherein Q is halogen.
(14) The ring-fused heterocyclic compound or a pharmaceutically acceptable salt thereof according to any one of the above (1) to (11), wherein Q is cyano.
(15) The ring-fused heterocyclic compound or a pharmaceutically acceptable salt thereof according to any one of the above (1) to (11), wherein Q is lower alkyl.

(16) The ring-fused heterocyclic compound or a pharmaceutically acceptable salt thereof according to any one of the above (1) to (15), wherein $W^1$ is C—$R^4$ (wherein, $R^4$ has the same meanings as described above).

(17) The ring-fused heterocyclic compound or a pharmaceutically acceptable salt thereof according to the above (16), wherein $R^4$ is a hydrogen atom.

(18) The ring-fused heterocyclic compound or a pharmaceutically acceptable salt thereof according to any one of the above (1) to (17), wherein $W^2$ is C—$R^5$ (wherein, $R^5$ has the same meanings as described above).

(19) The ring-fused heterocyclic compound or a pharmaceutically acceptable salt thereof according to the above (18), wherein $R^5$ is a hydrogen atom.

(20) The ring-fused heterocyclic compound or a pharmaceutically acceptable salt thereof according to the above (18), wherein $R^5$ is halogen.

(21) The ring-fused heterocyclic compound or a pharmaceutically acceptable salt thereof according to the above (18), wherein $R^5$ is lower alkyl.

(22) The ring-fused heterocyclic compound or a pharmaceutically acceptable salt thereof according to the above (1), wherein Q is cyano, $W^1$ is C—$R^4$ (wherein, $R^4$ has the same meanings as described above), and $W^2$ is C—$R^5$ (wherein, $R^5$ has the same meanings as described above).

(23) The ring-fused heterocyclic compound or a pharmaceutically acceptable salt thereof according to the above (22), wherein $R^3$ is —C(=O)NHR$^{3bA}$ (wherein, R$^{3bA}$ represents optionally substituted lower alkyl or an optionally substituted aliphatic heterocyclic group).

(24) The ring-fused heterocyclic compound or a pharmaceutically acceptable salt thereof according to the above (22) or (23), wherein $R^1$ is optionally substituted lower alkyl.

(25) The ring-fused heterocyclic compound or a pharmaceutically acceptable salt thereof according to any one of the above (22) to (24), wherein $R^2$ is cyclohexylmethyl which may have substituent(s) selected from the group consisting of halogen, hydroxy, cyano, or hydroxymethyl.

(26) The ring-fused heterocyclic compound or a pharmaceutically acceptable salt thereof according to any one of the above (22) to (25), wherein $R^4$ is a hydrogen atom.

(27) The ring-fused heterocyclic compound or a pharmaceutically acceptable salt thereof according to any one of the above (22) to (26), wherein $R^5$ is a hydrogen atom.

(28) The ring-fused heterocyclic compound or a pharmaceutically acceptable salt thereof according to any one of the above (22) to (26), wherein $R^5$ is halogen.

(29) The ring-fused heterocyclic compound or a pharmaceutically acceptable salt thereof according to any one of the above (22) to (26), wherein $R^5$ is lower alkyl.

(30) A pharmaceutical composition, which comprises, as an active ingredient, the ring-fused heterocyclic compound or a pharmaceutically acceptable salt thereof described in any one of the above (1) to (29).

(31) A T-type calcium channel inhibitor, which comprises, as an active ingredient, the ring-fused heterocyclic compound or a pharmaceutically acceptable salt thereof described in any one of the above (1) to (29).

(32) A therapeutic and/or preventive agent for a disease associated with a T-type calcium channel, which comprises, as an active ingredient, the ring-fused heterocyclic compound or a pharmaceutically acceptable salt thereof described in any one of the above (1) to (29).

(33) The agent described in the above (32), wherein the disease associated with a T-type calcium channel is pruritus.

(34) A method for treating and/or preventing a disease associated with a T-type calcium channel, which comprises a step of administering an effective amount of the ring-fused heterocyclic compound or a pharmaceutically acceptable salt thereof described in any one of the above (1) to (29).

(35) The method described in the above (34), wherein the disease associated with a T-type calcium channel is pruritus.

(36) The ring-fused heterocyclic compound or a pharmaceutically acceptable salt thereof descried in any one of the above (1) to (29) for use in treatment and/or prevention of a disease associated with a T-type calcium channel.

(37) The ring-fused heterocyclic compound or a pharmaceutically acceptable salt thereof described in the above (36), wherein the disease associated with a T-type calcium channel is pruritus.

(38) Use of the ring-fused heterocyclic compound or a pharmaceutically acceptable salt thereof described in any one of the above (1) to (29) for the manufacture of a therapeutic and/or preventive agent for a disease associated with a T-type calcium channel.

(39) The use described in the above (38), wherein the disease associated with a T-type calcium channel is pruritus.

Effects of the Invention

The ring-fused heterocyclic compound or a pharmaceutically acceptable salt thereof according to the prevent invention has a T-type calcium channel regulatory activity, and is useful, for example, as a therapeutic and/or preventive agent for pruritus and the like.

The invention provides a novel ring-fused heterocyclic compound or a pharmaceutically acceptable salt thereof, and the like, which has a T-type calcium channel inhibitory activity and is useful as a therapeutic and/or preventive agent for pruritus, and the like. In addition, the invention provides a T-type calcium channel inhibitor and the like comprising, as an active ingredient, the ring-fused heterocyclic compound or a pharmaceutically acceptable salt thereof.

MODE FOR CARRYING OUT THE INVENTION

Hereinafter, a compound represented by the general formula (I) is referred to as Compound (I). Compounds having the other formula numbers are referred to in the same manner.

In a definition of each group in the general formula (I), examples of the lower alkyl and the lower alkyl moiety of the lower alkanoyl, the lower alkoxy, the lower alkylsulfonyl, and the mono-lower alkylamino include linear or branched alkyl having 1 to 10 carbon atoms, more specifically, methyl, ethyl, propyl, isopropyl, butyl, isobutyl, sec-butyl, tert-butyl, pentyl, isopentyl, neopentyl, hexyl, heptyl, octyl, nonyl, decyl, and the like.

Examples of the lower alkenyl include a linear or branched alkenyl having 2 to 10 carbon atoms, more specifically, vinyl, allyl, 1-propenyl, butenyl, pentenyl, hexenyl, heptenyl, octenyl, nonenyl, decenyl, and the like.

Examples of the lower alkynyl include a linear or branched alkynyl having 2 to 10 carbon atoms, and more specifically include ethynyl, propynyl, butynyl, pentynyl, hexynyl, heptynyl, octynyl, nonynyl, decynyl, and the like.

Examples of the cycloalkyl include cycloalkyl having 3 to 8 carbon atoms, and more specifically include cyclopropyl, cyclobutyl, cyclopentyl, cyclohexyl, cycloheptyl, cyclooctyl, and the like.

Examples of the aralkyl include aralkyl having 7 to 16 carbon atoms, and more specifically include benzyl, phenetyl, phenylpropyl, phenylbutyl, phenylpentyl, phenylhexyl, phenylheptyl, phenyloctyl, penylnonyl, phenyldecyl, naphtylmethyl, naphtylethyl, naphtylpropyl, naphtylbutyl, naphtylpentyl, naphtylhexyl, anthrylmethyl, anthrylethyl, and the like.

Examples of the aryl include aryl having 6 to 14 carbon atoms, and more specifically include phenyl, naphthyl, azulenyl, anthryl, and the like.

Examples of the aliphatic heterocyclic group include a 3- to 7-membered monocyclic aliphatic heterocyclic group containing at least one atom selected from a nitrogen atom, an oxygen atom, and a sulfur atom, a bicyclic or tricyclic aliphatic heterocyclic group, in which 3- to 8-membered rings are fused, and which contains at least one atom selected from a nitrogen atom, an oxygen atom, and a sulfur atom, and the like. More specific examples include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzoxazolyl, dihydrobenzothioxazolyl, benzodioxolanyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, 1,4-dioxanyl, oxetanyl, 2-oxaspiro[3.5]nonanyl, oxepanyl, 2-oxaspiro[3.3]heptanyl, quinuclidinyl, 7-oxabicyclo[2.2.1]heptanyl, 1-azabicyclo[2.2.1]heptanyl, 7-azabicyclo[2.2.1]heptanyl, 3-oxabicyclo[3.1.0]hexanyl, 1,3-diazaadamantanyl, 8-azabicyclo[3.2.1]octanyl, 3-oxa-7-azabicyclo[3.3.1]nonanyl, and the like.

Examples of the aromatic heterocyclic group include a 5- or 6-membered monocyclic aromatic heterocyclic group containing at least one atom selected from a nitrogen atom, an oxygen atom, and a sulfur atom, a bicycle or tricycle aromatic heterocyclic group, in which 3- to 8-membered rings are fused, and which contains at least one atom selected from a nitrogen atom, an oxygen atom, and a sulfur atom, and the like. More specific examples include furyl, thienyl, pyrrolyl, imidazolyl, pyrazolyl, oxazolyl, isoxazolyl, oxadiazolyl, triazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl, 4,5,6,7-tetrahydrobenzimidazolyl, and the like.

Examples of the nitrogen-containing heterocyclic group formed together with the adjacent nitrogen atom include a 3- to 7-membered monocyclic heterocyclic group containing at least one nitrogen atom (wherein the monocyclic heterocyclic group may contain another nitrogen atom, an oxygen atom, or a sulfur atom), a bicyclic or tricyclic heterocyclic group, in which 3- to 8-membered rings are fused, and which contains at least one nitrogen atom (wherein the bicyclic or tricyclic heterocyclic group may contain another nitrogen atom, an oxygen atom, or a sulfur atom), and the like. More specific examples include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzoxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl, and the like.

The halogen means each atom of fluorine, chlorine, bromine, or iodine.

Examples of the substituents in the optionally substituted lower alkyl, the optionally substituted lower alkanoyl, the optionally substituted lower alkoxy, the optionally substituted mono-lower alkylamino, the optionally substituted lower alkenyl, the optionally substituted lower alkynyl, and the optionally substituted lower alkylsulfonyl, which may be the same or different and in number of 1 to 3, include substituents selected from the group comprising halogen, hydroxy, mercapto, nitro, cyano, carboxy, carbamoyl, optionally substituted $C_{3-8}$ cycloalkyl (examples of the substituent in the substituted $C_{3-8}$ cycloalkyl, which may be in number of 1 to 3, include halogen, hydroxy, cyano, hydroxymethyl, and the like), optionally substituted $C_{6-14}$ aryl (examples of the substituent in the substituted $C_{6-14}$ aryl, which may be in number of 1 to 3, include halogen, hydroxy, $C_{1-10}$ alkyl, $C_{1-10}$ alkoxy, and the like), an optionally substituted aliphatic heterocyclic group (examples of the substituent in the substituted aliphatic heterocyclic group, which may be in number of 1 to 3, include $C_{1-10}$ alkyl, oxo, hydroxy, $C_{1-10}$ alkoxy, and the like), an optionally substituted aromatic heterocyclic group (examples of the substituent in the substituted aromatic heterocyclic group, which may be in number of 1 to 3, include $C_{1-10}$ alkyl, and the like), $C_{1-10}$ alkoxy, $C_{3-8}$ cycloalkoxy, $C_{6-14}$ aryloxy, $C_{7-16}$ aralkyloxy, formyloxy, $C_{2-11}$ alkanoyloxy, $C_{7-15}$ aroyloxy, $C_{1-10}$ alkylthio, —NR$^X$R$^Y$ [wherein, R$^X$ and R$^Y$ may be the same or different, and each represents a hydrogen atom, optionally substituted $C_{1-10}$ alkyl (examples of the substituent in the substituted $C_{1-10}$ alkyl, which may be in number of 1 to 3, include hydroxy, and the like), $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl, and the like], $C_{2-11}$ alkanoyl, $C_{7-15}$ aroyl, $C_{1-10}$ alkoxycarbonyl, $C_{6-14}$ aryloxycarbonyl, $C_{1-10}$ alkylsulfonyl, —C(=O)—C(=O)R$^Z$ (wherein, R$^Z$ represents $C_{1-10}$ alkoxy, and the like), and —C(=O)—NR$^{X1}$R$^{Y1}$ [wherein, R$^{X1}$ and R$^{Y1}$ may be the same or different, and each represents a hydrogen atom, $C_{1-10}$ alkyl, $C_{6-14}$ aryl, an optionally substituted aliphatic heterocyclic group (examples of the substituent in the substituted aliphatic heterocyclic group, which may be in number of 1 to 3, include $C_{1-10}$ alkyl, and the like), and the like, or R$^{X1}$ and R$^{Y1}$ are combined together with the adjacent nitrogen atom thereto to form an optionally substituted nitrogen-containing heterocyclic group (examples of the substituent in the substituted nitrogen-containing heterocyclic group, which may be in number of 1 to 3, include halogen, or the like)], and the like.

Examples of the substituents in the optionally substituted aryl, the optionally substituted aromatic heterocyclic group, and the optionally substituted aralkyl, which may be the same or different and in number of 1 to 3, include substituents selected from the group comprising halogen, hydroxy, mercapto, nitro, cyano, carboxy, carbamoyl, $C_{1-10}$ alkyl, trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{X2}R^{Y2}$ (wherein, $R^{X2}$ and $R^{Y2}$ may be the same or different, and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl, and the like), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl, and the like.

Examples of the substituents in the optionally substituted cycloalkyl, the optionally substituted aliphatic heterocyclic group, and the optionally substituted nitrogen-containing heterocyclic group formed together with the adjacent nitrogen atom, which may be the same or different and in number of 1 to 3, include substituents selected from the group comprising oxo, halogen, hydroxy, mercapto, nitro, cyano, carboxy, carbamoyl, optionally substituted $C_{1-10}$ alkyl (examples of the substituent in the substituted $C_{1-10}$ alkyl, which may be in number of 1 to 3, include hydroxy, and the like), trifluoromethyl, $C_{3-8}$ cycloalkyl, $C_{6-14}$ aryl, an aliphatic heterocyclic group, an aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{X3}R^{Y3}$ (wherein, $R^{X3}$ and $R^{Y3}$ may be the same or different, and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl, and the like), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl, and the like.

Examples of the $C_{1-10}$ alkyl, and the $C_{1-10}$ alkyl moiety in the $C_{1-10}$ alkoxy, the $C_{2-11}$ alkanoyloxy, the $C_{1-10}$ alkylthio, the $C_{2-11}$ alkanoyl, the $C_{1-10}$ alkoxycarbonyl, the $C_{1-10}$ alkylsulfonyl, the $C_{1-10}$ alkylcarbamoyl, and the di-$C_{1-10}$ alkylcarbamoyl described herein include the groups mentioned as the examples of the lower alkyl described above. The two $C_{1-10}$ alkyl moieties in the di-$C_{1-10}$ alkylcarbamoyl may be the same or different.

Examples of the $C_{3-8}$ cycloalkyl, and the cycloalkyl moiety in the $C_{3-8}$ cycloalkoxy include the groups mentioned as the examples of the cycloalkyl described above.

Examples of the $C_{6-14}$ aryl, and the aryl moiety in the $C_{6-14}$ aryloxy, the $C_{7-15}$ aroyl, the $C_{7-15}$ aroyloxy, and the $C_{6-14}$ aryloxycarbonyl include the groups mentioned as the examples of the aryl described above.

Examples of the $C_{7-16}$ aralkyl, and the aralkyl moiety in the $C_{7-16}$ aralkyloxy and the $C_{7-16}$ aralkyloxycarbonyl include the groups mentioned as the examples of the aralkyl described above.

The aliphatic heterocyclic group, the aromatic heterocyclic group, and the halogen have the same meanings as described in the aliphatic heterocyclic group, the aromatic heterocyclic group, and the halogen described above, respectively.

As Compound (I), the following compounds are preferred in addition to the compounds described in the above (1) to (29).

For example, with regard to each group in Compound (I), a compound in which $R^1$ is $C_{1-10}$ alkyl substituted with 1 to 3 fluorine atoms is preferred, and more preferably a compound in which $R^1$ is trifluoromethyl or difluoroethyl is selected;

a compound in which $R^2$ is cyclohexylmethyl substituted with 1 to 3 halogen atoms or benzyl substituted with 1 to 3 halogen atoms is preferred, and more preferably a compound in which $R^2$ is (4,4-difluorocyclohexyl)methyl or 4-chlorobenzyl is selected;

a compound in which $R^3$ is —$CONHR^{3bB}$ [wherein, $R^{3bB}$ is optionally substituted $C_{1-10}$ alkyl (the substituent in the substituted $C_{1-10}$ alkyl is selected from the group comprising hydroxy, halogen, amino, $C_{1-10}$ alkoxy, $C_{3-8}$ cycloalkyl, $C_{6-14}$ aryl, $C_{2-11}$ alkanoyl, $C_{7-15}$ aroyl, $C_{1-10}$ alkoxycarbonyl, di-$C_{1-10}$ alkylamino, $C_{1-10}$ alkanoylamino, $C_{1-10}$ alkoxycarbonylamino, di-$C_{1-10}$ alkylcarbamoyl, $C_{1-10}$ alkylthio, $C_{1-10}$ alkylsulfonyl, an aliphatic heterocyclic group, an aromatic heterocyclic group, and the like), or an optionally substituted aliphatic heterocyclic group (the substituent in the substituted aliphatic heterocyclic group is selected from hydroxy, $C_{1-10}$ alkyl, and the like)] is preferred;

a compound in which Q is halogen, cyano, or $C_{1-10}$ alkyl is preferred, and more preferably a compound in which Q is cyano is selected, a compound in which $W^1$ is CH is preferred; and a compound in which $W^2$ is C—$R^5$ (wherein, $R^5$ represents a hydrogen atom, halogen, or $C_{1-10}$ alkyl) is preferred.

Further, a compound having a combination of any of the respective groups $R^1$, $R^2$, $R^3$, Q, $W^1$ and $W^2$ in the preferred compounds above is more preferred.

Examples of the diseases associated with a T-type calcium channel of the present invention include pruritus, epilepsy, sleep disorder, pain, migraine, heart diseases, kidney diseases, endocrine diseases, cancers, hearing impairment, and the like.

Examples of the pruritus include pruritus accompanied by skin lesion such as, for example, atopic dermatitis, neurodermatitis, senile cutaneous pruritus, seborrheic dermatitis, caterpillar dermatitis, urticaria, eczema and dermatitis, photosensitivity, autosensitive dermatitis, prurigo, insect bites and stings, scabies, mycosis, cutaneous pruritus, hypertrophic scar, psoriasis such as plaque psoriasis, hydroa, xeroderma, lichen, ringworm, burn; pruritus that are not necessarily accompanied by skin lesion, those caused by visceral diseases such as hepatic and biliary diseases (cirrhosis such as primary biliary cirrhosis, cholestasis, hepatitis, and the like), kidney diseases (kidney failure such as chronic kidney failure, kidney dialysis, and the like), endocrine and metabolic diseases (thyroid disease such as thyroid dysfunction, diabetes, and the like), and the like, cancers (such as malignant lymphoma and digestive system cancer), hematological disorders (such as polycythemia vera and hypoferric anemia), neurological disorders (such as multiple sclerosis and hematological disorders), AIDS, pregnancy, or drug side effects; pruritus associated with ophthalmic and otorhinolaryngological diseases; and the like.

As pruritus in the present invention, pruritus associated with atopic dermatitis or pruritus associated with kidney dialysis are preferred.

Examples of the pharmaceutically acceptable salt of compound (I) include pharmaceutically acceptable acid addition salts, metal salts, ammonium salts, organic amine addition salts, amino acid addition salts, and the like.

Examples of the pharmaceutically acceptable acid addition salts of compound (I) include inorganic acid salts such as hydrochloride, hydrobromate, nitrate, sulfate, and phosphate, and organic acid salts such as acetate, oxalate, maleate, fumarate, citrate, benzoate, and methanesulfonate, and the like. Examples of the pharmaceutically acceptable metal salts include alkali metal salts such as sodium salts and potassium salts, alkali-earth metal salts such as magnesium salts and calcium salts, aluminum salts, zinc salts, and the like. Examples of the pharmaceutically acceptable ammonium salts include salts of ammonium, tetramethylammonium, and the like. Examples of the pharmaceutically acceptable organic amine addition salts include addition salts of morpholine, piperidine, and the like. Examples of the pharmaceutically acceptable amino acid addition salts include addition salts of lysine, glycine, phenylalanine, aspartic acid, glutamic acid, and the like.

The present invention also include prodrug forms of Compound (I). The prodrug form of Compound (I) means a compound that is converted to Compound (I) by a reaction with an enzyme, a gastric acid, and the like, in the body. As the prodrug, many kinds thereof are known, and it is possible to select an appropriate prodrug form based on a known document (for example, Iyakuhin no Kaihatsu (development of medicament), Hirokawa Shoten, vol. 7, p. 163 (1990)) and to synthesize it by using a known method. As a prodrug form of Compound (I): in a case where Compound (I) has amino, a compound in which the amino is acylated, alkylated, or phosphorylated; in a case where Compound (I) has hydroxy, a compound in which the hydroxyl is acylated, alkylated, phosphorylated, or borated; in a case where Compound (I) has carboxy, a compound in which the carboxy is esterified or amidated; and the like can be exemplified. Further, the prodrug form of Compound (I) may be any of a hydrate, a non-hydrate, and a solvate thereof, and may form a salt with a pharmaceutically acceptable acid or base in the same manner as in Compound (I).

Among Compound (I) of the present invention, stereoisomers such as geometric isomers and optical isomers, and the like, tautomers, and the like, may exist. The present invention includes all possible isomers and mixtures thereof including them, and the mixing ratio of the mixtures may be any value.

Compound (I) or a pharmaceutically acceptable salt thereof of the invention may exist as an adduct with water or various solvent in some cases, and the present invention includes these adducts.

A part or all of the respective atoms in Compound (I) may be replaced by corresponding isotope atom(s), respectively, and the present invention also includes such compounds replaced by isotope atom(s). For example, a part or all of hydrogen atoms in Compound (I) may be a hydrogen atom having an atomic weight of 2 (deuterium atom).

For example, a compound in which a part or all of the respective atoms in Compound (I) is/are replaced by corresponding isotope atom(s), respectively can be produced in a same manner as in each of the methods described hereinbelow using building blocks of commercially available compounds. Also, a compound in which a part or all of hydrogen atoms in Compound (I) is/are replaced by deuterium atom(s) can also be synthesized by, for example: 1) a method using deuterium peroxide to deuterate carboxylic acid and the like under a basic condition (U.S. Pat. No. 3,849,458); 2) a method using iridium complex as a catalyst and using heavy water as a deuterium source to deuterate alcohol, a carboxylic acid, and the like [J. Am. Chem. Soc., Vol. 124, No. 10, 2092 (2002)]; 3) a method using palladium carbon as a catalyst and using only deuterium gas as a deuterium source to deuterate fatty acid [LIPIDS, Vol. 9, No. 11, 913 (1974)]; 4) a method using a metal such as platinum, palladium, rhodium, ruthenium, and iridium as a catalyst and using heavy water or heavy water and deuterium gas as a deuterium source to deuterate acrylic acid, methyl acrylate, methacrylic acid, methyl methacrylate, and the like (JPH5-19536, JPS61-277648 and JPS61-275241); 5) a method using palladium, nickel, copper, copper chromite, or the like as a catalyst and using heavy water as a deuterium source to deuterate acrylic acid, methyl methacrylate, and the like (JPS63-198638); and the like.

The isotope atom(s), as used herein, refer to atom(s) having a valence or a mass number different from a valence or a mass number generally found in nature. Examples of isotope atom(s) in the compound of the present invention include $^2$H, $^3$H, $^{13}$C, $^{14}$C, $^{15}$N, $^{17}$O, $^{18}$O, $^{31}$P, $^{32}$P, $^{35}$S, $^{18}$F, $^{36}$Cl, and the like.

Next, production methods of Compound (I) are explained.

Incidentally, in each of the production methods shown below, in the case where a defined group changes under the condition of the production methods or is unsuitable for carrying out the production methods, methods for introducing and removing a protective group commonly used in the organic synthetic chemistry [for example, the method described in Protective Groups in Organic Synthesis, third edition, T. W. Greene, John Wiley & Sons Inc. (1999), and the like] and the like, can be used to produce the target compound. Further, the order of the reaction steps such as a step for introducing a substituent and the like, may be changed, if necessary.

Production Method 1

Among Compound (I), Compound (a-12) in which $R^3$ is —C(=O)$NR^{3b}R^{3c}$ (wherein, $R^{3b}$ and $R^{3c}$ have the same meanings as described above, respectively), $R^2$ is —$CH_2R^{2aa}$ (wherein, $R^{2aa}$ represents the substituent in the optionally substituted lower alkyl of $R^2$ described above.) can be produced, for example, according to the following steps.

[Chemical Formula 7]

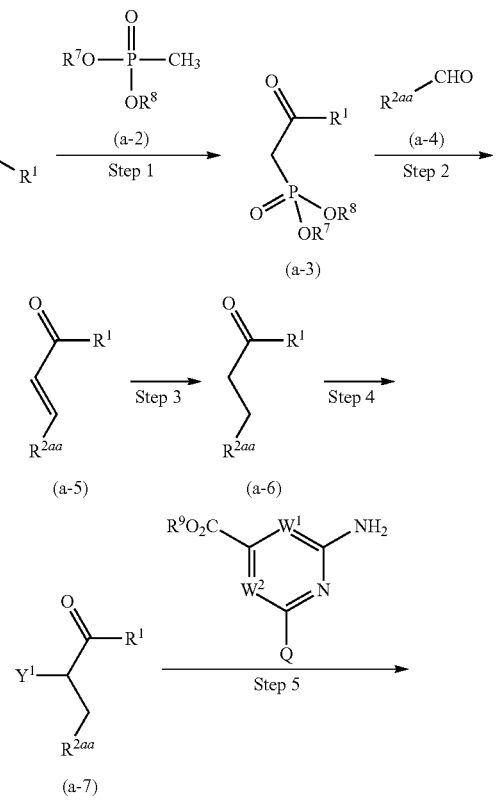

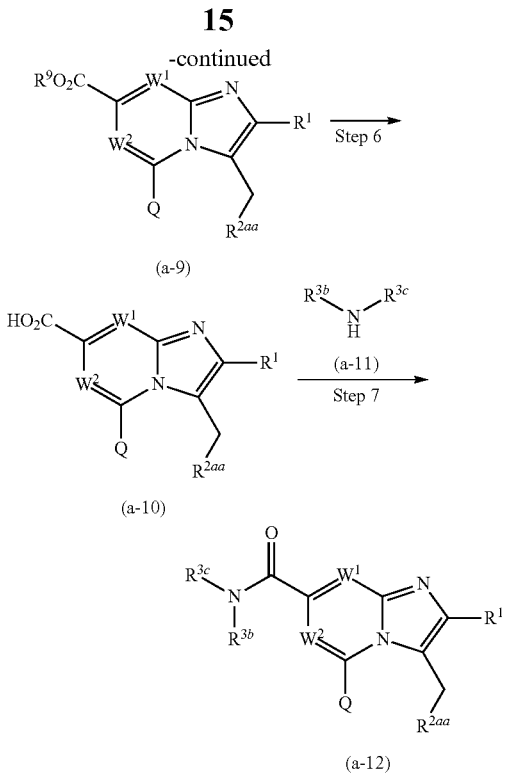

(wherein, $Y^1$ represents a chlorine atom, a bromine atom, or an iodine atom, $R^6$, $R^7$, and $R^8$ may be the same or different, and each represents $C_{1-6}$ alkyl or phenyl, $R^9$ represents $C_{1-10}$ alkyl or $C_{7-16}$ aralkyl, and $R^1$, $R^{2aa}$, $R^{3b}$, $R^{3c}$, Q, $W^1$, and $W^2$ have the same meanings as described above, respectively)

Step 1

Compound (a-3) can be produced by reacting Compound (a-1) with 1 to 20 equivalents of Compound (a-2) in a solvent or without solvent in the presence of 1 to 20 equivalents of a base at a temperature between −78° C. and the boiling point of the used solvent for 5 minutes to 72 hours.

Examples of the base include n-butyllithium and the like. Examples of the solvent include toluene, diethyl ether, tetrahydrofuran (THF), 1,2-dimethoxyethane (DME), dioxane, hexane, and the like. These may be used alone or as a mixture.

Compound (a-1) can be obtained as a commercially available product, or can be obtained by using a known method [for example, Jikken Kagaku Koza (Experimental Chemistry Course), the fourth edition, vol. 22, p. 43, Maruzen Co. Ltd. (1992), and the like], or a method based on such a method.

Compound (a-2) can be obtained as a commercially available product, or can be obtained by a known method [for example, Jikken Kagaku Koza (Experimental Chemistry Course), the fourth edition, vol. 24, p. 229, Maruzen Co. Ltd. (1992), and the like], or a method based on such a method.

Step 2

Compound (a-5) can be produced by reacting Compound (a-3) with 1 to 10 equivalents of Compound (a-4) in a solvent in the presence of 1 to 10 equivalents of a base at a temperature between −78° C. and a boiling point of the used solvent for 5 minutes to 72 hours.

Examples of the base include sodium hydride, potassium acetate, sodium hydrogen carbonate, potassium carbonate, potassium hydroxide, sodium hydroxide, sodium methoxide, potassium tert-butoxide, triethylamine, diisopropylethylamine, N-methylmorpholine, pyridine, 1,8-diazabycyclo [5.4.0]-7-undecene (DBU), and the like. Examples of the solvent include methanol, ethanol, dichloromethane, chloroform, 1,2-dichloroethane, toluene, ethyl acetate, acetonitrile, diethyl ether, THF, DME, dioxane, dimethylformamide (DMF), dimethylacetamide (DMA), N-methylpyrrolidone (NMP), and the like. These may be used alone or as a mixture.

Compound (a-4) can be obtained as a commercially available product, or can be obtained by a known method [for example, Jikken Kagaku Koza (Experimental Chemistry Course), the fourth edition, vol. 24, p. 229, Maruzen Co. Ltd. (1992), and the like], or a method based on such a method.

Incidentally, geometric isomers may exist in Compound (a-5) in some cases. Compound (a-5) encompasses the isomers and mixtures thereof.

Step 3

Compound (a-6) can be produced by treating Compound (a-5) in a solvent under a hydrogen atmosphere or in the presence of a hydrogen source in the presence of a catalyst at a temperature between −20° C. and the boiling point of the used solvent under a normal or increased pressure for 5 minutes to 72 hours.

Examples of the catalyst include palladium carbon, palladium, palladium hydroxide, palladium acetate, palladium black, and the like. These are used in 0.01 to 100 weight % with respect to Compound (a-5). Examples of the hydrogen source include formic acid, ammonium formate, sodium formate, cyclohexadiene, hydrazine, and the like. These are used in 2 equivalents to a large excess amount. Examples of the solvent include methanol, ethanol, toluene, ethyl acetate, acetonitrile, diethyl ether, THF, DME, dioxane, DMF, DMA, NMP, water, and the like. These are used alone or as a mixture.

Step 4

Compound (a-7) can be produced by treating Compound (a-6) in a solvent or without solvent in the presence of 1 to 5 equivalents of a halogenation agent at a temperature between −30° C. and 150° C. for 5 minutes to 72 hours.

Examples of the halogenation agent include chlorine, bromine, iodine, N,N,N,N-tetra-n-butylammonium tribromide, N-chlorosuccinimide, N-bromosuccinimide, N-iodosuccinimide, and the like. Examples of the solvent include acetone, 1,4-dioxane, acetonitrile, chloroform, dichloromethane, THF, DME, ethyl acetate, methanol, ethanol, DMF, acetic acid, water, and the like. These are used alone or as a mixture.

Step 5

Compound (a-9) can be produced by reacting Compound (a-7) with 0.1 to 10 equivalents of Compound (a-8) in a solvent or without solvent at a temperature between 0° C. and 300° C., if necessary, in the presence of 1 to 10 equivalents of a base, and if necessary, in the presence of 0.1 to 1000 weight % of an additive, for 5 minutes to 72 hours.

Examples of the base include potassium carbonate, sodium carbonate, potassium hydrogen carbonate, sodium hydrogen carbonate, potassium hydroxide, potassium hydroxide, triethylamine, diisopropylethylamine, N-methylmorpholine, pyridine, DBU, and the like. Examples of the additive include molecular sieves 4A, and the like. Examples of the solvent include methanol, ethanol, propanol, butanol, DMF, DMA, NMP, acetonitrile, diethyl ether, THF, DME, 1,4-dioxane, dimethyl sulfoxide (DMSO), and the like. These may be used alone or as a mixture.

Compound (a-8) can be obtained as a commercially available product, or can be obtained by a known method [for example, Jikken Kagaku Koza (Experimental Chemistry Course), the fourth edition, vol. 20, p. 290, Maruzen Co. Ltd. (1992), and the like] or a method based on such a method.

Step 6

Compound (a-10) can be produced by a method based on the method of removing a protective group described in, for example, Protective Groups in Organic Synthesis, T. W. Greene, John Wiley & Sons Inc. (1981), and the like, using Compound (a-9).

For example, in a case where $R^9$ is $C_{1-10}$ alkyl, Compound (a-10) can be produced by treating Compound (a-9) in a water-containing solvent in the presence of 1 equivalent to a large excess amount of a base at a temperature between 0° C. and the boiling point of the used solvent for 5 minutes to 72 hours.

Examples of the base include sodium hydroxide, potassium hydroxide, lithium hydroxide, and the like. Examples of the solvent include methanol, ethanol, propanol, THF, 1,4-dioxane, DME, toluene, dichloromethane, DMF, and the like, and a mixed solvent thereof with water can be used.

Further, for example, in a case where $R^9$ is tert-butyl, Compound (a-10) can be produced by treating Compound (a-9) in a solvent or without solvent in a presence of 1 equivalent to a large excess amount of an acid at a temperature between −30° C. to 100° C. for 5 minutes to 72 hours.

Examples of the acid include hydrochloric acid, sulfuric acid, trifluoroacetic acid, methanesulfonic acid, and the like. Examples of the solvent include methanol, ethanol, propanol, THF, 1,4-dioxane, DME, toluene, ethyl acetate, dichloromethane, DMF, water, and the like. These may be used alone or as a mixture.

In addition, the carboxyl group obtained by the conversion of the functional group in this step can also be obtained by hydrolysis of a cyano group at a corresponding substitution position in the same manner as in this step.

Step 7

Compound (a-12) can be produced by reacting Compound (a-10) in a solvent or without solvent in the presence of 1 to 30 equivalents of a condensing agent, if necessary, in the presence of 0.1 to 30 equivalents of an additive, with 1 to 30 equivalents of Compound (a-11), at a temperature between −30° C. and 150° C. for 5 minutes to 72 hours.

Examples of the condensing agent include dicyclohexyl carbodiimide (DCC), diisopropyl carbodiimide, N-(3-dimethylaminopropyl)-N'-ethyl carbodiimide (EDC), EDC hydrochloride, 4-(4,6-dimethoxy-1,3,5-triazin-2-yl)-4-methylmorpholinium chloride (DMT-MM), and the like. Examples of the additive include a 1-hydroxybenzotriazole hydrate, triethylamine, 4-dimethylaminopyridine (DMAP), potassium carbonate, sodium carbonate, sodium hydrogen carbonate, tetramethylethylenediamine (TMEDA), pyridine, diisopropylethylamine, DBU, and the like. Examples of the solvent include acetonitrile, dichloromethane, 1,2-dichloroethane, chloroform, DME, DMF, DMA, 1,4-dioxane, THF, diethyl ether, diisopropyl ether, benzene, toluene, xylene, pyridine, NMP, water, and the like. These may be used alone or as a mixture.

Compound (a-11) can be obtained as a commercially available product, or can be obtained by a known method [for example, Jikken Kagaku Koza (Experimental Chemistry Course), the fourth edition, vol. 20, p. 281, Maruzen Co. Ltd. (1992), and the like] or a method based on such a method.

Production Method 2

Among Compound (I), Compound (a-18) in which $R^2$ is $-SO_2NR^{2a}R^{2b}$ (wherein, $R^{2a}$ and $R^{2b}$ have the same meanings as describe above, respectively), Compound (a-20) in which $R^2$ is $-C(=O)C(=O)R^{2c}$ (wherein, $R^{2c}$ has the same meaning as described above), and Compound (a-25) in which $R^2$ is $-NR^{2d}R^{2e}$ (wherein, $R^{2d}$ and $R^{2e}$ have the same meanings as describe above, respectively) can be produced, for example, according to the following steps.

[Chemical Formula 8]

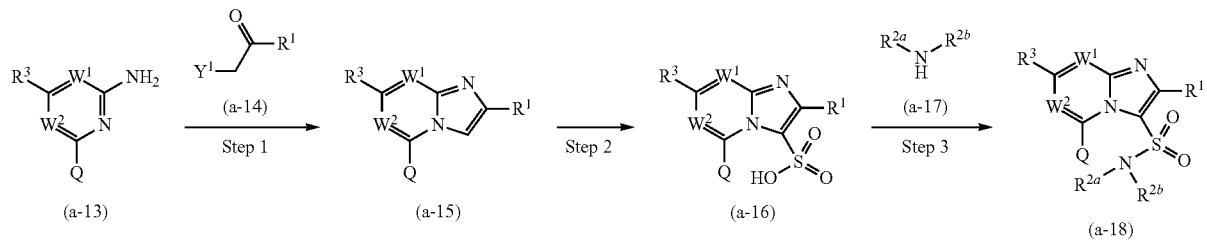

-continued

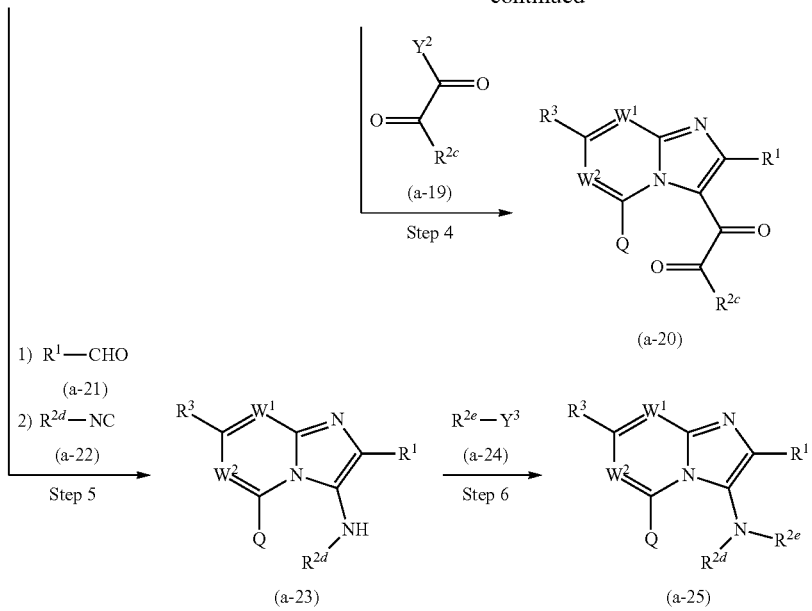

(wherein, $Y^2$ and $Y^3$ may be the same or different, and each represents a chlorine atom, a bromine atom, or an iodine atom, and $R^1$, $R^{2a}$, $R^{2b}$, $R^{2c}$, $R^{2d}$, $R^{2e}$, $R^3$, Q, $W^1$, $W^2$, and $Y^1$ have the same meanings as describe above, respectively)

Step 1

Compound (a-15) can be produced in the same manner as in Step 5 in Production Method 1 using Compound (a-13) and Compound (a-14).

Compound (a-13) can be obtained as a commercially available product, or can be obtained by a known method [for example, Jikken Kagaku Koza (Experimental Chemistry Course), the fourth edition, vol. 20, p. 290, Maruzen Co. Ltd. (1992), and the like] or a method based on such a method.

Compound (a-14) can be obtained as a commercially available product, or can be obtained by a known method [for example, Jikken Kagaku Koza (Experimental Chemistry Course), the fourth edition, vol. 19, p. 435, Maruzen Co. Ltd. (1992), and the like] or a method based on such a method.

Step 2

Compound (a-16) can be produced by treating Compound (a-15) in a solvent or without solvent in the presence of 0.5 to 10 equivalents of a sulfonylating agent at a temperature between −30° C. and the boiling point of the used solvent for 5 minutes to 72 hours.

Examples of the sulfonylating agent include chlorosulfonic acid, trimethylsilyl chlorosulfonate, fuming sulfuric acid, sulfur trioxide, sulfur dioxide, and the like. Examples of the solvent include 1,2-dichloroethane, chloroform, dichloromethane, sulfolane, ethyl acetate, and the like. These may be used alone or as a mixture. Among them, 1,2-dichloroethane or dichloromethane is preferred.

Step 3

Compound (a-18) can be produced by treating Compound (a-16) in a solvent or without solvent in the presence of 1 to 20 equivalents of an acid halogenation agent at a temperature between −20° C. and the boiling point of the used solvent for 5 minutes to 72 hours to obtain a sulfonic acid halide of Compound (a-16), and then reacting the resulting sulfonic acid halide of Compound (a-16), in a solvent in the presence of 1 to 10 equivalents of a base, with 0.5 to 5 equivalents of Compound (a-17) at a temperature between −20° C. and the boiling point of the used solvent for 5 minutes to 72 hours. In the treatment of Compound (a-16) with the acid halogenation agent, if necessary, 0.01 to 0.5 equivalents of DMF, pyridine, or the like, may be added.

Examples of the solvent to be used for treating Compound (a-16) with an acid halogenation agent include 1,2-dichloroethane, chloroform, dichloromethane, pyridine, THF, DME, toluene, DMF, dioxane, ethyl acetate and the like. These may be used alone or as a mixture. Among them, 1,2-dichloroethane, dichloromethane, or toluene is preferred. Further, examples of the acid halogenation agent include thionyl chloride, oxalyl chloride, phosphorus oxychloride, and the like.

Examples of the solvent to be used for the reaction of the sulfonic acid halide of Compound (a-16) with Compound (a-17) include 1,2-dichloroethane, chloroform, dichloromethane, pyridine, acetonitrile, THF, DME, toluene, DMF, dioxane, ethyl acetate, and the like. These may be used alone or as a mixture. Further, examples of the base include pyridine, triethylamine, 4-(dimethylamino)pyridine, N,N-diisopropylethylamine, a sodium hydrogen carbonate aqueous solution, a sodium hydroxide aqueous solution, and the like. Among them, triethylamine is preferred.

Compound (a-17) can be obtained as a commercially available product, or can be obtained by a known method [for example, Jikken Kagaku Koza (Experimental Chemistry Course), the fourth edition, vol. 20, p. 279, Maruzen Co. Ltd. (1992), and the like] or a method based on such a method.

Step 4

Compound (a-20) can be produced by reacting Compound (a-15), in a solvent or without solvent, with 0.5 to 10 equivalents of Compound (a-19) at a temperature between −30° C. and the boiling point of the used solvent for 5 minutes to 72 hours.

Examples of the solvent include 1,2-dichloroethane, chloroform, dichloromethane, pyridine, THF, DME, toluene, xylene, DMF, dioxane, ethyl acetate, and the like. These may be used alone or as a mixture. Among them, xylene or toluene is preferred.

Compound (a-19) can be obtained as a commercially available product, or can be obtained by a known method [for example, Jikken Kagaku Koza (Experimental Chemistry Course), the fourth edition, vol. 22, p. 116, Maruzen Co. Ltd. (1992), and the like] or a method based on such a method.

Step 5

Compound (a-23) can be produced by reacting Compound (a-13), in a solvent or without solvent, with 0.5 to 10 equivalents of Compound (a-21), in the presence of 0.05 to equivalents of an additive if necessary, at a temperature between −30° C. and the boiling point of the used solvent for 5 minutes to 72 hours, and further reacting the resultant with 0.5 to 10 equivalents of Compound (a-22) at a temperature between −30° C. and the boiling point of the used solvent for 5 minutes to 72 hours.

Examples of the additive include scandium(III) trifluoromethanesulfonate, ytterbium(III) trifluoromethanesulfonate, and the like. Examples of the solvent include methanol, 1,2-dichloroethane, chloroform, dichloromethane, sulfolane, ethyl acetate, and the like. These may be used alone or as a mixture. Among them, a mixed solvent of methanol and dichloromethane is preferred.

Compound (a-21) can be obtained as a commercially available product, or can be obtained by a known method [for example, Jikken Kagaku Koza (Experimental Chemistry Course), the fourth edition, vol. 21, p. 2, Maruzen Co. Ltd. (1992), and the like] or a method based on such a method.

Compound (a-22) can be obtained as a commercially available product, or can be obtained by a known method [for example, Jikken Kagaku Koza (Experimental Chemistry Course), the fourth edition, vol. 20, p. 463, Maruzen Co. Ltd. (1992), and the like] or a method based on such a method.

Step 6

Compound (a-25) can be produced by reacting Compound (a-23), in a solvent or without solvent, with 0.5 to 10 equivalents of Compound (a-24), in the presence of 1 to 10 equivalents of a base if necessary, at a temperature between −30° C. and the boiling point of the used solvent for 5 minutes to 72 hours.

Examples of the base include pyridine, triethylamine, 4-(dimethylamino)pyridine, N,N-diisopropylethylamine, sodium hydride, and the like. Examples of the solvent include methanol, 1,2-dichloroethane, chloroform, dichloromethane, sulfolane, THF, ethyl acetate, and the like. These may be used alone or as a mixture.

Compound (a-24) can be obtained as a commercially available product, or can be obtained by a known method [for example, Jikken Kagaku Koza (Experimental Chemistry Course), the fourth edition, vol. 19, p. 460, Maruzen Co. Ltd. (1992), and the like] or a method based on such a method.

Production Method 3

Among Compound (I), Compound (a-29) in which $R^3$ is —$CH_2C(=O)NR^{3b}R^{3c}$ (wherein, $R^{3b}$ and $R^{3c}$ have the same meanings as describe above, respectively) and Compound (a-31) in which $R^3$ is —$CHR^{3a}$—$C(=O)NR^{3b}R^{3c}$ (wherein, $R^{3a}$, $R^{3b}$, and $R^{3c}$ have the same meanings as describe above, respectively) can be produced, for example, according to the following steps.

[Chemical Formula 9]

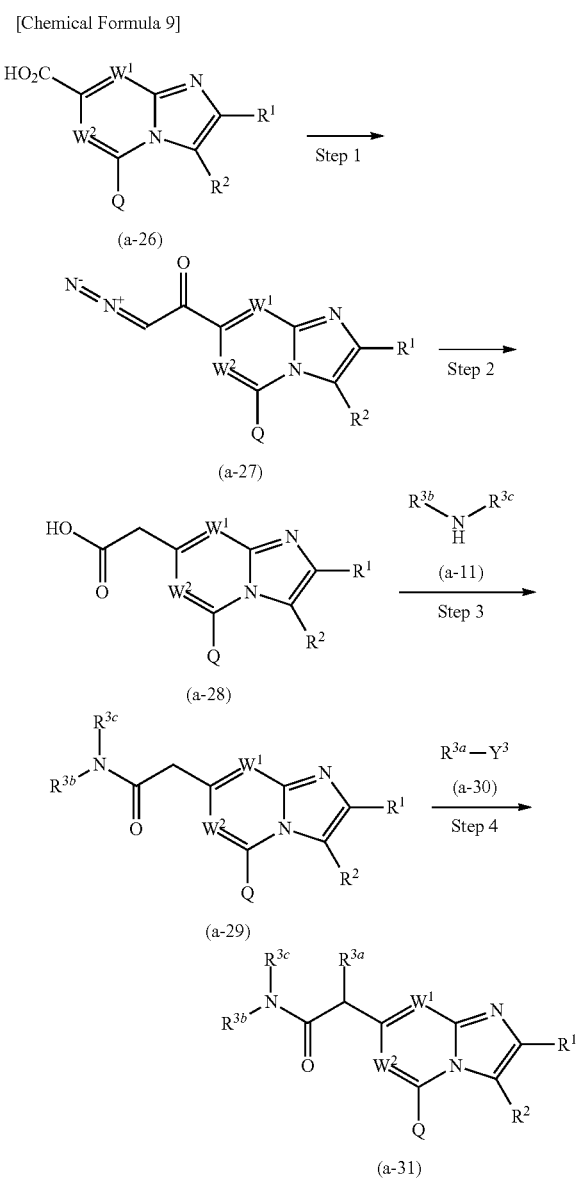

(wherein, $R^1$, $R^2$, $R^{3a}$, $R^{3b}$, $R^{3c}$, Q, $W^1$, $W^2$, and $Y^3$ have the same meanings as describe above, respectively)

Step 1

Compound (a-27) can be produced by reacting Compound (a-26) in a solvent or without solvent in the presence of to 10 equivalents of acid halogenation agent at a temperature between −30° C. and the boiling point of the used solvent for 5 minutes to 72 hours, and then treating the resultant in a solvent or without solvent in the presence of 1 to 10 equivalents of a diazotization agent at a temperature between −30° C. and the boiling point of the used solvent for 5 minutes to 72 hours.

Examples of the acid halogenation agent include thionyl chloride, oxalyl chloride, phosphorus oxychloride, and the like. Examples of the diazotization agent include trimethylsilyldiazomethane, diazomethane, and the like. Examples of the solvent include methanol, 1,2-dichloroethane, chloroform, dichloromethane, sulfolane, THF, DMF, acetonitrile, ethyl acetate, and the like. These may be used alone or as a mixture.

Compound (a-26) can be obtained by a method based on Production Method 1.

Step 2

Compound (a-28) can be produced by treating Compound (a-27) in a solvent or without solvent in the presence of 1 to 10 equivalents of an additive and 1 to 10 equivalents of a base at a temperature between −30° C. and the boiling point of the used solvent for 5 minutes to 72 hours.

Examples of the additive include silver trifluoroacetate, silver acetate, and the like. Examples of the base include triethylamine, pyridine, diisopropylethylamine, DBU, and the like. Examples of the solvent include methanol, THF, DMF, water, and the like. These may be used alone or as a mixture.

Step 3

Compound (a-29) can be produced in the same manner as in Step 7 of Production Method 1 using Compound (a-28) and Compound (a-11).

Step 4

Compound (a-31) can be produced by reacting Compound (a-29) in a solvent or without solvent with 0.5 to 10 equivalents of Compound (a-30), in the presence of 1 to 10 equivalents of a base if necessary, at a temperature between −30° C. and the boiling point of the used solvent for 5 minutes to 72 hours.

Examples of the base include pyridine, triethylamine, 4-(dimethylamino)pyridine, N,N-diisopropylethylamine, sodium hydride, and the like. Examples of the solvent include methanol, 1,2-dichloroethane, chloroform, dichloromethane, sulfolane, THF, DMF, ethyl acetate, and the like. These may be used alone or as a mixture.

Compound (a-30) can be obtained as a commercially available product, or can be obtained by a known method [for example, Jikken Kagaku Koza (Experimental Chemistry Course), the fourth edition, vol. 19, p. 460, Maruzen Co. Ltd. (1992), and the like] or a method based on such a method.

Production Method 4

Among Compound (I), Compound (a-34) in which $R^3$ is —CH═CHR$^{3f}$ (wherein, $R^f$ has the same meaning as described above), Compound (a-35) in which $R^3$ is —CH(OH)—CH(OH)R$^{3f}$ (wherein, $R^f$ has the same meaning as described above), and Compound (a-36) in which $R^3$ is —C(═O)—CH(OH)R$^{3f}$ (wherein, $R^f$ has the same meaning as described above) can be produced, for example, according to the following steps.

[Chemical Formula 10]

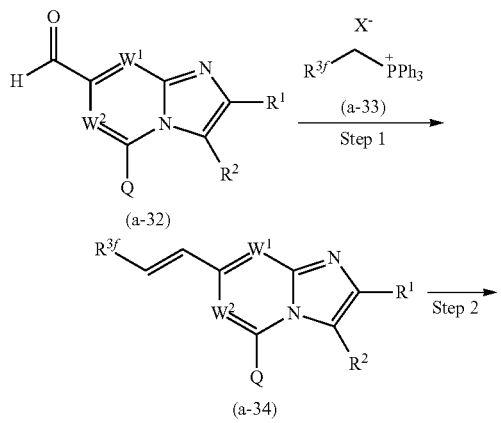

(a-32)

(a-34)

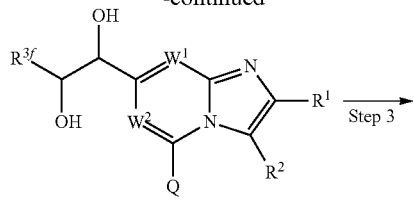

(a-35)

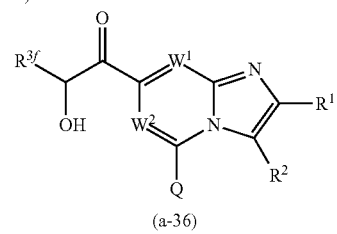

(a-36)

(wherein, X represents a chlorine atom, a bromine atom, or an iodine atom, and $R^1$, $R^2$, $R^{3f}$, Q, $W^1$, and $W^2$ have the same meanings as describe above, respectively)

Step 1

Compound (a-34) can be produced by reacting Compound (a-32) in a solvent or without solvent with 0.5 to 10 equivalents of Compound (a-33) in the presence of 1 to 10 equivalents of a base at a temperature between −30° C. and the boiling point of the used solvent for 5 minutes to 72 hours.

Examples of the base include pyridine, triethylamine, 4-(dimethylamino)pyridine, N,N-diisopropylethylamine, sodium hydride, and the like. Examples of the solvent include methanol, 1,2-dichloroethane, chloroform, dichloromethane, sulfolane, THF, DMF, ethyl acetate, and the like. These may be used alone or as a mixture.

Compound (a-32) can be obtained by a known method [for example, Jikken Kagaku Koza (Experimental Chemistry Course), the fourth edition, vol. 21, p. 83, Maruzen Co. Ltd. (1992), and the like] or a method based on such a method, using Compound (a-26).

Compound (a-33) can be obtained as a commercially available product, or can be obtained by a known method [for example, Jikken Kagaku Koza (Experimental Chemistry Course), the fourth edition, vol. 24, p. 252, Maruzen Co. Ltd. (1992), and the like] or a method based on such a method.

Incidentally, geometric isomers may exist in Compound (a-34) in some cases. Compound (a-34) encompasses the isomers and mixtures thereof.

Step 2

Compound (a-35) can be produced by treating Compound (a-34) in a solvent or without solvent in the presence of 0.1 to 10 equivalents of an oxidizing agent and 1 to 10 equivalents of a reoxidizing agent at a temperature between −30° C. and the boiling point of the used solvent for 5 minutes to 72 hours.

Examples of the oxidizing agent include osmium tetroxide, selenium dioxide, and the like. Examples of the reoxidizing agent include N-methylmorpholine N-oxide, tert-butylhydroperoxide, and the like. Examples of the solvent include methanol, 1,2-dichloroethane, chloroform, dichloromethane, sulfolane, butanol, THF, DMF, ethyl acetate, water, and the like. These may be used alone or as a mixture.

Incidentally, optical isomers may exist in Compound (a-35). Compound (a-34) encompasses the isomers and mixtures thereof.

Step 3

Compound (a-36) can be produced by treating Compound (a-35) in a solvent or without solvent in the presence of 0.1 to 10 equivalents of an oxidizing agent at a temperature between −30° C. and the boiling point of the used solvent for 5 minutes to 72 hours.

Examples of the oxidizing agent include manganese dioxide, potassium permanganate, and the like. Examples of the solvent include methanol, 1,2-dichloroethane, chloroform, dichloromethane, sulfolane, butanol, THF, DMF, ethyl acetate, water, and the like. These may be used alone or as a mixture.

Incidentally, optical isomers may exist in Compound (a-36). Compound (a-36) includes the isomers and mixtures thereof.

Production Method 5

Among Compound (I), Compound (a-37), Compound (a-39), Compound (a-41), Compound (a-42), Compound (a-44) and Compound (a-45) in which $R^3$ is a group represented by the following formula:

[Chemical Formula 11]

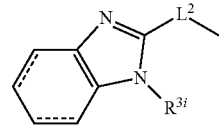

(wherein, $R^{3i}$, $L^2$, and $---$ have the same meanings as describe above, respectively) can be produced, for example, according to the following steps.

[Chemical Formula 12]

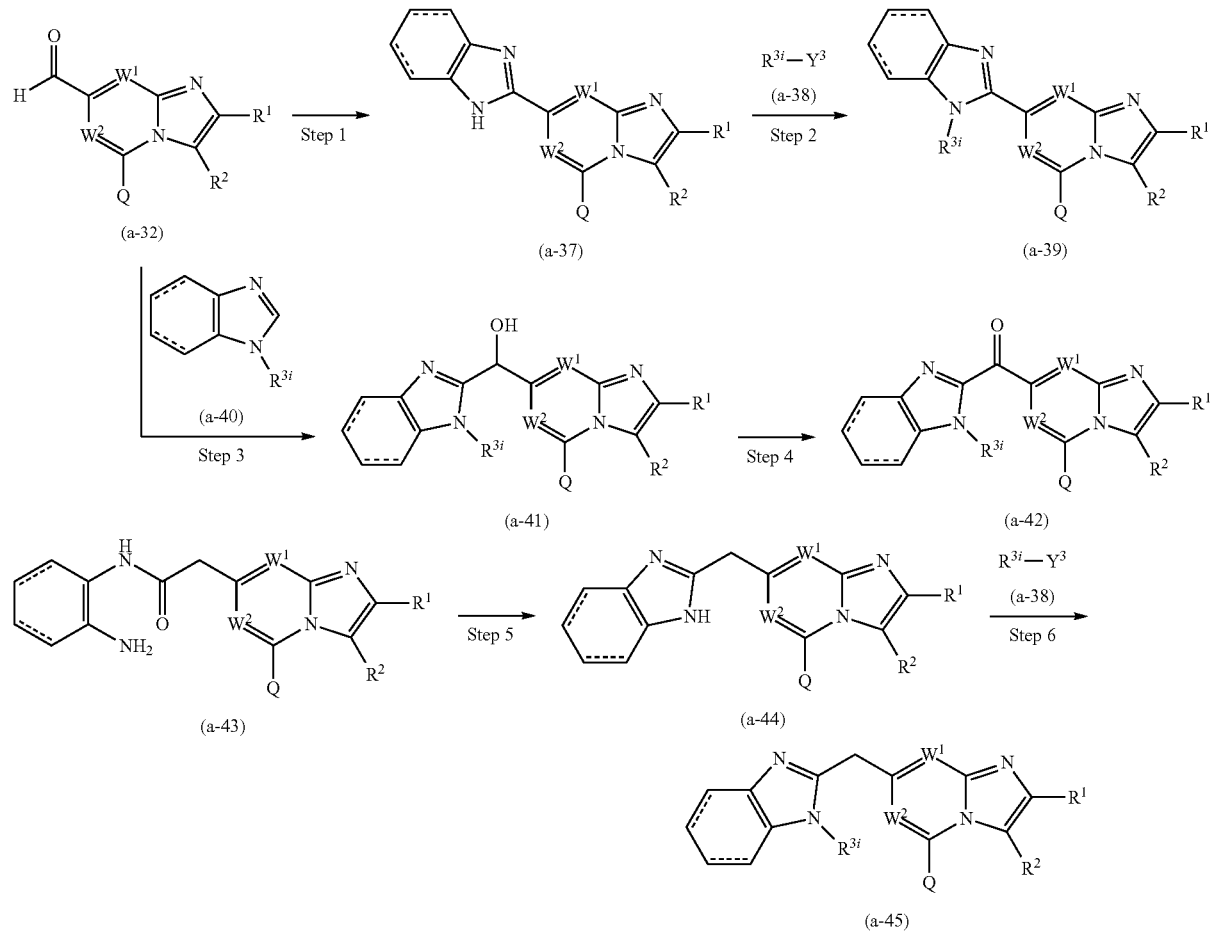

(wherein, $R^1$, $R^2$, $R^{3i}$, Q, $W^1$, $W^2$, $Y^3$, and $---$ have the same meanings as describe above, respectively)

Step 1

Compound (a-37) can be produced by reacting Compound (a-32) with 1 to 10 equivalents of a diketone compound in a solvent or without solvent in the presence of 0.1 to 10 equivalents of an additive at a temperature between −30° C. and the boiling point of the used solvent for 5 minutes to 72 hours.

Examples of the diketone compound include cyclohexane-1,2-dione and 3,5-cyclohexadiene-1,2-dione, which are commercially available, and the like. Examples of the additive include ammonium acetate, ammonium chloride, and the like. Examples of the solvent include methanol, 1,2-dichloroethane, chloroform, dichloromethane, sulfolane, butanol, THF, DMF, ethyl acetate, acetic acid, water, and the like. These may be used alone or as a mixture.
Step 2
Compound (a-39) can be produced in the same manner as in step 4 of Production Method 3 using compound (a-37) and compound (a-38).
Compound (a-38) can be obtained as a commercially available product, or can be obtained by a known method [for example, Jikken Kagaku Koza (Experimental Chemistry Course), the fourth edition, vol. 19, p. 460, Maruzen Co. Ltd. (1992), and the like] or a method based on such a method.
Step 3
Compound (a-41) can be produced by reacting Compound (a-32) with 1 to 10 equivalents of Compound (a-40) in the presence of 1 to 10 equivalents of a base at a temperature between −78° C. and the boiling point of the used solvent for 5 minutes to 72 hours.
Examples of the base include n-butyllithium, lithium aluminum hydride, and the like. Examples of the solvent include methanol, 1,2-dichloroethane, chloroform, dichloromethane, sulfolane, butanol, THF, DMF, ethyl acetate, acetic acid, water, and the like. These may be used alone or as a mixture.
Compound (a-40) can be obtained as a commercially available product, or can be obtained by a known method [for example, the method described in Tetrahedron Lett., vol. 46, p. 5081 (2005), and the like] or a method based on such a method.
Step 4
Compound (a-42) can be produced by treating Compound (a-41) in a solvent or without solvent in the presence of 0.1 to 10 equivalents of an oxidizing agent at a temperature between −30° C. and the boiling point of the used solvent for 5 minutes to 72 hours.
Examples of the oxidizing agent include Dess-Martin Periodinane, manganese dioxide, and the like. Examples of the solvent include methanol, 1,2-dichloroethane, chloroform, dichloromethane, sulfolane, butanol, THF, DMF, ethyl acetate, acetic acid, water, and the like. These may be used alone or as a mixture.
Step 5
Compound (a-44) can be produced by treating Compound (a-43) in a solvent or without solvent at a temperature between −30° C. and the boiling point of the used solvent for 5 minutes to 72 hours.
Examples of the solvent include methanol, 1,2-dichloroethane, chloroform, dichloromethane, sulfolane, butanol, THF, DMF, ethyl acetate, acetic acid, water, and the like. These may be used alone or as a mixture.
Compound (a-43) can be obtained, for example, in the same manner as in Production Method 3.
Step 6
Compound (a-45) can be produced in the same manner as in step 4 of Production Method 3 using compound (a-44) and compound (a-38).
Production Process 6
Among Compound (I), Compound (a-48) in which $R^3$ is an optionally substituted aromatic heterocyclic group can be produced, for example, according to the following steps.

[Chemical Formula 13]

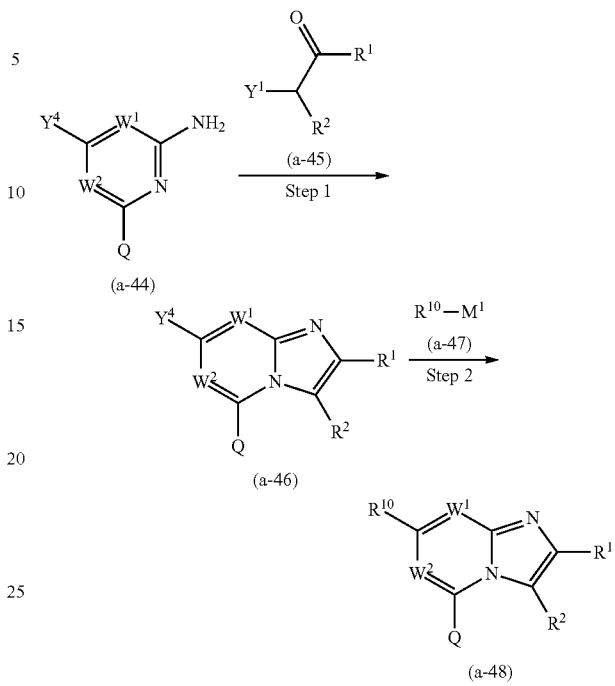

[wherein, $R^{10}$ represents the optionally substituted aromatic heterocyclic group in the definition of $R^3$, $M^1$ represents $B(OR^{11})(OR^{12})$ (wherein, $R^{11}$ and $R^{11}$ may be the same or different, and each represents a hydrogen atom or $C_{1-6}$ alkyl, or $R^{11}$ and $R^{12}$ are combined together to represent $C_{1-6}$ alkylene), or $SnR^{13}R^{14}R^{15}$ (wherein, $R^{13}$, $R^{24}$, and $R^{15}$ may be the same or different, and each represents $C_{1-6}$ alkyl or phenyl), $Y^4$ represents a chlorine atom, a bromine atom, or an iodine atom, and $R^1$, $R^2$, Q, $W^1$, $W^2$, and $Y^1$ have the same meanings as describe above, respectively]
Step 1
Compound (a-46) can be produced in the same manner as in step 5 of Production Method 1 using compound (a-44) and compound (a-45).
Compound (a-44) can be obtained as a commercially available product, or can be obtained by a known method [for example, the method described in WO2010/90716, and the like] or a method based on such a method.
Compound (a-45) can be obtained as a commercially available product, or can be obtained by a known method [for example, Jikken Kagaku Koza (Experimental Chemistry Course), the fourth edition, vol. 19, p. 435, Maruzen Co. Ltd. (1992), and the like] or a method based on such a method.
Step 2
Compound (a-48) can be produced by reacting Compound (a-46) with 1 to 10 equivalents of Compound (a-47) in a solvent or without solvent in the presence of 1 to 10 equivalents of an additive and 1 to 10 equivalents of a base at a temperature between −30° C. and the boiling point of the used solvent for 5 minutes to 72 hours.
Examples of the additive include palladium acetate, tetrakis(triphenylphsphine)palladium, and the like. Examples of the base include sodium hydrogen carbonate, cesium carbonate, potassium phosphate, and the like. Examples of the solvent include 1,2-dichloroethane, chloroform, dichloromethane, toluene, sulfolane, dioxane, THF, DMF, ethyl acetate, water, and the like. These may be used alone or as a mixture.

Compound (a-47) can be obtained as a commercially available product, or can be obtained by a known method [for example, Jikken Kagaku Koza (Experimental Chemistry Course), the fourth edition, vol. 24, p. 80, Maruzen Co. Ltd. (1992), and the like] or a method based on such a method.

Production Method 7

Among Compound (I), Compound (a-52) in which Q is cyano can be produced, for example, according to the following steps.

[Chemical Formula 14]

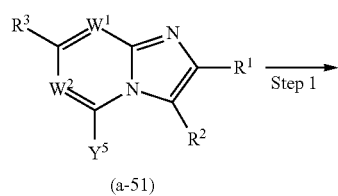

(a-51)

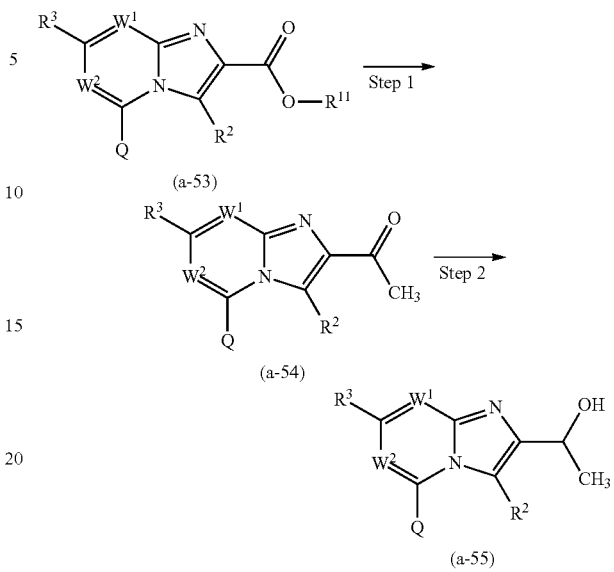

(wherein, $Y^5$ represents a chlorine atom, a bromine atom, or an iodine atom, and $R^1$, $R^2$, $R^3$, $W^1$, and $W^2$ have the same meanings as describe above, respectively)

Step 1

Compound (a-52) can be produced by treating Compound (a-51) in a solvent or without solvent in the presence of 0.1 to 1 equivalents of an additive and 1 to 10 equivalents of a cyanating agent at a temperature between −30° C. and the boiling point of the used solvent for 5 minutes to 72 hours.

Examples of the additive include palladium acetate, tetrakis(triphenylphosphine)palladium, and the like. Examples of a cyanating agent include potassium cyanide, copper cyanide, zinc dicyanide, and the like. Examples of the solvent include 1,2-dichloroethane, chloroform, dichloromethane, toluene, sulfolane, dioxane, THF, DMF, ethyl acetate, and the like. These may be used alone or as a mixture.

Compound (a-51) can be obtained by combining methods described in Production Methods 1 to 6 or methods based thereon.

Production Method 8

Among Compound (I), Compound (a-54) in which $R^2$ is —C(=O)CH$_3$, and Compound (a-55) in which $R^2$ is —CH(OH)CH$_3$ can be produced, for example, according to the following steps.

[Chemical Formula 15]

(wherein, $R^{11}$ represents $C_{1-10}$ alkyl, and $R^2$, $R^3$, Q, $W^1$, and $W^2$ have the same meanings as describe above, respectively)

Step 1

Compound (a-54) can be produced by reacting Compound (a-53), in a solvent or without solvent, with 1 to 10 equivalents of a nucleophilic agent at a temperature between −78° C. and the boiling point of the used solvent for 5 minutes to 72 hours.

Examples of the nucleophilic agent include methylmagnesium bromide, methyllithium, and the like. Examples of the solvent include 1,2-dichloroethane, chloroform, dichloromethane, toluene, sulfolane, diethyl ether, dioxane, THF, DMF, ethyl acetate, and the like. These may be used alone or as a mixture.

Compound (a-53) can be obtained by combining methods described in Production Methods 1 to 6 or methods based thereon.

Step 2

Compound (a-55) can be produced by treating Compound (a-54) in a solvent or without solvent in the presence of 1 to 10 equivalents of a reducing agent at a temperature between −30° C. and the boiling point of the used solvent for 5 minutes to 72 hours.

Examples of the reducing agent include lithium aluminum hydride, sodium borohydride, lithium borohydride, and the like. Examples of the solvent include methanol, ethanol, 1,2-dichloroethane, chloroform, dichloromethane, toluene, sulfolane, dioxane, THF, DMF, ethyl acetate, water, and the like. These may be used alone or as a mixture.

Production Method 9

Compound (a-9) mentioned above, which is a synthetic intermediate for Compound (I), can be produced, for example, according to the following steps.

[Chemical Formula 16]

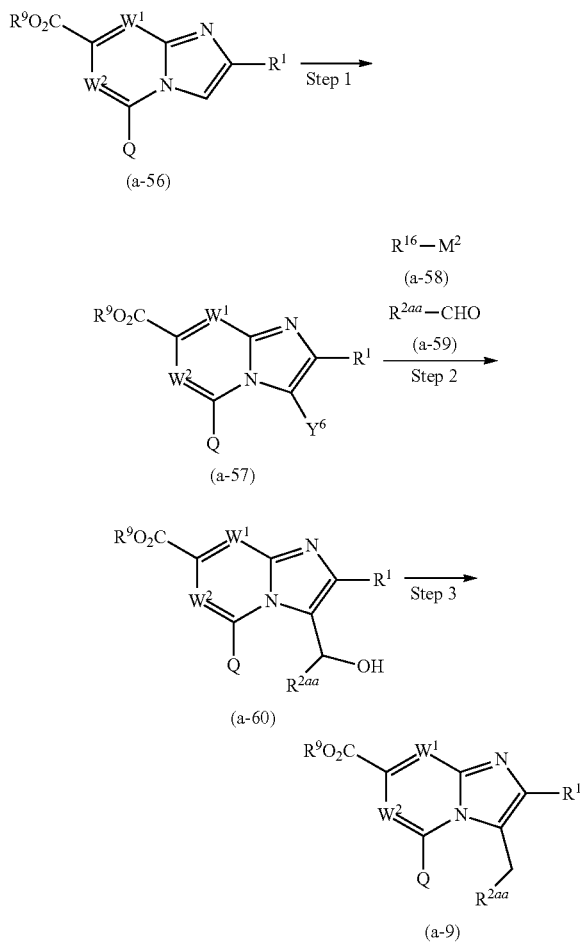

(wherein, $R^1$, $R^{2aa}$, $R^9$, Q, $W^1$, and $W^2$ have the same meanings as described above, respectively, $Y^6$ represents a chlorine atom, a bromine atom, or an iodine atom, $M^2$ represents a metal group such as MgBr, MgCl, and Li, and $R^{16}$ represents $C_{1-6}$ alkyl or phenyl)

Step 1

Compound (a-57) can be produced by treating Compound (a-56) in a solvent or without solvent in the presence of to 5 equivalents of a halogenation agent at a temperature between −30° C. and 150° C. for 5 minutes to 72 hours.

Examples of the halogenation agent include chlorine, bromine, iodine, N,N,N,N-tetra-n-butylammonium tribromide, N-chlorosuccinimide, N-bromosuccinimide, N-iodosuccinimide, and the like. Examples of the solvent include acetone, 1,4-dioxane, acetonitrile, chloroform, dichloromethane, THF, DME, ethyl acetate, methanol, ethanol, DMF, acetic acid, water, and the like. These may be used alone or as a mixture.

Compound (a-56) can be produced in the same manner as in step 5 of Production Method 1 using compound (a-8) and compound (a-14).

Step 2

Compound (a-60) can be produced by reacting Compound (a-57) with 1 to 10 equivalents of Compound (a-58) and 1 to 10 equivalents of Compound (a-59) in a solvent at a temperature between −78° C. and the boiling point of the used solvent for 5 minutes to 72 hours.

Examples of the solvent include toluene, diethyl ether, THF, DME, dioxane, hexane, and the like. These may be used alone or as a mixture.

Compound (a-58) can be obtained as a commercially available product, or can be obtained by a known method [for example, the fifth edition's Jikken Kagaku Koza (Experimental Chemistry Course), vol. 18: Yukikagobutsu no Gosei (Synthesis of Organic Compounds)VI, Kinzoku wo Motiiru Yukigosei (Organic Synthesis Using Metals), the fifth edition, p. 59, Maruzen (2005)] or a method based on such a method.

Compound (a-59) can be obtained as a commercially available product, or can be obtained by a known method [for example, Jikken Kagaku Koza (Experimental Chemistry Course), the fourth edition, vol. 21, p. 1, Maruzen Co. Ltd. (1992), and the like] or a method based on such a method.

Step 3

Compound (a-9) can be produced by treating Compound (a-60) in the presence of 1 equivalent to a large excess amount of alkylchlorosilane and 1 equivalent to a large excess amount of sodium iodide in a solvent at a temperature between −20° C. and the boiling point of the used solvent for 5 minutes to 72 hours.

Examples of the alkylchlorosilane include trimethylchlorosilane, triethylchlorosilane, dimethyldichlorosilane, and the like. Examples of the solvent include dichloromethane, hexane, and acetonitrile. These may be used alone or as a mixture Further, Compound (a-9) can be produced by reacting Compound (a-60) in a solvent in the presence of 1 to 10 equivalents of a reducing agent, and in the presence of 1 to 10 equivalents of a Btornsted acid if necessary, at a temperature between −78° C. and the boiling point of the used solvent for 5 minutes to 72 hours.

Examples of the reducing agent include sodium borohydride, lithium borohydride, triethylsilane, and the like. Examples of the Broensted acid include hydrochloric acid, sulfuric acid, trifluoroacetic acid, acetic acid, methanesulfonic acid, and the like. Examples of the solvent include toluene, THF, DME, 1,4-dioxane, DMF, and the like. These may be used alone or as a mixture.

Production Method 10

Among Compound (I), Compound (a-52) in which Q is cyano can be produced, for example, according to the following steps.

[Chemical Formula 17]

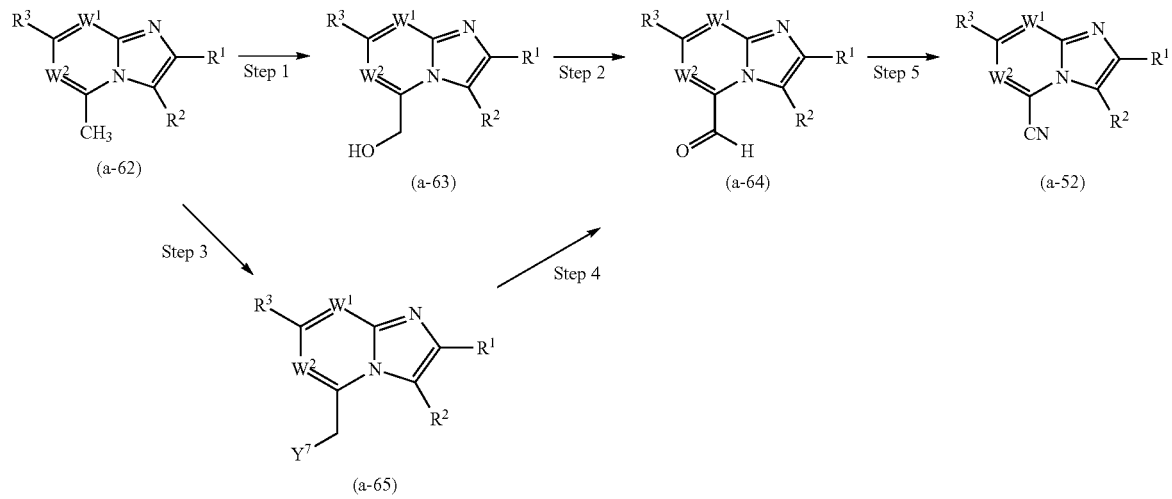

(wherein, $Y^7$ represents a chlorine atom, a bromine atom, or an iodine atom, and $R^1$, $R^2$, $R^3$, $W^1$, and $W^2$ have the same meanings as describe above, respectively)

Step 1

Compound (a-63) can be produced by treating Compound (a-62) in the presence of 1 to 10 equivalents of an oxidizing agent in a solvent at a temperature between −78° C. and the boiling point of the used solvent for 5 minutes to 72 hours.

Examples of the oxidizing agent include selenium dioxide and the like. Examples of the solvent include dioxane and the like.

Compound (a-62) can be obtained by combining methods described in Production Methods 1 to 9 or methods based thereon.

Step 2

Compound (a-64) can be produced by treating Compound (a-63) in a solvent in the presence of 1 to 10 equivalents of an oxidizing agent at a temperature between −78° C. and the boiling point of the used solvent for 5 minutes to 72 hours.

Examples of the oxidizing agent include manganese dioxide, chromic acid, pyridinium chlorochromate, pyridinium dichromate, potassium permanganate, sulfur trioxide-pyridine, Oxone, DMSO/oxalyl chloride, Dess-Martin Periodinane, and the like. Examples of the solvent include dichloromethane, chloroform, 1,2-dichloroethane, toluene, ethyl acetate, acetonitrile, diethyl ether, THF, DME, dioxane, DMF, DMA, NMP, DMSO, pyridine, hydrochloric acid, acetic acid, propionic acid, acetic anhydride, sulfuric acid, water, and the like. These may be used alone or as a mixture.

Step 3

Compound (a-65) can be produced by treating compound (a-62) in a solvent or without solvent in the presence of to 5 equivalents of a halogenation agent, in the presence of a catalytic amount to 10 equivalents of a radical initiator if necessary, at a temperature between −30° C. and 150° C. for 5 minutes to 72 hours.

Examples of the halogenation agent include chlorine, bromine, iodine, N,N,N,N-tetra-n-butylammonium tribromide, N-chlorosuccinimide, N-bromosuccinimide, N-iodosuccinimide, and the like. Examples of a radical initiator include azobisisobutyronitrile, and the like. Examples of the solvent include acetone, 1,4-dioxane, acetonitrile, chloroform, dichloromethane, THF, DME, ethyl acetate, methanol, ethanol, DMF, acetic acid, water, and the like. These may be used alone or as a mixture.

Step 4

Compound (a-64) can be produced by treating Compound (a-65) in a solvent or without solvent in the presence of 1 to 5 equivalents of an oxidizing agent, in the presence of 0.1 to 1000 weight % of an additive if necessary, at a temperature between −78° C. and the boiling point of the used solvent for 5 minutes to 72 hours.

Examples of the oxidizing agent include N-methylmorpholine N-oxide and the like. Examples of the additive include molecular sieves 4A and the like. Examples of the solvent include acetonitrile and the like.

Step 5

Compound (a-52) can be produced by treating Compound (a-64) in a solvent or without solvent in the presence of 1 to 2 equivalents of hydroxylamine hydrochloride and 1 to equivalents of a dehydrating agent at a temperature between −78° C. and the boiling point of the used solvent for 5 minutes to 72 hours.

Examples of the dehydrating agent include acetic anhydride and the like. Examples of the solvent include NMP and the like.

Production Method 11

Among Compound (I), Compound (a-69) in which Q is a chlorine atom and $W^2$ is C—$Y^8$ (wherein, $Y^8$ represents a chlorine atom, a bromine atom, or an iodine atom) can be produced, for example, according to the following steps.

[Chemical Formula 18]

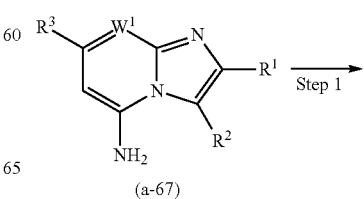

-continued

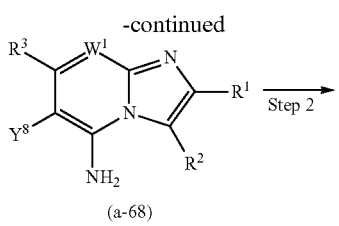

(a-68)

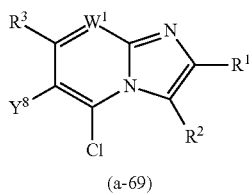

(a-69)

(wherein, $R^1$, $R^2$, $R^3$, $W^1$, and $Y^8$ have the same meanings as described above, respectively)

Step 1

Compound (a-68) can be produced by treating Compound (a-67) in a solvent or without solvent in the presence of to 5 equivalents of a halogenation agent at a temperature between −30° C. and 150° C. for 5 minutes to 72 hours.

Examples of the halogenation agent include chlorine, bromine, iodine, N,N,N,N-tetra-n-butylammonium tribromide, N-chlorosuccinimide, N-bromosuccinimide, N-iodosuccinimide, and the like. Examples of the solvent include acetone, 1,4-dioxane, acetonitrile, chloroform, dichloromethane, THF, DME, ethyl acetate, methanol, ethanol, DMF, acetic acid, water, and the like. These may be used alone or as a mixture.

Compound (a-67) can be obtained by combining methods described in Production Methods 1 to 10 or methods based thereon.

Step 2

Compound (a-69) can be produced by treating Compound (a-68) in a solvent or without solvent in the presence of to 5 equivalents of a nitrite salt and 1 to 5 equivalents of a metal chloride, and in the presence of 1 to 300 equivalents of hydrochloric acid if necessary, at a temperature between and −78° C. and the boiling point of the used solvent for 5 minutes to 72 hours.

Examples of the nitrite salt include sodium nitrite, isoamyl nitrite, and the like. Examples of the metal chloride include cuprous chloride and the like. Examples of the solvent include acetonitrile and the like.

The conversions of the functional groups contained in $R^1$, $R^2$, $R^3$, Q, $W^1$, $W^2$, and the like, of Compound (I) and each intermediates in the above production methods can also be carried out according to a known method [for example, a method described in Comprehensive Organic Transformations 2nd edition, R. C. Larock, Vch Verlagsgesellschaft Mbh (1999), and the like] or a method based thereon.

The intermediates in each production method described above and the target compounds can be isolated and purified by being subjected to separation and purification methods commonly used in the organic synthetic chemistry, including, for example, filtration, extraction, washing, drying, concentration, recrystallization, various chromatography, and the like. Further, the intermediates can also be used in the next reaction without being purified.

To obtain a salt of Compound (I), when Compound (I) is obtained in a form of salt, it may be purified as it is. Or when Compound (I) is obtained in a form of free, it may be dissolved or suspended in a suitable solvent, followed by addition of an acid or a base to form a salt, and then the salt may be isolated and purified.

Specific examples of Compound (I) of the present invention are shown in Table 1 to Table 24. However, the compounds of the present invention are not limited thereto.

TABLE 1

| Compound No. | $R^3$— | —Q | —$W^2$— | —$R^1$ |
|---|---|---|---|---|
| 1 | (tetrahydropyran-4-yl)NH-C(=O)- | $CH_3$ | C—H | -C($CH_3$)$_2$-O-$CH_3$ |
| 2 | (2-methyltetrahydrofuran-2-yl)CH$_2$-NH-C(=O)- | CN | C—H | -CF$_3$ |

TABLE 1-continued

[Structure: imidazo-pyrimidine core with R³ at position 7, W² at position 6, Q at position 5, R¹ at position 2, and a (4,4-difluorocyclohexyl)methyl group at position 3]

| Compound No. | R³— | —Q | —W²— | —R¹ |
|---|---|---|---|---|
| 3 | [tetrahydrofuran-3-ylmethyl-NH-C(=O)-] | CN | C—H | —CF₃ (–C(F)(F)F) |
| 4 | [tetrahydropyran-4-yl-NH-C(=O)-] | CH₃ | C—H | —C(CH₃)₃ (tert-butyl) |
| 5 | [phenyl-NH-C(=O)-] | H | C—Cl | —CF₂CH₃ |
| 6 | [phenyl-NH-C(=O)-] | H | C—Cl | —cyclopropyl |
| 7 | [phenyl-NH-C(=O)-] | H | C—Cl | —(3,3-difluorocyclobutyl) |
| 8 | [phenyl-NH-C(=O)-] | CH₃ | C—H | —C(CH₃)₂OH |

TABLE 2

| Compound No. | R³— | —Q | —W²— | —R¹ |
|---|---|---|---|---|
| 9 | [4,4-difluorocyclohexyl-NH-C(=O)-] | CH₃ | C—H | —C(CH₃)₂OH |

TABLE 2-continued

| Compound No. | R³— | —Q | —W²— | —R¹ |
|---|---|---|---|---|
| 10 | 3,3-difluorocyclobutyl-NH-C(=O)- | CH₃ | C—H | -C(CH₃)₂-OH |
| 11 | tetrahydropyran-4-yl-NH-C(=O)- | CH₃ | C—H | -C(CH₃)₂-O-CD₂H (OCHD₂ with D's) |
| 12 | phenyl-NH-C(=O)- | CH₃ | C—H | -CH₂-S(=O)₂-CH₃ |
| 13 | phenyl-NH-C(=O)- | CH₃ | C—H | -CH(CH₃)-S(=O)₂-CH₃ |
| 14 | 4,4-difluorocyclohexyl-NH-C(=O)- | H | C—Cl | cyclopropyl |
| 15 | 4,4-difluorocyclohexyl-NH-C(=O)- | H | C—Cl | -C(CH₃)(F)-F (1,1-difluoroethyl) |
| 16 | phenyl-NH-C(=O)- | CH₃ | C—H | -CH₂OH |
| 17 | phenyl-NH-C(=O)- | CH₃ | C—H | -CH(CH₃)-S(=O)₂-CH₂CH₃ |

TABLE 3

| Compound No. | R³— | —Q | —W²— | —R¹ |
|---|---|---|---|---|
| 18 | tetrahydropyran-4-yl-NH-C(=O)- | CH₃ | C—H | -CHF₂ |

TABLE 3-continued

| Compound No. | R³— | —Q | —W²— | —R¹ |
|---|---|---|---|---|
| 19 | phenyl-NH-C(=O)- | CH₃ | C—H | -C(=O)CH₃ |
| 20 | phenyl-NH-C(=O)- | CH₃ | C—H | -CH(OH)CH₃ |
| 21 | cyclopropyl-CH₂-NH-C(=O)- | H | C—Cl | -C(F)(F)CH₃ |
| 22 | cyclobutyl-NH-C(=O)- | H | C—Cl | -C(F)(F)CH₃ |
| 23 | 2,2-dimethyl-tetrahydropyran-4-yl-NH-C(=O)- | H | C—Cl | -C(F)(F)CH₃ |
| 24 | tetrahydrofuran-3-yl-CH₂-NH-C(=O)- | H | C—Cl | -C(F)(F)CH₃ |
| 25 | trans-4-hydroxycyclohexyl-NH-C(=O)- | H | C—Cl | -C(F)(F)CH₃ |
| 26 | (CH₃)₂C(OH)-CH₂-NH-C(=O)- | H | C—Cl | -C(F)(F)CH₃ |

TABLE 4

| Compound No. | R³— | —Q | —W²— | —R² | —R¹ |
|---|---|---|---|---|---|
| 27 | 4-(tetrahydropyran-4-ylamino)carbonyl | CH₃ | C—H | (4,4-difluorocyclohexyl)methyl | 1,1-difluoropropyl (CF₂CH₃ with extra F) |
| 28 | 3-methylisoxazol-5-ylaminocarbonyl | H | C—Cl | 3,3-difluoroazetidin-1-ylsulfonyl | 2-chloro-2-methylpropan-2-yl (C(CH₃)₂Cl) |
| 29 | 4-chloro-3-methylisoxazol-5-ylaminocarbonyl | H | C—Cl | 3,3-difluoroazetidin-1-ylsulfonyl | 2-chloro-2-methylpropan-2-yl (C(CH₃)₂Cl) |
| 30 | phenylaminocarbonyl | H | C—H | ethoxyoxalyl (−C(=O)C(=O)OCH₂CH₃) | CF₃ |
| 31 | phenylaminocarbonyl | CH₃ | C—H | N-cyclohexyl-N-acetyl-amino | isopropyl (CH(CH₃)₂) |
| 32 | tetrahydropyran-4-ylaminocarbonyl | CH₃ | C—H | N-cyclohexyl-N-acetyl-amino | isopropyl (CH(CH₃)₂) |

TABLE 5

| Compound No. | R³— | —Q | —W²— | —R² | —R¹ |
|---|---|---|---|---|---|
| 33 | phenylaminocarbonyl | H | C—H | −C(=O)C(=O)NH−C(CH₃)₂CH₃ (tert-butylaminooxalyl) | CF₃ |

TABLE 5-continued

| Compound No. | R³— | —Q | —W²— | —R² | —R¹ |
|---|---|---|---|---|---|
| 34 | tetrahydropyran-4-yl-NH-C(=O)- | CH₃ | C—H | cyclohexyl-N(CH₃)- | isopropyl (CH(CH₃)₂) |
| 35 | tetrahydropyran-4-yl-NH-C(=O)- | CH₃ | C—H | cyclohexyl-NH- | isopropyl (CH(CH₃)₂) |
| 36 | phenyl-NH-C(=O)- | H | C—H | -CH(OH)C(=O)OCH₂CH₃ | -CF₃ |
| 37 | phenyl-NH-C(=O)- | H | C—H | -C(=O)C(=O)-piperidin-1-yl | -CF₃ |
| 38 | phenyl-NH-C(=O)- | H | C—H | -C(=O)C(=O)-morpholin-4-yl | -CF₃ |

TABLE 6

| Compound No. | —Q |
|---|---|
| 39 | —Br |
| 40 | —CN |

TABLE 6-continued

[Structure: N-(tetrahydropyran-4-yl) imidazo[1,2-a]pyridine-7-carboxamide with 2-CF₃, 3-(4,4-difluorocyclohexylmethyl), and Q substituent at 5-position]

| Compound No. | —Q |
|---|---|
| 41 | —C(O)CH₃ |
| 42 | —S(O)₂CH₃ |
| 43 | —OCH₃ |
| 44 | —CH=CH₂ |
| 45 | —CHO |
| 46 | —CH₂OH |
| 47 | —CH₂F |
| 48 | —CHF₂ |
| 49 | —OH |
| 50 | —C≡CH |

TABLE 7

[Structure: imidazo[1,2-a]pyridine with R³ at 7-position, 2-CF₃, 5-CH, and 3-(4,4-difluorocyclohexylmethyl)]

| Compound No. | R³— |
|---|---|
| 51 | H₃C—C(OH)(CH₃)—CH₂—NH—C(O)— |
| 52 | 2-aminophenyl—NH—C(O)— |
| 53 | cyclopropyl-CH₂—NH—C(O)— |
| 54 | cyclobutyl—NH—C(O)— |
| 55 | H₃C—C(OCH₃)(CH₃)—CH₂—NH—C(O)— |
| 56 | trans-4-hydroxycyclohexyl—NH—C(O)— |
| 57 | 2,2-dimethyltetrahydropyran-4-yl—NH—C(O)— |
| 58 | 4-(hydroxymethyl)tetrahydropyran-4-yl—NH—C(O)— |

TABLE 7-continued

[Structure: imidazo[1,2-a]pyridine core with R³ at 7-position, CH₃ at 5-position, 2-CF₃, and 3-CH₂-(4,4-difluorocyclohexyl) substituent]

| Compound No. | R³— |
|---|---|
| 59 | 1,4-dioxan-2-ylmethyl-NH-C(O)- |
| 60 | oxetan-3-yl-NH-C(O)- |
| 61 | (4-hydroxytetrahydropyran-4-yl)methyl-NH-C(O)- |
| 62 | tetrahydrofuran-3-yl-NH-C(O)- |
| 63 | 2-(tetrahydropyran-4-yl)propan-2-yl-NH-C(O)- |
| 64 | tetrahydropyran-3-yl-NH-C(O)- |
| 65 | tetrahydropyran-4-yl-O-NH-C(O)- |
| 66 | [1-(tetrahydropyran-4-yl)cyclopropyl]-NH-C(O)- |
| 67 | (phenacyl)-NH-C(O)- |
| 68 | (2-hydroxypropyl)-NH-C(O)- |
| 69 | (1-hydroxycyclopropyl)methyl-NH-C(O)- |
| 70 | 2-oxaspiro[3.5]nonan-7-yl-NH-C(O)- |
| 71 | (2-oxopropyl)-NH-C(O)- |

TABLE 8
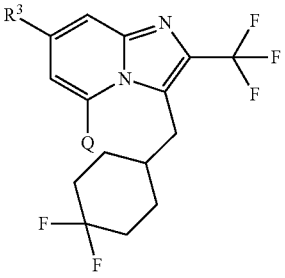
| Compound No. | R3— | —Q |
|---|---|---|
| 72 | 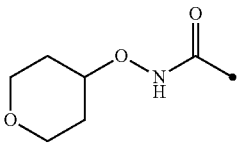 | CH₃ |
| 73 | 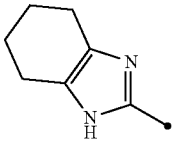 | CH₃ |
| 74 | 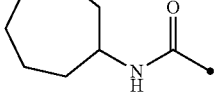 | CH₃ |
| 75 | 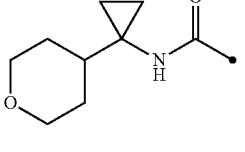 | CH₃ |
| 76 | 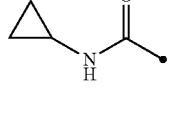 | CN |
| 77 | 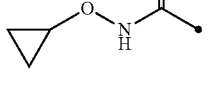 | Cl |
| 78 | 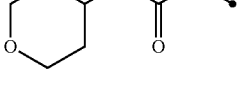 | CH₃ |
| 79 | 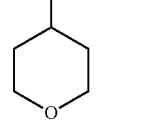 | CH₃ |
TABLE 8-continued
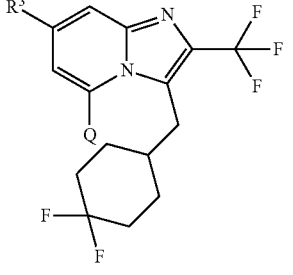
| Compound No. | R3— | —Q |
|---|---|---|
| 80 | 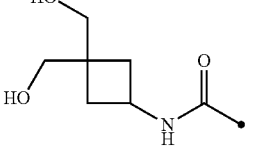 | CH₃ |
| 81 | 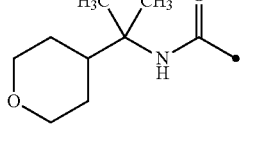 | Cl |
| 82 | 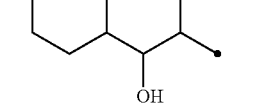 | CH₃ |
| 83 | 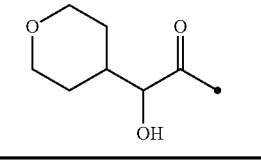 | CH₃ |
TABLE 9
| Compound No. | R³— | —Q |
|---|---|---|
| 84 | 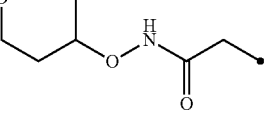 | CH₃ |
| 85 | 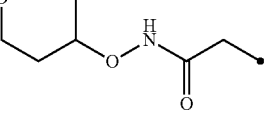 | CH₃ |
| 86 | 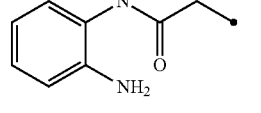 | Cl |

TABLE 9-continued

| Compound No. | R³— | —Q |
|---|---|---|
| 87 | 2-ethyl-1H-benzimidazole | CH₃ |
| 88 | 2-oxaspiro[3.3]heptan-6-yl acetamide | CH₃ |
| 89 | N-(tetrahydro-2H-pyran-4-yl)-2-methylpropanamide | CH₃ |
| 90 | cis-cinnamyl | CH₃ |
| 91 | trans-cinnamyl | CH₃ |
| 92 | (Z)-2-(pyridin-4-yl)vinyl | CH₃ |
| 93 | (E)-2-(pyridin-4-yl)vinyl | CH₃ |
| 94 | 1-phenyl-1,2-dihydroxyethyl | CH₃ |
| 95 | 3,3-bis(hydroxymethyl)cyclobutyl acetamide | Cl |

TABLE 10

| Compound No. | R³— | —Q |
|---|---|---|
| 96 | N-(2-morpholinoethyl)acetamide | Cl |
| 97 | N-(pyridin-4-ylmethyl)acetamide | Cl |
| 98 | N-benzylacetamide | Cl |
| 99 | N-(2-(piperidin-1-yl)ethyl)acetamide | Cl |
| 100 | N-(3-(1H-imidazol-1-yl)propyl)acetamide | Cl |
| 101 | (E)-N-(tetrahydro-2H-pyran-4-yl)but-2-enamide | CH₃ |
| 102 | N-(2-hydroxyethyl)acetamide | Cl |
| 103 | N-(3-hydroxybenzyl)acetamide | Cl |
| 104 | N-(2-(1H-imidazol-4-yl)ethyl)acetamide | Cl |
| 105 | N-(pyridin-3-ylmethyl)acetamide | Cl |
| 106 | N-(pyridin-2-ylmethyl)acetamide | Cl |

TABLE 10-continued

| Compound No. | R³— | —Q |
|---|---|---|
| 107 | (benzoyl hydrazide acetyl) | Cl |
| 108 | (serinol amide) | Cl |
| 109 | (bis(2-hydroxyethyl)amino ethyl amide) | Cl |
| 110 | (ethyl glycinate amide) | Cl |
| 111 | (1H-benzimidazol-2-yl carbonyl) | CH₃ |

TABLE 11

| Compound No. | R³— | —Q |
|---|---|---|
| 112 | (1-(1H-benzimidazol-2-yl)ethanol) | CH₃ |
| 113 | (N-acetyl ethylenediamine amide) | Cl |
| 114 | (N,N-dimethyl ethylenediamine amide) | Cl |
| 115 | (Boc-ethylenediamine amide) | Cl |

TABLE 11-continued

| Compound No. | R³— | —Q |
|---|---|---|
| 116 | (4-hydroxy-tetrahydropyran-4-ylmethyl crotonamide) | CH₃ |
| 117 | (2-hydroxy-2-methylpropyl crotonamide) | CH₃ |
| 118 | (tetrahydropyran-4-yloxy crotonamide) | CH₃ |
| 119 | (2,2-dimethyl-tetrahydropyran-4-yl crotonamide) | CH₃ |
| 120 | (1-(1-methyl-1H-benzimidazol-2-yl)ethanol) | CH₃ |
| 121 | (1-methyl-1H-benzimidazol-2-yl carbonyl) | CH₃ |
| 122 | (2,2-dimethyl-tetrahydropyran-4-yl dihydroxybutanamide) | CH₃ |
| 123 | (ethyl lactate amide) | Cl |
| 124 | (ethyl 2-oxoglycinate amide) | CH₃ |

TABLE 11-continued

| Compound No. | R³— | —Q |
|---|---|---|
| 125 | HO-[1-(hydroxymethyl)cyclopropyl]methyl-NH-C(=O)- | Cl |
| 126 | 2-oxaspiro[3.5]non-7-yl-NH-C(=O)- | CH₃ |

TABLE 12

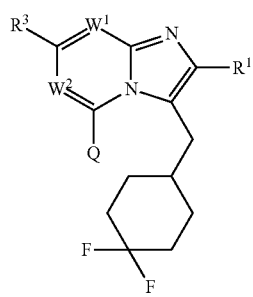

| Compound No. | R³— | —Q | —W¹— | —W²— | —R¹ |
|---|---|---|---|---|---|
| 127 | 2-oxaspiro[3.5]non-7-yl-NH-C(=O)- | H | C—H | C—Cl | -C(F)(F)(CH₃) |
| 128 | (tetrahydropyran-4-yl)NH-C(=O)-CH(CH₃)-NH-C(=O)- | Cl | C—H | C—H | -CF₃ |
| 129 | 2-oxaspiro[3.3]hept-6-yl-NH-C(=O)- | Cl | C—H | C—H | -CF₃ |
| 130 | (tetrahydropyran-4-yl)NH-C(=O)-CH₂-NH-C(=O)- | Cl | C—H | C—H | -CF₃ |
| 131 | (tetrahydrofuran-3-yl)NH-C(=O)-CH₂-NH-C(=O)- | Cl | C—H | C—H | -CF₃ |
| 132 | (2,2-dimethyltetrahydropyran-4-yl)NH-C(=O)-CH₂-NH-C(=O)- | Cl | C—H | C—H | -CF₃ |

TABLE 12-continued

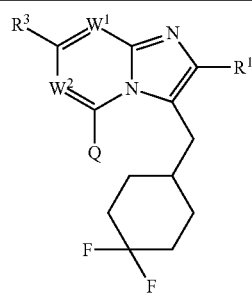

| Compound No. | R³— | —Q | —W¹— | —W²— | —R¹ |
|---|---|---|---|---|---|
| 133 | ![tetrahydropyran-NHC(O)-] | CH₃ | C—OCH₃ | C—H | CF₃ |

TABLE 13

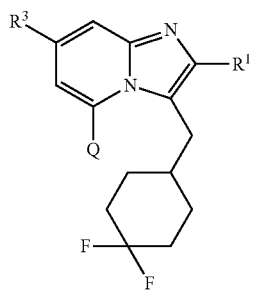

| Compound No. | R³— | —Q | —R¹ |
|---|---|---|---|
| 134 | H₃C-C(NH₂)(CH₃)-CH₂-NHC(O)- | CN | CF₃ |
| 135 | ethyl 1-(acetamido)cyclopropanecarboxylate | Cl | CF₃ |
| 136 | 2-oxaspiro[3.3]heptan-6-yl-NHC(O)- | CH₃ | C(CH₃)F₂ |
| 137 | 2-oxaspiro[3.3]heptan-6-yl-NHC(O)- | CH₃ | C(CH₃)₃ |

TABLE 13-continued

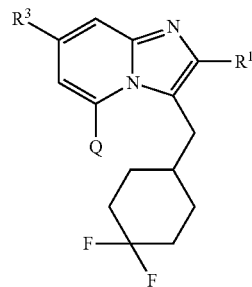

| Compound No. | R³— | —Q | —R¹ |
|---|---|---|---|
| 138 | 3-methylisoxazol-5-yl-NHC(O)- | CN | CF₃ |
| 139 | ethyl 2-(acetamido)acetate | CN | CF₃ |
| 140 | 2-oxotetrahydrofuran-3-yl-NHC(O)- | CN | CF₃ |

TABLE 14

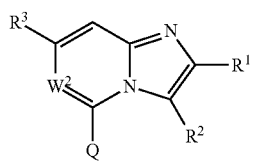

| Compound No. | R³— | —Q | —W²— | —R² | —R¹ |
|---|---|---|---|---|---|
| 141 | (4-methoxytetrahydropyran-4-yl)methyl-NH-C(O)- | CN | C—H | 4,4-difluorocyclohexylmethyl | CF₃ |
| 142 | cyclopropyl-C(O)-NH-NH-C(O)- | Cl | C—H | 4,4-difluorocyclohexylmethyl | CF₃ |
| 143 | (tetrahydropyran-4-yl)CH₂-C(O)-NH-NH-C(O)- | Cl | C—H | 4,4-difluorocyclohexylmethyl | CF₃ |
| 144 | phenyl-NH-C(O)- | H | C—H | n-butyl | isopropyl |
| 145 | 2-oxaspiro[3.3]heptan-6-yl-NH-C(O)- | CH₃ | C—H | 4,4-difluorocyclohexylmethyl | isopropyl |
| 146 | 2-oxaspiro[3.3]heptan-6-yl-NH-C(O)- | CN | C—H | 4,4-difluorocyclohexylmethyl | CF₃ |
| 147 | 2-oxaspiro[3.3]heptan-6-yl-NH-C(O)- | H | C—Cl | 4,4-difluorocyclohexylmethyl | CF₂CH₃ |

TABLE 15

| Compound No. | R³— | —Q | —W²— | —R² | —R¹ |
|---|---|---|---|---|---|
| 148 | (oxaspiro cyclobutane)-NH-C(=O)- | H | C—Cl | 4,4-difluorocyclohexyl-CH₂- | -C(CH₃)₃ |
| 149 | (2-oxopyrrolidin-1-yl)-(CH₂)₃-NH-C(=O)- | CN | C—H | 4,4-difluorocyclohexyl-CH₂- | -CF₃ |
| 150 | (2-oxooxazolidin-3-yl)-C(=O)- | CN | C—H | 4,4-difluorocyclohexyl-CH₂- | -CF₃ |
| 151 | PhNH-C(=O)-CH₂-NH-C(=O)- | Cl | C—H | 4,4-difluorocyclohexyl-CH₂- | -CF₃ |
| 152 | (3-methyl-1H-pyrazol-5-yl)-CH₂-NH-C(=O)- | Cl | C—H | 4,4-difluorocyclohexyl-CH₂- | -CF₃ |
| 153 | 5-(ethoxycarbonyl)oxazol-2-yl- | CH₃ | C—H | 4,4-difluorocyclohexyl-CH₂- | -CF₃ |
| 154 | (5-methylisoxazol-3-yl)-CH₂-NH-C(=O)- | Cl | C—H | 4,4-difluorocyclohexyl-CH₂- | -CF₃ |
| 155 | HOCH₂-C(CH₃)₂-CH₂-NH-C(=O)- | CN | C—H | 4,4-difluorocyclohexyl-CH₂- | -CF₃ |

TABLE 16

| Compound No. | R³— | —Q | —W² | —R² | —R¹ |
|---|---|---|---|---|---|
| 156 | (CH₃)₂N-C(CH₃)₂-CH₂-NH-C(=O)- | CN | C—H | 4,4-difluorocyclohexyl-CH₂- | -CF₃ |
| 157 | HC(=O)-O-CH₂-C(CH₃)₂-CH₂-NH-C(=O)- | CN | C—H | 4,4-difluorocyclohexyl-CH₂- | -CF₃ |
| 158 | tetrahydropyran-4-yl-NH-C(=O)- | CHO | C—H | 4,4-difluorocyclohexyl-CH₂- | -CF₂CH₃ |
| 159 | tetrahydropyran-4-yl-NH-C(=O)- | CN | C—H | 4,4-difluorocyclohexyl-CH₂- | -CF₂CH₃ |
| 160 | (CH₃)₃C-C(=O)-CH₂-NH-C(=O)- | CN | C—H | 4,4-difluorocyclohexyl-CH₂- | -CF₃ |
| 161 | H₃C-CH₂-O-C(=O)-C(cyclopropyl)-NH-C(=O)- | CN | C—H | 4,4-difluorocyclohexyl-CH₂- | -CF₃ |
| 162 | HO-CH₂-C(CH₃)₂-NH-C(=O)- | CN | C—H | 4,4-difluorocyclohexyl-CH₂- | -CF₃ |

TABLE 17

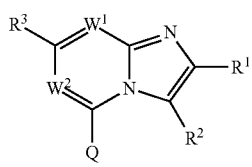

| Compound No. | R³— | —Q | —W¹— | —W²— | —R² | —R¹ |
|---|---|---|---|---|---|---|
| 163 | PhNHC(O)CH₂— (N-phenylacetamide) | H | C—H | C—H | 2-phenoxypropan-2-yl | CF₃ |
| 164 | (2-methoxy-2-methylpropyl)aminocarbonylmethyl | CN | C—H | C—H | (4,4-difluorocyclohexyl)methyl | C(CH₃)F₂ |
| 165 | methyl 1-(acetamido)cyclopropane-1-carboxylate | CN | C—H | C—H | (4,4-difluorocyclohexyl)methyl | C(CH₃)F₂ |
| 166 | (tetrahydro-2H-pyran-4-yl)aminocarbonylmethyl | CH₃ | C—CH₃ | C—H | (4,4-difluorocyclohexyl)methyl | CF₃ |
| 167 | (tetrahydro-2H-pyran-4-yl)aminocarbonylmethyl | CH₃ | C—H | C—CH₃ | (4,4-difluorocyclohexyl)methyl | CF₃ |
| 168 | (tetrahydro-2H-pyran-4-yl)aminocarbonylmethyl | CN | C—H | C—Cl | (4,4-difluorocyclohexyl)methyl | CF₃ |
| 169 | (quinuclidin-3-yl)aminocarbonylmethyl | CN | C—H | C—H | (4,4-difluorocyclohexyl)methyl | CF₃ |

TABLE 18

| Compound No. | R³— | —Q | —W¹— | —W²— | —R² | —R¹ |
|---|---|---|---|---|---|---|
| 170 | 3,3-difluorocyclobutyl-NH-C(=O)- | CN | C—H | C—H | 4,4-difluorocyclohexyl-CH₂- | -CH(CH₃)₂ |
| 171 | CF₃CH₂-NH-C(=O)- | CN | C—H | C—H | 4,4-difluorocyclohexyl-CH₂- | -CH(CH₃)₂ |
| 172 | 3,3-difluoroazetidinyl-C(=O)-CH₂-NH-C(=O)- | Cl | C—H | C—H | 4,4-difluorocyclohexyl-CH₂- | -CF₃ |
| 173 | (CH₃)₂C(OCH₃)-CH₂-NH-C(=O)- | CN | C—H | C—Cl | 4,4-difluorocyclohexyl-CH₂- | -CF₃ |
| 174 | HO-CH₂-(cyclopropyl)-CH₂-NH-C(=O)- | Cl | C—H | C—H | 4,4-difluorocyclohexyl-CH₂- | -CF₃ |
| 175 | 1-cyanocyclopropyl-NH-C(=O)- | Cl | C—H | C—H | 4,4-difluorocyclohexyl-CH₂- | -CF₃ |
| 176 | 1-cyanocyclopropyl-CH₂-NH-C(=O)- | Cl | C—H | C—H | 4,4-difluorocyclohexyl-CH₂- | -CF₃ |
| 177 | CH₃CF₂-CH₂-NH-C(=O)- | CN | C—H | C—H | 4,4-difluorocyclohexyl-CH₂- | -CH(CH₃)₂ |

TABLE 18-continued
| Compound No. | R³— | —Q | —W¹— | —W²— | —R² | —R¹ |
|---|---|---|---|---|---|---|
| 178 | 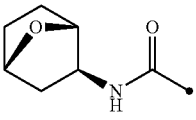 | CN | C—H | C—H | 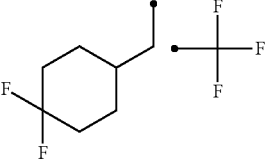 | 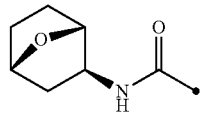 |
TABLE 19
| Compound No. | R³— | —Q | —W¹— | —W²— | —R² | —R¹ |
|---|---|---|---|---|---|---|
| 179 | 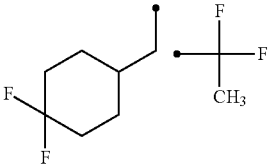 | CHO | C—H | C—H | 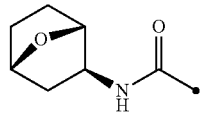 | 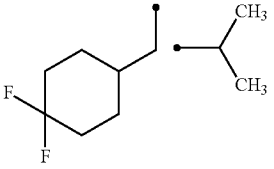 |
| 180 | 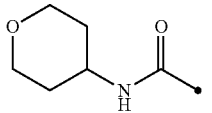 | CN | C—H | C—H | 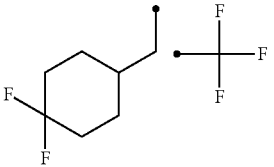 | 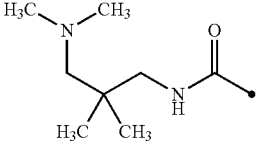 |
| 181 | 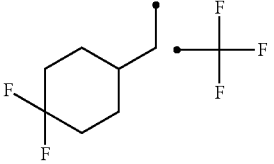 | CN | C—H | C—CH₃ | | |
| 182 | 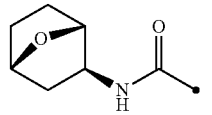 | CN | C—H | C—H | | |
| 183 | 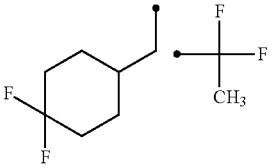 | CN | C—H | C—H | | |
| 184 | 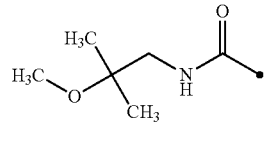 | CN | C—H | C—CH₃ | 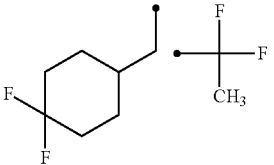 | |

TABLE 19-continued

| Compound No. | R³— | —Q | —W¹— | —W²— | —R² | —R¹ |
|---|---|---|---|---|---|---|
| 185 | tetrahydropyran-4-yl-NH-C(O)- | CN | C—H | C—CH₃ | 4,4-difluorocyclohexyl-CH₂- | -C(F)(F)(CH₃) |
| 186 | CD₂H-C(CH₃)₂-O-... H₃C, CH₃ with NH-C(O)- | CN | C—H | C—H | 4,4-difluorocyclohexyl-CH₂- | -CF₃ |
| 187 | (CH₃)₂N-C(O)-CH(CH₃)-NH-C(O)- | CN | C—H | C—H | 4,4-difluorocyclohexyl-CH₂- | -CF₃ |

TABLE 20

| Compound No. | R³— | —Q | —W¹— | —W²— | —R² | —R¹ |
|---|---|---|---|---|---|---|
| 188 | quinuclidin-4-yl-NH-C(O)- | CN | C—H | C—H | 4,4-difluorocyclohexyl-CH₂- | -CF₃ |
| 189 | CH₃-S(O)₂-C(CH₃)₂-CH₂-NH-C(O)- | CN | C—H | C—H | 4,4-difluorocyclohexyl-CH₂- | -CF₃ |
| 190 | CD₂H-O-C(CH₃)₂-CH₂-NH-C(O)- | CN | C—H | C—CH₃ | 4,4-difluorocyclohexyl-CH₂- | -CF₃ |
| 191 | H₃C-C(O)-N-azabicyclic-NH-C(O)- | CN | C—H | C—H | 4,4-difluorocyclohexyl-CH₂- | -CF₃ |

TABLE 20-continued

| Compound No. | R³— | —Q | —W¹— | —W²— | —R² | —R¹ |
|---|---|---|---|---|---|---|
| 192 | ![R3 structure with CD2-O-C(CH3)2-CH2-NH-C(O)-] | CH₂OH | C—H | C—H | ![4,4-difluorocyclohexyl-CH2-] | ![C(F)2CH3 with F] |
| 193 | ![tetrahydropyran-4-yl-NH-C(O)-] | Cl | C—H | C—Cl | ![4,4-difluorocyclohexyl-CH2-] | ![CF3] |
| 194 | ![R3 structure with CD2-O-C(CH3)2-CH2-NH-C(O)-] | CN | C—H | C—H | ![4,4-difluorocyclohexyl-CH2-] | ![C(F)2CH3] |
| 195 | ![tetrahydropyran-4-yl-NH-C(O)-] | Cl | C—H | C—CH₃ | ![4,4-difluorocyclohexyl-CH2-] | ![CF3] |
| 196 | ![oxabicyclic structure-NH-C(O)-] | Cl | C—H | C—H | ![4,4-difluorocyclohexyl-CH2-] | ![CF3] |

TABLE 21

| Compound No. | R³— | —Q | —W¹— | —W²— | —R² | —R¹ |
|---|---|---|---|---|---|---|
| 197 | ![H3C-S(O)2-C(CH3)2-CH2-NH-C(O)-] | Cl | C—H | C—H | ![4,4-difluorocyclohexyl-CH2-] | ![CF3] |
| 198 | ![(CH3)3C-NH-C(O)-] | CN | C—H | C—H | ![4,4-difluorocyclohexyl-CH2-] | ![CF3] |

TABLE 21-continued

| Compound No. | R³— | —Q | —W¹— | —W²— | —R² | —R¹ |
|---|---|---|---|---|---|---|
| 199 | (diazabicyclic-NH-C(O)-) | CN | C—H | C—H | 4,4-difluorocyclohexylmethyl | CF₃ |
| 200 | (6-methylpyrazin-2-yl-NH-C(O)-) | CN | C—H | C—H | 4,4-difluorocyclohexylmethyl | CF₃ |
| 201 | (tetrahydropyran-4-yl-C(O)-NH-C(O)-) | CN | C—H | C—H | 4,4-difluorocyclohexylmethyl | CF₃ |
| 202 | (cyclopropyl-C(O)-NH-C(O)-) | CN | C—H | C—H | 4,4-difluorocyclohexylmethyl | CF₃ |
| 203 | (tert-butyl-C(O)-NH-C(O)-) | CN | C—H | C—H | 4,4-difluorocyclohexylmethyl | CF₃ |
| 204 | (azabicyclic-CH₂-NH-C(O)-, HCl) | CN | C—H | C—H | 4,4-difluorocyclohexylmethyl | CF₃ |
| 205 | (2,2-dimethyltetrahydropyran-4-yl-NH-C(O)-) | Cl | C—H | C—Cl | 4,4-difluorocyclohexylmethyl | CF₃ |

TABLE 22

| Compound No. | R³— | —Q | —W¹— | —W²— | —R² | —R¹ |
|---|---|---|---|---|---|---|
| 206 | (tetrahydropyran-4-yl-NH-C(O)-) | CH₃ | C—H | C—H | benzyl | CF₃ |

TABLE 22-continued

| Compound No. | R³— | —Q | —W¹— | —W²— | —R² | —R¹ |
|---|---|---|---|---|---|---|
| 207 | tetrahydropyran-4-yl-NH-C(O)- | CH₃ | C—H | C—H | 4-methylbenzyl | CF₃ |
| 208 | tetrahydropyran-4-yl-NH-C(O)- | CH₃ | C—H | C—H | 4-chlorobenzyl | CF₃ |
| 209 | tetrahydropyran-4-yl-NH-C(O)- | CH₃ | C—H | C—H | 4-methoxybenzyl | CF₃ |
| 210 | 2-oxa-5-azabicyclo[2.2.1]heptan-3-one-5-yl-C(O)- | CN | C—H | C—H | 4,4-difluorocyclohexylmethyl | CF₃ |
| 211 | tetrahydropyran-4-yl-NH-C(O)- | CN | C—H | C—H | 4-chlorobenzyl | CF₃ |
| 212 | tetrahydropyran-4-yl-NH-C(O)- | CH₃ | C—H | C—H | 4-fluorobenzyl | CF₃ |
| 213 | (CH₃)₂C(SCH₃)CH₂NH-C(O)- | Cl | C—H | C—Cl | 4,4-difluorocyclohexylmethyl | CF₃ |
| 214 | tetrahydropyran-4-yl-NH-C(O)- | CH₃ | C—H | C—H | 4-chlorobenzyl | CHF₂CH₃ |

TABLE 23

| Compound No. | R³— | —Q | —W¹— | —W²— | —R² | —R¹ |
|---|---|---|---|---|---|---|
| 215 | (7-oxabicyclo[2.2.1]heptyl)-NH-C(=O)- | CH₃ | C—H | C—H | 4-Cl-phenyl-CH< | -C(F)(F)(CH₃) |
| 216 | H₃C-S(=O)₂-C(CH₃)₂-CH₂-NH-C(=O)- | Cl | C—H | C—Cl | 4,4-difluorocyclohexyl-CH< | -C(F)(F)(F) |
| 217 | (CH₃)₃C-NH-C(=O)- | CH₃ | C—H | C—H | 4,4-difluorocyclohexyl-CH< | -C(F)(F)(F) |
| 218 | (CH₃)₃C-NH-C(=O)- | CH₃ | C—H | C—H | 4,4-difluorocyclohexyl-CH< | -C(F)(F)(CH₃) |
| 219 | (CH₃)₃C-NH-C(=O)- | CH₃ | C—H | C—H | 4,4-difluorocyclohexyl-CH< | -CH(CH₃)₂ |
| 220 | (CH₃)₃C-NH-C(=O)- | Cl | C—H | C—H | 4,4-difluorocyclohexyl-CH< | -C(F)(F)(F) |
| 221 | (tetrahydropyran-4-yl)-NH-C(=O)- | CN | C—H | C—H | 4-Cl-phenyl-CH< | -C(F)(F)(CH₃) |
| 222 | (7-oxabicyclo[2.2.1]heptyl)-NH-C(=O)- | CN | C—H | C—H | 4-Cl-phenyl-CH< | -C(F)(F)(CH₃) |
| 223 | CD₃-O-C(CH₃)₂-CH₂-NH-C(=O)- | CN | C—H | C—H | 4-Cl-phenyl-CH< | -C(F)(F)(CH₃) |

TABLE 24

| Compound No. | R³— | —Q | —W¹— | —W²— | —R² | —R¹ |
|---|---|---|---|---|---|---|
| 224 | (tetrahydropyran-4-yl)NHC(O)— | CH₃ | C—H | C—H | 4-Cl-phenyl-CH₂— | —CH(CH₃)₂ |
| 225 | (CH₃)₂C(NHC(O)CH₃)— | CN | C—H | C—H | 4-F-cyclohexyl-CH₂— | —C(CH₃)F₂ |
| 226 | (CH₃)₂C(NHC(O)CH₃)— | CN | C—H | C—H | 4-F-cyclohexyl-CH₂— | —CH(CH₃)₂ |
| 227 | (CH₃)₂C(NHC(O)CH₃)— | Cl | C—H | C—Cl | 4-F-cyclohexyl-CH₂— | —CF₃ |

Next, the pharmacological effects of the representative compounds (I) and (IA) are described in detail with reference to Test Examples.

TEST EXAMPLE 1

Inhibitory Effect for Intracellular Calcium Response Via Cav3.2 T-Type $Ca^{2+}$ Channels Intracellular calcium response was measured with an FLIPR Calcium 3 Assay Kit (Molecular Devices). The fluorescence indicator attached to the kit was dissolved in an assay buffer containing 20 mmol/L HEPES-NaOH (pH 7.4), 0.5 mmol/L $CaCl_2$, 0.407 mmol/L $MgSO_4$, 0.75 mg/mL amaranth, and Hanks' Balanced Salt Solutions (calcium and magnesium free) to prepare an indicator solution.

A human Cav3.2 T-type $Ca^{2+}$ channel-expressing cell line was produced according to a known method [Analytical Biochemistry, Vol. 400, p. 163 (2010)], using KJMGER8 cells (Namalwa cell-derived cell line) as a host. The cells were suspended in the indicator solution in 1×10⁶ cells/mL density, and plated in a 384-well clear-bottom black plate (Nunc) in 40 μL/well portions, then incubated in a $CO_2$ incubator (95% air, 5% $CO_2$) at 37° C. for 30 minutes. By using an FDSS 6000 (Hamamatsu Photonics K.K.), 5 μL/well of a solution containing the test compound in 10-fold concentration of the final concentration (prepared using an assay buffer containing 1 vol % DMSO and 0.2 vol % bovine serum albumin) was added and incubated for 5 minutes. Then, 5 μL/well of an assay buffer containing 50 mmol/L $CaCl_2$ (final concentration 5 mmol/L) was added to induce the reaction, and the fluorescence (excitation wavelength 480 nm, fluorescence wavelength 540 nm) was measured every two seconds for 2 minutes and 40 seconds.

The difference between the minimum value and the maximum value of the fluorescence values after the addition of $CaCl_2$ was used as the index of calcium response. The calcium response in the absence of the test compound was taken as 100% with respect to the calcium response in the presence of 3 μmol/L mibefradil (T-type $Ca^{2+}$ channel inhibitor; Sigma-Aldrich), and the test compound concentration that shows a 50% inhibitory effect ($IC_{50}$ value) was calculated.

As a result, the $IC_{50}$ of compounds 1, 2, 3, 4, 5, 6, 7, 8, 9, 10, 11, 14, 15, 19, 20, 21, 22, 23, 24, 25, 26, 27, 28, 34, 39, 40, 45, 47, 48, 49, 50, 51, 52, 53, 54, 55, 56, 57, 58, 59, 60, 61, 62, 63, 64, 65, 66, 67, 68, 69, 70, 72, 73, 74, 75, 76, 77, 78, 80, 81, 82, 83, 84, 85, 86, 87, 88, 89, 94, 95, 96, 97, 98, 99, 100, 103, 104, 106, 107, 109, 110, 112, 115, 120, 123, 124, 125, 126, 127, 128, 129, 131, 133, 135, 136, 137, 138, 139, 140, 141, 142, 143, 144, 145, 146, 147, 148, 149, 150, 151, 152, 154, 155, 156, 157, 158, 159, 160, 161, 162, 163, 164, 165, 166, 167, 168, 170, 171, 172, 173, 174, 175, 176, 177, 178, 179, 180, 181, 182, 183, 184, 185, 186, 187, 188, 189, 190, 191, 192, 193, 194, 195, 196, 197, 198, 201, 202, 203, 204, 205, 206, 207, 208, 209, 210, 211, 212, 213, 214, 215, 216, 217, 218, 219, 220, 221, 222, 223, 224, 225, 226 and 227 for the human Cav3.2 T-type $Ca^{2+}$ current was equal to or lower than 100 nmol/L. It was confirmed that compound (I) and pharmaceutically acceptable salts thereof inhibit the human Cav3.2 T-type $Ca^{2+}$ current. Therefore, compound (I) and pharmaceutically acceptable salts thereof were considered to be useful as therapeutic and/or preventive agents for diseases associated with the T-type calcium channels.

Thus, compound (I) and pharmaceutically acceptable salts thereof were considered to be useful as therapeutic and/or preventive agent for diseases associated with the T-type calcium channels, such as, epilepsy (for example, absence epilepsy, and the like), sleep disorder (for example, insomnia, and the like), pain (for example, neuropathic pain, trigeminal neuralgia, diabetic pain, postherpetic neuralgia, neuropathic low back pain, HIV-related pain, fibromyalgia syndrome, cancer pain, inflammatory pain, acute pain, chronic pain, postoperative pain, acute pain after tooth extraction, chronic musculoskeletal pain, nociceptive pain, psychogenic pain, menstrual pain, and the like), migraine, pruritus [for example, pruritus accompanied by skin lesion, including, for example, atopic dermatitis, neurodermatitis, senile cutaneous pruritus, seborrheic dermatitis, caterpillar dermatitis, urticaria, eczema and dermatitis, photosensitivity, autosensitive dermatitis, prurigo, insect bites and stings, scabies, mycosis, cutaneous pruritus, hypertrophic scar, psoriasis such as plaque psoriasis, hydroa, xeroderma, lichen, ringworm, burn, and the like; visceral diseases such as hepatic and biliary tract diseases (for example, cirrhosis such as primary biliary cirrhosis, cholestasis, hepatitis, and the like), kidney diseases (for example, kidney failure such as chronic kidney failure, kidney dialysis, and the like), endocrine and metabolic diseases (for example, thyroid disease such as thyroid dysfunction, diabetes, and the like), and the like; cancers (for example, malignant lymphoma, digestive cancer, and the like); hematological disorders (for example, polycythemia vera, hypoferric anemia, and the like); neurological disorders (for example, multiple sclerosis, neurosis, and the like); AIDS; pregnancy; pruritus that are not necessarily accompanied by skin lesion due to drug side effects; pruritus associated with ophthalmic or otorhinolaryngological diseases; and the like], heart diseases (for example, cardiac hypertrophy, heart failure, myocardial infarction, cardiac arrhythmia, atrial fibrillation, hypertension, and the like), kidney diseases (for example, nephritis, nephropathy, kidney failure, and the like), endocrine diseases (for example, aldosteronism, Cushing's syndrome, hyperthyroidism, hyperinsulinemia, and the like), cancers (for example, prostate cancer, breast cancer, leukemia, neuroblastoma, retinoblastoma, and the like), hearing impairment (for example, noise-induced hearing impairment, and the like), and the like.

TEST EXAMPLE 2

Inhibitory Effect for Pruritus in Morphine-Induced Pruritus Mice

Morphine (1 nmol/5 μL, dissolved in physiological saline) or physiological saline was intrathecally administered between the fifth and sixth lumbar vertebrae of male ddY mice using a microsyringe fitted with a 30-gauge injection needle. Mice to which only morphine was administered were referred to as a control group, and mice to which only physiological saline was administered were referred to as a physiological saline-administered group.

The number of scratching behavior with the hind legs which began to be observed immediately after the morphine administration was measured for 30 minutes. Because mice show continuous scratching actions in each scratching behavior, a series of such actions was counted as a single scratching behavior.

Each test compound was administered 30 minutes or 1 hour before the morphine administration. The test compound was suspended in a 0.5% methylcellulose solution and was prepared plural administration solutions of different concentrations, and each of them was orally administered in a volume of 10 mL/kg.

As a result, Compounds 15, 40, 53, 55, and 129 inhibited the increase of the scratching behavior observed in the morphine-induced pruritus mice by the administration of them at a dose of 30 mg/kg or less. Compounds 164, 173, 176, 178, 180, 181, 182, 183, 184, 185, 186, 189, 190, 193, 194, 197, and 208 inhibited the increase of the scratching behavior observed in the morphine-induced pruritus mice by the administration of them at a dose of 10 mg/kg or less.

Therefore, it was confirmed that compound (I) or pharmaceutically acceptable salts thereof were useful as therapeutic and/or preventive agents for pruritus, and useful as therapeutic and/or preventive agents for pruritus, such as pruritus accompanied by skin lesion, including, for example, atopic dermatitis, neurodermatitis, senile cutaneous pruritus, seborrheic dermatitis, caterpillar dermatitis, urticaria, eczema and dermatitis, photosensitivity, autosensitive dermatitis, prurigo, insect bites and stings, scabies, mycosis, cutaneous pruritus, hypertrophic scar, psoriasis such as plaque psoriasis, hydroa, xeroderma, lichen, ringworm, burn, and the like; pruritus that are not necessarily accompanied by skin lesion, which is caused by visceral diseases such as hepatic and biliary diseases (cirrhosis such as primary biliary cirrhosis, cholestasis, hepatitis, and the like), kidney diseases (kidney failure such as chronic kidney failure, kidney dialysis, and the like), endocrine and metabolic diseases (thyroid disease such as thyroid dysfunction, diabetes, and the like), and the like, cancers (malignant lymphoma, digestive system cancer, and the like), hematological disorders (polycythemia vera, hypoferric anemia, and the like), neurological disorders (multiple sclerosis, hematological disorders, and the like), AIDS, pregnancy, or drug side effects; pruritus associated with ophthalmic and otorhinolaryngological diseases, and the like.

Compound (I) or a pharmaceutically acceptable salt thereof can be administered alone as it is. However, usually, compound (I) or a pharmaceutically acceptable salt thereof are preferably provided in various pharmaceutical preparations. Also, the pharmaceutical preparations are used for animals or humans.

The pharmaceutical preparations according to the present invention may contain compound (I) or a pharmaceutically acceptable salt thereof as an active ingredient, either alone or as a mixture with any other active ingredient for other treatments. Further, the pharmaceutical preparations are prepared by mixing the active ingredient with one or more pharmaceutically acceptable carriers (for example, diluent, solvent, excipient, and the like) and then subjecting the mixture to any method well known in the technical field of pharmaceutics.

As for the administration route, it is preferred to select the most effective route for the treatment. Examples of the administration route include oral administration, parenteral administration such as intravenous administration, and the like.

Examples of the dosage form include a tablet, injection, and the like.

Suitable dosage forms for the oral administration, for example, tablets and the like, can be prepared by using excipients such as lactose and the like, disintegrators such as starch and the like, lubricants such as magnesium stearate and the like, binders such as hydroxypropyl cellulose and the like, and the like.

Suitable dosage forms for the parenteral administration, for example, injections and the like, can be prepared by using diluents, or solvents, or the like, such as a salt solution, a glucose solution, a mixture of brine with a glucose solution, and the like.

The doses and the frequencies of administration of compound (I) or a pharmaceutically acceptable salt thereof may vary depending upon dosage form, age and body weight of a patient, nature or seriousness of the symptom to be treated, and the like. In the oral administration, in general, a dose of 0.01 to 1,000 mg, preferably, 0.05 to 100 mg, is administered to an adult patient once or several times a day. In parenteral administration such as intravenous administration, a dose of 0.001 to 1,000 mg, preferably, 0.01 to 100 mg, is administered to an adult patient once or several times a day. However, these doses and frequencies of administration vary by the various conditions described above.

The present invention is explained below more specifically with reference to Examples. However, it should be noted that the scope of the present invention is not limited by these Examples.

Incidentally, the proton nuclear magnetic resonance spectra $^1$H NMR) used in Examples were measured at 270 MHz, 300 MHz, or 400 MHz, and exchangeable protons may not be clearly observed depending on the compound and measurement conditions. Common notation is used to represent signal multiplicity. The symbol br denotes apparently wide signal. Further, the synthesized compounds were denominated, if necessary, by using ChemBioDraw Ultra 11.0.1.

EXAMPLE 1

3-[(4,4-Difluorocyclohexyl)methyl]-2-(2-ethoxypropan-2-yl)-5-methyl-N-(tetrahydro-2H-pyran-4-yl)imidazo[1,2-a]pyridine-7-carboxamide (Compound 1)

Step 1

60% Sodium hydride (1.40 g, 35.0 mmol) was suspended in THF (50 mL), and ethyl diethylphosphonoacetate (7.00 mL, 35.3 mmol) was added dropwise under ice-cooled condition. After completing the addition, the mixture was stirred at room temperature for 10 minutes, then, under ice-cooled condition, a mixture of 4,4-difluorocyclohexanecarbaldehyde (3.50 g, 23.6 mmol) and THF (10 mL) were added dropwise in a manner that the internal temperature did not exceed 10° C. After completing the addition, the mixture was stirred at room temperature for 1 hour. A saturated aqueous ammonium chloride solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=90/10), whereby ethyl (E)-3-(4,4-difluorocyclohexyl)acrylate (4.78 g, yield 93%) was obtained.

$^1$H NMR (270 MHz, CDCl$_3$, δ): 6.90 (dd, J=15.9, 6.9 Hz, 1H), 5.83 (dd, J=15.9, 1.5 Hz, 1H), 4.20 (q, J=7.2 Hz, 2H), 2.36-1.43 (m, 9H), 1.29 (t, J=7.1 Hz, 3H).

Step 2

Ethyl (E)-3-(4,4-difluorocyclohexyl)acrylate (520 mg, 2.39 mmol) obtained in Step 1 was dissolved in ethanol (8.0 mL), and 10% palladium/carbon (containing water) (200 mg) was added. After displacing the inside of the reaction vessel with hydrogen gas, the mixture was stirred at room temperature overnight. The reaction mixture was filtrated through Celite (registered trademark), and the solvent was evaporated under reduced pressure, whereby ethyl 3-(4,4-difluorocyclohexyl)propionate (522 mg, yield 99%) was obtained.

$^1$H NMR (270 MHz, CDCl$_3$, δ): 4.13 (q, J=7.1 Hz, 2H), 2.32 (t, J=7.7 Hz, 2H), 2.15-1.99 (m, 2H), 2.14-2.00 (m, 2H), 1.83-1.17 (m, 7H), 1.26 (t, J=7.1 Hz, 3H).

Step 3

Ethyl 3-(4,4-difluorocyclohexyl)propionate (0.550 g, 2.50 mmol) obtained in Step 2 was dissolved in ethanol (1.0 mL), sodium ethoxide (20% solution in ethanol) (1.16 mL, 3.00 mmol) and diethyl oxalate (0.405 mL, 3.00 mmol) were added, and the mixture was stirred for 2 hours under reflux with heating. The reaction mixture was cooled to room temperature, and then the solvent was evaporated under reduced pressure. Diethyl ether was added to the residue, and the mixture was extracted with water. Conc. sulfuric acid (0.160 mL, 3.00 mmol) was added to the aqueous layer, and the mixture was extracted with ethyl acetate. The organic layer was washed with saturated brine and dried over anhydrous magnesium sulfate, and the solvent was evaporated under reduced pressure. The residue was dissolved in a mixed solvent of DMSO and water (10:1) (3.3 mL), sodium chloride (0.117 g, 3.03 mmol) was added thereto, and the mixture was stirred at 150° C. for 30 minutes. After cooling the reaction mixture to room temperature, water was added, and the mixture was extracted with diethyl ether. The organic layer was washed with saturated brine and dried over anhydrous magnesium sulfate, and the solvent was evaporated under reduced pressure. The residue was purified by silica gel column chromatography (hexane/ethyl acetate=90/10 to 80/20), whereby ethyl 4-(4,4-difluorocyclohexyl)-2-oxobutanoate (0.146 g, yield 39%) was obtained.

$^1$H NMR (270 MHz, CDCl$_3$, δ): 4.33 (q, J=7.1 Hz, 2H), 2.87 (t, J=7.6 Hz, 2H), 2.16-2.01 (m, 2H), 1.82-1.53 (m, 6H), 1.42-1.21 (m, 6H).

Step 4

Ethyl 4-(4,4-difluorocyclohexyl)-2-oxobutanoate (240 mg, 0.967 mmol) obtained in Step 3 was dissolved in ethanol (2 mL), tetra-n-butylammonium tribromide (559 mg, 1.16 mmol) was added thereto, and the mixture was stirred for 1 hour under reflux with heating. After cooling the reaction mixture to room temperature, an aqueous sodium hydrogen carbonate solution was added, and the mixture was extracted with ethyl acetate. The organic layer was washed with saturated brine and dried over anhydrous sodium sulfate, and the solvent was evaporated under reduced pressure. The residue was purified by silica gel column chromatography (hexane/ethyl acetate=90/10), whereby ethyl 3-bromo-4-(4,4-difluorocyclohexyl)-2-oxobutanoate (0.206 g, yield 65%) was obtained.

$^1$H NMR (300 MHz, CDCl$_3$, δ): 5.11 (dd, J=8.8, 6.2 Hz, 1H), 4.39 (q, J=7.1 Hz, 2H), 2.17-1.18 (m, 14H).

Step 5

Ethyl 3-bromo-4-(4,4-difluorocyclohexyl)-2-oxobutanoate obtained in Step 4 (400 mg, 1.22 mmol), 2-amino-6-methylisonicotinonitrile obtained by a method described in WO2010/90716 (163 mg, 1.22 mmol), and molecular sieves 4A (400 mg) were suspended in n-butanol (2 mL), and the mixture was stirred at 130° C. overnight. After cooling the reaction mixture to room temperature, an aqueous sodium hydrogen carbonate solution was added, and the mixture was filtrated through Celite (registered trademark). The filtrate was extracted with ethyl acetate. The organic layer was washed with water and saturated brine and dried over anhydrous sodium sulfate, and the solvent was evaporated under reduced pressure. The residue was purified by silica gel column chromatography (hexane/ethyl acetate=9/1 to 2/1), whereby ethyl 7-cyano-3-[(4,4-difluorocyclohexyl)methyl]-5-methylimidazo[1,2-a]pyridine-2-carboxylate (0.106 g, yield 24%) and buthyl 7-cyano-3-[(4,4-difluorocyclohexyl)methyl]-5-methylimidazo[1,2-a]pyridine-2-carboxylate (0.101 g, yield 21%) were obtained, respectively.

Ethyl 7-cyano-3-[(4,4-difluorocyclohexyl)methyl]-5-methylimidazo[1,2-a]pyridine-2-carboxylate $^1$H NMR (300 MHz, CDCl$_3$, δ): 7.97 (s, 1H), 6.71 (s, 1H), 4.48 (q, J=7.2 Hz, 2H), 3.60 (d, J=6.2 Hz, 2H), 2.89 (s, 3H), 2.16-2.04 (m, 2H), 1.74-1.51 (m, 7H), 1.46 (t, J=7.2 Hz, 3H); ESIMS m/z: [M+H]$^+$ 362.

Butyl 7-cyano-3-[(4,4-difluorocyclohexyl)methyl]-5-methylimidazo[1,2-a]pyridine-2-carboxylate $^1$H NMR (300 MHz, CDCl$_3$, δ): 7.97 (s, 1H), 6.70 (s, 1H), 4.42 (t, J=7.0 Hz, 2H), 3.59 (d, J=6.6 Hz, 2H), 2.89 (s, 3H), 2.19-2.02 (m, 2H), 1.71-1.51 (m, 11H), 0.98 (t, J=7.3 Hz, 3H); ESIMS m/z: [M+H]$^+$ 390.

Step 6

Ethyl 7-cyano-3-[(4,4-difluorocyclohexyl)methyl]-5-methylimidazo[1,2-a]pyridine-2-carboxylate obtained in Step 5 (1.64 g, 4.54 mmol) was dissolved in THF (30 mL), a solution of methylmagnesium bromide in THF (1.1 mol/L) (16.2 mL, 18.2 mmol) was added at −50° C. and the mixture was stirred at −50° C. for 2 hours and further stirred at 0° C. for 30 minutes. Under ice-cooled condition, a saturated aqueous ammonium chloride solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=80/20 to 65/35), whereby 3-[(4,4-difluorocyclohexyl)methyl]-2-(2-hydroxypropan-2-yl)-5-methylimidazo[1,2-a]pyridine-7-carbonitrile (928 mg, yield 59%) and 2-acetyl-3-[(4,4-difluorocyclohexyl)methyl]-5-methylimidazo[1,2-a]pyridine-7-carbonitrile (110 mg, yield 7%) were obtained, respectively.

3-[(4,4-Difluorocyclohexyl)methyl]-2-(2-hydroxypropan-2-yl)-5-methylimidazo[1,2-a]pyridine-7-carbonitrile $^1$H NMR (300 MHz, CDCl$_3$, δ): 7.81 (s, 1H), 6.63 (s, 1H), 3.39 (d, J=6.6 Hz, 2H), 2.84 (s, 3H), 2.41 (br s, 1H), 2.14-2.02 (m, 2H), 1.71 (s, 6H), 1.67-1.39 (m, 7H); ESIMS m/z: [M+H]$^+$ 348.

2-Acetyl-3-[(4,4-difluorocyclohexyl)methyl]-5-methylimidazo[1,2-a]pyridine-7-carbonitrile $^1$H NMR (300 MHz, CDCl$_3$, δ): 7.93 (d, J=1.5 Hz, 1H), 6.70 (d, J=1.5 Hz, 1H), 3.57 (d, J=6.2 Hz, 2H), 2.88 (s, 3H), 2.75 (s, 3H), 2.16-2.02 (m, 2H), 1.71-1.49 (m, 7H); ESIMS m/z: [M+H]$^+$ 332.

Step 7

3-[(4,4-Difluorocyclohexyl)methyl]-2-(2-hydroxypropan-2-yl)-5-methylimidazo[1,2-a]pyridine-7-carbonitrile obtained in Step 6 (43.5 mg, 0.125 mmol) was dissolved in THF (1 mL), 60% sodium hydride (6.0 mg, 0.015 mmol) and iodoethane (0.015 mL, 0.188 mmol) were added under ice-cooled condition, and the mixture was stirred at 50° C. for 2 hours. Further, under ice-cooled condition, additional 60% sodium hydride (6.0 mg, 0.015 mmol) and iodoethane (0.015 mL, 0.188 mmol) were added thereto, and the mixture was stirred at 50° C. for 2 hours. A saturated aqueous ammonium chloride solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (hexane/ethyl acetate=80/20 to 70/30), whereby 3-[(4,4-difluorocyclohexyl)methyl]-2-(2-ethoxypropan-2-yl)-5-methylimidazo[1,2-a]pyridine-7-carbonitrile (9.1 mg, yield 19%) was obtained.

$^1$H NMR (300 MHz, CDCl$_3$, δ): 7.82 (d, J=1.1 Hz, 1H), 6.61 (d, J=1.1 Hz, 1H), 3.48 (q, J=7.0 Hz, 2H), 3.43 (d, J=7.3 Hz, 2H), 2.83 (s, 3H), 2.15-2.00 (m, 2H), 1.65-1.47 (m, 13H), 1.24 (t, J=7.0 Hz, 3H); ESIMS m/z: [M+H]$^+$ 376.

Step 8

3-[(4,4-Difluorocyclohexyl)methyl]-2-(2-ethoxypropan-2-yl)-5-methylimidazo[1,2-a]pyridine-7-carbonitrile (9.0 mg, 0.024 mmol) obtained in Step 7 was dissolved in a 50% aqueous ethanol solution (0.2 mL), lithium hydroxide monohydrate (7.2 mg, 0.172 mmol) was added, and the mixture was stirred for 4 hours under reflux with heating. Under ice-cooled condition, 3 mol/L hydrochloric acid (0.06 mL) was added to the reaction mixture, and the mixture was extracted with a mixed solvent of chloroform and isopropanol (6/1). The organic layer was washed with saturated brine and dried over anhydrous magnesium sulfate, and the solvent was evaporated under reduced pressure, whereby 3-[(4,4-difluorocyclohexyl)methyl]-2-(2-ethoxypropan-2-yl)-5-methylimidazo[1,2-a]pyridine-7-carboxylic acid (8.4 mg, yield 89%) was obtained.

$^1$H NMR (300 MHz, CDCl$_3$, δ): 8.34 (s, 1H), 7.20 (s, 1H), 3.49 (q, J=7.0 Hz, 2H), 3.45 (d, J=7.0 Hz, 2H), 2.85 (s, 3H), 2.16-1.99 (m, 2H), 1.73 (s, 6H), 1.72-1.41 (m, 7H), 1.25 (t, J=7.0 Hz, 3H); ESIMS m/z: [M+H]$^+$ 395.

Step 9

3-[(4,4-Difluorocyclohexyl)methyl]-2-(2-ethoxypropan-2-yl)-5-methylimidazo[1,2-a]pyridine-7-carboxylic acid obtained in Step 8 (8.4 mg, 0.021 mmol) was dissolved in THF (0.5 mL), tetrahydro-2H-pyran-4-amine (6.5 mg, 0.064 mmol), EDC.HCl (8.2 mg, 0.043 mmol), and HOBt.H$_2$O (3.3 mg, 0.021 mmol) were added, and the mixture was stirred at room temperature overnight. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (hexane/ethyl acetate=80/20 to 70/30), whereby Compound 1 (5.2 mg, yield 51%) was obtained.

$^1$H NMR (300 MHz, CDCl$_3$, δ): 7.73 (d, J=1.8 Hz, 1H), 6.98 (d, J=1.8 Hz, 1H), 5.99 (d, J=7.7 Hz, 1H), 4.25-4.13 (m, 1H), 4.04-3.95 (m, 2H), 3.59-3.50 (m, 2H), 3.47 (q, J=7.0 Hz, 2H), 3.40 (d, J=7.3 Hz, 2H), 2.83 (s, 3H), 2.13-1.36 (m, 13H), 1.68 (s, 6H), 1.24 (t, J=7.0 Hz, 3H); ESIMS m/z: [M+H]$^+$ 478.

EXAMPLE 2

5-Cyano-3-[(4,4-difluorocyclohexyl)methyl]-N-[(2-methyltetrahydrofuran-2-yl)methyl]-2-(trifluoromethyl)imidazo[1,2-a]pyridine-7-carboxamide (Compound 2)

Compound 2 (10.3 mg, yield 27%) was obtained in the same manner as in Step 9 of Example 1, using 5-cyano-3-

[(4,4-difluorocyclohexyl)methyl]-2-(trifluoromethyl)imidazo[1,2-a]pyridine-7-carboxylic acid obtained in Step 3 of Example 37 and (2-methyltetrahydrofuran-2-yl)methanamine.

$^1$H NMR (300 MHz, CDCl$_3$, δ): 8.23 (d, J=1.8 Hz, 1H), 8.07 (d, J=1.8 Hz, 1H), 6.61 (br s, 1H), 3.92-3.85 (m, 2H), 3.55 (ddd, J=24.2, 13.6, 5.5 Hz, 2H), 3.36 (d, J=6.6 Hz, 2H), 2.17-1.47 (m, 13H), 1.25 (s, 3H); ESIMS m/z: [M+H]$^+$ 485.

EXAMPLE 3

5-Cyano-3-[(4,4-difluorocyclohexyl)methyl]-N-[(tetrahydrofuran-3-yl)methyl]-2-(trifluoromethyl)imidazo[1,2-a]pyridine-7-carboxamide (Compound 3)

Compound 3 (8.50 mg, yield 23%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and (tetrahydrofuran-3-yl)methanamine.

$^1$H NMR (300 MHz, CDCl$_3$, δ): 8.18 (d, J=1.5 Hz, 1H), 8.06 (d, J=1.8 Hz, 1H), 6.54 (s, 1H), 3.97 (td, J=8.4, 5.1 Hz, 2H), 3.84-3.68 (m, 2H), 3.54 (td, J=5.9, 1.8 Hz, 2H), 3.36 (d, J=7.0 Hz, 2H), 2.65-2.62 (m, 1H), 2.14-2.08 (m, 4H), 1.70-1.59 (m, 7H); ESIMS m/z: [M+H]$^+$ 471.

EXAMPLE 4

2-tert-Butyl-3-[(4,4-difluorocyclohexyl)methyl]-5-methyl-N-(tetrahydro-2H-pyran-4-yl)imidazo[1,2-a]pyridine-7-carboxamide (Compound 4)

Step 1

Ethyl 2-tert-butyl-5-methylimidazo[1,2-a]pyridine-7-carboxylate (537 mg, yield 12%) was obtained in the same manner as in Step 5 of Example 1, using ethyl 2-amino-6-methylpyridine-4-carboxylate obtained by a method described in WO2008/009750 and 1-bromo-3,3-dimethylbutan-2-one.

$^1$H NMR (300 MHz, CDCl$_3$, δ): 8.28 (s, 1H), 7.32 (s, 1H), 7.20 (s, 1H), 4.38 (q, J=7.2 Hz, 2H), 2.61 (s, 3H), 1.44 (s, 9H), 1.39 (t, J=7.2 Hz, 3H); ESIMS m/z: [M+H]$^+$ 261.

Step 2

Ethyl 2-tert-butyl-5-methylimidazo[1,2-a]pyridine-7-carboxylate obtained in Step 1 (530 mg, 2.04 mmol) was dissolved in DMF (8 mL), N-iodosuccinimide (504 mg, 2.24 mmol) was added thereto, and the mixture was stirred at 50° C. for 2 hours. After cooling the reaction mixture to room temperature, an aqueous sodium hydrogen carbonate solution was added, and the mixture was extracted with a mixed solvent of ethyl acetate and hexane. The organic layer was washed with saturated brine and dried over anhydrous magnesium sulfate, and the solvent was evaporated under reduced pressure. The residue was purified by silica gel column chromatography (hexane/ethyl acetate=80/20 to 50/50), whereby ethyl 2-tert-butyl-3-iodo-5-methylimidazo[1,2-a]pyridine-7-carboxylate (677 mg, yield 86%) was obtained.

$^1$H NMR (300 MHz, CDCl$_3$, δ): 8.24 (d, J=1.8 Hz, 1H), 7.07 (d, J=1.8 Hz, 1H), 4.37 (q, J=7.1 Hz, 2H), 3.27 (s, 3H), 1.59 (s, 9H), 1.38 (t, J=7.1 Hz, 3H)

Step 3

Ethyl 2-tert-butyl-3-iodo-5-methylimidazo[1,2-a]pyridine-7-carboxylate obtained in Step 2 (670 mg, 1.74 mmol) was dissolved in THF (15 mL), isopropylmagnesium bromide (2 mol/L solution in THF) (2.6 mL, 5.20 mmol) was added thereto at −78° C. After raising the temperature to −20° C., the mixture was stirred for 10 minutes. 4,4-Difluorocyclohexanecarboxyaldehyde (771 mg, 5.20 mmol) was added to the reaction mixture, and the mixture was stirred at room temperature for 30 minutes. A saturated aqueous ammonium chloride solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=90/10 to 70/30), whereby ethyl 2-tert-butyl-3-[(4,4-difluorocyclohexyl) (hydroxy)methyl]-5-methylimidazo[1,2-a]pyridine-7-carboxylate (366 mg, yield 51%) was obtained.

$^1$H NMR (300 MHz, CDCl$_3$, δ): 8.23 (d, J=1.1 Hz, 1H), 7.21 (d, J=1.1 Hz, 1H), 5.38-5.35 (m, 1H), 4.38 (q, J=7.1 Hz, 2H), 3.52 (d, J=6.2 Hz, 1H), 3.01 (s, 3H), 2.53-2.43 (m, 1H), 2.27-1.24 (m, 8H), 1.52 (s, 9H), 1.39 (t, J=7.1 Hz, 3H); ESIMS m/z: [M+H]$^+$ 409.

Step 4

Sodium iodide (1.32 g, 8.81 mmol) was suspended in a mixed solvent of dichloromethane/acetonitrile (1:1) (10 mL). Dichlorodimethylsilane (0.527 mL, 4.41 mmol) was added thereto under ice-cooled condition, and the mixture was stirred for 15 minutes. A solution (5 mL) of ethyl 2-tert-butyl-3-[(4,4-difluorocyclohexyl)(hydroxy)methyl]-5-methylimidazo[1,2-a]pyridine-7-carboxylate obtained in Step 3 (360 mg, 0.881 mmol) in dichloromethane was added to the reaction mixture, and the mixture was stirred at room temperature for 30 minutes. A saturated aqueous sodium hydrogen carbonate solution and a saturated aqueous sodium thiosulfate solution were added to the reaction mixture, the mixture was filtrated through Presep (registered trademark; diatomite, granular type M, 4.5 g/25 mL), and the solvent was evaporated under reduced pressure. The residue was purified by silica gel column chromatography (heptane/ethyl acetate=80/20 to 65/35), whereby ethyl 2-tert-butyl-3-[(4,4-difluorocyclohexyl)methyl]-5-methylimidazo[1,2-a]pyridine-7-carboxylate (195 mg, yield 56%) was obtained.

$^1$H NMR (300 MHz, CDCl$_3$, δ): 8.21 (s, 1H), 7.07 (s, 1H), 4.37 (q, J=7.1 Hz, 2H), 3.22 (d, J=6.6 Hz, 2H), 2.80 (s, 3H), 2.14-2.01 (m, 2H), 1.65-1.33 (m, 7H), 1.50 (s, 9H), 1.38 (t, J=7.1 Hz, 3H); ESIMS m/z: [M+H]$^+$ 393.

Step 5

2-tert-Butyl-3-[(4,4-difluorocyclohexyl)methyl]-5-methylimidazo[1,2-a]pyridine-7-carboxylic acid (164 mg, yield 91%) was obtained in the same manner as in Step 8 of Example 1, using ethyl 2-tert-butyl-3-[(4,4-difluorocyclohexyl)methyl]-5-methylimidazo[1,2-a]pyridine-7-carboxylate obtained in Step 4 (195 mg, 0.497 mmol).

$^1$H NMR (300 MHz, CDCl$_3$, δ): 8.35 (s, 1H), 7.19 (s, 1H), 3.24 (d, J=6.6 Hz, 2H), 2.82 (s, 3H), 2.19-1.99 (m, 2H), 1.68-1.32 (m, 7H), 1.53 (s, 9H); ESIMS m/z: [M−H]$^-$ 363.

Step 6

Compound 4 (86.7 mg, yield 88%) was obtained in the same manner as in Step 9 of Example 1, using 2-tert-butyl-3-[(4,4-difluorocyclohexyl)methyl]-5-methylimidazo[1,2-a]pyridine-7-carboxylic acid obtained in Step 5, tetrahydro-2H-pyran-4-amine hydrochloride, and potassium carbonate.

$^1$H NMR (300 MHz, CDCl$_3$, δ): 7.73 (d, J=1.8 Hz, 1H), 6.97 (d, J=1.8 Hz, 1H), 5.98 (d, J=7.0 Hz, 1H), 4.24-4.13 (m, 1H), 4.03-3.96 (m, 2H), 3.59-3.49 (m, 2H), 3.21 (d, J=6.6 Hz, 2H), 2.80 (s, 3H), 2.11-1.96 (m, 4H), 1.65-1.23 (m, 9H), 1.49 (s, 9H); ESIMS m/z: [M+H]$^+$ 448.

EXAMPLE 5

6-Chloro-3-[(4,4-difluorocyclohexyl)methyl]-2-(1,1-difluoroethyl)-N-phenylimidazo[1,2-a]pyridine-7-carboxamide (Compound 5)

Step 1

2-Amino-4-cyanopyridine (8.00 g, 67.2 mmol) was dissolved in DMF (40 mL), N-chlorosuccinimide (8.97 g, 67.2 mmol) was added thereto, and the mixture was stirred at 50° C. for 1 hour. Under ice-cooled condition, an aqueous sodium hydrogen carbonate solution was added to the reaction mixture, and the precipitated solid was collected by filtration. The resulting solid was purified by silica gel column chromatography (chloroform/methanol=95/5 to 90/10, heptane/ethyl acetate=65/35 to 50/50), whereby 2-amino-5-chloro-4-cyanopyridine (6.23 g, yield 60%) and 2-amino-3-chloro-4-cyanopyridine (0.254 g, yield 2%) were obtained respectively.

2-Amino-5-chloro-4-cyanopyridine $^1$H NMR (300 MHz, CDCl$_3$, δ): 8.20 (s, 1H), 6.73 (s, 1H), 4.71 (s, 2H).

2-Amino-3-chloro-4-cyanopyridine $^1$H NMR (300 MHz, CDCl$_3$, δ): 8.10 (d, J=5.1 Hz, 1H), 6.89 (d, J=5.1 Hz, 1H), 5.14 (s, 2H).

Step 2

Dimethyl methylphosphonate (6.32 mL, 59.1 mmol) was dissolved in THF (80 mL), n-butyllithium (2.7 mol/L solution in n-hexane) (21.9 mL, 59.1 mmol) was added thereto at −78° C., and the mixture was stirred at −78° C. for minutes. A solution of ethyl 2,2-difluoropropionate (6.80 g, 49.2 mmol) in THF (20 mL) was gently added to the reaction mixture. After raising the temperature to room temperature, the mixture was stirred for 30 minutes. A saturated aqueous ammonium chloride solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=98/2 to 95/5), whereby dimethyl 3,3-difluoro-2-oxobutylphosphonate (8.83 g, yield 83%) was obtained.

$^1$H NMR (300 MHz, CDCl$_3$, δ): 3.82 (d, J=11.4 Hz, 6H), 3.36 (dt, J=22.1, 1.2 Hz, 2H), 1.74 (t, J=19.2 Hz, 3H).

Step 3

1-(4,4-Difluorocyclohexyl)-4,4-difluoropent-1-en-3-one (113 mg, yield 21%) was obtained in the same manner as in Step 1 of Example 1, using dimethyl 3,3-difluoro-2-oxobutylphosphonate obtained in Step 2 and 4,4-difluorocyclohexanecarbaldehyde.

$^1$H NMR (300 MHz, CDCl$_3$, δ): 7.14 (dd, J=15.8, 6.6 Hz, 1H), 6.58-6.50 (m, 1H), 2.41-2.26 (m, 1H), 2.24-2.09 (m, 3H), 1.97-1.51 (m, 8H).

Step 4

1-(4,4-Difluorohexyl)-4,4-difluoropent-1-en-3-one obtained in Step 3 (1.15 g, 4.83 mmol) was dissolved in ethanol (15 mL), and the solution was reacted by using H-cube (registered trademark) (manufactured by ThalesNano Technologies, 10% Pd/C CatCart (30 mm), full H2mode) at 25° C., whereby 1-(4,4-difluorocyclohexyl)-4,4-difluoropentan-3-one (0.973 g, yield 84%) was obtained.

$^1$H NMR (300 MHz, CDCl$_3$, δ): 2.72 (tt, J=7.3, 1.5 Hz, 2H), 2.15-2.01 (m, 2H), 1.82-1.21 (m, 12H).

Step 5

1-(4,4-Difluorocyclohexyl)-4,4-difluoropentan-3-one obtained in Step 4 (50 mg, 0.208 mmol) was dissolved in THF (1.0 mL), DBU (0.063 mL, 0.416 mmol) and chlorotriethylsilane (0.070 mL, 0.416 mmol) were added thereto under ice-cooled condition, and the mixture was stirred at 0° C. for 30 minutes. A saturated aqueous sodium hydrogen carbonate solution was added to the reaction mixture, and the mixture was extracted with heptane. The organic layer was washed with saturated brine and dried over anhydrous magnesium sulfate, and the solvent was evaporated under reduced pressure. The residue was purified by silica gel column chromatography (hexane/ethyl acetate=95/5 to 90/10), whereby [1-(4,4-difluorocyclohexyl)-4,4-difluoropent-2-en-3-yloxy]triethylsilane (31.5 mg, yield 43%) was obtained.

$^1$H NMR (300 MHz, CDCl$_3$, δ): 5.12 (t, J=7.3 Hz, 1H), 2.16-1.21 (m, 14H), 0.99 (t, J=7.9 Hz, 9H), 0.71 (q, J=7.9 Hz, 6H).

Step 6

[1-(4,4-Difluorocyclohexyl)-4,4-difluoropent-2-en-3-yloxy]triethylsilane obtained in Step 5 (1.09 g, 3.07 mmol) was dissolved in dichloromethane (10 mL). Under ice-cooled condition, a solution (5 mL) of bromine (541 mg, 3.38 mmmol) in dichloromethane was added thereto, and the mixture was stirred at room temperature for 1 hour. A saturated aqueous sodium hydrogen carbonate solution and an aqueous sodium thiosulfate solution were added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=90/10 to 80/20), whereby 2-bromo-1-(4,4-difluorocyclohexyl)-4,4-difluoropentan-3-one (947 mg, yield 97%) was obtained.

$^1$H NMR (300 MHz, CDCl$_3$, δ): 4.85-4.78 (m, 1H), 2.18-1.23 (m, 14H).

Step 7

6-Chloro-3-[(4,4-difluorocyclohexyl)methyl]-2-(1,1-difluoroethyl)imidazo[1,2-a]pyridine-7-carbonitrile (491 mg, yield 45%) was obtained in the same manner as in Step of Example 1, using 2-amino-5-chloro-4-cyanopyridine obtained in Step 1 and 2-bromo-1-(4,4-difluorocyclohexyl)-4,4-difluoropentan-3-one obtained in Step 6.

$^1$H NMR (300 MHz, CDCl$_3$, δ): 8.08 (s, 1H), 8.05 (s, 1H), 3.03 (d, J=7.0 Hz, 2H), 2.20-2.07 (m, 5H), 1.80-1.40 (m, 7H); ESIMS m/z: [M+H]$^+$ 374.

Step 8

6-Chloro-3-[(4,4-difluorocyclohexyl)methyl]-2-(1,1-difluoroethyl)imidazo[1,2-a]pyridine-7-carboxylic acid (480 mg, yield 94%) was obtained in the same manner as in Step 8 of Example 1, using 6-chloro-3-[(4,4-difluorocyclohexyl)methyl]-2-(1,1-difluoroethyl)imidazo[1,2-a]pyridine-7-carbonitrile obtained in Step 7.

$^1$H NMR (300 MHz, DMSO-d$_6$, δ): 8.85 (s, 1H), 8.03 (s, 1H), 3.06 (d, J=7.3 Hz, 2H), 2.08 (t, J=19.1 Hz, 3H), 2.00-1.19 (m, 9H); ESIMS m/z: [M+H]$^+$ 393.

Step 9

Compound 5 (57.3 mg, yield 69%) was obtained in the same manner as in Step 9 of Example 1, using 6-chloro-3-[(4,4-difluorocyclohexyl)methyl]-2-(1,1-difluoroethyl)imidazo[1,2-a]pyridine-7-carboxylic acid obtained in Step 8 and aniline.

$^1$H NMR (300 MHz, CDCl$_3$, δ): 8.06-8.03 (m, 2H), 7.84 (s, 1H), 7.67-7.60 (m, 2H), 7.44-7.36 (m, 2H), 7.24-7.17 (m,

1H), 3.03 (d, J=7.2 Hz, 2H), 2.16-2.01 (m, 2H), 2.14 (t, J=19.4 Hz, 3H), 1.83-1.43 (m, 7H); ESIMS m/z: [M+H]$^+$ 468.

EXAMPLE 6

6-Chloro-2-cyclopropyl-3-[(4,4-difluorocyclohexyl)methyl]-N-phenylimidazo[1,2-a]pyridine-7-carboxamide (Compound 6)

Step 1

1-Cyclopropyl-3-(4,4-difluorocyclohexyl)prop-2-en-1-one (2.69 g, yield 80%) was obtained in the same manner as in Step 1 of Example 1, using dimethyl 2-cyclopropyl-2-oxoethylphosphonate obtained by a method described in US2009/82317 and 4,4-difluorocyclohexanecarbaldehyde.

$^1$H NMR (300 MHz, CDCl$_3$, δ): 6.81 (dd, J=15.8, 6.9 Hz, 1H), 6.24 (dd, J=15.8, 1.5 Hz, 1H), 2.40-1.46 (m, 10H), 1.15-1.03 (m, 2H), 0.95-0.88 (m, 2H).

Step 2

1-Cyclopropyl-3-(4,4-difluorocyclohexyl)propan-1-one (1.68 g, yield 63%) was obtained in the same manner as in Step 2 of Example 1, using 1-cyclopropyl-3-(4,4-difluorocyclohexyl)prop-2-en-1-one obtained in Step 1.

$^1$H NMR (300 MHz, CDCl$_3$, δ): 2.58 (t, J=7.5 Hz, 2H), 2.14-2.00 (m, 2H), 1.98-1.87 (m, 1H), 1.84-1.18 (m, 9H), 1.07-0.98 (m, 2H), 0.91-0.81 (m, 2H).

Step 3

2-Bromo-1-cyclopropyl-3-(4,4-difluorocyclohexyl)propan-1-one (2.05 g, yield 91%) was obtained in the same manner as in Step 6 of Example 5, using 1-cyclopropyl-3-(4,4-difluorocyclohexyl)propan-1-one obtained in Step 2.

$^1$H NMR (300 MHz, CDCl$_3$, δ): 4.44 (dd, J=8.6, 6.6 Hz, 1H), 2.25-1.25 (m, 12H), 1.17-0.95 (m, 4H).

Step 4

6-Chloro-2-cyclopropyl-3-[(4,4-difluorocyclohexyl)methyl]imidazo[1,2-a]pyridine-7-carbonitrile (441 mg, yield 29%) was obtained in the same manner as in Step 5 of Example 1, using 2-bromo-1-cyclopropyl-3-(4,4-difluorocyclohexyl)propan-1-one obtained in Step 3 and 2-amino-5-chloro-4-cyanopyridine obtained in Step 1 of Example 5.

$^1$H NMR (300 MHz, CDCl$_3$, δ): 7.93 (d, J=0.7 Hz, 1H), 7.87 (d, J=0.7 Hz, 1H), 2.92 (d, J=7.0 Hz, 2H), 2.19-2.06 (m, 2H), 1.98-1.89 (m, 1H), 1.83-1.42 (m, 7H), 1.14-1.02 (m, 4H); ESIMS m/z: [M+H]$^+$ 350.

Step 5

6-Chloro-2-cyclopropyl-3-[(4,4-difluorocyclohexyl)methyl]imidazo[1,2-a]pyridine-7-carboxylic acid (424 mg, yield 86%) was obtained in the same manner as in Step 8 of Example 1, using 6-chloro-2-cyclopropyl-3-[(4,4-difluorocyclohexyl)methyl]imidazo[1,2-a]pyridine-7-carbonitrile obtained in Step 4.

$^1$H NMR (300 MHz, DMSO-d$_6$, δ): 13.38 (br s, 1H), 8.66 (s, 1H), 7.90 (s, 1H), 3.01 (d, J=7.0 Hz, 2H), 2.15-1.63 (m, 8H), 1.43-1.23 (m, 2H), 1.00-0.87 (m, 4H); ESIMS m/z: [M+H]$^+$ 369.

Step 6

Compound 6 (27.1 mg, yield 32%) was obtained in the same manner as in Step 9 of Example 1, using 6-chloro-2-cyclopropyl-3-[(4,4-difluorocyclohexyl)methyl]imidazo[1,2-a]pyridine-7-carboxylic acid obtained in Step 5 and aniline.

$^1$H NMR (300 MHz, CDCl$_3$, δ): 7.95-7.90 (m, 3H), 7.66-7.61 (m, 2H), 7.42-7.34 (m, 2H), 7.22-7.15 (m, 1H), 2.92 (d, J=6.6 Hz, 2H), 2.18-2.05 (m, 2H), 1.99-1.87 (m, 1H), 1.84-1.40 (m, 7H), 1.13-0.99 (m, 4H); ESIMS m/z: [M+H]$^+$ 444.

EXAMPLE 7

6-Chloro-2-(3,3-difluorocyclobutyl)-3-[(4,4-difluorocyclohexyl)methyl]-N-phenylimidazo[1,2-a]pyridine-7-carboxamide (Compound 7)

Step 1

3,3-Difluoro-N-methoxy-N-methylcyclobutanecarboxamide (5.44 g, yield 83%) was obtained in the same manner as in Step 9 of Example 1, using 3,3-difluorocyclobutylcarboxylic acid, N,O-dimethylhydroxylamine hydrochloride, and triethylamine.

$^1$H NMR (300 MHz, CDCl$_3$, δ): 3.69 (s, 3H), 3.34-3.21 (m, 1H), 3.21 (s, 3H), 3.01-2.60 (m, 4H).

Step 2

Dimethyl 2-(3,3-difluorocyclobutyl)-2-oxoethylphsphonate (5.69 g, yield 78%) was obtained in the same manner as in Step 2 of Example 5, using 3,3-difluoro-N-methoxy-N-methylcyclobutanecarboxamide obtained in Step 1 and dimethyl methylphsphonate.

$^1$H NMR (300 MHz, CDCl$_3$, δ): 3.80 (d, J=11.2 Hz, 6H), 3.40-3.26 (m, 1H), 3.12 (d, J=23.0 Hz, 2H), 2.93-2.66 (m, 4H).

Step 3

1-(3,3-Difluorocyclobutyl)-3-(4,4-difluorocyclohexyl)prop-2-en-1-one (4.00 g, yield 67%) was obtained in the same manner as in Step 1 of Example 1, using dimethyl 2-(3,3-difluorocyclobutyl)-2-oxoethylphsphonate obtained in Step 2 and 4,4-difluorocyclohexanecarbaldehyde.

$^1$H NMR (300 MHz, CDCl$_3$, δ): 6.78 (dd, J=16.1, 6.6 Hz, 1H), 6.12 (dd, J=16.1, 1.3 Hz, 1H), 3.38-3.19 (m, 1H), 2.97-2.64 (m, 4H), 2.39-2.06 (m, 3H), 1.97-1.44 (m, 6H).

Step 4

1-(3,3-Difluorocyclobutyl)-3-(4,4-difluorocyclohexyl)propan-1-one (4.03 g, yield quantitative) was obtained in the same manner as in Step 2 of Example 1, using 1-(3,3-difluorocyclobutyl)-3-(4,4-difluorocyclohexyl)prop-2-en-1-one obtained in Step 3.

$^1$H NMR (300 MHz, CDCl$_3$, δ): 3.13-2.99 (m, 1H), 2.87-2.61 (m, 4H), 2.47 (t, J=7.5 Hz, 2H), 2.15-2.01 (m, 2H), 1.80-1.49 (m, 5H), 1.38-1.18 (m, 4H).

Step 5

2-Bromo-1-(3,3-difluorocyclobutyl)-3-(4,4-difluorocyclohexyl)propan-1-one (3.52 g, yield 91%) was obtained in the same manner as in Step 6 of Example 5, using 1-(3,3-difluorocyclobutyl)-3-(4,4-difluorocyclohexyl)propan-1-one obtained in Step 4.

Step 6

6-Chloro-2-(3,3-difluorocyclobutyl)-3-[(4,4-difluorocyclohexyl)methyl]imidazo[1,2-a]pyridine-7-carbonitrile (685 mg, yield 30%) was obtained in the same manner as in Step 5 of Example 1, using 2-bromo-1-(3,3-difluorocyclobutyl)-3-(4,4-difluorocyclohexyl)propan-1-one obtained in Step 5 and 2-amino-5-chloro-4-cyanopyridine obtained in Step 1 of Example 5.

$^1$H NMR (300 MHz, CDCl$_3$, δ): 8.01 (s, 1H), 7.97 (s, 1H), 3.51-3.37 (m, 1H), 3.19-2.86 (m, 4H), 2.83 (d, J=7.0 Hz, 2H), 2.20-1.37 (m, 9H); ESIMS m/z: [M+H]$^+$ 400.

Step 7

6-Chloro-2-(3,3-difluorocyclobutyl)-3-[(4,4-difluorocyclohexyl)methyl]imidazo[1,2-a]pyridine-7-carboxylic acid (543 mg, yield 76%) was obtained in the same manner as in Step 8 of Example 1, using 6-chloro-2-(3,3-difluorocyclobutyl)-3-[(4,4-difluorocyclohexyl)methyl]imidazo[1,2-a]pyridine-7-carboxamide obtained in Step 6.

$^1$H NMR (300 MHz, DMSO-$d_6$, δ): 8.37-8.35 (m, 1H), 7.35-7.27 (m, 1H), 3.55-3.41 (m, 1H), 2.99-2.81 (m, 6H), 2.03-1.55 (m, 7H), 1.34-1.17 (m, 2H); ESIMS m/z: [M+H]$^+$ 419.

Step 8

Compound 7 (56.5 mg, yield 68%) was obtained in the same manner as in Step 9 of Example 1, using 6-chloro-2-(3,3-difluorocyclobutyl)-3-[(4,4-difluorocyclohexyl)methyl]imidazo[1,2-a]pyridine-7-carboxylic acid obtained in Step 7 and aniline.

$^1$H NMR (300 MHz, CDCl$_3$, δ): 8.05 (s, 1H), 7.95 (s, 1H), 7.82 (br s, 1H), 7.67-7.60 (m, 2H), 7.45-7.34 (m, 2H), 7.24-7.16 (m, 1H), 3.53-3.31 (m, 1H), 3.20-2.88 (m, 4H), 2.83 (d, J=6.6 Hz, 2H), 2.22-2.05 (m, 2H), 1.83-1.10 (m, 7H); ESIMS m/z: [M+H]$^+$ 494.

EXAMPLE 8

3-[(4,4-Difluorocyclohexyl)methyl]-2-(2-hydroxypropan-2-yl)-5-methyl-N-phenylimidazo[1,2-a]pyridine-7-carboxamide (Compound 8)

Step 1

3-[(4,4-Difluorocyclohexyl)methyl]-2-(2-hydroxypropan-2-yl)-5-methylimidazo[1,2-a]pyridine-7-carboxylic acid (40.9 mg, yield 72%) was obtained in the same manner as in Step 8 of Example 1, using 3-[(4,4-difluorocyclohexyl)methyl]-2-(2-hydroxypropan-2-yl)-5-methylimidazo[1,2-a]pyridine-7-carbonitrile obtained in Step 6 of Example 1.

$^1$H NMR (300 MHz, DMSO-$d_6$, δ): 7.83 (s, 1H), 7.05 (s, 1H), 5.07 (s, 1H), 3.46 (d, J=6.6 Hz, 2H), 2.85 (s, 3H), 2.03-1.89 (m, 2H), 1.84-1.64 (m, 4H), 1.56 (s, 6H), 1.42-1.22 (m, 3H); ESIMS m/z: [M+H]$^+$ 367.

Step 2

Compound 8 (43.5 mg, yield 60%) was obtained in the same manner as in Step 9 of Example 1, using 3-[(4,4-difluorocyclohexyl)methyl]-2-(2-hydroxypropan-2-yl)-5-methylimidazo[1,2-a]pyridine-7-carboxylic acid obtained in Step 1 and aniline.

$^1$H NMR (300 MHz, CDCl$_3$, δ): 7.85 (d, J=1.5 Hz, 1H), 7.81 (s, 1H), 7.65-7.60 (m, 2H), 7.42-7.36 (m, 2H), 7.20-7.14 (m, 1H), 7.08 (d, J=1.5 Hz, 1H), 3.38 (d, J=6.6 Hz, 2H), 2.87 (s, 3H), 2.57 (s, 1H), 2.16-2.02 (m, 2H), 1.72 (s, 6H), 1.70-1.41 (m, 7H); ESIMS m/z: [M+H]$^+$ 442.

EXAMPLE 9

3-[(4,4-Difluorocyclohexyl)methyl]-2-(2-methoxy-$d_3$-propan-2-yl)-5-methyl-N-(tetrahydro-2H-pyran-4-yl)imidazo[1,2-a]pyridine-7-carboxamide (Compound 11)

Step 1

3-[(4,4-Difluorocyclohexyl)methyl]-2-(2-methoxy-$d_3$-propan-2-yl)-5-methylimidazo[1,2-a]pyridine-7-carbonitrile (66.5 mg, yield 63%) was obtained in the same manner as in Step 7 of Example 1, using 3-[(4,4-difluorocyclohexyl)methyl]-2-(2-hydroxypropan-2-yl)-5-methylimidazo[1,2-a]pyridine-7-carbonitrile obtained in Step 6 of Example 1 and iodomethane-$d_3$.

$^1$H NMR (300 MHz, CDCl$_3$, δ): 7.82 (s, 1H), 6.62 (s, 1H), 3.36 (d, J=7.0 Hz, 2H), 2.83 (s, 3H), 2.16-2.00 (m, 2H), 1.66 (s, 6H), 1.65-1.23 (m, 7H); ESIMS m/z: [M+H]$^+$ 365.

Step 2

3-[(4,4-Difluorocyclohexyl)methyl]-2-(2-methoxy-$d_3$-propan-2-yl)-5-methylimidazo[1,2-a]pyridine-7-carboxylic acid (67.9 mg, yield 99%) was obtained in the same manner as in Step 8 of Example 1, using 3-[(4,4-difluorocyclohexyl)methyl]-2-(2-methoxy-$d_3$-propan-2-yl)-5-methylimidazo[1,2-a]pyridine-7-carbonitrile obtained in Step 1.

$^1$H NMR (300 MHz, CDCl$_3$, δ): 8.57 (s, 1H), 7.47 (s, 1H), 3.41 (d, J=6.6 Hz, 2H), 2.96 (s, 3H), 2.16-2.02 (m, 2H), 1.81 (s, 6H), 1.79-1.41 (m, 7H); ESIMS m/z: [M+H]$^+$ 384.

Step 3

Compound 11 (45.2 mg, yield 62%) was obtained in the same manner as in Step 6 of Example 4, using 3-[(4,4-difluorocyclohexyl)methyl]-2-(2-methoxy-$d_3$-propan-2-yl)-5-methylimidazo[1,2-a]pyridine-7-carboxylic acid obtained in Step 2 and tetrahydro-2H-pyran-4-amine hydrochloride.

$^1$H NMR (300 MHz, CDCl$_3$, δ): 7.73 (d, J=1.5 Hz, 1H), 6.99 (d, J=1.5 Hz, 1H), 5.98 (d, J=7.3 Hz, 1H), 4.24-4.12 (m, 1H), 4.04-3.95 (m, 2H), 3.59-3.49 (m, 2H), 3.34 (d, J=7.0 Hz, 2H), 2.83 (s, 3H), 2.14-1.97 (m, 4H), 1.67 (s, 6H), 1.66-1.37 (m, 9H); ESIMS m/z: [M+H]$^+$ 467.

EXAMPLE 10

3-[(4,4-Difluorocyclohexyl)methyl]-5-methyl-2-(methylsulfonylmethyl)-N-phenylimidazo[1,2-a]pyridine-7-carboxamide (Compound 12)

Step 1

Butyl 7-cyano-3-[(4,4-difluorocyclohexyl)methyl]-5-methylimidazo[1,2-a]pyridine-2-carboxylate (2.00 g, 5.14 mmol) obtained in Step 5 of Example 1 was dissolved in a mixed solvent of THF (20 mL) and methanol (4.0 mL). Under ice-cooled condition, lithium borohydride (447 mg, 0.55 mmol) was added thereto, and the mixture was stirred at room temperature for 2 hours. Acetone and a saturated aqueous sodium hydrogen carbonate solution were added to the reaction mixture, and the mixture was extracted with ethyl acetate. The organic layer was washed with saturated brine and dried over anhydrous sodium sulfate, and the solvent was evaporated under reduced pressure. The residue was purified by silica gel column chromatography (chloroform/methanol=9/1), whereby 3-[(4,4-difluorocyclohexyl)methyl]-2-(hydroxymethyl)-5-methylimidazo[1,2-a]pyridine-7-carbonitrile (636 mg, yield 39%) was obtained.

$^1$H NMR (300 MHz, CDCl$_3$, δ): 7.87 (d, J=1.1 Hz, 1H), 6.67 (d, J=1.1 Hz, 1H), 4.81 (s, 2H), 3.10 (d, J=6.6 Hz, 2H), 2.86 (s, 3H), 2.15-2.03 (m, 2H), 1.78-1.37 (m, 7H) ESIMS m/z: [M+H]$^+$ 320.

Step 2

3-[(4,4-Difluorocyclohexyl)methyl]-2-(hydroxymethyl)-5-methylimidazo[1,2-a]pyridine-7-carbonitrile (630 mg, 1.97 mmol) obtained in Step 1 was dissolved in THF (10 mL). Under ice-cooled condition, triethylamine (0.550 mL, 3.95 mmol) and methanesulfonyl chloride (0.231 mL, 2.96 mmol) were added thereto, and the mixture was stirred at 0° C. for 30 minutes. An aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=50/50 to 0/100), whereby {7-cyano-3-[(4,4-difluorocyclohexyl)methyl]-5-methylimidazo[1,2-a]pyridin-2-yl}methyl methanesulfonate (746 mg, yield 95%) was obtained.

$^1$H NMR (300 MHz, CDCl$_3$, δ): 7.88 (d, J=1.1 Hz, 1H), 6.70 (d, J=1.1 Hz, 1H), 5.39 (s, 2H), 3.15 (d, J=6.2 Hz, 2H), 3.09 (s, 3H), 2.87 (s, 3H), 2.17-2.07 (m, 2H), 1.77-1.39 (m, 7H); ESIMS m/z: [M+H]⁺ 398.

Step 3

{7-Cyano-3-[(4,4-difluorocyclohexyl)methyl]-5-methyl-imidazo[1,2-a]pyridin-2-yl}methyl methanesulfonate obtained in Step 2 (750 mg, 1.89 mmol) was dissolved in DMSO (10 mL), sodium methanesulfinate (771 mg, 7.55 mmol) was added thereto, and the mixture was stirred at room temperature for 1 hour. Water was added to the reaction mixture, and the mixture was extracted with a mixed solvent of ethyl acetate and heptane. The organic layer was washed with saturated brine and dried over anhydrous magnesium sulfate, and the solvent was evaporated under reduced pressure. The residue was purified by silica gel column chromatography (hexane/ethyl acetate=50/50 to 0/100), whereby 3-[(4,4-difluorocyclohexyl)methyl]-5-methyl-2-(methylsulfonylmethyl)imidazo[1,2-a]pyridine-7-carbonitrile (339 mg, yield 47%) was obtained.

¹H NMR (300 MHz, CDCl₃, δ): 7.84 (s, 1H), 6.71 (s, 1H), 4.44 (s, 2H), 3.19 (d, J=6.6 Hz, 2H), 3.03 (s, 3H), 2.87 (s, 3H), 2.24-1.93 (m, 2H), 1.78-1.36 (m, 7H); ESIMS m/z: [M+H]⁺ 382.

Step 4

3-[(4,4-Difluorocyclohexyl)methyl]-5-methyl-2-(methylsulfonylmethyl)imidazo[1,2-a]pyridine-7-carboxylic acid (30.3 mg, yield 93%) was obtained in the same manner as in Step 8 of Example 1, using 3-[(4,4-difluorocyclohexyl)methyl]-5-methyl-2-(methylsulfonylmethyl)imidazo[1,2-a]pyridine-7-carbonitrile obtained in Step 3.

¹H NMR (300 MHz, DMSO-d₆, δ): 13.19 (br s, 1H), 7.93 (d, J=1.3 Hz, 1H), 7.15 (d, J=1.3 Hz, 1H), 4.64 (s, 2H), 3.15 (d, J=6.6 Hz, 2H), 3.13 (s, 3H), 2.90 (s, 3H), 2.03-1.20 (m, 9H); ESIMS m/z: [M+H]⁺ 401.

Step 5

Compound 12 (20.5 mg, yield 96%) was obtained in the same manner as in Step 9 of Example 1, using 3-[(4,4-difluorocyclohexyl)methyl]-5-methyl-2-(methylsulfonylmethyl)imidazo[1,2-a]pyridine-7-carboxylic acid obtained in Step 4 and aniline.

¹H NMR (300 MHz, CDCl₃, δ): 7.95 (br s, 1H), 7.78 (d, J=1.5 Hz, 1H), 7.44-7.36 (m, 2H), 7.35-7.33 (m, 2H), 7.22-7.17 (m, 1H), 7.12 (d, J=1.5 Hz, 1H), 4.45 (s, 2H), 3.13 (d, J=6.6 Hz, 2H), 3.13 (s, 3H), 2.87 (s, 3H), 2.17-2.04 (m, 2H), 1.73-1.35 (m, 7H); ESIMS m/z: [M+H]⁺ 476.

EXAMPLE 11

3-[(4,4-Difluorocyclohexyl)methyl]-5-methyl-2-[1-(methylsulfonyl)ethyl]-N-phenylimidazo[1,2-a]pyridine-7-carboxamide (Compound 13)

Step 1

3-[(4,4-Difluorocyclohexyl)methyl]-5-methyl-2-(methylsulfonylmethyl)imidazo[1,2-a]pyridine-7-carbonitrile obtained in Step 3 of Example 10 (50 mg, 0.131 mmol) was dissolved in THF (1.0 mL). Under ice-cooled condition, 60% sodium hydride (6.9 mg, 0.029 mmol) and iodomethane (0.025 mL, 0.393 mmol) were added thereto, and the mixture was stirred at room temperature overnight. A saturated aqueous ammonium chloride solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=98/2 to 95/5), whereby 3-[(4,4-difluorocyclohexyl)methyl]-5-methyl-2-[1-(methylsulfonyl)ethyl]imidazo[1,2-a]pyridine-7-carbonitrile (49.8 mg, yield 96%) was obtained.

¹H NMR (300 MHz, CDCl₃, δ): 7.85 (s, 1H), 6.70 (s, 1H), 4.30 (q, J=7.3 Hz, 1H), 3.29 (dd, J=16.1, 3.8 Hz, 1H), 3.09 (dd, J=16.1, 8.4 Hz, 1H), 2.91 (s, 3H), 2.87 (s, 3H), 2.18-2.05 (m, 2H), 1.96 (d, J=7.3 Hz, 3H), 1.72-1.41 (m, 7H); ESIMS m/z: [M+H]⁺ 396.

Step 2

3-[(4,4-Difluorocyclohexyl)methyl]-5-methyl-2-[1-(methylsulfonyl)ethyl]imidazo[1,2-a]pyridine-7-carboxylic acid (47.3 mg, yield 92%) was obtained in the same manner as in Step 8 of Example 1, using 3-[(4,4-difluorocyclohexyl)methyl]-5-methyl-2-[1-(methylsulfonyl)ethyl]imidazo[1,2-a]pyridine-7-carbonitrile obtained in Step 1.

¹H NMR (300 MHz, DMSO-d₆, δ): 7.93 (d, J=0.7 Hz, 1H), 7.14 (d, J=0.7 Hz, 1H), 4.65 (q, J=7.0 Hz, 1H), 3.37-2.99 (m, 2H), 2.99 (s, 3H), 2.89 (s, 3H), 2.08-1.25 (m, 9H), 1.76 (d, J=7.0 Hz, 3H); ESIMS m/z: [M+H]⁺ 415.

Step 3

Compound 13 (52.3 mg, yield 98%) was obtained in the same manner as in Step 9 of Example 1, using 3-[(4,4-difluorocyclohexyl)methyl]-5-methyl-2-[1-(methylsulfonyl)ethyl]imidazo[1,2-a]pyridine-7-carboxylic acid obtained in Step 2 and aniline.

¹H NMR (300 MHz, CDCl₃, δ): 8.06 (s, 1H), 7.74-7.65 (m, 3H), 7.44-7.36 (m, 2H), 7.22-7.15 (m, 1H), 7.11 (d, J=0.7 Hz, 1H), 4.31 (q, J=7.1 Hz, 1H), 3.20 (dd, J=16.1, 4.2 Hz, 1H), 3.11 (s, 3H), 2.91 (dd, J=16.1, 10.3 Hz, 1H), 2.82 (s, 3H), 2.17-2.00 (m, 2H), 1.96 (d, J=7.1 Hz, 3H), 1.79-1.17 (m, 7H); ESIMS m/z: [M+H]⁺ 490.

EXAMPLE 12

3-[(4,4-Difluorocyclohexyl)methyl]-2-(hydroxymethyl)-5-methyl-N-phenylimidazo[1,2-a]pyridine-7-carboxamide (Compound 16)

Step 1

3-[(4,4-Difluorocyclohexyl)methyl]-2-(hydroxymethyl)-5-methylimidazo[1,2-a]pyridine-7-carboxylic acid (37.9 mg, yield 71%) was obtained in the same manner as in Step 8 of Example 1, using 3-[(4,4-difluorocyclohexyl)methyl]-2-(hydroxymethyl)-5-methylimidazo[1,2-a]pyridine-7-carbonitrile obtained in Step 1 of Example 10.

¹H NMR (300 MHz, DMSO-d₆, δ): 13.08 (br s, 1H), 7.88 (d, J=1.5 Hz, 1H), 7.08 (d, J=1.5 Hz, 1H), 5.08 (t, J=4.4 Hz, 1H), 4.57 (d, J=4.4 Hz, 2H), 3.11 (d, J=6.6 Hz, 2H), 2.88 (s, 3H), 2.05-1.21 (m, 9H); ESIMS m/z: [M+H]⁺ 339.

Step 2

Compound 16 (12.0 mg, yield 98%) was obtained in the same manner as in Step 9 of Example 1, using 3-[(4,4-difluorocyclohexyl)methyl]-2-(hydroxymethyl)-5-methylimidazo[1,2-a]pyridine-7-carboxylic acid obtained in Step 1 and aniline.

¹H NMR (300 MHz, CDCl₃, δ): 8.38 (s, 1H), 7.90 (d, J=1.5 Hz, 1H), 7.70-7.65 (m, 2H), 7.40-7.33 (m, 2H), 7.19-7.12 (m, 1H), 7.09 (d, J=1.5 Hz, 1H), 4.81 (s, 2H), 3.04 (d, J=6.6 Hz, 2H), 2.83 (s, 3H), 2.16-2.01 (m, 2H), 1.65-1.42 (m, 7H); ESIMS m/z: [M+H]⁺ 414.

EXAMPLE 13

3-[(4,4-Difluorocyclohexyl)methyl]-2-[1-(ethylsulfonyl)ethyl]-5-methyl-N-phenylimidazo[1,2-a]pyridine-7-carboxamide (Compound 17)

Step 1

3-[(4,4-Difluorocyclohexyl)methyl]-5-methyl-2-[1-(methylsulfonyl)ethyl]imidazo[1,2-a]pyridine-7-carbonitrile obtained in Step 1 of Example 11 (35 mg, 0.089 mmol) was dissolved in THF (1.0 mL), n-butyllithium (1.63 mol/L, solution in n-hexane) (0.060 mL, 0.097 mmol) was added thereto at −78° C., and the mixture was stirred at −78° C. for 10 minutes. Iodomethane (0.011 mL, 0.177 mmol) was added to the reaction mixture, the temperature was raised to 0° C., and the mixture was stirred for 1 hour. A saturated aqueous ammonium chloride solution was added to the reaction mixture, the mixture was filtrated through Presep (registered trademark; diatomite, granular type M, 4.5 g/25 mL), and the solvent was evaporated under reduced pressure. The residue was purified by preparative thin-layer chromatography (chloroform/methanol=30/1), whereby 3-[(4,4-difluorocyclohexyl)methyl]-2-[1-(ethylsulfonyl)ethyl]-5-methylimidazo[1,2-a]pyridine-7-carbonitrile (9.3 mg, 26%) was obtained.

$^1$H NMR (300 MHz, CDCl$_3$, δ): 7.84 (d, J=1.1 Hz, 1H), 6.69 (d, J=1.1 Hz, 1H), 4.36 (q, J=7.2 Hz, 1H), 3.33-3.04 (m, 4H), 2.86 (s, 3H), 1.95 (d, J=7.2 Hz, 3H), 1.87-1.44 (m, 9H), 1.32 (t, J=7.5 Hz, 3H); ESIMS m/z: [M+H]$^+$ 410.

Step 2

3-[(4,4-Difluorocyclohexyl)methyl]-2-[1-(ethylsulfonyl)ethyl]-5-methylimidazo[1,2-a]pyridine-7-carboxylic acid (17.7 mg, yield quantitative) was obtained in the same manner as in Step 8 of Example 1, using 3-[(4,4-difluorocyclohexyl)methyl]-2-[1-(ethylsulfonyl)ethyl]-5-methylimidazo[1,2-a]pyridine-7-carbonitrile obtained in Step 1.

$^1$H NMR (300 MHz, DMSO-d$_6$, δ): 7.90 (s, 1H), 7.14 (s, 1H), 4.66 (q, J=7.0 Hz, 2H), 4.03 (q, J=7.0 Hz, 1H), 3.21-2.94 (m, 2H), 2.88 (s, 3H), 2.23-1.83 (m, 2H), 1.76 (d, J=7.0 Hz, 3H), 1.69-1.23 (m, 7H), 1.15 (t, J=7.0 Hz, 3H); ESIMS m/z: [M+H]$^+$ 429.

Step 3

Compound 17 (15.4 mg, yield 87%) was obtained in the same manner as in Step 9 of Example 1, using 3-[(4,4-difluorocyclohexyl)methyl]-2-[1-(ethylsulfonyl)ethyl]-5-methylimidazo[1,2-a]pyridine-7-carboxylic acid obtained in Step 2 and aniline.

$^1$H NMR (300 MHz, CDCl$_3$, δ): 7.99 (s, 1H), 7.73-7.66 (m, 3H), 7.45-7.35 (m, 2H), 7.21-7.17 (m, 1H), 7.11 (s, 1H), 4.38 (q, J=7.0 Hz, 1H), 3.41 (dd, J=13.7, 7.1 Hz, 1H), 3.21 (q, J=7.0 Hz, 2H), 2.97 (dd, J=13.7, 9.5 Hz, 1H), 2.84 (s, 3H), 2.21-2.02 (m, 2H), 1.96 (d, J=7.0 Hz, 3H), 1.85-1.48 (m, 7H), 1.39 (t, J=7.0 Hz, 3H); ESIMS m/z: [M+H]$^+$ 504.

EXAMPLE 14

3-[(4,4-Difluorocyclohexyl)methyl]-2-(difluoromethyl)-5-methyl-N-(tetrahydro-2H-pyran-4-yl)imidazo[1,2-a]pyridine-7-carboxamide (Compound 18)

Step 1

3-[(4,4-Difluorocyclohexyl)methyl]-2-(hydroxymethyl)-5-methyl-N-(tetrahydro-2H-pyran-4-yl)imidazo[1,2-a]pyridine-7-carboxamide (32.1 mg, yield 49%) was obtained in the same manner as in Step 6 of Example 4, using 3-[(4,4-difluorocyclohexyl)methyl]-2-(hydroxymethyl)-5-methylimidazo[1,2-a]pyridine-7-carboxylic acid obtained in Step 1 of Example 12 and tetrahydro-2H-pyran-4-amine hydrochloride.

$^1$H NMR (300 MHz, CDCl$_3$, δ): 7.74 (s, 1H), 7.01 (s, 1H), 6.01 (d, J=6.6 Hz, 1H), 4.78 (s, 2H), 4.31-4.12 (m, 1H), 4.05-3.98 (m, 2H), 3.60-3.49 (m, 2H), 3.06 (d, J=7.0 Hz, 2H), 2.85 (s, 3H), 2.18-1.96 (m, 5H), 1.82-1.33 (m, 9H); ESIMS m/z: [M+H]$^+$ 422.

Step 2

3-[(4,4-Difluorocyclohexyl)methyl]-2-(hydroxymethyl)-5-methyl-N-(tetrahydro-2H-pyran-4-yl)imidazo[1,2-a]pyridine-7-carboxamide obtained in Step 1 (29.0 mg, 0.069 mmol) was dissolved in dichloromethane (1.0 mL). Under ice-cooled condition, Dess-Martin Periodinane (35.0 mg, 0.083 mmol) was added thereto, and the mixture was stirred at room temperature for 1 hour. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=98/2 to 95/5), whereby 3-[(4,4-difluorocyclohexyl)methyl]-2-formyl-5-methyl-N-(tetrahydro-2H-pyran-4-yl)imidazo[1,2-a]pyridine-7-carboxamide (29.0 mg, yield quantitative) was obtained.

$^1$H NMR (300 MHz, CDCl$_3$, δ): 10.24 (s, 1H), 7.82 (s, 1H), 7.08 (s, 1H), 6.01 (d, J=7.0 Hz, 1H), 4.25-4.15 (m, 1H), 4.05-3.99 (m, 2H), 3.61-3.48 (m, 4H), 2.89 (s, 3H), 2.13-1.98 (m, 4H), 1.78-1.47 (m, 9H); ESIMS m/z: [M+H]$^+$ 420.

Step 3

3-[(4,4-Difluorocyclohexyl)methyl]-2-formyl-5-methyl-N-(tetrahydro-2H-pyran-4-yl)imidazo[1,2-a]pyridine-7-carboxamide obtained in Step 3 (27.0 mg, 0.064 mmol) was dissolved in dichloromethane (1.0 mL). Under ice-cooled condition, bis(2-methoxyethyl)aminosulfur trifluoride (0.237 mL, 1.29 mmol) was added thereto, and the mixture was stirred at room temperature for 2 hours. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=98/2 to 95/5), whereby Compound 18 (20.7 mg, yield 73%) was obtained.

$^1$H NMR (300 MHz, CDCl$_3$, δ): 7.76 (d, J=1.8 Hz, 1H), 7.06 (d, J=1.8 Hz, 1H), 6.87 (t, J=54.3 Hz, 1H), 6.01 (d, J=7.7 Hz, 1H), 4.25-4.14 (m, 1H), 4.05-3.98 (m, 2H), 3.59-3.49 (m, 2H), 3.20 (d, J=7.3 Hz, 2H), 2.88 (s, 3H), 2.16-1.98 (m, 4H), 1.73-1.41 (m, 9H); ESIMS m/z: [M+H]$^+$ 442.

EXAMPLE 15

2-Acetyl-3-[(4,4-difluorocyclohexyl)methyl]-5-methyl-N-phenylimidazo[1,2-a]pyridine-7-carboxamide (Compound 19)

Step 1

2-Acetyl-3-[(4,4-difluorocyclohexyl)methyl]-5-methylimidazo[1,2-a]pyridine-7-carboxylic acid (115 mg, yield 99%) was obtained in the same manner as in Step 8 of Example 1, using 2-acetyl-3-[(4,4-difluorocyclohexyl)methyl]-5-methylimidazo[1,2-a]pyridine-7-carbonitrile obtained in Step 6 of Example 1.

$^1$H NMR (300 MHz, DMSO-d$_6$, δ): 7.91 (d, J=1.5 Hz, 1H), 7.19 (d, J=1.5 Hz, 1H), 3.51 (d, J=7.0 Hz, 2H), 2.88 (s, 3H), 2.63 (s, 3H), 2.02-1.17 (m, 9H); ESIMS m/z: [M+H]$^+$ 351.

Step 2

Compound 19 (77.7 mg, yield 91%) was obtained in the same manner as in Step 9 of Example 1, using 2-acetyl-3-[(4,4-difluorocyclohexyl)methyl]-5-methylimidazo[1,2-a]pyridine-7-carboxylic acid obtained in Step 1 and aniline.

$^1$H NMR (300 MHz, CDCl$_3$, δ): 7.96 (d, J=1.3 Hz, 1H), 7.82 (br s, 1H), 7.65-7.61 (m, 2H), 7.44-7.37 (m, 2H), 7.23-7.17 (m, 1H), 7.15 (d, J=1.3 Hz, 1H), 3.58 (d, J=6.3 Hz, 2H), 2.91 (s, 3H), 2.76 (s, 3H), 2.12-2.02 (m, 2H), 1.70-1.48 (m, 7H); ESIMS m/z: [M+H]$^+$ 426.

EXAMPLE 16

3-[(4,4-Difluorocyclohexyl)methyl]-2-(1-hydroxyethyl)-5-methyl-N-phenylimidazo[1,2-a]pyridine-7-carboxamide (Compound 20)

Compound 19 (52.0 mg, 0.122 mmol) was dissolved in a mixed solvent of THF, methanol, and water (10:2:1) (1.3 mL). Under ice-cooled condition, sodium borohydride (9.3 mg, 0.24 mmol) was added thereto, and the mixture was stirred at room temperature for 1 hour. Under ice-cooled condition, acetone and a saturated aqueous sodium hydrogen carbonate solution were added to the reaction mixture. The mixture was filtrated through Presep (registered trademark; diatomite, granular type M, 4.5 g/25 mL), and the solvent was evaporated under reduced pressure. The residue was purified by silica gel column chromatography (heptane/ethyl acetate=50/50 to 0/100), whereby Compound 20 (51.2 mg, yield 98%) was obtained.

$^1$H NMR (300 MHz, CDCl$_3$, δ): 7.89 (d, J=1.5 Hz, 1H), 7.86 (s, 1H), 7.66-7.61 (m, 2H), 7.43-7.36 (m, 2H), 7.21-7.15 (m, 1H), 7.10 (d, J=1.5 Hz, 1H), 5.01 (q, J=6.5 Hz, 1H), 3.20-2.96 (m, 2H), 2.88 (s, 3H), 2.17-2.05 (m, 2H), 1.86-1.38 (m, 10H); ESIMS m/z: [M+H]$^+$ 428.

EXAMPLE 17

3-[(4,4-Difluorocyclohexyl)methyl]-2-(1,1-difluoropropyl)-5-methyl-N-(tetrahydro-2H-pyran-4-yl)imidazo[1,2-a]pyridine-7-carboxamide (Compound 27)

Step 1
2-Amino-N,N-diethyl-6-methylisonicotinamide (2.22 g, yield 81%) was obtained in the same manner as in Step 9 of Example 1, using 2-amino-6-methylisonicotinic acid obtained by a method described in US2010/261687 and diethylamine.

$^1$H NMR (300 MHz, CDCl$_3$, δ): 6.46 (s, 1H), 6.25 (s, 1H), 4.46 (br s, 2H), 3.51 (q, J=7.1 Hz, 2H), 3.23 (q, J=7.1 Hz, 2H), 2.39 (s, 3H), 1.23 (t, J=7.1 Hz, 3H), 1.10 (t, J=7.1 Hz, 3H).
Step 2
Butyl 7-(diethylcarbamoyl)-3-[(4,4-difluorocyclohexyl)methyl]-5-methylimidazo[1,2-a]pyridine-2-carboxylate (294 mg, yield 23%) was obtained in the same manner as in Step 5 of Example 1, using 2-amino-N,N-diethyl-6-methylisonicotinamide obtained in Step 1 and ethyl 3-bromo-4-(4,4-difluorocyclohexyl)-2-oxobutanoate obtained in Step 4 of Example 1.

$^1$H NMR (300 MHz, CDCl$_3$, δ): 7.53 (d, J=1.5 Hz, 1H), 6.67 (d, J=1.5 Hz, 1H), 4.41 (t, J=7.0 Hz, 2H), 3.57 (d, J=6.2 Hz, 2H), 3.55-3.34 (m, 4H), 2.85 (s, 3H), 2.15-2.02 (m, 2H), 1.88-1.77 (m, 2H), 1.72-1.15 (m, 15H), 0.97 (t, J=7.3 Hz, 3H); ESIMS m/z: [M+H]$^+$ 464.
Step 3
7-(Diethylcarbamoyl)-3-[(4,4-difluorocyclohexyl)methyl]-5-methylimidazo[1,2-a]pyridine-2-carboxylic acid (245 mg, yield 96%) was obtained in the same manner as in Step 8 of Example 1, using butyl 7-(diethylcarbamoyl)-3-[(4,4-difluorocyclohexyl)methyl]-5-methylimidazo[1,2-a]pyridine-2-carboxylate obtained in Step 2.

$^1$H NMR (300 MHz, CDCl$_3$, δ): 7.67 (br s, 1H), 6.71 (s, 1H), 3.59 (d, J=5.9 Hz, 2H), 3.55-3.36 (m, 4H), 2.88 (s, 3H), 2.17-1.50 (m, 9H), 1.29-1.22 (m, 6H); ESIMS m/z: [M+H]$^+$ 408.
Step 4
3-[(4,4-Difluorocyclohexyl)methyl]-7-(N,N-diethylcarbamoyl)-N,5-dimethyl-N-methoxyimidazo[1,2-a]pyridine-2-carboxamide (95.7 mg, yield 87%) was obtained in the same manner as in Step 6 of Example 4, using 7-(diethylcarbamoyl)-3-[(4,4-difluorocyclohexyl)methyl]-5-methylimidazo[1,2-a]pyridine-2-carboxylic acid obtained in Step 3.

$^1$H NMR (300 MHz, CDCl$_3$, δ): 7.45 (s, 1H), 6.63 (s, 1H), 3.85 (s, 3H), 3.54-3.42 (m, 7H), 3.33 (d, J=6.6 Hz, 2H), 2.84 (s, 3H), 2.13-2.00 (m, 2H), 1.75-1.18 (m, 13H); ESIMS m/z: [M+H]$^+$ 451.
Step 5
3-[(4,4-Difluorocyclohexyl)methyl]-7-(N,N-diethylcarbamoyl)-N,5-dimethyl-N-methoxyimidazo[1,2-a]pyridine-2-carboxamide obtained in Step 4 (390 mg, 0.866 mmol) was dissolved in THF (4.0 mL), a solution of ethylmagnesium bromide in THF (1.0 mol/L) (3.46 mL, 3.46 mmol) was added thereto at 0° C., and the mixture was stirred at 0° C. for 4 hours. Under ice-cooled condition, a saturated aqueous ammonium chloride solution was added to the reaction mixture. The mixture was filtrated through Presep (registered trademark; diatomite, granular type M, 4.5 g/25 mL), and the solvent was evaporated under reduced pressure. The residue was purified by silica gel column chromatography (chloroform/methanol=98/2 to 95/5), whereby 3-[(4,4-difluorocyclohexyl)methyl]-N,N-diethyl-5-methyl-2-propionylimidazo[1,2-a]pyridine-7-carboxamide (249 mg, yield 69%) was obtained.

$^1$H NMR (300 MHz, CDCl$_3$, δ): 7.47 (s, 1H), 6.62 (s, 1H), 3.55 (d, J=6.2 Hz, 2H), 3.52-3.40 (br m, 4H), 3.25-3.20 (m, 2H), 2.84 (s, 3H), 2.17-2.00 (m, 2H), 1.76-1.43 (m, 7H), 1.33-1.17 (m, 9H); ESIMS m/z: [M+H]$^+$ 420.
Step 6
3-[(4,4-Difluorocyclohexyl)methyl]-N,N-diethyl-5-methyl-2-propionylimidazo[1,2-a]pyridine-7-carboxamide obtained in Step 5 (175 mg, 0.417 mmol) was dissolved in isobutyl alcohol (1.0 mL), 10 mol/L aqueous potassium hydroxide solution (0.42 mL) was added thereto, and the mixture was stirred under reflux with heating overnight. Diethyl ether was added to the reaction mixture, the mixture was stirred, and then the aqueous layer was separated. 3 mol/L hydrochloric acid (1.4 mL) was added to the aqueous layer, and the mixture was extracted with a mixed solvent of chloroform and isopropanol (6/1). The organic layer was washed with saturated brine and dried over anhydrous magnesium sulfate, and the solvent was evaporated under reduced pressure, whereby 3-[(4,4-difluorocyclohexyl)methyl]-5-methyl-2-propionylimidazo[1,2-a]pyridine-7-carboxylic acid (53.8 mg, yield 35%) was obtained.

$^1$H NMR (300 MHz, CDCl$_3$, δ): 8.33 (s, 1H), 7.16 (s, 1H), 3.59 (d, J=6.6 Hz, 2H), 3.26 (q, J=7.3 Hz, 2H), 2.89 (s, 3H), 2.14-1.95 (m, 2H), 1.71-1.45 (m, 7H), 1.23 (t, J=7.3 Hz, 3H); ESIMS m/z: [M+H]$^+$ 365.
Step 7
3-[(4,4-Difluorocyclohexyl)methyl]-5-methyl-2-propionyl-N-(tetrahydro-2H-pyran-4-yl)imidazo[1,2-a]pyridine-7-carboxamide (58.0 mg, yield 94%) was obtained in the same manner as in Step 6 of Example 4, using 3-[(4,4-difluorocyclohexyl)methyl]-5-methyl-2-propionylimidazo[1,2-a]pyridine-7-carboxylic acid obtained in Step 6 and tetrahydro-2H-pyran-4-amine hydrochloride.

¹H NMR (300 MHz, CDCl₃, δ): 7.83 (s, 1H), 7.04 (s, 1H), 6.22 (d, J=7.3 Hz, 1H), 4.27-4.09 (m, 1H), 4.06-3.96 (m, 2H), 3.61-3.44 (m, 4H), 3.23 (q, J=7.0 Hz, 2H), 2.88 (s, 3H), 2.13-1.96 (m, 4H), 1.73-1.41 (m, 9H), 1.21 (t, J=7.0 Hz, 3H); ESIMS m/z: [M+H]⁺ 448.

Step 8

To 3-[(4,4-difluorocyclohexyl)methyl]-5-methyl-2-propionyl-N-(tetrahydro-2H-pyran-4-yl)imidazo[1,2-a]pyridine-7-carboxamide obtained in Step 7 (10 mg, 0.022 mmol), bis(2-methoxyethyl)aminosulfur trifuloride (0.20 mL, 1.09 mmol) and ethanol (0.13 μL, 2.2 μmol) were added thereto, and the mixture was stirred at 80° C. overnight. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=98/2 to 95/5) and further purified by preparative thin-layer chromatography (hexane/ethyl acetate=25/75), whereby Compound 27 (1.1 mg, yield 10%) was obtained.

¹H NMR (300 MHz, CDCl₃, δ): 7.77 (d, J=1.5 Hz, 1H), 7.05 (d, J=1.5 Hz, 1H), 5.99 (d, J=7.7 Hz, 1H), 4.27-4.16 (m, 1H), 4.05-3.95 (m, 2H), 3.59-3.47 (m, 2H), 3.26 (d, J=6.6 Hz, 2H), 2.88 (s, 3H), 2.48 (td, J=17.0, 7.5 Hz, 2H), 2.15-1.97 (m, 4H), 1.72-1.37 (m, 9H), 1.08 (t, J=7.5 Hz, 3H); ESIMS m/z: [M+H]⁺ 470.

EXAMPLE 18

6-Chloro-2-(2-chloropropan-2-yl)-3-(3,3-difluoroazetidin-1-ylsulfonyl)-N-(3-methylisoxazol-5-yl)imidazo[1,2-a]pyridine-7-carboxamide (Compound 28)

6-chloro-N-(4-chloro-3-methylisoxazol-5-yl)-2-(2-chloropropan-2-yl)-3-(3,3-difluoroazetidin-1-ylsulfonyl)imidazo[1,2-a]pyridine-7-carboxamide (Compound 29)

Step 1

6-Chloro-2-isopropylimidazo[1,2-a]pyridine-7-carbonitrile (1.46 g, yield 51%) was obtained in the same manner as in Step 5 of Example 1, using 2-amino-5-chloro-4-cyanopyridine obtained in Step 1 of Example 5 and 1-bromo-3-methylbutan-2-one.

¹H NMR (300 MHz, CDCl₃, δ): 8.23 (d, J=0.7 Hz, 1H), 7.96 (s, 1H), 7.47 (s, 1H), 3.16-3.11 (m, 1H), 1.37 (d, J=6.9 Hz, 6H).

Step 2

6-Chloro-2-isopropylimidazo[1,2-a]pyridine-7-carbonitrile obtained in Step 1 (1.35 g, 6.15 mmol) was dissolved in dichloroethane (10 mL). Under ice-cooled condition, trimethylsilyl chlorosulfonate (2.32 g, 12.3 mmol) was added thereto, and the mixture was stirred at 90° C. for 5 hours. The solvent in the reaction mixture was evaporated under reduced pressure. The residue was purified by slurry in heptane, whereby 6-chloro-7-cyano-2-isopropylimidazo[1,2-a]pyridine-3-sulfonic acid (1.83 g, yield 99%) was obtained.

¹H NMR (300 MHz, DMSO-d₆, δ): 8.98 (s, 1H), 8.57 (s, 1H), 3.90-3.84 (m, 1H), 1.25 (d, J=6.6 Hz, 6H).

Step 3

6-Chloro-7-cyano-2-isopropylimidazo[1,2-a]pyridine-3-sulfonic acid obtained in Step 2 (2.16 g, 7.21 mmol) was dissolved in dichloroethane (20 mL), triethylamine (2.01 mL, 14.4 mmol) and phosphorus oxychloride (1.34 mL, 14.4 mmol) were added thereto, and the mixture was stirred at 100° C. for 4 hours. Water was added to the reaction mixture, and the mixture was extracted with chloroform. The organic layer was dried over anhydrous magnesium sulfate, and the solvent was evaporated under reduced pressure. The residue was purified by silica gel column chromatography (heptane/ethyl acetate=90/10 to 80/20), whereby 6-chloro-7-cyano-2-isopropylimidazo[1,2-a]pyridine-3-sulfonylchloride (1.73 g, yield 75%) was obtained.

¹H NMR (300 MHz, CDCl₃, δ): 8.96 (d, J=0.9 Hz, 1H), 8.15 (d, J=0.9 Hz, 1H), 3.84-3.75 (m, 1H), 1.41 (d, J=7.0 Hz, 6H).

Step 4

6-Chloro-7-cyano-2-isopropylimidazo[1,2-a]pyridine-3-sulfonyl chloride (1.00 g, 3.14 mmol) obtained in Step 3 was dissolved in acetonitrile (10 mL), 3,3-difluoroazetidine hydrochloride (611 mg, 4.71 mmol) and triethylamine (1.31 mL, 9.43 mmol) were added thereto, and the mixture was stirred at room temperature for 1.25 hours. A saturated aqueous sodium hydrogen carbonate solution was added to the reaction mixture, and the precipitated solid was collected by filtration and washed with water. The resulting solid was purified by silica gel column chromatography (heptane/ethyl acetate=80/20 to 50/50), whereby 6-chloro-3-(3,3-difluoroazetidin-1-ylsulfonyl)-2-isopropylimidazo[1,2-a]pyridine-7-carbonitrile (1.10 g, yield 93%) was obtained.

¹H NMR (300 MHz, CDCl₃, δ): 8.78 (s, 1H), 8.09 (s, 1H), 4.31 (t, J=11.7 Hz, 4H), 3.75-3.68 (m, 1H), 1.37 (d, J=6.8 Hz, 6H).

Step 5

6-Chloro-3-(3,3-difluoroazetidin-1-ylsulfonyl)-2-isopropylimidazo[1,2-a]pyridine-7-carboxylic acid (462 mg, yield 76%) was obtained in the same manner as in Step 8 of Example 1, using 6-chloro-3-(3,3-difluoroazetidin-1-ylsulfonyl)-2-isopropylimidazo[1,2-a]pyridine-7-carbonitrile obtained in Step 4.

¹H NMR (300 MHz, DMSO-d₆, δ): 8.72 (s, 1H), 8.23 (s, 1H), 4.41 (t, J=12.5 Hz, 4H), 3.68-3.55 (m, 1H), 1.31 (d, J=7.0 Hz, 6H).

Step 6

6-Chloro-3-(3,3-difluoroazetidin-1-ylsulfonyl)-2-isopropylimidazo[1,2-a]pyridine-7-carboxylic acid obtained in Step 5 (250 mg, 0.635 mmol) was dissolved in dichloroethane (3.0 mL). Under ice-cooled condition, oxalyl chloride (0.111 mL, 1.27 mmol) and DMF (0.00492 mL, 0.063 mmol) were added thereto, and the mixture was stirred at room temperature for 45 minutes. The solvent in the reaction mixture was evaporated under reduced pressure, and dichloroethane (3.0 mL) was added to the residue. N,N-diisopropylethylamine (0.333 mL, 1.91 mmol) and 3-methylisoxazole-5-amine (125 mg, 1.27 mmol) were added to the mixture, and the mixture was stirred at room temperature for 2 hours. A saturated aqueous sodium hydrogen carbonate solution was added to the reaction mixture, and the mixture was filtrated through Presep (registered trademark; diatomite, granular type M, 4.5 g/25 mL). The solvent was evaporated under reduced pressure. The residue was purified by silica gel column chromatography (heptane/ethyl acetate=80/20 to 65/35) and further purified by amino-silica gel column chromatography (heptane/ethyl acetate=50/50, chloroform/methanol=100/0 to 90/10), whereby 6-chloro-3-(3,3-difluoroazetidin-1-ylsulfonyl)-2-isopropyl-N-(3-methylisoxazol-5-yl)imidazo[1,2-a]pyridine-7-carboxamide (173 mg, yield 29%) was obtained.

¹H NMR (300 MHz, CDCl₃, δ): 8.90 (s, 1H), 8.78 (d, J=0.7 Hz, 1H), 8.21 (s, 1H), 6.44 (s, 1H), 4.30 (t, J=11.7 Hz, 4H), 3.77-3.68 (m, 1H), 2.33 (s, 3H), 1.38 (d, J=7.0 Hz, 6H); ESIMS m/z: [M+H]⁺ 474.

Step 7

Compound 28 (11.8 mg, 22%) and Compound 29 (8.40 mg, 15%) were obtained in the same manner as in Step 1 of Example 5, using 6-chloro-3-(3,3-difluoroazetidin-1-ylsulfonyl)-2-isopropyl-N-(3-methylisoxazol-5-yl)imidazo[1,2-a]pyridine-7-carboxamide obtained in Step 6.

Compound 28

¹H NMR (300 MHz, CDCl₃, δ): 8.88 (s, 1H), 8.83 (d, J=0.7 Hz, 1H), 8.25 (s, 1H), 6.44 (s, 1H), 4.44 (t, J=11.9 Hz, 4H), 2.34 (s, 3H), 2.19 (s, 6H); ESIMS m/z: [M+H]⁺ 509.

Compound 29

¹H NMR (300 MHz, CDCl₃, δ): 8.83 (s, 1H), 8.23 (s, 1H), 8.17 (s, 1H), 4.44 (t, J=11.9 Hz, 4H), 2.33 (s, 3H), 2.19 (s, 6H); ESIMS m/z: [M+H]⁺ 542.

EXAMPLE 19

Ethyl 2-oxo-2-[7-(phenylcarbamoyl)-2-(trifluoromethyl)imidazo[1,2-a]pyridin-3-yl]acetate (Compound 30)

Step 1

2-(Trifluoromethyl)imidazo[1,2-a]pyridine-7-carbonitrile (9.64 g, 54%) was obtained in the same manner as in Step 5 of Example 1, using 2-aminoisonicotinonitrile and 3-bromo-1,1,1-trifluoropropan-2-one.

¹H NMR (300 MHz, CDCl₃, δ): 8.27 (dd, J=7.1, 1.0 Hz, 1H), 8.11 (s, 1H), 8.04 (s, 1H), 7.08 (dd, J=7.1, 1.5 Hz, 1H).

Step 2

2-(Trifluoromethyl)imidazo[1,2-a]pyridine-7-carbonitrile obtained in Step 1 (3.00 g, 14.2 mmol) was dissolved in 50% aqueous ethanol solution (30 mL), and lithium hydroxide monohydrate (1.79 g, 42.6 mmol) was added thereto. Under reflux with heating, the mixture was stirred for 1 hour. Under ice-cooled condition, 2 mol/L hydrochloric acid was added to the reaction mixture, and the solvent in the reaction mixture was evaporated under reduced pressure. Methanol was added to the residue, the insoluble matter was removed by filtration, and the solvent was evaporated. The residue was dissolved in DMF (20 mL), aniline (1.63 mL, 17.8 mmol), EDC.HCl (3.41 g, 17.8 mmol), and HOBt.H₂O (2.73 g, 17.8 mmol) were added thereto, and the mixture was stirred at room temperature overnight. A saturated aqueous sodium hydrogen carbonate solution was added to the reaction mixture, and the precipitated crystal was collected by filtration, whereby N-phenyl-2-(trifluoromethyl)imidazo[1,2-a]pyridine-7-carboxamide (2.25 g, 83%) was obtained.

¹H NMR (300 MHz, CDCl₃, δ): 8.26 (d, J=7.0 Hz, 1H), 8.16-8.12 (m, 2H), 7.99 (s, 1H), 7.66 (d, J=7.7 Hz, 2H), 7.51 (d, J=7.0 Hz, 1H), 7.41 (t, J=7.7 Hz, 2H), 7.20 (t, J=7.7 Hz, 1H).

Step 3

N-Phenyl-2-(trifluoromethyl)imidazo[1,2-a]pyridine-7-carboxamide obtained in Step 2 (0.10 g, 0.328 mmol) was dissolved in xylene (1.0 mL), and ethyl 2-chloro-2-oxoacetate (0.183 mL, 1.64 mmol) was added. Under reflux with heating, the mixture was stirred overnight. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (heptane/ethyl acetate=80/20 to 65/35), whereby Compound 30 (57.0 mg, 43%) was obtained.

¹H NMR (300 MHz, CDCl₃, δ): 9.64-9.59 (m, 1H), 8.32 (s, 1H), 7.94 (s, 1H), 7.78 (dd, J=7.3, 1.8 Hz, 1H), 7.68-7.62 (m, 2H), 7.46-7.37 (m, 2H), 7.26-7.21 (m, 1H), 4.47 (q, J=7.2 Hz, 2H), 1.43 (t, J=7.2 Hz, 3H); ESIMS m/z: [M+H]% 406.

EXAMPLE 20

3-(N-Cyclohexylacetamide)-2-isopropyl-5-methyl-N-phenylimidazo[1,2-a]pyridine-7-carboxamide (Compound 31)

Step 1

Ethyl 2-amino-6-methylpyridine-4-carboxylate obtained by a method described in WO2008/009750 (200 mg, 1.11 mmol) was dissolved in a mixed solvent of methanol and dichloromethane (2:1) (4.5 mL), isobutylaldehyde (0.101 mL, 1.11 mmol) and scandium (III) trifluoromethanesulfonate (55 mg, 0.11 mmol) were added, and the mixture was stirred at room temperature for 10 minutes. Isocyanocyclohexane (0.138 mL, 1.11 mmol) was added to the reaction mixture, and the mixture was stirred at room temperature for 3 hours. The solvent in the reaction mixture was evaporated under reduced pressure. The residue was purified by silica gel column chromatography (chloroform/methanol=98/2 to 95/5), whereby ethyl 3-(cyclohexylamino)-2-isopropyl-5-methylimidazo[1,2-a]pyridine-7-carboxylate (218 mg, 0.635 mmol) was obtained.

¹H NMR (300 MHz, CDCl₃, δ): 8.11 (s, 1H), 6.97 (s, 1H), 4.36 (q, J=7.1 Hz, 2H), 3.12 (sep, J=7.0, 1H), 2.93 (s, 3H), 2.89-2.71 (br m, 2H), 1.90-1.60 (m, 6H), 1.37 (t, J=7.1 Hz, 3H), 1.36 (d, J=7.0 Hz, 6H), 1.29-1.15 (m, 4H); ESIMS m/z: [M+H]⁺ 344.

Step 2

Ethyl 3-(cyclohexylamino)-2-isopropyl-5-methylimidazo[1,2-a]pyridine-7-carboxylate obtained in Step 1 (50 mg, 0.146 mmol) was dissolved in dichloromethane (0.5 mL), triethylamine (0.041 mL, 0.291 mmol) and acetylchloride (0.016 mL, 0.218 mmol) were added thereto, and the mixture was stirred at room temperature for 1 hour. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (heptane/ethyl acetate=80/20 to 65/35), whereby ethyl 3-(N-cyclohexylacetamide)-2-isopropyl-5-methylimidazo[1,2-a]pyridine-7-carboxylate (34.8 mg, 0.090 mmol) was obtained.

ESIMS m/z: [M+H]⁺ 386.

Step 3

3-(N-Cyclohexylacetamide)-2-isopropyl-5-methylimidazo[1,2-a]pyridine-7-carboxylic acid (30.1 mg, yield 98%) was obtained in the same manner as in Step 8 of Example 1, using ethyl 3-(N-cyclohexylacetamide)-2-isopropyl-5-methylimidazo[1,2-a]pyridine-7-carboxylate obtained in Step 2.

ESIMS m/z: [M+H]⁺ 358.

Step 4

Compound 31 (13.7 mg, yield 75%) was obtained in the same manner as in Step 9 of Example 1, using 3-(N-cyclohexylacetamide)-2-isopropyl-5-methylimidazo[1,2-a]pyridine-7-carboxylic acid obtained in Step 3 above and aniline.

¹H NMR (300 MHz, CDCl₃, δ): 7.91 (d, J=1.1 Hz, 1H), 7.81 (br s, 1H), 7.65-7.60 (m, 2H), 7.41-7.39 (m, 2H), 7.21-7.19 (m, 1H), 7.13 (d, J=1.1 Hz, 1H), 3.13 (q, J=6.6 Hz, 1H), 2.62 (s, 3H), 2.55-2.45 (m, 1H), 1.83-1.76 (m, 2H), 1.69-1.60 (m, 2H), 1.45 (d, J=6.6 Hz, 3H), 1.36 (d, J=6.6 Hz, 3H), 1.32-1.22 (m, 9H); ESIMS m/z: [M+H]$^+$ 433.

EXAMPLE 21

3-[2-(tert-Butylamino)-2-oxoacetyl]-N-phenyl-2-(trifluoromethyl)imidazo[1,2-a]pyridine-7-carboxamide (Compound 33)

Step 1

Compound 30 (40.0 mg, 0.0990 mmol) was dissolved in a 50% aqueous ethanol solution (1.0 mL), 4 mol/L aqueous sodium hydroxide solution (0.0740 mL, 0.296 mmol) was added thereto, and the mixture was stirred at room temperature for 5 minutes. Under ice-cooled condition, 4 mol/L hydrochloric acid (0.0740 mL, 0.296 mmol) was added to the reaction mixture, and the mixture was extracted with a mixed solvent of chloroform and methanol. The organic layer was dried over anhydrous magnesium sulfate, and the solvent was evaporated under reduced pressure, whereby 2-oxo-2-[7-(phenylcarbamoyl)-2-(trifluoromethyl)imidazo[1,2-a]pyridin-3-yl]acetic acid (26.0 mg, 70%) was obtained.

$^1$H NMR (300 MHz, DMSO-d$_6$, δ): 10.66 (s, 1H), 9.49-9.44 (m, 1H), 8.65 (s, 1H), 7.94-7.89 (m, 1H), 7.84-7.78 (m, 2H), 7.41 (t, J=8.1 Hz, 2H), 7.17 (t, J=7.3 Hz, 1H).

Step 2

Compound 33 (7.00 mg, yield 24%) was obtained in the same manner as in Step 9 of Example 1, using 2-oxo-2-[7-(phenylcarbamoyl)-2-(trifluoromethyl)imidazo[1,2-a]pyridin-3-yl]acetic acid obtained in Step 1 and tert-butylamine.

$^1$H NMR (300 MHz, CDCl$_3$, δ): 9.15 (d, J=7.3 Hz, 1H), 8.25 (s, 1H), 7.89 (s, 1H), 7.71-7.62 (m, 3H), 7.42 (t, J=7.9 Hz, 2H), 7.25-7.19 (m, 1H), 6.58 (s, 1H), 1.49 (s, 9H); ESIMS m/z: [M+H]$^+$ 433.

EXAMPLE 22

3-[Cyclohexyl(methyl)amino]-2-isopropyl-5-methyl-N-(tetrahydro-2H-pyran-4-yl)imidazo[1,2-a]pyridine-7-carboxamide (Compound 34)

Step 1

Ethyl 3-[cyclohexyl(methyl)amino]-2-isopropyl-5-methylimidazo[1,2-a]pyridine-7-carboxylate (12.2 mg, yield 6%) was obtained in the same manner as in Step 1 of Example 11, using ethyl 3-(cyclohexylamino)-2-isopropyl-5-methylimidazo[1,2-a]pyridine-7-carboxylate obtained in Step 1 of Example 20 (200 mg, 0.582 mmol).

$^1$H NMR (300 MHz, CDCl$_3$, δ): 8.12 (d, J=1.1 Hz, 1H), 6.99 (d, J=1.1 Hz, 1H), 4.36 (q, J=7.2 Hz, 2H), 3.15-3.06 (m, 1H), 3.00-2.91 (m, 1H), 2.85 (s, 3H), 2.82 (s, 3H), 2.16-0.88 (m, 19H); ESIMS m/z: [M+H]$^+$ 358.

Step 2

3-[Cyclohexyl(methyl)amino]-2-isopropyl-5-methylimidazo[1,2-a]pyridine-7-carboxylic acid (20 mg, yield 99%) was obtained in the same manner as in Step 8 of Example 1, using ethyl 3-[cyclohexyl(methyl)amino]-2-isopropyl-5-methylimidazo[1,2-a]pyridine-7-carboxylate obtained in Step 1.

$^1$H NMR (300 MHz, CDCl$_3$, δ): 8.93 (br s, 1H), 8.40 (s, 1H), 7.34 (s, 1H), 3.21-3.12 (m, 1H), 3.01-2.90 (m, 1H), 2.86 (s, 3H), 2.84 (s, 3H), 2.07-0.85 (m, 15H); ESIMS m/z: [M+H]$^+$ 330.

Step 3

Compound 34 (18.0 mg, yield 72%) was obtained in the same manner as in Step 6 of Example 4, using 3-[cyclohexyl(methyl)amino]-2-isopropyl-5-methylimidazo[1,2-a]pyridine-7-carboxylic acid obtained in Step 2 and tetrahydro-2H-pyran-4-amine hydrochloride.

$^1$H NMR (300 MHz, CDCl$_3$, δ): 7.66 (d, J=1.5 Hz, 1H), 6.87 (d, J=1.5 Hz, 1H), 5.95 (d, J=8.1 Hz, 1H), 4.21-4.10 (m, 1H), 4.04-3.95 (m, 2H), 3.60-3.48 (m, 2H), 3.16-3.04 (m, 1H), 3.01-2.90 (m, 1H), 2.85 (s, 3H), 2.82 (s, 3H), 2.07-1.04 (m, 20H); ESIMS m/z: [M+H]$^+$ 413.

EXAMPLE 23

3-(Cyclohexylamino)-2-isopropyl-5-methyl-N-(tetrahydro-2H-pyran-4-yl)imidazo[1,2-a]pyridine-7-carboxamide (Compound 35)

Step 1

3-(Cyclohexylamino)-2-isopropyl-5-methylimidazo[1,2-a]pyridine-7-carboxylic acid (172 mg, yield 94%) was obtained in the same manner as in Step 8 of Example 1, using ethyl 3-(cyclohexylamino)-2-isopropyl-5-methylimidazo[1,2-a]pyridine-7-carboxylate obtained in Step 1 of Example 20.

$^1$H NMR (300 MHz, DMSO-d$_6$, δ): 7.76 (d, J=1.1 Hz, 1H), 6.92 (d, J=1.1 Hz, 1H), 4.32 (d, J=5.9 Hz, 1H), 3.23-3.13 (m, 1H), 2.91 (s, 3H), 2.77 (br s, 1H), 1.79-1.51 (m, 4H), 1.26-1.12 (m, 12H); ESIMS m/z: [M+H]$^+$ 316.

Step 2

Compound 35 (40.5 mg, yield 80%) was obtained in the same manner as in Step 6 of Example 4, using 3-(cyclohexylamino)-2-isopropyl-5-methylimidazo[1,2-a]pyridine-7-carboxylic acid obtained in Step 1 and tetrahydro-2H-pyran-4-amine hydrochloride.

$^1$H NMR (300 MHz, CDCl$_3$, δ): 7.66 (d, J=1.5 Hz, 1H), 6.86 (d, J=1.5 Hz, 1H), 5.94 (d, J=8.1 Hz, 1H), 4.25-4.10 (m, 1H), 4.03-3.94 (m, 2H), 3.60-3.48 (m, 2H), 3.17-3.06 (m, 1H), 2.93 (s, 3H), 2.89-2.67 (m, 2H), 2.05-1.47 (m, 14H), 1.34 (d, J=7.0 Hz, 6H); ESIMS m/z: [M+H]$^+$ 399.

EXAMPLE 24

Ethyl 2-hydroxy-2-{7-(phenylcarbamoyl)-2-(trifluoromethyl)imidazo[1,2-a]pyridin-3-yl}acetate (Compound 36)

Compound 30 (30.0 mg, 0.0740 mmol) was dissolved in THF (1.0 mL). Under ice-cooled condition, sodium borohydride (0.980 mg, 0.0260 mmol) was added thereto at 0° C., and the mixture was stirred at room temperature for 30 minutes. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (heptane/ethyl acetate=80/20 to 50/50), whereby Compound 36 (8.50 mg, 28%) was obtained.

$^1$H NMR (300 MHz, CDCl$_3$, δ): 8.40 (d, J=7.3 Hz, 1H), 8.07 (s, 1H), 8.05 (s, 1H), 7.64 (d, J=7.8 Hz, 2H), 7.44-7.37 (m, 3H), 7.20 (t, J=7.8 Hz, 1H), 5.92 (s, 1H), 4.35-4.13 (m, 2H), 3.95 (s, 1H), 1.18 (t, J=7.1 Hz, 3H); ESIMS m/z: [M+H]$^+$ 408.

EXAMPLE 25

5-Bromo-3-[(4,4-difluorocyclohexyl)methyl]-Netrahydro-2H-pyran-4-yl)-2-(trifluoromethyl)imidazo[1,2-a]pyridine-7-carboxamide (Compound 39)

Step 1

3-(4,4-Difluorocyclohexyl)propionic acid (3.84 g, quantitative) was obtained in the same manner as in Step 8 in Example 1, using ethyl 3-(4,4-difluorocyclohexyl)propionate obtained in Step 2 of Example 1.

$^1$H NMR (270 MHz, CDCl$_3$, δ): 2.39 (t, J=7.7 Hz, 2H), 2.18-2.01 (m, 2H), 1.85-1.21 (m, 9H).

Step 2

3-(4,4-Difluorocyclohexyl)propionic acid obtained in Step 1 above (500 mg, 2.60 mmol) was dissolved in dichloromethane (5.0 mL), oxalyl chloride (0.430 mL, 5.12 mmol) and DMF (0.010 mL) were added thereto, and the mixture was stirred at room temperature for 30 minutes. The solvent in the reaction mixture was evaporated under reduced pressure. After dissolving the residue in dichloromethane (10 mL), the solution was cooled to −10° C., trifluoroacetic anhydride (2.20 mL, 15.8 mmol) and pyridine (1.70 mL, 21.3 mmol) were added thereto, and the mixture was stirred at room temperature for 2 hours. The reaction mixture was cooled to −10° C., water was gently added in a manner that the internal temperature did not exceed 0° C., and the mixture was extracted with dichloromethane. The organic layer was washed with 3 mol/L hydrochloric acid, a saturated aqueous sodium hydrogen carbonate solution, and saturated brine and dried over anhydrous sodium sulfate, and the solvent was evaporated under reduced pressure. The residue was purified by silica gel column chromatography (hexane/ethyl acetate=70/30), whereby 4-(4,4-difluorocyclohexyl)-1,1,1-trifluorobutan-2-one (204 mg, yield 35%) was obtained.

$^1$H NMR (300 MHz, CDCl$_3$, δ): 2.75 (t, J=7.3 Hz, 2H), 2.16-2.02 (m, 2H), 1.84-1.60 (m, 6H), 1.43-1.22 (m, 3H).

Step 3

4-(4,4-Difluorocyclohexyl)-1,1,1-trifluorobutan-2-one (100 mg, 0.410 mmol) obtained in Step 2 was dissolved in DMF (1.0 mL). Under ice-cooled condition, triethylamine (0.110 mL, 0.788 mmol) and chlorotrimethylsilane (0.0570 mL, 0.450 mmol) were added, and the mixture was stirred at 0° C. for 30 minutes. A saturated sodium hydrogen carbonate solution was added to the reaction mixture, and the mixture was extracted with hexane. The organic layer was washed with saturated brine and dried over anhydrous magnesium sulfate, and the solvent was evaporated under reduced pressure. The residue was dissolved in dichloromethane (1.0 mL), bromine (73.0 mg, 0.456 mmol) was added thereto under ice-cooled condition, and the mixture was stirred at room temperature for 30 minutes. A saturated aqueous sodium hydrogen carbonate solution and an aqueous trisodium thiosulfate solution were added to the reaction mixture, the mixture was filtrated through Presep (registered trademark; diatomite, granular type M, 4.5 g/25 mL), and the solvent was evaporated under reduced pressure. The residue was purified by silica gel column chromatography (hexane/ethyl acetate=80/20), whereby 3-bromo-4-(4,4-difluorocyclohexyl)-1,1,1-trifluorobutan-2-one (73.8 mg, yield 56%) was obtained.

$^1$H NMR (270 MHz, CDCl$_3$, δ): 4.67 (dd, J=8.6, 6.6 Hz, 1H), 2.17-1.23 (m, 11H).

Step 4

Methyl 5-amino-3-[(4,4-difluorocyclohexyl)methyl]-2-(trifluoromethyl)imidazo[1,2-a]pyridine-7-carboxylate (451 mg, yield 19%) was obtained in the same manner as in Step 5 of Example 1, using 3-bromo-4-(4,4-difluorocyclohexyl)-1,1,1-trifluorobutan-2-one obtained in Step 3 and methyl 2,6-diaminoisonicotinate.

$^1$H NMR (400 MHz, CDCl$_3$, δ): 7.91 (s, 1H), 6.69 (s, 1H), 4.40 (s, 2H), 3.94 (s, 3H), 3.22 (d, J=6.8 Hz, 2H), 2.12-2.09 (m, 2H), 1.90-1.88 (m, 1H), 1.68-1.40 (m, 6H); ESIMS m/z: [M+H]$^+$ 392.

Step 5

Methyl 5-amino-3-[(4,4-difluorocyclohexyl)methyl]-2-(trifluoromethyl)imidazo[1,2-a]pyridine-7-carboxylate obtained in Step 4 (50.0 mg, 0.130 mmol) was dissolved in acetonitrile (1.0 mL), isoamyl nitrite (44.9 mg, 0.380 mmol) and copper(I) bromide (55.0 mg, 0.380 mmol) were added thereto, and the mixture was stirred at 65° C. for 6 hours. An aqueous sodium hydrogen carbonate solution was added to the reaction mixture, and the mixture was extracted with ethyl acetate. The organic layer was dried over anhydrous magnesium sulfate, and the solvent was evaporated under reduced pressure. The residue was purified by silica gel column chromatography (heptane/ethyl acetate=100/0 to 80/20), whereby methyl 5-bromo-3-[(4,4-difluorocyclohexyl)methyl]-2-(trifluoromethyl)imidazo[1,2-a]pyridine-7-carboxylate (5.20 mg, yield 9%) was obtained.

$^1$H NMR (300 MHz, CDCl$_3$, δ): 8.35 (d, J=1.5 Hz, 1H), 7.74 (d, J=1.5 Hz, 1H), 3.98 (s, 3H), 3.38 (d, J=7.3 Hz, 2H), 2.22-1.24 (m, 9H); ESIMS m/z: [M+H]$^+$ 455.

Step 6

A crude product of 5-bromo-3-[(4,4-difluorocyclohexyl)methyl]-2-(trifluoromethyl)imidazo[1,2-a]pyridine-7-carboxylic acid was obtained in the same manner as in Step 8 of Example 1, using methyl 5-bromo-3-[(4,4-difluorocyclohexyl)methyl]-2-(trifluoromethyl)imidazo[1,2-a]pyridine-7-carboxylate obtained in Step 5 (5.00 mg, 0.011 mmol), and the product was used in the next reaction without purification.

Step 7

Compound 39 (1.00 mg, yield 34%) was obtained in the same manner as in Step 9 of Example 1, using the crude product of 5-bromo-3-[(4,4-difluorocyclohexyl)methyl]-2-(trifluoromethyl)imidazo[1,2-a]pyridine-7-carboxylic acid obtained in Step 6 and 4-aminotetrahydropyran.

$^1$H NMR (300 MHz, CDCl$_3$, δ): 7.92 (d, J=1.5 Hz, 1H), 7.63 (d, J=1.8 Hz, 1H), 5.97 (d, J=8.1 Hz, 1H), 4.04-3.99 (m, 2H), 3.54 (td, J=11.7, 2.1 Hz, 2H), 3.37 (d, J=7.0 Hz, 2H), 2.17-1.43 (m, 14H); ESIMS m/z: [M+H]$^+$ 524.

EXAMPLE 26

5-Cyano-3-[(4,4-difluorocyclohexyl)methyl]-Netrahydro-2H-pyran-4-yl)-2-(trifluoromethyl)imidazo[1,2-a]pyridine-7-carboxamide (Compound 40)

Step 1

2-Amino-6-chloroisonicotinic acid (500 mg, 2.90 mmol) was dissolved in ethanol (29.0 mL), thienyl chloride (1.06 mL, 14.5 mmol) was added thereto, and the mixture was stirred for 3 hours under reflux with heating. The solvent in the reaction mixture was evaporated under reduced pressure. An aqueous sodium hydrogen carbonate solution was added to the residue, and the mixture was extracted with chloroform. The organic layer was dried over anhydrous sodium sulfate, and the solvent was evaporated under reduced pressure, whereby ethyl 2-amino-6-chloroisonicotinate (510 mg, yield 88%) was obtained.

¹H NMR (400 MHz, CDCl₃, δ): 7.18 (d, J=1.0 Hz, 1H), 6.96 (d, J=1.0 Hz, 1H), 4.70 (s, 2H), 4.37 (q, J=7.2 Hz, 2H), 1.39 (t, J=7.1 Hz, 3H).
Step 2
Ethyl 5-chloro-3-[(4,4-difluorocyclohexyl)methyl]-2-(trifluoromethyl)imidazo[1,2-a]pyridine-7-carboxylate (62.0 mg, yield 5.7%) was obtained in the same manner as in Step 5 of Example 1, using ethyl 2-amino-6-chloroisonicotinate obtained in Step 1 and 3-bromo-4-(4,4-difluorocyclohexyl)-1,1,1-trifluorobutan-2-one obtained in Step 3 of Example 25.
¹H NMR (400 MHz, CDCl₃, δ): 8.35-8.33 (m, 1H), 7.53-7.52 (m, 1H), 4.43 (q, J=7.1 Hz, 2H), 3.36 (d, J=6.8 Hz, 2H), 2.12-1.40 (m, 12H); ESIMS m/z: [M+H]⁺ 425.
Step 3
5-Chloro-3-[(4,4-difluorocyclohexyl)methyl]-2-(trifluoromethyl)imidazo[1,2-a]pyridine-7-carboxylic acid (66 mg) was obtained in the same manner as in Step 8 of Example 1, using ethyl 5-chloro-3-[(4,4-difluorocyclohexyl)methyl]-2-(trifluoromethyl)imidazo[1,2-a]pyridine-7-carboxylate obtained in Step 2 (62 mg, 0.146 mmol).
ESIMS m/z: [M−H]⁻ 395.
Step 4
5-Chloro-3-[(4,4-difluorocyclohexyl)methyl]-Netrahydro-2H-pyran-4-yl)-2-(trifluoromethyl)imidazo[1,2-a]pyridine-7-carboxamide (14.0 mg, yield 40%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 3 and tetrahydro-2H-pyran-4-amine hydrochloride.
¹H NMR (300 MHz, CDCl₃, δ): 7.88 (s, 1H), 7.42 (d, J=2.0 Hz, 1H), 5.98 (d, J=7.8 Hz, 1H), 4.20 (d, J=7.8 Hz, 1H), 4.02 (d, J=10.7 Hz, 2H), 3.54 (dd, J=11.7, 9.8 Hz, 2H), 3.35 (d, J=6.8 Hz, 2H), 2.06 (t, J=18.1 Hz, 4H), 1.57-1.12 (m, 9H); ESIMS m/z: [M+H]⁺ 480.
Step 5
5-Chloro-3-[(4,4-difluorocyclohexyl)methyl]-N-(tetrahydro-2H-pyran-4-yl)-2-(trifluoromethyl)imidazo[1,2-a]pyridine-7-carboxamide obtained in Step 4 (20.0 mg, 0.042 mmol) was dissolved in DMA (0.5 mL). Zinc(II) cyanide (5.4 mg, 0.046 mmol), tris(dibenzylideneacetone)dipalladium(0) (3.8 mg, 0.004 mmol), 1,3-bis(diphenylphophino)propane (2.6 mg, 0.006 mmol), and zinc powder (5.5 mg, 0.083 mmol) were added thereto, and the mixture was stirred at 150° C. for 2 hours. After cooling the reaction mixture to room temperature, a saturated aqueous sodium hydrogen carbonate solution was added thereto. The mixture was filtrated through Presep (registered trademark; diatomite, granular type M, 4.5 g/25 mL), and the solvent was evaporated under reduced pressure. The residue was purified by preparative thin-layer chromatography (heptane/ethyl acetate=20/80), whereby Compound 40 (19.1 mg, yield 97%) was obtained.
¹H NMR (300 MHz, CDCl₃, δ): 8.19 (d, J=1.5 Hz, 1H), 8.03 (d, J=1.5 Hz, 1H), 6.05 (d, J=7.3 Hz, 1H), 4.28-4.16 (m, 1H), 4.07-3.99 (m, 2H), 3.60-3.49 (m, 2H), 3.36 (d, J=7.0 Hz, 2H), 2.16-1.99 (m, 4H), 1.86-1.44 (m, 9H); ESIMS m/z: [M+H]⁺ 471.

EXAMPLE 27

5-Acetyl-3-[(4,4-difluorocyclohexyl)methyl]-Netrahydro-2H-pyran-4-yl)-2-(trifluoromethyl)imidazo[1,2-a]pyridine-7-carboxamide (Compound 41)

5-Chloro-3-[(4,4-difluorocyclohexyl)methyl]-Netrahydro-2H-pyran-4-yl)-2-(trifluoromethyl)imidazo[1,2-a]pyridine-7-carboxamide (20.0 mg, 0.042 mmol) obtained in Step 4 of Example 26 was suspended in toluene (0.5 mL), tributyl(1-ethoxyvinyl)tin (0.028 mL, 0.083 mmol) and dichlorobis(triphenylphosphine)palladium (2.9 mg, 0.004 mmol) were added thereto, and the mixture was stirred at 100° C. for 2 hours. Under ice-cooled condition, conc. hydrochloric acid (0.1 mL) was added to the reaction mixture, and the mixture was stirred at room temperature for 1 hour. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by amino-silica gel column chromatography (heptane/ethyl acetate=50/50 to 0/100), and further purified by silica gel column chromatography (chloroform/methanol=98/2 to 95/5), whereby Compound 41 (11.5 mg, yield 57%) was obtained.
¹H NMR (300 MHz, CDCl₃, δ): 8.09 (d, J=1.5 Hz, 1H), 8.01 (d, J=1.5 Hz, 1H), 6.08 (d, J=8.1 Hz, 1H), 4.29-4.17 (m, 1H), 4.07-3.99 (m, 2H), 3.61-3.50 (m, 2H), 3.05 (d, J=6.6 Hz, 2H), 2.81 (s, 3H), 2.12-1.98 (m, 4H), 1.71-1.22 (m, 9H); ESIMS m/z: [M+H]⁺ 488.

EXAMPLE 28

3-[(4,4-Difluorocyclohexyl)methyl]-5-(methylsulfonyl)-N-(tetrahydro-2H-pyran-4-yl)-2-(trifluoromethyl)imidazo[1,2-a]pyridine-7-carboxamide (Compound 42)

5-Chloro-3-[(4,4-difluorocyclohexyl)methyl]-Netrahydro-2H-pyran-4-yl)-2-(trifluoromethyl)imidazo[1,2-a]pyridine-7-carboxamide obtained in Step 4 of Example 26 (20.0 mg, 0.042 mmol) was dissolved in DMF (0.5 mL), sodium methanesulfinate (16 mg, 0.157 mmol) was added thereto, and the mixture was stirred at 100° C. for 7 hours. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by preparative thin-layer chromatography (ethyl acetate), whereby Compound 42 (4.5 mg, yield 21%) was obtained.
¹H NMR (300 MHz, CDCl₃, δ): 8.15 (d, J=7.3 Hz, 1H), 7.05 (d, J=7.3 Hz, 1H), 5.95 (d, J=8.1 Hz, 1H), 4.30-4.18 (m, 1H), 4.02-3.94 (m, 2H), 3.67 (s, 3H), 3.57-3.47 (m, 2H), 3.03 (d, J=7.0 Hz, 2H), 2.18-2.00 (m, 4H), 1.81-1.38 (m, 9H); ESIMS m/z: [M+H]⁺ 524.

EXAMPLE 29

3-[(4,4-Difluorocyclohexyl)methyl]-5-methoxy-N-(tetrahydro-2H-pyran-4-yl)-2-(trifluoromethyl)imidazo[1,2-a]pyridine-7-carboxamide (Compound 43)

5-Chloro-3-[(4,4-difluorocyclohexyl)methyl]-Netrahydro-2H-pyran-4-yl)-2-(trifluoromethyl)imidazo[1,2-a]pyridine-7-carboxamide obtained in Step 4 of Example 26 (10.0 mg, 0.021 mmol) was dissolved in DMF (0.5 mL), 28% sodium methoxide (solution in methanol) (0.012 mL, 0.063 mmol) was added thereto, and the mixture was stirred at 100° C. for 30 minutes using microwave chemical synthesis apparatus (CEM Discover). Water was added to the reaction mixture, the mixture was filtrated through Presep (registered trademark; diatomite, granular type M, 4.5 g/25 mL), and the solvent was evaporated under reduced pressure. The residue was purified by preparative thin-layer chromatography (ethyl acetate), whereby Compound 43 (1.6 mg, yield 16%) was obtained.

$^1$H NMR (300 MHz, CDCl$_3$, δ): 7.48 (d, J=1.5 Hz, 1H), 6.61 (d, J=1.5 Hz, 1H), 6.06 (d, J=7.7 Hz, 1H), 4.26-4.14 (m, 1H), 4.12 (s, 3H), 4.05-3.98 (m, 2H), 3.61-3.49 (m, 2H), 3.22 (d, J=7.0 Hz, 2H), 2.17-1.95 (m, 4H), 1.81-1.36 (m, 9H); ESIMS m/z: [M+H]$^+$ 476.

EXAMPLE 30

3-[(4,4-Difluorocyclohexyl)methyl]-Netrahydro-2H-pyran-4-yl)-2-(trifluoromethyl)-5-vinylimidazo[1,2-a]pyridine-7-carboxamide (Compound 44)

5-Chloro-3-[(4,4-difluorocyclohexyl)methyl]-Netrahydro-2H-pyran-4-yl)-2-(trifluoromethyl)imidazo[1,2-a]pyridine-7-carboxamide obtained in Step 4 of Example 26 (6 mg, 0.013 mmol) was dissolved in a mixted solvent of DME (0.50 ml) and water (0.50 ml), potassium vinyltrifluoroborate (3.35 mg, 0.025 mmol), tetrakistriphenylphosphine palladium (1.45 mg, 0.001 mmol), and sodium carbonate (5.30 mg, 0.050 mmol) were added thereto, and the mixture was stirred at 80° C. for 3 hours. An aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=100/0 to 90/10), whereby Compound 44 (2.20 mg, yield 37%) was obtained.

$^1$H NMR (300 MHz, CDCl$_3$, δ): 7.87 (d, J=1.8 Hz, 1H), 7.31 (dd, J=1.8, 0.7 Hz, 1H), 7.19 (dd, J=17.0, 10.8 Hz, 1H), 6.02 (d, J=8.1 Hz, 1H), 5.96 (dd, J=17.2, 0.7 Hz, 1H), 5.72 (dd, J=10.8, 0.9 Hz, 1H), 5.36-5.33 (m, 1H), 4.23-4.18 (m, 1H), 4.03-4.01 (m, 2H), 3.55 (td, J=11.6, 2.1 Hz, 2H), 3.16 (d, J=6.6 Hz, 2H), 2.13-1.24 (m, 12H); ESIMS m/z: [M+H]$^+$ 472.

EXAMPLE 31

3-[(4,4-Difluorocyclohexyl)methyl]-5-formyl-N-(tetrahydro-2H-pyran-4-yl)-2-(trifluoromethyl)imidazo[1,2-a]pyridine-7-carboxamide (Compound 45)

Compound 45 (10.9 mg, yield quantitative) was obtained in the same manner as in Step 2 of Example 14, using Compound 46.

$^1$H NMR (300 MHz, CDCl$_3$, δ): 9.99 (s, 1H), 8.26 (d, J=1.8 Hz, 1H), 8.18 (d, J=1.8 Hz, 1H), 6.27 (d, J=8.1 Hz, 1H), 4.33-4.19 (m, 1H), 4.08-3.99 (m, 2H), 3.61-3.50 (m, 2H), 3.40 (d, J=3.7 Hz, 2H), 2.11-1.96 (m, 4H), 1.71-1.25 (m, 9H); ESIMS m/z: [M+H]$^+$ 474.

EXAMPLE 32

3-[(4,4-Difluorocyclohexyl)methyl]-5-(hydroxymethyl)-N-(tetrahydro-2H-pyran-4-yl)-2-(trifluoromethyl)imidazo[1,2-a]pyridine-7-carboxamide (Compound 46)

Step 1

Ethyl 3-[(4,4-difluorocyclohexyl)methyl]-5-methyl-2-(trifluoromethyl)imidazo[1,2-a]pyridine-7-carboxylate (148 mg, yield 19%) was obtained in the same manner as in Step 5 of Example 1, using 3-bromo-4-(4,4-difluorocyclohexyl)-1,1,1-trifluorobutan-2-one obtained in Step 3 of Example and ethyl 2-amino-6-methylpyridine-4-carboxylate obtained by a method described in WO2008/009750.

$^1$H NMR (270 MHz, CDCl$_3$, δ): 8.26 (s, 1H), 7.22 (s, 1H), 4.41 (q, J=7.1 Hz, 2H), 3.23 (d, J=6.2 Hz, 2H), 2.89 (s, 3H), 2.15-2.03 (br m, 2H), 1.83-1.29 (m, 7H), 1.41 (t, J=7.1 Hz, 3H); ESIMS m/z: [M+H]$^+$ 405.

Step 2

3-[(4,4-Difluorocyclohexyl)methyl]-5-methyl-2-(trifluoromethyl)imidazo[1,2-a]pyridine-7-carboxylic acid (114 mg, yield 84%) was obtained in the same manner as in Step 8 of Example 1, using ethyl 3-[(4,4-difluorocyclohexyl)methyl]-5-methyl-2-(trifluoromethyl)imidazo[1,2-a]pyridine-7-carboxylate obtained in Step 1.

$^1$H NMR (300 MHz, DMSO-d$_6$, δ): 7.75 (s, 1H), 7.25 (s, 1H), 3.14 (d, J=7.0 Hz, 2H), 2.86 (s, 3H), 2.04-1.58 (m, 7H), 1.33-1.15 (m, 2H); ESIMS m/z: [M+H]$^+$ 376.

Step 3

3-[(4,4-Difluorocyclohexyl)methyl]-5-methyl-N-(tetrahydro-2H-pyran-4-yl)-2-(trifluoromethyl)imidazo[1,2-a]pyridine-7-carboxamide (52.8 mg, yield 72%) was obtained in the same manner as in Step 9 of Example 1, using 3-[(4,4-difluorocyclohexyl)methyl]-5-methyl-2-(trifluoromethyl)imidazo[1,2-a]pyridine-7-carboxylic acid obtained in Step 2 and 4-aminotetrahydropyran.

$^1$H NMR (300 MHz, CDCl$_3$, δ): 7.80 (d, J=1.5 Hz, 1H), 7.11 (d, J=1.5 Hz, 1H), 6.17 (d, J=7.7 Hz, 1H), 4.26-4.13 (m, 1H), 4.05-3.97 (m, 2H), 3.59-3.49 (m, 2H), 3.21 (d, J=5.5 Hz, 2H), 2.89 (s, 3H), 2.18-1.96 (m, 4H), 1.75-1.42 (m, 9H); ESIMS m/z: [M+H]$^+$ 460.

Step 4

Selenium dioxide (16.0 mg, 0.141 mmol) was suspended in 1,4-dioxane (1.0 mL), and the mixture was stirred at 80° C. for 30 minutes. 3-[(4,4-Difluorocyclohexyl)methyl]-5-methyl-N-(tetrahydro-2H-pyran-4-yl)-2-(trifluoromethyl)imidazo[1,2-a]pyridine-7-carboxamide obtained in Step 3 (50.0 mg, 0.109 mmol) was added thereto, and the mixture was stirred at 80° C. for 1 hour, and then stirred at 100° C. overnight. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by preparative thin-layer chromatography (chloroform/methanol=30/1), whereby Compound 46 (11.0 mg, yield 21%) was obtained.

$^1$H NMR (300 MHz, CDCl$_3$, δ): 7.82 (d, J=1.5 Hz, 1H), 7.35 (d, J=1.5 Hz, 1H), 6.68 (br s, 1H), 4.97 (d, J=4.0 Hz, 2H), 4.04-3.90 (m, 3H), 3.51-3.42 (m, 2H), 3.32 (d, J=5.9 Hz, 2H), 2.14-2.02 (m, 3H), 1.95-1.83 (m, 2H), 1.74-1.40 (m, 9H); ESIMS m/z: [M+H]$^+$ 476.

EXAMPLE 33

3-[(4,4-Difluorocyclohexyl)methyl]-5-(fluoromethyl)-N-(tetrahydro-2H-pyran-4-yl)-2-(trifluoromethyl)imidazo[1,2-a]pyridine-7-carboxamide (Compound 47)

Compound 47 (8.5 mg, yield 85%) was obtained in the same manner as in Step 3 of Example 14, using Compound 46.

$^1$H NMR (300 MHz, CDCl$_3$, δ): 8.00 (dd, J=2.2, 2.2 Hz, 1H), 7.51 (dd, J=4.0, 2.2 Hz, 1H), 6.02 (d, J=7.3 Hz, 1H), 5.68 (d, J=47.7 Hz, 2H), 4.27-4.15 (m, 1H), 4.06-3.98 (m,

2H), 3.60-3.49 (m, 2H), 3.20 (d, J=5.5 Hz, 2H), 2.14-1.98 (m, 4H), 1.75-1.45 (m, 9H); ESIMS m/z: [M+H]$^+$ 478.

EXAMPLE 34

3-[(4,4-Difluorocyclohexyl)methyl]-5-(difluoromethyl)-N-(tetrahydro-2H-pyran-4-yl)-2-(trifluoromethyl)imidazo[1,2-a]pyridine-7-carboxamide (Compound 48)

Compound 47 (7.9 mg, yield 75%) was obtained in the same manner as in Step 3 of Example 14, using Compound 45.

$^1$H NMR (300 MHz, CDCl$_3$, δ): 8.09 (s, 1H), 7.81 (s, 1H), 7.00 (t, J=53.5 Hz, 1H), 6.03 (d, J=8.1 Hz, 1H), 4.29-4.14 (m, 1H), 4.07-3.98 (m, 2H), 3.60-3.49 (m, 2H), 3.18 (d, J=6.2 Hz, 2H), 2.15-1.99 (m, 4H), 1.73-1.41 (m, 9H); ESIMS m/z: [M+H]$^+$ 496.

EXAMPLE 35

3-[(4,4-Difluorocyclohexyl)methyl]-5-hydroxy-N-(tetrahydro-2H-pyran-4-yl)-2-(trifluoromethyl)imidazo[1,2-a]pyridine-7-carboxamide (Compound 49)

Step 1
5-Amino-3-[(4,4-difluorocyclohexyl)methyl]-2-(trifluoromethyl)imidazo[1,2-a]pyridine-7-carboxylic acid (74.5 mg, yield 77%) was obtained in the same manner as in Step 8 of Example 1, using methyl 5-amino-3-[(4,4-difluorocyclohexyl)methyl]-2-(trifluoromethyl)imidazo[1,2-a]pyridine-7-carboxylate obtained in Step 4 of Example 25.

$^1$H NMR (270 MHz, DMSO-d$_6$, δ): 7.48 (d, J=1.6 Hz, 1H), 6.67 (d, J=1.6 Hz, 1H), 6.33 (s, 2H), 3.21 (d, J=7.2 Hz, 2H), 2.01-1.51 (m, 9H).

Step 2
5-Amino-3-[(4,4-difluorocyclohexyl)methyl]-Netrahydro-2H-pyran-4-yl)-2-(trifluoromethyl)imidazo[1,2-a]pyridine-7-carboxamide (80.0 mg, yield 91%) was obtained in the same manner as in Step 9 of Example 1, using 5-amino-3-[(4,4-difluorocyclohexyl)methyl]-2-(trifluoromethyl)imidazo[1,2-a]pyridine-7-carboxylic acid obtained in Step 1 and 4-aminotetrahydropyran hydrochloride.

$^1$H NMR (300 MHz, CDCl$_3$, δ): 7.42 (d, J=1.7 Hz, 1H), 6.59 (d, J=1.7 Hz, 1H), 6.09 (d, J=7.3 Hz, 1H), 4.53 (s, 2H), 4.19-4.16 (m, 1H), 4.05-3.96 (m, 2H), 3.55-3.51 (m, 2H), 3.20 (d, J=7.0 Hz, 2H), 2.18-1.42 (m, 13H).

Step 3
5-Amino-3-[(4,4-difluorocyclohexyl)methyl]-Netrahydro-2H-pyran-4-yl)-2-(trifluoromethyl)imidazo[1,2-a]pyridine-7-carboxamide obtained in Step 2 above (32.0 mg, 0.0690 mmol) was dissolved in acetonitrile (1.0 mL), and sulfuric acid (0.5 mL) was added thereto at −40° C. A solution of sodium nitrite (5.75 mg, 0.0830 mmol) dissolved in water (0.5 mL) was added to the reaction mixture, and the mixture was stirred at 0° C. for 1 hour. The reaction mixture was neutralized with 2 mol/L aqueous sodium hydroxide solution, and the mixture was extracted with chloroform. The organic layer was dried over anhydrous magnesium sulfate, and the solvent was evaporated under reduced pressure. The residue was purified by silica gel column chromatography (chloroform/methanol=98/2 to 95/5), whereby Compound 49 (5.30 mg, yield 17%) was obtained.

$^1$H NMR (300 MHz, CDCl$_3$, δ): 11.21 (s, 1H), 7.80 (s, 1H), 7.65 (s, 1H), 6.33 (d, J=6.2 Hz, 1H), 4.27-4.17 (m, 1H), 4.07-4.00 (m, 2H), 3.60-3.50 (m, 2H), 2.95 (d, J=7.0 Hz, 2H), 2.14-1.99 (m, 4H), 1.78-1.38 (m, 9H); ESIMS m/z: [M+H]$^+$ 462.

EXAMPLE 36

3-[(4,4-Difluorocyclohexyl)methyl]-5-ethynyl-N-(tetrahydro-2H-pyran-4-yl)-2-(trifluoromethyl)imidazo[1,2-a]pyridine-7-carboxamide (Compound 50)

Compound 45 (7.80 mg, 0.016 mmol) was dissolved in methanol (2.0 ml), potassium carbonate (4.55 mg, 0.033 mmol) and dimethyl (1-diazo-2-oxopropyl)phosphonate (4.11 mg, 0.021 mmol) were added thereto, and the mixture was stirred at room temperature for 2 hours. An aqueous sodium hydrogen carbonate solution was added to the reaction mixture, and the solvent was evaporated under reduced pressure. Water was added to the residue, and the precipitated solid was collected by filtration, whereby Compound 50 (1.60 mg, yield 20%) was obtained.

$^1$H NMR (300 MHz, CDCl$_3$, δ): 7.99 (d, J=1.8 Hz, 1H), 7.66 (d, J=1.5 Hz, 1H), 6.01 (d, J=7.3 Hz, 1H), 4.24-4.20 (m, 1H), 4.04-4.00 (m, 2H), 3.81 (s, 1H), 3.54 (td, J=11.7, 2.2 Hz, 2H), 3.42 (d, J=7.3 Hz, 2H), 2.17-1.36 (m, 13H); ESIMS m/z: [M+H]$^+$ 470.

EXAMPLE 37

5-Cyano-3-[(4,4-difluorocyclohexyl)methyl]-N-(2-hydroxy-2-methylpropyl)-2-(trifluoromethyl)imidazo[1,2-a]pyridine-7-carboxamide (Compound 51)

Step 1
Methyl 5-amino-3-[(4,4-difluorocyclohexyl)methyl]-2-(trifluoromethyl)imidazo[1,2-a]pyridine-7-carboxylate obtained in Step 4 of Example 25 (0.516 g, 1.32 mmol) was dissolved in acetonitrile (13 mL). Under ice-cooled condition, 12 mol/L hydrochloric acid (8.0 mL), sodium nitrite (0.273 g, 3.96 mmol), and copper(I) chloride (0.196 g, 1.98 mmol) were added thereto, and the mixture was stirred at 50° C. for 1.5 hours. Under ice-cooled condition, the reaction mixture was neutralized with a saturated aqueous sodium hydrogen carbonate solution. The mixture was filtrated through Celite (registered trademark) and the filtrate was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=90/10 to 85/15), whereby methyl 5-chloro-3-[(4,4-difluorocyclohexyl)methyl]-2-(trifluoromethyl)imidazo[1,2-a]pyridine-7-carboxylate (216 mg, yield 40%) was obtained.

$^1$H NMR (300 MHz, CDCl$_3$, δ): 8.31 (d, J=1.5 Hz, 1H), 7.53 (d, J=1.5 Hz, 1H), 3.98 (s, 3H), 3.36 (d, J=7.0 Hz, 2H), 2.18-1.99 (m, 2H), 1.94-1.37 (m, 7H).

Step 2
Methyl 5-chloro-3-[(4,4-difluorocyclohexyl)methyl]-2-(trifluoromethyl)imidazo[1,2-a]pyridine-7-carboxylate obtained in Step 1 (210 mg, 0.511 mmol), tetrakistriphenylphosphine palladium (59.0 mg, 0.0510 mmol), and zinc dicyanide (90.0 mg, 0.767 mmol) were dissolved in DMF (2.0 mL), and the mixture was stirred at 150° C. for 30 minutes using microwave chemical synthesis apparatus (CEM Discover). A saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=90/10 to 65/35), whereby methyl 5-cyano-3-[(4,4-difluorocyclohexyl)methyl]-2-(trifluoromethyl)imidazo[1,2-a]pyridine-7-carboxylate (141 mg, yield 69%) was obtained.

$^1$H NMR (300 MHz, CDCl$_3$, δ): 8.61 (d, J=1.8 Hz, 1H), 8.12 (d, J=1.8 Hz, 1H), 4.02 (s, 3H), 3.37 (d, J=7.0 Hz, 2H), 2.19-1.24 (m, 9H).

Step 3

5-Cyano-3-[(4,4-difluorocyclohexyl)methyl]-2-(trifluoromethyl)imidazo[1,2-a]pyridine-7-carboxylic acid (188 mg, yield 97%) was obtained in the same manner as in Step 8 of Example 1, using methyl 5-cyano-3-[(4,4-difluorocyclohexyl)methyl]-2-(trifluoromethyl)imidazo[1,2-a]pyridine-7-carboxylate obtained in Step 2.

$^1$H NMR (400 MHz, DMSO-d$_6$, δ): 8.53-8.52 (m, 1H), 8.23-8.22 (m, 1H), 3.27 (d, J=7.8 Hz, 2H), 2.08-1.25 (m, 9H).

Step 4

Compound 51 (17.9 mg, 84%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 and 1-amino-2-methylpropan-2-ol.

$^1$H NMR (300 MHz, CDCl$_3$, δ): 8.29 (d, J=1.8 Hz, 1H), 8.08 (d, J=1.8 Hz, 1H), 6.79 (s, 1H), 3.51 (d, J=5.9 Hz, 2H), 3.36 (d, J=7.0 Hz, 2H), 2.17-2.10 (m, 2H), 1.82-1.47 (m, 7H), 1.32 (s, 6H); ESIMS m/z: [M+H]$^+$ 459.

EXAMPLE 38

5-Cyano-3-[(4,4-difluorocyclohexyl)methyl]-N-(2-methoxy-2-methylpropyl)-2-(trifluoromethyl)imidazo[1,2-a]pyridine-7-carboxamide (Compound 55)

Compound 55 (21.7 mg, 89%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and 2-methoxy-2-methylpropan-1-amine.

$^1$H NMR (270 MHz, CDCl$_3$, δ): 8.25 (d, J=1.6 Hz, 1H), 8.07 (d, J=1.6 Hz, 1H), 6.66-6.63 (m, 1H), 3.49 (d, J=5.6 Hz, 2H), 3.36 (d, J=6.9 Hz, 2H), 3.25 (s, 3H), 2.25-2.04 (m, 2H), 1.87-1.12 (m, 13H); ESIMS m/z: [M+H]$^+$ 473.

EXAMPLE 39

5-Cyano-3-[(4,4-difluorocyclohexyl)methyl]-N-(2-oxopropyl)-2-(trifluoromethyl)imidazo[1,2-a]pyridine-7-carboxamide (Compound 71)

Compound 71 (26.1 mg, 97%) was obtained in the same manner as in Step 2 of Example 14, using Compound 68 (27.0 mg, 0.0610 mmol).

$^1$H NMR (300 MHz, CDCl$_3$, δ): 8.33 (d, J=1.8 Hz, 1H), 8.05 (d, J=1.8 Hz, 1H), 7.07 (s, 1H), 4.39 (d, J=4.4 Hz, 2H), 3.37 (d, J=7.0 Hz, 2H), 2.32 (s, 3H), 2.18-2.04 (m, 2H), 1.85-1.41 (m, 7H); ESIMS m/z: [M+H]$^+$ 443.

EXAMPLE 40

3-[(4,4-Difluorocyclohexyl)methyl]-5-methyl-N-(tetrahydro-2H-pyran-4-yloxy)-2-(trifluoromethyl)imidazo[1,2-a]pyridine-7-carboxamide (Compound 72)

Step 1

Triphenylphosphine (1.93 g, 7.34 mmol) and 2-hydroxyisoindoline-1,3-dione (1.20 g, 7.34 mmol) were dissolved in THF (10 mL), tetrahydro-2H-pyran-4-ol (0.500 g, 4.90 mmol) and diethyl azodicarboxylate (2.2 mol/L solution in toluene) (3.34 mL, 7.34 mmol) were added thereto, and the mixture was stirred at room temperature overnight. The solvent in the reaction mixture was evaporated under reduced pressure. The residue was purified by silica gel column chromatography (heptane/ethyl acetate=90/10 to 80/20 to 50/50), whereby 2-(tetrahydro-2H-pyran-4-yloxy)isoindoline-1,3-dione (1.03 g, 85%) was obtained.

$^1$H NMR (300 MHz, CDCl$_3$, δ): 7.87-7.82 (m, 2H), 7.79-7.75 (m, 2H), 4.49-4.41 (m, 1H), 4.11-4.03 (m, 2H), 3.53-3.45 (m, 2H), 2.10-1.83 (m, 4H).

Step 2

2-(Tetrahydro-2H-pyran-4-yloxy)isoindoline-1,3-dione obtained in Step 1 above (0.500 g, 2.02 mmol) was dissolved in ethanol (5.0 mL), hydrazine monohydrate (0.118 mL, 2.43 mmol) was added thereto, and the mixture was stirred for 1 hour under reflux with heating. After cooling the reaction mixture to room temperature, the precipitated solid was removed by filtration, 2 mol/L hydrochloric acid (1.01 mL, 2.02 mmol) was added to the filtrate, and the solvent was evaporated under reduced pressure. Diethyl ether was added to the residue, and the precipitated crystal was collected by filtration, whereby O-(tetrahydro-2H-pyran-4-yl)hydroxylamine hydrochloride (264 mg, 85%) was obtained.

$^1$H NMR (400 MHz, DMSO-d$_6$, δ): 11.06 (br s, 2H), 4.33-4.27 (m, 1H), 3.84-3.76 (m, 2H), 3.38-3.35 (m, 2H), 2.00-1.96 (m, 2H), 1.53-1.50 (m, 2H).

Step 3

Compound 72 (53.6 mg, yield 57%) was obtained in the same manner as in Step 9 of Example 1, using O-(tetrahydro-2H-pyran-4-yl)hydroxylamine hydrochloride obtained in Step 2 and 3-[(4,4-difluorocyclohexyl)methyl]-5-methyl-2-(trifluoromethyl)imidazo[1,2-a]pyridine-7-carboxylic acid obtained in Step 2 of Example 32.

$^1$H NMR (300 MHz, DMSO-d$_6$, δ): 11.77 (s, 1H), 7.91 (s, 1H), 7.16 (s, 1H), 4.12 (s, 1H), 3.88-3.86 (m, 2H), 3.51-3.42 (m, 2H), 3.17 (d, J=6.6 Hz, 2H), 3.08 (s, 1H), 2.91 (s, 3H), 1.92-1.76 (m, 12H); ESIMS m/z: [M+H]$^+$ 476.

EXAMPLE 41

2-{3-[(4,4-Difluorocyclohexyl)methyl]-5-methyl-2-(trifluoromethyl)imidazo[1,2-a]pyridin-7-yl}-4,5,6,7-tetrahydro-1H-benzo[d]imidazol (Compound 73)

Step 1

3-[(4,4-Difluorocyclohexyl)methyl]-N-methoxy-N,5-dimethyl-2-(trifluoromethyl)imidazo[1,2-a]pyridine-7-carboxamide (936 mg, yield 84%) was obtained in the same manner as in Step 9 of Example 1, using 3-[(4,4-difluorocyclohexyl)methyl]-5-methyl-2-(trifluoromethyl)imidazo[1,2-a]pyridine-7-carboxylic acid obtained in Step 2 of Example 32 and N,O-dimethylhydroxylamine hydrochloride.

$^1$H NMR (300 MHz, CDCl$_3$, δ): 8.03-8.02 (m, 1H), 7.02-7.01 (m, 1H), 3.64 (s, 3H), 3.40 (s, 3H), 3.22 (d, J=6.2 Hz, 2H), 2.87 (s, 3H), 2.10 (s, 2H), 1.60-1.36 (m, 7H).

Step 2

3-[(4,4-Difluorocyclohexyl)methyl]-N-methoxy-N,5-dimethyl-2-(trifluoromethyl)imidazo[1,2-a]pyridine-7-carboxamide obtained in Step 1 (480 mg, 1.15 mmol) was dissolved in THF (5.0 mL). Under ice-cooled condition, lithium aluminum hydride (52.0 mg, 1.37 mmol) was added thereto, and the mixture was stirred at room temperature for 2.5 hours. Under ice-cooled condition, water (0.0550 mL), 2 mol/L aqueous sodium hydroxide solution (0.0550 mL), and water (0.165 mL) were sequentially added to the reaction mixture, and the mixture was stirred at room temperature for 2 hours. The reaction mixture was filtrated through Celite (registered trademark), and the solvent was evaporated under reduced pressure. The residue was purified by silica gel column chromatography (heptane/ethyl acetate=80/20 to 50/50), whereby 3-[(4,4-difluorocyclohexyl)methyl]-5-methyl-2-(trifluoromethyl)imidazo[1,2-a]pyridine-7-carbaldehyde (220 mg, 53%) was obtained.

$^1$H NMR (300 MHz, CDCl$_3$, δ): 9.98 (s, 1H), 8.02 (d, J=1.1 Hz, 1H), 7.15-7.14 (m, 1H), 3.24 (d, J=6.2 Hz, 2H), 2.91 (s, 3H), 2.11-2.08 (m, 2H), 1.70-1.40 (m, 7H).

Step 3

3-[(4,4-Difluorocyclohexyl)methyl]-5-methyl-2-(trifluoromethyl)imidazo[1,2-a]pyridine-7-carbaldehyde obtained in Step 2 (50.0 mg, 0.139 mmol) was dissolved in acetic acid (1.0 mL), ammonium acetate (107 mg, 1.39 mmol) and cyclohexane-1,2-dione (19.0 mg, 0.167 mmol) were added thereto, and the mixture was stirred at 100° C. for 3 hours. After cooling the reaction mixture to room temperature, the mixture was neutralized using 2 mol/L aqueous sodium hydroxide solution, and the mixture was extracted with chloroform. The organic layer was dried over anhydrous magnesium sulfate, and the solvent was evaporated under reduced pressure. The residue was purified by silica gel column chromatography (chloroform/methanol=100/0 to 95/5) and purified by preparative HPLC (Waters, XBridge™ Prep C18 OBD Column, 5 μm, 19×100 mm) (MeCN/10 mmol/L aqueous ammonium acetate solution), whereby Compound 73 (5.00 mg, yield 8%) was obtained.

$^1$H NMR (300 MHz, CDCl$_3$, δ): 7.60 (s, 1H), 7.40 (s, 1H), 3.15 (s, 2H), 2.88 (s, 3H), 2.65 (s, 4H), 2.20-2.11 (m, 3H), 1.84 (s, 4H), 1.76-1.21 (m, 6H); ESIMS m/z: [M+H]$^+$ 453.

EXAMPLE 42

5-Chloro-N-(cyclopropylmethyl)-3-[(4,4-difluorocyclohexyl)methyl]-2-(trifluoromethyl)imidazo[1,2-a]pyridine-7-carboxamide (Compound 77)

Step 1

5-Chloro-3-[(4,4-difluorocyclohexyl)methyl]-2-(trifluoromethyl)imidazo[1,2-a]pyridine-7-carboxylic acid (29.0 mg, 95%) was obtained in the same manner as in Step of Example 1, using methyl 5-chloro-3-[(4,4-difluorocyclohexyl)methyl]-2-(trifluoromethyl)imidazo[1,2-a]pyridine-7-carboxylate obtained in Step 1 of Example 37.

Step 2

Compound 77 (12.0 mg, yield 25%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 1 and cyclopropylmethanamine.

$^1$H NMR (300 MHz, CDCl$_3$, δ): 7.89 (d, J=1.6 Hz, 1H), 7.45 (d, J=1.6 Hz, 1H), 6.21 (s, 1H), 3.35-3.32 (m, 4H), 2.09 (s, 2H), 1.71-0.88 (m, 8H), 0.60 (dd, J=12.7, 5.4 Hz, 2H), 0.30 (dd, J=4.9, 2.5 Hz, 2H); ESIMS m/z: [M+H]$^+$ 450.

EXAMPLE 43

2-{3-[(4,4-Difluorocyclohexyl)methyl]-5-methyl-2-(trifluoromethyl)imidazo[1,2-a]pyridin-7-yl}-N-(tetrahydro-2H-pyran-4-yl)acetamide (Compound 78)

Step 1

3-[(4,4-Difluorocyclohexyl)methyl]-5-methyl-2-(trifluoromethyl)imidazo[1,2-a]pyridine-7-carboxylic acid obtained in Step 2 of Example 32 (1.13 g, 3.00 mmol) was dissolved in 1,2-dichloroethane (10 mL), and thionyl chloride (0.438 mL, 6.00 mol) and DMF (1 drop) were added thereto. Under reflux with heating, the mixture was stirred for 30 minutes. The solvent in the reaction mixture was evaporated under reduced pressure. The residue was dissolved in a mixed solvent of THF (5.0 mL) and acetonitrile (2.0 mL), trimethylsilyldiazomethane (0.6 mol/L hexane solution) (7.50 mL, 4.50 mmol) was added thereto, and the mixture was stirred at room temperature overnight. Ethyl acetate was added to the reaction mixture, and the mixture was washed sequentially with 5% aqueous citric acid solution, a saturated aqueous sodium hydrogen carbonate solution, and saturated brine. The organic layer was dried over anhydrous magnesium sulfate, and the solvent was evaporated under reduced pressure. The residue was purified by silica gel column chromatography (hexane/ethyl acetate=90/10 to 50/50), whereby 2-diazo-1-{3-[(4,4-difluorocyclohexyl)methyl]-5-methyl-2-(trifluoromethyl)imidazo[1,2-a]pyridin-7-yl}ethanone (643 mg, yield 54%) was obtained.

$^1$H NMR (400 MHz, CDCl$_3$, δ): 7.80 (s, 1H), 7.19 (s, 1H), 5.93 (s, 1H), 3.22 (d, J=6.8 Hz, 2H), 2.89 (s, 3H), 2.18-2.06 (m, 2H), 1.74-1.26 (m, 7H).

Step 2

2-Diazo-1-{3-[(4,4-difluorocyclohexyl)methyl]-5-methyl-2-(trifluoromethyl)imidazo[1,2-a]pyridin-7-yl}ethanone obtained in Step 1 (615 mg, 1.54 mmol) was dissolved in a mixed solvent of THF (5.0 mL) and water (0.5 mL). After cooling the mixture to −20° C., a solution of silver trifluoroacetate (170 mg, 0.768 mmol) dissolved in triethylamine (1.29 mL, 9.22 mmol) was added thereto, and the mixture was stirred at room temperature overnight. Then, 2 mol/L hydrochloric acid and ethyl acetate were added to the reaction mixture, and the precipitated insoluble matter was removed by filtration through Celite (registered trademark). Then, 2 mol/L aqueous sodium hydroxide solution was added to the filtrate, and the mixture was extracted with an aqueous sodium hydroxide solution. The aqueous layer was washed with ethyl acetate, 2 mol/L hydrochloric acid was added to adjust pH to 4.5, and the mixture was extracted with a mixed solvent of chloroform and methanol. The organic layer was dried over anhydrous magnesium sulfate, the solvent was evaporated under reduced pressure, whereby 2-{3-[(4,4-difluorocyclohexyl)methyl]-5-methyl-2-(trifluoromethyl)imidazo[1,2-a]pyridin-7-yl}acetic acid (426 mg, 71%) was obtained.

$^1$H NMR (300 MHz, DMSO-d$_6$, δ): 8.32 (s, 1H), 7.38 (s, 1H), 6.76 (s, 1H), 3.64 (s, 2H), 3.13 (d, J=7.0 Hz, 2H), 2.85 (s, 3H), 1.92-1.68 (m, 9H).

Step 3

Compound 78 (98.4 mg, yield 81%) was obtained in the same manner as in Step 9 of Example 1, using 2-{3-[(4,4-difluorocyclohexyl)methyl]-5-methyl-2-(trifluoromethyl)imidazo[1,2-a]pyridin-7-yl}acetic acid obtained in Step 2 and 4-aminotetrahydropyran hydrochloride.

$^1$H NMR (300 MHz, CDCl$_3$, δ): 7.36 (s, 1H), 6.66 (d, J=0.7 Hz, 1H), 5.42 (d, J=7.7 Hz, 1H), 4.00-3.95 (m, 3H), 3.50-3.40 (m, 4H), 3.18 (d, J=6.2 Hz, 2H), 2.83 (s, 3H), 2.12-2.09 (m, 2H), 1.89-1.86 (m, 2H), 1.74-1.18 (m, 7H), 0.89-0.79 (m, 2H); ESIMS m/z: [M+H]$^+$ 474.

EXAMPLE 44

(Z)-3-[(4,4-Difluorocyclohexyl)methyl]-5-methyl-7-(2-tetrahydro-2H-pyran-4-ylvinyl)-2-(trifluoromethyl)imidazo[1,2-a]pyridine (Compound 79)

Step 1

(Tetrahydro-2H-pyran-4-yl)methanol (1.00 g, 8.61 mmol) was dissolved in THF (3.0 mL), a solution of sodium hydroxide (0.689 g, 17.2 mmol) dissolved in water (0.69 mL) and a solution of p-toluenesulfonyl chloride (3.28 g, 17.2 mmol) dissolved in THF (3.0 mL) were added thereto, and the mixture was stirred at room temperature overnight. Then, 12 mol/L hydrochloric acid (2.0 mL) was added to the reaction mixture, and the mixture was extracted with ethyl acetate. The organic layer was dried over anhydrous magnesium sulfate, and the solvent was evaporated under reduced pressure. The residue was purified by silica gel column chromatography (heptane/ethyl acetate=80/20 to 50/50), whereby (tetrahydro-2H-pyran-4-yl)methyl 4-methylbenzenesulfonate (1.22 g, yield 52%) was obtained.

$^1$H NMR (300 MHz, CDCl$_3$, δ): 7.82-7.76 (m, 2H), 7.37-7.33 (m, 2H), 3.98-3.90 (m, 2H), 3.86 (d, J=6.6 Hz, 2H), 3.34 (td, J=11.7, 2.2 Hz, 2H), 2.46 (s, 3H), 2.01-1.87 (m, 1H), 1.61-1.56 (m, 2H), 1.30-1.24 (m, 2H).

Step 2

(Tetrahydro-2H-pyran-4-yl)methyl 4-methylbenzenesulfonate obtained in Step 1 (1.20 g, 4.44 mmol) was dissolved in acetone (15 mL), sodium iodide (2.00 g, 13.3 mmol) was added thereto, and under reflux with heating, the mixture was stirred for 4 hours. After cooling the reaction mixture to room temperature, the precipitated solid was removed by filtration, and the filtrate was evaporated under reduced pressure. Chloroform was added to the residue, and the precipitated solid was removed by filtration. The filtrate was concentrated under reduced pressure, whereby 4-(iodomethyl)tetrahydro-2H-pyran (0.946 g, 94%) was obtained.

$^1$H NMR (300 MHz, CDCl$_3$, δ): 3.99-3.96 (m, 2H), 3.37 (td, J=11.7, 2.1 Hz, 2H), 3.10 (d, J=6.6 Hz, 2H), 1.81-1.65 (m, 3H), 1.37-1.24 (m, 2H).

Step 3

4-(Iodomethyl)tetrahydro-2H-pyran obtained in Step 2 (0.940 g, 4.16 mmol) was dissolved in acetonitrile (10 mL), triphenylphosphine (1.09 g, 4.16 mmol) was added thereto, and the mixture was stirred for 13 hours under reflux with heating. The solvent in the reaction mixture was evaporated under reduced pressure, diethyl ether was added to the residue, and the precipitated crystal was collected by filtration, whereby triphenyl[(tetrahydro-2H-pyran-4-yl)methyl]phosphonium iodide (0.600 g, 30%) was obtained.

$^1$H NMR (300 MHz, DMSO-d$_6$, δ): 7.90-7.74 (m, 15H), 3.68-3.61 (m, 4H), 3.16-3.13 (m, 2H), 2.02-1.91 (m, 1H), 1.41-1.31 (m, 4H).

Step 4

Compound 79 (43.5 mg, yield 35%) was obtained in the same manner as in Step 1 of Example 1, using triphenyl[(tetrahydro-2H-pyran-4-yl)methyl]phosphonium iodide obtained in Step 3 and 3-[(4,4-difluorocyclohexyl)methyl]-5-methyl-2-(trifluoromethyl)imidazo[1,2-a]pyridine-7-carbaldehyde obtained in Step 2 of Example 41.

$^1$H NMR (300 MHz, CDCl$_3$, δ): 7.42 (s, 1H), 6.48 (s, 1H), 6.24 (d, J=11.6 Hz, 1H), 5.63 (dd, J=11.6, 10.1 Hz, 1H), 4.00-3.91 (m, 2H), 3.43 (td, J=11.3, 3.2 Hz, 2H), 3.19 (d, J=6.2 Hz, 2H), 2.93-2.81 (m, 4H), 2.22-2.01 (m, 2H), 1.76-1.40 (m, 11H); ESIMS m/z: [M+H]$^+$ 443.

EXAMPLE 45

1-{3-[(4,4-Difluorocyclohexyl)methyl]-5-methyl-2-(trifluoromethyl)imidazo[1,2-a]pyridin-7-yl}-2-(tetrahydro-2H-pyran-4-yl)ethane-1,2-diol (Compound 82)

Compound 79 (33.0 mg, 0.0750 mol) was dissolved in a mixed solvent of tert-butanol (1.0 mL) and water (0.25 mL), osmium tetraoxide (2.5% solution in tert-butanol) (0.187 mL, 0.0150 mmol) and N-methylmorpholine N-oxide (17.0 mg, 0.149 mmol) were added thereto, and the mixture was stirred at room temperature overnight. An aqueous sodium thiosulfate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=80/20 to 50/50 to chloroform/methanol=90/10), whereby Compound 82 (30.5 mg, yield 86%) was obtained.

$^1$H NMR (400 MHz, CDCl$_3$, δ): 7.49 (s, 1H), 6.81 (s, 1H), 4.72 (d, J=4.9 Hz, 1H), 4.00-3.94 (m, 2H), 3.70 (t, J=5.4 Hz, 1H), 3.34-3.31 (m, 2H), 3.18 (d, J=5.9 Hz, 2H), 2.84 (s, 3H), 2.73 (s, 1H), 2.26-2.21 (m, 1H), 2.16-2.06 (m, 2H), 1.83-1.40 (m, 12H); ESIMS m/z: [M+H]$^+$ 477.

EXAMPLE 46

1-{3-[(4,4-Difluorocyclohexyl)methyl]-5-methyl-2-(trifluoromethyl)imidazo[1,2-a]pyridin-7-yl}-2-hydroxy-2-(tetrahydro-2H-pyran-4-yl)ethanone (Compound 83)

Compound 82 (23.0 mg, 0.0480 mmol) was dissolved in dichloromethane (2.0 mL), manganese dioxide (150 mg, 1.73 mmol) was added thereto, and the mixture was stirred at room temperature for 1 hour. The reaction mixture was filtrated through Celite (registered trademark), and the solvent was evaporated under reduced pressure. The residue was purified by preparative thin-layer chromatography (chloroform/methanol=95/5), whereby Compound 83 (12.6 mg, 55%) was obtained.

$^1$H NMR (300 MHz, CDCl$_3$, δ): 8.13-8.10 (m, 1H), 7.22-7.20 (m, 1H), 4.97 (dd, J=6.8, 2.7 Hz, 1H), 4.00-3.93 (m, 2H), 3.49-3.15 (m, 5H), 2.92 (s, 3H), 2.22-1.26 (m, 14H); ESIMS m/z: [M+H]$^+$ 475.

EXAMPLE 47

2-{3-[(4,4-Difluorocyclohexyl)methyl]-5-methyl-2-(trifluoromethyl)imidazo[1,2-a]pyridin-7-yl}-N-(tetrahydro-2H-pyran-4-yloxy)acetamide (Compound 84)

Compound 84 (12.0 mg, yield 19%) was obtained in the same manner as in Step 9 of Example 1, using 2-{3-[(4,4-difluorocyclohexyl)methyl]-5-methyl-2-(trifluoromethyl)imidazo[1,2-a]pyridin-7-yl}acetic acid obtained in Step 2 of Example 43 and O-(tetrahydro-2H-pyran-4-yl)hydroxylamine hydrochloride obtained in Step 2 of Example 40.

$^1$H NMR (300 MHz, DMSO-d$_6$, δ): 11.13 (s, 1H), 7.34 (s, 1H), 6.73 (s, 1H), 3.99-3.91 (m, 1H), 3.84-3.77 (m, 2H), 3.37-3.29 (m, 4H), 3.13 (d, J=6.6 Hz, 2H), 2.85 (s, 3H), 2.03-1.24 (m, 13H); ESIMS m/z: [M+H]$^+$ 490.

EXAMPLE 48

2-({3-[(4,4-Difluorocyclohexyl)methyl]-5-methyl-2-(trifluoromethyl)imidazo[1,2-a]pyridin-7-yl}methyl)-1H-benzo[d]imidazol (Compound 87)

Compound 85 (79.0 mg, 0.164 mmol) was dissolved in acetic acid (1.0 mL), and the mixture was stirred at 100° C. overnight. A saturated aqueous sodium hydrogen carbonate solution was added to the reaction mixture, and the precipitated crystal was collected by filtration and washed with water. The resulting crystal was purified by silica gel column chromatography (chloroform/methanol=100/0 to 95/5), whereby Compound 87 (59.4 mg, yield 78%) was obtained.

$^1$H NMR (300 MHz, CDCl$_3$, δ): 7.51 (br s, 1H), 7.40 (s, 1H), 7.24-7.22 (m, 4H), 6.69 (s, 1H), 4.24 (s, 2H), 3.13 (d, J=6.2 Hz, 2H), 2.74 (s, 3H), 2.09-2.06 (m, 2H), 1.59-1.47 (m, 7H); ESIMS m/z: [M+H]$^+$ 463.

EXAMPLE 49

3-[(4,4-Difluorocyclohexyl)methyl]-5-methyl-N-(2-oxaspiro[3.3]heptan-6-yl)-2-(trifluoromethyl)imidazo[1,2-a]pyridine-7-carboxamide (Compound 88)

Compound 80 (93.7 mg, 0.191 mmol) was dissolved in DMF (2.0 mL). Under ice-cooled condition, 60% sodium hydride (23 mg, 0.547 mmol) and p-toluenesulfonyl chloride (40 mg, 0.211 mmol) were added thereto, and the mixture was stirred at room temperature for 2 hours. A saturated aqueous sodium hydrogen carbonate solution was added to the reaction mixture, and the mixture was extracted with a mixed solvent of ethyl acetate and heptane. The organic layer was washed with saturated brine and dried over anhydrous magnesium sulfate, and the solvent was evaporated under reduced pressure. The residue was purified by silica gel column chromatography (chloroform/methanol=98/2 to 95/5) and further purified by amino-silica gel column chromatography (heptane/ethyl acetate=50/50 to 0/100), whereby Compound 88 (8.5 mg, yield 9%) was obtained.

$^1$H NMR (300 MHz, CDCl$_3$, δ): 7.73 (d, J=1.1 Hz, 1H), 7.08 (d, J=1.1 Hz, 1H), 6.28 (d, J=7.0 Hz, 1H), 4.71 (d, J=36.7 Hz, 4H), 4.44-4.30 (m, 1H), 3.21 (d, J=6.2 Hz, 2H), 2.87 (s, 3H), 2.85-2.76 (m, 2H), 2.24-1.37 (m, 11H); ESIMS m/z: [M+H]$^+$ 472.

EXAMPLE 50

2-{3-[(4,4-Difluorocyclohexyl)methyl]-5-methyl-2-(trifluoromethyl)imidazo[1,2-a]pyridin-7-yl}-N-(tetrahydro-2H-pyran-4-yl)propanamide (Compound 89)

Compound 89 (14.4 mg, yield 23%) was obtained in the same manner as in Step 1 of Example 11, using Compound 78 (60.0 mg, 0.127 mmol) was obtained.

$^1$H NMR (300 MHz, CDCl$_3$, δ): 7.38 (s, 1H), 6.69 (s, 1H), 5.45 (d, J=7.7 Hz, 1H), 4.01-3.88 (m, 3H), 3.52-3.38 (m, 3H), 3.17 (d, J=6.2 Hz, 2H), 2.82 (s, 3H), 2.22-1.23 (m, 16H); ESIMS m/z: [M+H]$^+$ 488.

EXAMPLE 51

(Z)-3-[(4,4-Difluorocyclohexyl)methyl]-5-methyl-7-styryl-2-(trifluoromethyl)imidazo[1,2-a]pyridine (Compound 90), (E)-3-[(4,4-difluorocyclohexyl)methyl]-5-methyl-7-styryl-2-(trifluoromethyl)imidazo[1,2-a]pyridine (Compound 91)

Potassium tert-butoxide (47.0 mg, 0.416 mmol) and benzylphosphonium iodide (160 mg, 0.333 mmol) were dissolved in THF (1.0 mL), and the mixture was stirred at room temperature for 30 minutes. A solution of 3-[(4,4-difluorocyclohexyl)methyl]-5-methyl-2-(trifluoromethyl)imidazo[1,2-a]pyridine-7-carbaldehyde obtained in Step 2 of Example 41 (100 mg, 0.278 mmol) in THF (1.0 mL) was added to the reaction mixture, and the mixture was stirred at room temperature for 3 hours. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (heptane/ethyl acetate=80/20 to 65/35), whereby Compound 90 (53.4 mg, yield 44%) and Compound 91 (51.5 mg, yield 43%) were obtained, respectively.

Compound 90

$^1$H NMR (300 MHz, CDCl$_3$, δ): 7.41 (s, 1H), 7.28-7.27 (m, 5H), 6.77 (d, J=12.7 Hz, 1H), 6.49 (d, J=12.7 Hz, 1H), 6.43 (s, 1H), 3.14 (d, J=6.6 Hz, 2H), 2.64 (s, 3H), 2.12-2.08 (m, 2H), 1.62-1.50 (m, 7H); ESIMS m/z: [M+H]$^+$ 435.

Compound 91

$^1$H NMR (300 MHz, CDCl$_3$, δ): 7.55-7.53 (m, 2H), 7.49 (s, 1H), 7.39 (t, J=7.3 Hz, 2H), 7.33-7.31 (m, 1H), 7.15 (d, J=16.3 Hz, 1H), 7.05 (d, J=16.3 Hz, 1H), 6.90 (s, 1H), 3.19 (d, J=6.2 Hz, 2H), 2.87 (s, 3H), 2.13-2.09 (m, 2H), 1.60-1.35 (m, 7H); ESIMS m/z: [M+H]$^+$ 435.

EXAMPLE 52

1-{3-[(4,4-Difluorocyclohexyl)methyl]-5-methyl-2-(trifluoromethyl)imidazo[1,2-a]pyridin-7-yl}-2-phenylethane-1,2-diol (Compound 94)

Compound 94 (43.7 mg, yield 84%) was obtained in the same manner as Example 45, using Compound 91.

$^1$H NMR (300 MHz, CDCl$_3$, δ): 7.35-7.21 (m, 6H), 6.42 (s, 1H), 4.76-4.73 (m, 2H), 3.16-3.14 (m, 3H), 2.81-2.79 (m, 1H), 2.74 (s, 3H), 2.15-2.05 (m, 2H), 1.74-1.25 (m, 7H); ESIMS m/z: [M+H]$^+$ 469.

EXAMPLE 53

(E)-3-{3-[(4,4-Difluorocyclohexyl)methyl]-5-methyl-2-(trifluoromethyl)imidazo[1,2-a]pyridin-7-yl}-N-(tetrahydro-2H-pyran-4-yl)acrylamide (Compound 101)

Step 1

Ethyl (E)-3-{3-[(4,4-difluorocyclohexyl)methyl]-5-methyl-2-(trifluoromethyl)imidazo[1,2-a]pyridin-7-yl}acrylate (130 mg, quantitative) was obtained in the same manner as in Step 1 of Example 1, using 3-[(4,4-difluorocyclohexyl)methyl]-5-methyl-2-(trifluoromethyl)imidazo[1,2-a]pyridine-7-carbaldehyde obtained in Step 2 of Example 41 and ethyl 2-(diethoxyphosphoryl)acetate.

$^1$H NMR (300 MHz, CDCl$_3$, δ): 7.64-7.57 (m, 2H), 6.79 (s, 1H), 6.45 (d, J=16.1 Hz, 1H), 4.29 (q, J=7.1 Hz, 2H), 3.20 (d, J=6.2 Hz, 2H), 2.86 (s, 3H), 2.17-2.06 (m, 2H), 1.71-1.27 (m, 10H).

Step 2

(E)-3-{3-[(4,4-Difluorocyclohexyl)methyl]-5-methyl-2-(trifluoromethyl)imidazo[1,2-a]pyridin-7-yl}acrylic acid (105 mg, yield 93%) was obtained in the same manner as in Step 8 of Example 1, using ethyl (E)-3-{3-[(4,4-difluorocyclohexyl)methyl]-5-methyl-2-(trifluoromethyl)imidazo[1,2-a]pyridin-7-yl}acrylate obtained in Step 1.

$^1$H NMR (400 MHz, DMSO-d$_6$, δ): 12.58 (s, 1H), 7.82 (s, 1H), 7.60 (d, J=16.1 Hz, 1H), 7.33 (s, 1H), 6.67 (d, J=16.1 Hz, 1H), 3.14 (d, J=6.8 Hz, 2H), 2.89 (s, 3H), 1.88-1.70 (m, 6H), 1.28-1.25 (m, 3H).

Step 3

Compound 101 (34.8 mg, yield 96%) was obtained in the same manner as in Step 9 of Example 1, using (E)-3-{3-[(4,4-difluorocyclohexyl)methyl]-5-methyl-2-(trifluoromethyl)imidazo[1,2-a]pyridin-7-yl}acrylic acid obtained in Step 2 and 4-aminotetrahydropyran hydrochloride.

$^1$H NMR (300 MHz, CDCl$_3$, δ): 7.61 (s, 1H), 7.55 (d, J=15.4 Hz, 1H), 6.74 (s, 1H), 6.40 (d, J=15.4 Hz, 1H), 5.56 (d, J=8.1 Hz, 1H), 4.21-4.11 (m, 1H), 3.99 (d, J=9.9 Hz, 2H), 3.55-3.51 (m, 2H), 3.19 (d, J=6.6 Hz, 2H), 2.85 (s, 3H), 2.11-1.96 (m, 4H), 1.59-1.51 (m, 9H); ESIMS m/z: [M+H]$^+$ 486.

EXAMPLE 54

N'-Benzyl-5-chloro-3-[(4,4-difluorocyclohexyl)methyl]-2-(trifluoromethyl)imidazo[1,2-a]pyridine-7-carbohydrazide (Compound 107)

Step 1

To methyl 5-chloro-3-[(4,4-difluorocyclohexyl)methyl]-2-(trifluoromethyl)imidazo[1,2-a]pyridine-7-carboxylate obtained in Step 1 of Example 37 (10.0 mg, 0.0240 mmol), methanol (2.0 mL) and hydrazine monohydrate (24.0 mg, 0.487 mmol) were added thereto, and the mixture was stirred at room temperature overnight. The solvent in the reaction mixture was evaporated under reduced pressure, and the residue was purified by preparative thin-layer chromatography (chloroform/methanol=90/10), whereby 5-chloro-3-[(4,4-difluorocyclohexyl)methyl]-2-(trifluoromethyl)imidazo[1,2-a]pyridine-7-carbohydrazine (10.0 mg, yield quantitative) was obtained.

$^1$H NMR (300 MHz, CDCl$_3$, δ): 7.88 (d, J=1.6 Hz, 1H), 7.42 (br s, 1H), 7.41 (d, J=1.6 Hz, 1H), 4.18 (s, 2H), 3.35 (d, J=6.6 Hz, 2H), 2.09 (s, 2H), 1.71-1.20 (m, 7H).

Step 2

To 5-chloro-3-[(4,4-difluorocyclohexyl)methyl]-2-(trifluoromethyl)imidazo[1,2-a]pyridine-7-carbohydrazine obtained in Step 1 (10.0 mg, 0.0240 mmol), Dichloromethane (5.0 mL), pyridine (2.17 μL, 0.0270 mmol), and a solution of benzoyl chloride (3.76 mg, 0.0270 mmol) in dichloromethane (1.0 mL) were added thereto, and the mixture was stirred at room temperature overnight. Water was added to the reaction mixture, and the mixture was extracted with chloroform. The organic layer was dried over anhydrous sodium sulfate, and the solvent was evaporated under reduced pressure. The residue was purified by preparative thin-layer chromatography (chloroform/methanol=90/10), whereby Compound 107 (9.5 mg, yield 74%) was obtained.

$^1$H NMR (300 MHz, CD$_3$OD, δ): 8.19 (s, 1H), 7.93 (d, J=7.6 Hz, 2H), 7.60-7.54 (m, 4H), 3.39 (d, J=6.6 Hz, 2H), 2.12-1.12 (m, 9H); ESIMS m/z: [M+H]$^+$ 515.

EXAMPLE 55

(1H-Benzo[d]imidazol-2-yl){3-[(4,4-difluorocyclohexyl)methyl]-5-methyl-2-(trifluoromethyl)imidazo[1,2-a]pyridin-7-yl}methanone (Compound 111)

Compound 111 (4.1 mg, yield 45%) was obtained in the same manner as in Step 2 of Example 14, using Compound 112.

$^1$H NMR (300 MHz, CDCl$_3$, δ): 10.26 (br s, 1H), 9.64 (d, J=1.5 Hz, 1H), 7.96-7.92 (m, 1H), 7.62-7.57 (m, 2H), 7.51-7.37 (m, 2H), 3.26 (d, J=6.2 Hz, 2H), 2.95 (s, 3H), 2.19-2.05 (m, 2H), 1.76-1.44 (m, 7H); ESIMS m/z: [M+H]$^+$ 477.

EXAMPLE 56

(1H-Benzo[d]imidazol-2-yl){3-[(4,4-difluorocyclohexyl)methyl]-5-methyl-2-(trifluoromethyl)imidazo[1,2-a]pyridin-7-yl}methanol (Compound 112)

1-(Dimethoxymethyl)-1H-benzo[d]imidazol obtained by a method described in Tetrahedron Lett., vol. 46, p. 5081 (2005) (19 mg, 0.10 mmol) was dissolved in THF (0.5 mL), n-butyllithium (1.6 mol/L, solution in n-hexane) (0.062 mL, 0.10 mmol) was added thereto at −78° C., and the mixture was stirred at −78° C. for 10 minutes. After a solution of 3-[(4,4-difluorocyclohexyl)methyl]-5-methyl-2-(trifluoromethyl)imidazo[1,2-a]pyridine-7-carbaldehyde obtained in Step 2 of Example 41 (30 mg, 0.84 mmol) in THF (0.5 mL) was gently added to the reaction mixture, the temperature was raised to 0° C., and the mixture was stirred for 1 hour. Then, 3 mol/L hydrochloric acid (0.2 mL) was added to the reaction mixture, and the mixture was stirred at room temperature for 10 minutes. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=98/2 to 94/6), and then purified by preparative thin-layer chromatography (ethyl acetate), whereby Compound 112 (9.3 mg, yield 23%) was obtained.

$^1$H NMR (300 MHz, CDCl$_3$, δ): 7.68 (s, 1H), 7.50-7.37 (br m, 2H), 7.16-7.12 (m, 2H), 6.70 (s, 1H), 6.09 (s, 1H), 3.02 (d, J=6.2 Hz, 2H), 2.63 (s, 3H), 2.12-1.98 (m, 2H), 1.72-1.22 (m, 7H); ESIMS m/z: [M+H]$^+$ 479.

EXAMPLE 57

{3-[(4,4-Difluorocyclohexyl)methyl]-5-methyl-2-(trifluoromethyl)imidazo[1,2-a]pyridin-7-yl}(1-methyl-1H-benzo[d]imidazol-2-yl)methanol(Compound 120)

1-Methyl-1H-benzimidazol (22 mg, 0.17 mmol) was dissolved in THF (1.0 mL), n-butyllithium (1.6 mol/L, solution in n-hexane) (0.104 mL, 0.167 mmol) was added thereto at −78° C., and the mixture was stirred for 10 minutes. After gently adding a solution of 3-[(4,4-difluorocyclohexyl)methyl]-5-methyl-2-(trifluoromethyl)imidazo[1,2-a]pyridine-7-carbaldehyde obtained in Step 2 of Example 41 (50 mg, 0.14 mmol) in THF (1 mL) to the reaction mixture at −78° C., the temperature was raised to 0° C., and the mixture was stirred for 1 hour. A saturated aqueous ammonium chloride solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=98/2 to 94/6), whereby Compound 120 (14.3 mg, yield 21%) was obtained.

$^1$H NMR (300 MHz, CDCl$_3$, δ): 7.75-7.68 (m, 1H), 7.64 (s, 1H), 7.30-7.20 (m, 3H), 6.60 (s, 1H), 6.08 (s, 1H), 5.94 (br s, 1H), 3.63 (s, 3H), 3.13 (d, J=6.1 Hz, 2H), 2.72 (s, 3H), 2.15-1.98 (m, 2H), 1.75-1.34 (m, 7H); ESIMS m/z: [M+H]$^+$ 493.

EXAMPLE 58

{3-[(4,4-Difluorocyclohexyl)methyl]-5-methyl-2-(trifluoromethyl)imidazo[1,2-a]pyridin-7-yl}(1-methyl-1H-benzo[d]imidazol-2-yl)methanone (Compound 121)

Compound 121 (6.8 mg, yield 57%) was obtained in the same manner as in Step 2 of Example 14, using Compound 120.

$^1$H NMR (300 MHz, CDCl$_3$, δ): 9.04 (s, 1H), 7.92-7.88 (m, 1H), 7.52-7.47 (m, 3H), 7.45-7.38 (m, 1H), 4.20 (s, 3H), 3.25 (d, J=6.3 Hz, 2H), 2.93 (s, 3H), 2.19-2.06 (m, 2H), 1.77-1.42 (m, 7H); ESIMS m/z: [M+H]$^+$ 491.

EXAMPLE 59

3-{3-[(4,4-Difluorocyclohexyl)methyl]-5-methyl-2-(trifluoromethyl)imidazo[1,2-a]pyridin-7-yl}-N-(2,2-dimethyltetrahydro-2H-pyran-4-yl)-2,3-dihydroxypropanamide (Compound 122)

Compound 122 (11.8 mg, yield 48%) was obtained in the same manner as in Example 45, using Compound 119.

$^1$H NMR (300 MHz, CDCl$_3$, δ): 7.56 (s, 1H), 6.77-6.70 (m, 2H), 5.17-5.14 (m, 2H), 4.39-4.12 (m, 3H), 3.80-3.68 (m, 2H), 3.10 (d, J=6.3 Hz, 2H), 2.77 (s, 3H), 2.08-1.23 (m, 19H); ESIMS m/z: [M+H]$^+$ 548.

EXAMPLE 60

Ethyl 3-{3-[(4,4-difluorocyclohexyl)methyl]-5-methyl-2-(trifluoromethyl)imidazo[1,2-a]pyridine-7-carboxamide}-2-oxopropanoate (Compound 124)

Step 1

3-[(4,4-Difluorocyclohexyl)methyl]-5-methyl-2-(trifluoromethyl)imidazo[1,2-a]pyridine-7-carboxamide (489 mg, yield 95%) was obtained in the same manner as in Step 9 of Example 1, using 3-[(4,4-difluorocyclohexyl)methyl]-5-methyl-2-(trifluoromethyl)imidazo[1,2-a]pyridine-7-carboxylic acid obtained in Step 2 of Example 32 and ammonium chloride.

$^1$H NMR (300 MHz, CDCl$_3$, δ): 7.87-7.86 (m, 1H), 7.18-7.17 (m, 1H), 3.22 (d, J=6.2 Hz, 2H), 2.89 (s, 3H), 2.17-2.05 (m, 2H), 1.73-1.41 (m, 9H).

Step 2

3-[(4,4-Difluorocyclohexyl)methyl]-5-methyl-2-(trifluoromethyl)imidazo[1,2-a]pyridine-7-carboxamide obtained in Step 1 above (200 mg, 0.533 mmol) was dissolved in THF (5.0 mL), and sodium hydrogen carbonate (224 mg, 2.66 mmol) and ethyl bromopyruvate (0.223 mL, 1.60 mmol) were added thereto. Under reflux with heating, the mixture was stirred for 7 hours. Ethyl bromopyruvate (0.223 mL, 1.60 mmol) was added to the reaction mixture, and under reflux with heating, the mixture was stirred overnight. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (heptane/ethyl acetat=50/50), whereby Compound 124 (178 mg, 68%) was obtained.

$^1$H NMR (400 MHz, CDCl$_3$, δ): 8.13 (s, 1H), 7.28-7.27 (m, 2H), 4.85 (d, J=9.8 Hz, 1H), 4.46 (d, J=10.7 Hz, 1H), 4.41-4.30 (m, 2H), 3.22 (d, J=5.9 Hz, 2H), 2.87 (s, 3H), 2.16-2.06 (m, 2H), 1.72-1.27 (m, 10H); ESIMS m/z: [M+H]$^+$ 490.

EXAMPLE 61

3-[(4,4-Difluorocyclohexyl)methyl]-5-methyl-N-(2-oxaspiro[3.5]nonan-7-yl)-2-(trifluoromethyl)imidazo[1,2-a]pyridine-7-carboxamide (Compound 126)

Step 1

Ethyl 1,4-dioxaspiro[4.5]decane-8-carboxylate obtained by a method described in U.S. Pat. No. 4,985,411 (5.36 g, 25.0 mmol) was dissolved in THF (150 mL), lithium diisopropylamide (2.0 mol/L solution in THF/heptane/ethylbenzene) (15.0 mL, 30.0 mmol) was added thereto at −78° C., and the mixture was stirred for 1 hours. Ethyl chloroformate (3.6 mL, 27.5 mL) was added to the reaction mixture at −78° C., and the mixture was stirred for 1 hour. A saturated aqueous ammonium chloride solution was added to the reaction mixture, and the mixture was extracted with ethyl acetate. The organic layer was dried over anhydrous magnesium sulfate, and the solvent was evaporated under reduced pressure. The residue was purified by silica gel column column chromatography (hexane/ethyl acetate=90/10), whereby diethyl 1,4-dioxaspiro[4.5]decane-8,8-dicarboxylate (6.94 g, yield 97%) was obtained.

$^1$H NMR (270 MHz, CDCl$_3$, δ): 1.25 (t, J=7.1 Hz, 6H), 1.66-1.71 (m, 4H), 2.16-2.21 (m, 4H), 3.94 (s, 4H), 4.19 (q, J=7.1 Hz, 4H).

Step 2

Lithium aluminum hydride (0.725 g, 19.1 mmol) was suspended in THF (30 mL), diethyl 1,4-dioxaspiro[4.5]decane-8,8-dicarboxylate obtained in Step 1 (4.56 g, 15.9 mmol) was added thereto at 0° C., and the mixture was stirred for 1 hour. Lithium aluminum hydride (0.725 g, 19.1 mmol) was added to the reaction mixture, and the mixture was stirred at room temperature for 1 hour. Water (0.73 mL), 10 mol/L aqueous sodium hydroxide solution (0.32 mL), water (2.2 mL), and sodium sulfate were sequentially added to the reaction mixture, and the mixture was stirred overnight. The reaction mixture was filtrated through Celite (registered trademark), and the solvent in the filtrate was evaporated under reduced pressure. The residue was reslurried in a mixed solvent of hexane and ethyl acetate (5:1), whereby 1,4-dioxaspiro[4.5]decane-8,8-diyldimethanol (2.46 g, yield 76%) was obtained.

$^1$H NMR (270 MHz, CDCl$_3$, δ): 1.57 (m, 4H), 1.63 (m, 4H), 2.21 (t, J=3.9 Hz, 2H), 3.66 (d, J=3.9 Hz, 4H), 3.95 (s, 4H).

Step 3

1,4-Dioxaspiro[4.5]decane-8,8-diyldimethanol obtained in Step 2 (3.17 g, 15.7 mmol) was dissolved in THF (150 mL), n-butyllithium (6.81 mL, 18.8 mmol) was added thereto at 0° C., and the mixture was stirred for 30 minutes. A solution (30 mL) of p-toluenesulfonyl chloride (3.59 g, 18.8 mmol) in THF was added to the reaction mixture, and the mixture was stirred at room temperature for 1 hour. n-Butyllithium (6.81 mL, 18.8 mmol) was added to the reaction mixture at 0° C., and the mixture was stirred at 65° C. for 1 hour. A saturated aqueous sodium hydrogen carbonate solution was added to the reaction mixture, and the mixture was extracted with ethyl acetate. The organic layer was dried over anhydrous magnesium sulfate, and the solvent was evaporated under reduced pressure. The residue was purified by silica gel column chromatography (hexane/ ethyl acetate=80/20), whereby 1,4,10-trioxaspiro[3.4.5]tridecane (2.48 g, yield 86%) was obtained.

¹H NMR (300 MHz, CDCl₃, δ): 1.58 (t, J=6.2 Hz, 4H), 1.92 (t, J=6.2 Hz, 4H), 3.93 (s, 4H), 4.41 (s, 4H).

Step 4

1,4,10-Trioxaspiro[3.4.5]tridecane obtained in Step (25 g, 0.135 mol) was dissolved in THF (100 mL), 0.2% hydrochloric acid (290 mL) was added thereto, and the mixture was stirred at room temperature overnight. The reaction mixture was neutralized with a saturated aqueous sodium hydrogen carbonate solution, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=80/20) whereby 2-oxaspiro[3.5]nonan-7-one (17.1 g, yield 90%) was obtained.

¹H NMR (400 MHz, CDCl₃, δ): 2.18 (t, J=6.8 Hz, 4H), 2.33 (t, J=6.8 Hz, 4H), 4.56 (s, 4H).

Step 5

2-Oxaspiro[3.5]nonan-7-one obtained in Step 4 above (200 mg, 1.43 mmol) was dissolved in dichloroethane (4.0 mL), benzylamine (0.187 mL, 1.71 mmol) and sodium triacetoxyborohydride (363 mg, 1.71 mmol) were added thereto, and the mixture was stirred at room temperature for 1 hour. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (ethyl acetate/methanol=90/10), and then purified by amino-silica gel column chromatography (heptane/ethyl acetate=65/35 to 50/50), whereby N-benzyl-2-oxaspiro[3.5]nonan-7-amine (123 mg, yield 37%) was obtained.

¹H NMR (300 MHz, CDCl₃, δ): 7.35-7.22 (m, 5H), 4.38 (d, J 27.3 Hz, 4H), 3.80 (s, 2H), 2.52-2.44 (m, 1H), 2.16-2.10 (m, 2H), 1.88-1.81 (m, 2H), 1.57-1.40 (m, 2H), 1.20-1.07 (m, 2H).

Step 6

N-Benzyl-2-oxaspiro[3.5]nonan-7-amine obtained in Step 5 (120 mg, 0.519 mmol) was dissolved in THF (2.0 mL), and 10% palladium carbon (containing water) (120 mg) was added thereto. After displacing the inside of the reaction vessel with hydrogen gas, the mixture was stirred at room temperature for 5 hours. The reaction mixture was filtrated through Celite (registered trademark), the solvent was evaporated under reduced pressure, whereby 2-oxaspiro[3.5]nonan-7-amine (68.1 mg, yield 93%) was obtained.

¹H NMR (300 MHz, CDCl₃, δ): 4.38 (d, J=21.3 Hz, 4H), 2.69-2.58 (m, 1H), 2.16-2.08 (m, 2H), 1.89-1.71 (m, 2H), 1.53-1.40 (m, 2H), 1.26 (br s, 2H), 1.12-0.98 (m, 2H).

Step 7

Compound 126 (37.7 mg, yield 95%) was obtained in the same manner as in Step 9 of Example 1, using 2-oxaspiro[3.5]nonan-7-amine obtained in Step 6 and 3-[(4,4-difluorocyclohexyl)methyl]-5-methyl-2-(trifluoromethyl)imidazo[1,2-a]pyridine-7-carboxylic acid obtained in Step 2 of Example 32.

¹H NMR (300 MHz, CDCl₃, δ): 7.75 (s, 1H), 7.09 (s, 1H), 5.90 (d, J=7.0 Hz, 1H), 4.43 (d, J=19.1 Hz, 4H), 4.01-3.85 (m, 1H), 3.21 (d, J=6.2 Hz, 2H), 2.88 (s, 3H), 2.22-1.21 (m, 17H); ESIMS m/z: [M+H]⁺ 500.

EXAMPLE 62

5-Chloro-3-[(4,4-difluorocyclohexyl)methyl]-N-[1-oxo-1-(tetrahydro-2H-pyran-4-ylamino)propan-2-yl]-2-(trifluoromethyl)imidazo[1,2-a]pyridine-7-carboxamide (Compound 128)

Step 1

2-{5-Chloro-3-[(4,4-difluorocyclohexyl)methyl]-2-(trifluoromethyl)imidazo[1,2-a]pyridine-7-carboxamide}propionic acid (29.0 mg, yield 93%) was obtained in the same manner as in Step 8 of Example 1, using Compound 123.

¹H NMR (300 MHz, CD₃OD, δ): 8.16 (d, J=2.0 Hz, 1H), 7.62 (d, J=2.0 Hz, 1H), 4.45 (q, J=7.2 Hz, 1H), 3.37 (d, J=6.8 Hz, 2H), 2.03-1.96 (m, 2H), 1.76-1.29 (m, 10H); ESIMS m/z: [M−H]⁻ 466.

Step 2

Compound 128 (9.5 mg, yield 73%) was obtained in the same manner as in Step 9 of Example 1, using 2-{5-chloro-3-[(4,4-difluorocyclohexyl)methyl]-2-(trifluoromethyl)imidazo[1,2-a]pyridine-7-carboxamide}propionic acid obtained in Step 1 and tetrahydro-2H-pyran-4-amine hydrochloride.

¹H NMR (300 MHz, CDCl₃, δ): 8.07 (d, J=2.0 Hz, 1H), 7.43 (s, 1H), 7.36 (d, J=6.8 Hz, 1H), 6.08 (d, J=7.8 Hz, 1H), 4.65-4.59 (m, 1H), 4.06-3.94 (m, 3H), 3.53-3.46 (m, 2H), 3.35 (d, J=6.8 Hz, 2H), 2.11-1.26 (m, 16H); ESIMS m/z: [M+H]⁺ 551.

EXAMPLE 63

5-Chloro-3-[(4,4-difluorocyclohexyl)methyl]-N-(2-oxaspiro[3.3]heptan-6-yl)-2-(trifluoromethyl)imidazo[1,2-a]pyridine-7-carboxamide (Compound 129)

Compound 129 (37.7 mg, yield 95%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 1 of Example 42 and a commercially available product of 2-oxaspiro[3.3]heptan-6-amine hydrochloride (Pharma Block, catalog No. PBN2011614).

¹H NMR (300 MHz, CDCl₃, δ): 7.83 (d, J=1.5 Hz, 1H), 7.41 (d, J=1.5 Hz, 1H), 6.21 (d, J=6.6 Hz, 1H), 4.78 (s, 2H), 4.66 (s, 2H), 4.42-4.32 (m, 1H), 3.35 (d, J=7.3 Hz, 2H), 2.86-2.77 (m, 2H), 2.24-2.05 (m, 4H), 1.72-1.40 (m, 7H); ESIMS m/z: [M+H]⁺ 492.

EXAMPLE 64

5-Chloro-3-[(4,4-difluorocyclohexyl)methyl]-N-[2-oxo-2-(tetrahydro-2H-pyran-4-ylamino)ethyl]-2-(trifluoromethyl)imidazo[1,2-a]pyridine-7-carboxamide (Compound 130)

Step 1

2-{5-Chloro-3-[(4,4-difluorocyclohexyl)methyl]-2-(trifluoromethyl)imidazo[1,2-a]pyridine-7-carboxamide}acetic acid (14.0 mg, yield 97%) was obtained in the same manner as in Step 8 of Example 1, using Compound 110.

¹H NMR (300 MHz, CD₃OD, δ): 8.15 (s, 1H), 7.62 (d, J=2.0 Hz, 1H), 3.97 (s, 2H), 3.38 (d, J=6.8 Hz, 2H), 2.06-1.29 (m, 9H); ESIMS m/z: [M−H]⁻ 452.

Step 2

Compound 130 (9.4 mg, yield 94%) was obtained in the same manner as in Step 9 of Example 1, using 2-{5-chloro-3-[(4,4-difluorocyclohexyl)methyl]-2-(trifluoromethyl)imidazo[1,2-a]pyridine-7-carboxamide}acetic acid obtained in Step 1 and tetrahydro-2H-pyran-4-amine hydrochloride.

$^1$H NMR (300 MHz, CDCl$_3$, δ): 8.05 (s, 1H), 7.44 (d, J=2.0 Hz, 1H), 7.28 (d, J=5.9 Hz, 1H), 5.86 (d, J=7.8 Hz, 1H), 4.11 (d, J=4.9 Hz, 2H), 4.04-3.99 (m, 3H), 3.49 (td, J=11.7, 2.0 Hz, 2H), 3.35 (d, J=6.8 Hz, 2H), 2.11 (t, J=25.4 Hz, 2H), 1.89 (dd, J=22.4, 20.5 Hz, 3H), 1.68-1.25 (m, 8H); ESIMS m/z: [M+H]$^+$ 537.

EXAMPLE 65

3-[(4,4-Difluorocyclohexyl)methyl]-8-methoxy-5-methyl-N-(tetrahydro-2H-pyran-4-yl)-2-(trifluoromethyl)imidazo[1,2-a]pyridine-7-carboxamide (Compound 133)

Step 1

{3-[(4,4-Difluorocyclohexyl)methyl]-7-(tetrahydro-2H-pyran-4-ylcarbamoyl)-2-(trifluoromethyl)imidazo[1,2-a]pyridin-5-yl}methyl methanesulfonate (29.9 mg, yield 66%) was obtained in the same manner as in Step 2 of Example 10, using Compound 46.

$^1$H NMR (300 MHz, CDCl$_3$, δ): 8.04 (d, J=1.8 Hz, 1H), 7.57 (d, J=1.8 Hz, 1H), 6.19 (d, J=8.1 Hz, 1H), 5.56 (s, 2H), 4.31-4.15 (m, 1H), 4.07-3.96 (m, 2H), 3.63-3.45 (m, 2H), 3.20 (d, J=5.1 Hz, 2H), 3.08 (s, 3H), 2.19-1.95 (m, 4H), 1.88-1.40 (m, 9H); ESIMS m/z: [M+H]$^+$ 554.

Step 2

{3-[(4,4-Difluorocyclohexyl)methyl]-7-(tetrahydro-2H-pyran-4-ylcarbamoyl)-2-(trifluoromethyl)imidazo[1,2-a]pyridin-5-yl}methyl methanesulfonate obtained in Step 1 (240 mg, 0.434 mmol) was suspended in 1,4-dioxane (10 mL), 28% sodium methoxide (solution in methanol) (0.172 mL, 0.867 mmol) was added thereto, and the mixture was stirred at room temperature for 10 minutes. Acetone and saturated aqueous sodium hydrogen carbonate solution were added to the reaction mixture, and the mixture was extracted with ethyl acetate. The organic layer was washed with saturated brine and dried over anhydrous sodium sulfate, and the solvent was evaporated under reduced pressure. The residue was purified by silica gel column chromatography (chloroform/methanol=98/2 to 95/5), whereby Compound 133 (158 mg, yield 74%) was obtained.

$^1$H NMR (300 MHz, CDCl$_3$, δ): 7.94 (d, J=7.3 Hz, 1H), 7.29 (s, 1H), 4.39 (s, 3H), 4.28-4.15 (m, 1H), 4.02-3.93 (m, 2H), 3.63-3.51 (m, 2H), 3.19 (d, J=6.2 Hz, 2H), 2.80 (s, 3H), 2.19-1.96 (m, 4H), 1.75-1.19 (m, 9H); ESIMS m/z: [M+H]$^+$ 490.

EXAMPLE 66

Ethyl 1-{5-chloro-3-[(4,4-difluorocyclohexyl)methyl]-2-(trifluoromethyl)imidazo[1,2-a]pyridine-7-carboxamide}cyclopropanecarboxylate (Compound 135)

Compound 135 (64.6 mg, yield 98%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 1 of Example 42 and ethyl 1-aminocyclopropanecarboxylate hydrochloride.

$^1$H NMR (300 MHz, CDCl$_3$, δ): 7.93 (d, J=2.0 Hz, 1H), 7.46 (s, 1H), 7.01 (s, 1H), 4.17 (q, J=7.2 Hz, 2H), 3.34 (d, J=6.8 Hz, 2H), 2.14 (d, J=27.3 Hz, 2H), 1.83-0.86 (m, 14H); ESIMS m/z: [M+H]$^+$ 508.

EXAMPLE 67

3-[(4,4-Difluorocyclohexyl)methyl]-2-(1,1-difluoroethyl)-5-methyl-N-(2-oxaspiro[3.3]heptan-6-yl)imidazo[1,2-a]pyridine-7-carboxamide (Compound 136)

Step 1

Ethyl 3-[(4,4-difluorocyclohexyl)methyl]-2-(1,1-difluoroethyl)-5-methylimidazo[1,2-a]pyridine-7-carboxylate (7.90 mg, yield 13%) was obtained in the same manner as in Step 5 of Example 1, using ethyl 2-bromo-1-(4,4-difluorocyclohexyl)-4,4-difluoropentan-3-one obtained in Step 6 of Example 5 and ethyl 2-amino-6-methylpyridine-4-carboxylate.

$^1$H NMR (300 MHz, CDCl$_3$, δ): 8.22 (d, J=1.1 Hz, 1H), 7.16 (d, J=1.1 Hz, 1H), 4.40 (q, J=7.1 Hz, 3H), 3.28 (d, J=6.6 Hz, 2H), 2.88 (s, 3H), 2.26-1.33 (m, 14H); ESIMS m/z: [M+H]$^+$ 401.

Step 2

3-[(4,4-Difluorocyclohexyl)methyl]-2-(1,1-difluoroethyl)-5-methylimidazo[1,2-a]pyridine-7-carboxylic acid (179 mg, yield 75%) was obtained in the same manner as in Step 8 of Example 1, using ethyl 3-[(4,4-difluorocyclohexyl)methyl]-2-(1,1-difluoroethyl)-5-methylimidazo[1,2-a]pyridine-7-carboxylate obtained in Step 1.

$^1$H NMR (300 MHz, DMSO-d$_6$, δ): 13.30 (br s, 1H), 7.97 (d, J=1.1 Hz, 1H), 7.19 (d, J=1.1 Hz, 1H), 3.21 (d, J=7.0 Hz, 2H), 2.91 (s, 3H), 2.10 (t, J=19.1 Hz, 3H), 2.02-1.18 (m, 9H); ESIMS m/z: [M+H]$^+$ 373.

Step 3

Compound 136 (3.3 mg, yield 52%) was obtained in the same manner as in Step 9 of Example 1, using 3-[(4,4-difluorocyclohexyl)methyl]-2-(1,1-difluoroethyl)-5-methylimidazo[1,2-a]pyridine-7-carboxylic acid obtained in Step 2 and 2-oxaspiro[3.3]heptan-6-amine.

$^1$H NMR (300 MHz, CDCl$_3$, δ): 7.74 (d, J=1.1 Hz, 1H), 7.04 (d, J=1.1 Hz, 1H), 6.24 (d, J=7.0 Hz, 1H), 4.78 (s, 2H), 4.66 (s, 2H), 4.44-4.30 (m, 1H), 3.26 (d, J=6.6 Hz, 2H), 2.86 (s, 3H), 2.85-2.76 (m, 2H), 2.23-2.01 (m, 7H), 1.74-1.38 (m, 7H); ESIMS m/z: [M+H]$^+$ 468.

EXAMPLE 68

2-tert-Butyl-3-[(4,4-difluorocyclohexyl)methyl]-5-methyl-N-(2-oxaspiro[3.3]heptan-6-yl)imidazo[1,2-a]pyridine-7-carboxamide (Compound 137)

Compound 137 (15.0 mg, yield 79%) was obtained in the same manner as in Step 9 of Example 1, using 2-tert-butyl-3-[(4,4-difluorocyclohexyl)methyl]-5-methylimidazo[1,2-a]pyridine-7-carboxylic acid obtained in Step 5 of Example 4 and 2-oxaspiro[3.3]heptan-6-amine.

$^1$H NMR (300 MHz, CDCl$_3$, δ): 7.71 (d, J=1.8 Hz, 1H), 6.96 (d, J=1.8 Hz, 1H), 6.26 (d, J=7.3 Hz, 1H), 4.77 (s, 2H), 4.65 (s, 2H), 4.43-4.29 (m, 1H), 3.20 (d, J=6.6 Hz, 2H), 2.83-2.74 (m, 5H), 2.18-2.00 (m, 4H), 1.69-1.22 (m, 16H); ESIMS m/z: [M+H]$^+$ 460.

EXAMPLE 69

5-Cyano-3-[(4,4-difluorocyclohexyl)methyl]-N-[(4-methoxytetrahydro-2H-pyran-4-yl)methyl]-2-(trifluoromethyl)imidazo[1,2-a]pyridine-7-carboxamide (Compound 141)

Compound 141 (11.1 mg, yield 28%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and (4-methoxytetrahydro-2H-pyran-4-yl)methanamine hydrochloride.

$^1$H NMR (300 MHz, CDCl$_3$, δ): 8.23 (d, J=1.8 Hz, 1H), 8.06 (d, J=1.8 Hz, 1H), 6.42 (br s, 1H), 3.74 (dd, J=7.0, 3.7 Hz, 4H), 3.58 (d, J=5.1 Hz, 2H), 3.36 (d, J=7.0 Hz, 2H), 3.26 (s, 3H), 2.14-2.11 (m, 2H), 1.83-1.44 (m, 11H); ESIMS m/z: [M+H]$^+$ 515.

EXAMPLE 70

3-Butyl-2-isopropyl-N-phenylimidazo[1,2-a]pyridine-7-carboxamide (Compound 144)

Step 1

2-Isopropylimidazo[1,2-a]pyridine-7-carbonitrile (15.6 g, yield 60%) was obtained in the same manner as in Step 5 of Example 1, using 2-aminoisonicotinonitrile and 1-bromo-3-methylbutan-2-one.

$^1$H NMR (300 MHz, CDCl$_3$, δ): 8.13 (d, J=6.8 Hz, 1H), 7.94 (s, 1H), 7.50 (s, 1H), 6.89 (dd, J=6.8, 2.0 Hz, 1H), 3.21-3.11 (m, 1H), 1.38 (d, J=6.8 Hz, 6H).

Step 2

2-Isopropylimidazo[1,2-a]pyridine-7-carboxylic acid was obtained in the same manner as in Step 8 of Example 1, using 2-isopropylimidazo[1,2-a]pyridine-7-carbonitrile obtained in Step 1, and the product was used in the next reaction without purification.

Step 3

2-Isopropyl-N-phenylimidazo[1,2-a]pyridine-7-carboxamide (1.50 g, yield quantitative) was obtained in the same manner as in Step 9 of Example 1, using 2-isopropylimidazo[1,2-a]pyridine-7-carboxylic acid obtained in Step 2 and aniline.

$^1$H NMR (300 MHz, CDCl$_3$, δ): $^1$H-NMR (CDCl$_3$) δ: 8.14 (dd, J=7.1, 0.9 Hz, 1H), 8.01 (d, J=0.7 Hz, 1H), 7.92 (br s, 1H), 7.64 (dd, J=8.6, 0.9 Hz, 2H), 7.46 (s, 1H), 7.42-7.37 (m, 2H), 7.31 (dd, J=7.1, 1.6 Hz, 1H), 7.21-7.15 (m, 1H), 3.20-3.11 (m, 1H), 1.39 (d, J=7.0 Hz, 6H).

Step 4

2-Isopropyl-N-phenylimidazo[1,2-a]pyridine-7-carboxamide obtained in Step 3 (100 mg, 0.36 mmol) was dissolved in acetic acid (1.0 ml), n-butylaldehyde (3.27 g, 45.3 mmol) was added thereto, and the mixture was stirred at 80° C. overnight. The solvent in the reaction mixture was evaporated under reduced pressure. A saturated aqueous sodium hydrogen carbonate solution was added to the residue, and the mixture was extracted with ethyl acetate. The organic layer was dried over anhydrous magnesium sulfate, and the solvent was evaporated under reduced pressure. The residue was purified by silica gel column chromatography (heptane/ethyl acetate=100/0 to 80/20), whereby (E)-3-(1-butenyl)-2-isopropyl-N-phenylimidazo[1,2-a]pyridine-7-carboxamide (85.3 mg, yield 72%) was obtained.

$^1$H NMR (300 MHz, CDCl$_3$, δ): 8.18 (dd, J=7.0, 1.1 Hz, 1H), 8.04 (d, J=1.1 Hz, 1H), 7.82 (br s, 1H), 7.64-7.63 (m, 2H), 7.41-7.36 (m, 3H), 7.19-7.16 (m, 1H), 6.47 (dt, J=16.1, 1.5 Hz, 1H), 6.21 (dt, J=16.1, 6.4 Hz, 1H), 3.28 (td, J=14.2, 7.6 Hz, 1H), 2.38 (tt, J=13.7, 4.6 Hz, 2H), 1.40 (d, J=7.0 Hz, 6H), 1.19 (t, J=7.5 Hz, 3H).

Step 5

Compound 144 (21.0 mg, yield 78%) was obtained in the same manner as in Step 2 of Example 1, using (E)-3-(buten-1-yl)-2-isopropyl-N-phenylimidazo[1,2-a]pyridine-7-carboxamide obtained in Step 4.

$^1$H NMR (300 MHz, CDCl$_3$, δ): 8.04 (s, 1H), 7.95 (d, J=7.0 Hz, 1H), 7.88 (s, 1H), 7.64 (d, J=7.7 Hz, 2H), 7.42-7.34 (m, 3H), 7.17 (t, J=7.3 Hz, 1H), 3.21-3.12 (m, 1H), 2.92 (t, J=7.5 Hz, 2H), 1.66-1.56 (m, 3H), 1.43 (dt, J=19.9, 6.2 Hz, 2H), 1.38 (d, J=7.0 Hz, 6H), 0.97 (t, J=7.3 Hz, 3H); ESIMS m/z: [M+H]$^+$ 336.

EXAMPLE 71

3-[(4,4-Difluorocyclohexyl)methyl]-2-isopropyl-5-methyl-N-(2-oxaspiro[3.3]heptan-6-yl)imidazo[1,2-a]pyridine-7-carboxamide (Compound 145)

Step 1

Ethyl 2-isopropyl-5-methylimidazo[1,2-a]pyridine-7-carboxylate (835 mg, yield 21%) was obtained in the same manner as in Step 5 of Example 1, using 1-bromo-3-methylbutan-2-one and ethyl 2-amino-6-methylpyridine-4-carboxylate.

$^1$H NMR (300 MHz, CDCl$_3$, δ): 8.24-8.22 (m, 1H), 7.32-7.31 (m, 1H), 7.21-7.20 (m, 1H), 4.39 (q, J=7.2 Hz, 2H), 3.22-3.13 (m, 1H), 2.61 (s, 3H), 1.43-1.38 (m, 9H).

Step 2

Ethyl 3-iodo-2-isopropyl-5-methylimidazo[1,2-a]pyridine-7-carboxylate (971 mg, yield 77%) was obtained in the same manner as in Step 2 of Example 4, using ethyl 2-isopropyl-5-methylimidazo[1,2-a]pyridine-7-carboxylate obtained in Step 1.

$^1$H NMR (300 MHz, CDCl$_3$, δ): 8.23 (d, J=1.0 Hz, 1H), 7.08 (d, J=1.0 Hz, 1H), 4.37 (q, J=7.1 Hz, 2H), 3.30-3.19 (m, 1H), 3.22 (s, 3H), 1.39 (t, J=7.1 Hz, 3H), 1.35 (d, J=6.9 Hz, 6H).

Step 3

Ethyl 3-[(4,4-difluorocyclohexyl)(hydroxy)methyl]-2-isopropyl-5-methylimidazo[1,2-a]pyridine-7-carboxylate (276 mg, yield 52%) was obtained in the same manner as in Step 3 of Example 4, using ethyl 3-iodo-2-isopropyl-5-methylimidazo[1,2-a]pyridine-7-carboxylate obtained in Step 2 and 4,4-difluorocyclohexanecarbaldehyde.

$^1$H NMR (300 MHz, CDCl$_3$, δ): 8.22 (d, J=1.8 Hz, 1H), 7.14 (d, J=1.8 Hz, 1H), 5.25 (d, J=9.2 Hz, 1H), 4.38 (q, J=7.1 Hz, 2H), 3.50-3.38 (m, 1H), 2.87 (s, 3H), 2.50-0.73 (m, 19H); ESIMS m/z: [M+H]$^+$ 395.

Step 4

Ethyl 3-[(4,4-difluorocyclohexyl)methyl]-2-isopropyl-5-methylimidazo[1,2-a]pyridine-7-carboxylate (78.1 mg, yield 37%) was obtained in the same manner as in Step 4 of Example 4, using ethyl 3-[(4,4-difluorocyclohexyl)(hydroxy)methyl]-2-isopropyl-5-methylimidazo[1,2-a]pyridine-7-carboxylate obtained in Step 3.

$^1$H NMR (300 MHz, CDCl$_3$, δ): 8.21 (d, J=1.8 Hz, 1H), 7.07 (d, J=1.8 Hz, 1H), 4.37 (q, J=7.1 Hz, 2H), 3.14-3.05 (m, 1H), 3.03 (d, J=7.0 Hz, 2H), 2.83 (s, 3H), 2.16-2.03 (m, 2H), 1.77-1.32 (m, 16H); ESIMS m/z: [M+H]$^+$ 379.

Step 5

3-[(4,4-Difluorocyclohexyl)methyl]-2-isopropyl-5-methylimidazo[1,2-a]pyridine-7-carboxylic acid (123 mg, yield 83%) was obtained in the same manner as in Step 8 of Example 1, using ethyl 3-[(4,4-difluorocyclohexyl)methyl]-2-isopropyl-5-methylimidazo[1,2-a]pyridine-7-carboxylate obtained in Step 4.

$^1$H NMR (300 MHz, DMSO-d$_6$, δ): 7.86 (s, 1H), 7.05 (s, 1H), 3.17-3.08 (m, 1H), 3.03 (d, J=7.0 Hz, 2H), 2.86 (s, 3H), 2.03-1.59 (m, 7H), 1.33-1.25 (m, 8H); ESIMS m/z: [M+H]$^+$ 351.

Step 6

Compound 145 (24.1 mg, yield 95%) was obtained in the same manner as in Step 9 of Example 1, using 3-[(4,4-difluorocyclohexyl)methyl]-2-isopropyl-5-methylimidazo[1,2-a]pyridine-7-carboxylic acid obtained in Step 5 and 2-oxaspiro[3.3]heptan-6-amine.

$^1$H NMR (300 MHz, CDCl$_3$, δ): 7.70 (s, 1H), 6.96 (s, 1H), 6.17 (d, J=7.3 Hz, 1H), 4.77 (s, 2H), 4.65 (s, 2H), 4.41-4.28 (m, 1H), 3.07 (sep, J=6.8 Hz, 1H), 3.01 (d, J=6.6 Hz, 2H), 2.85-2.73 (m, 5H), 2.19-2.03 (m, 4H), 1.79-1.48 (m, 7H), 1.34 (d, J=6.8 Hz, 6H); ESIMS m/z: [M+H]$^+$ 446.

EXAMPLE 72

5-Cyano-3-[(4,4-difluorocyclohexyl)methyl]-N-(2-oxaspiro[3.3]heptan-6-yl)-2-(trifluoromethyl)imidazo[1,2-a]pyridine-7-carboxamide (Compound 146)

Compound 146 (18.2 mg, yield 73%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and 2-oxaspiro[3.3]heptan-6-amine.

$^1$H NMR (300 MHz, CDCl$_3$, δ): 8.15 (d, J=1.8 Hz, 1H), 8.02 (d, J=1.8 Hz, 1H), 6.26 (d, J=7.0 Hz, 1H), 4.79 (s, 2H), 4.67 (s, 2H), 4.44-4.30 (m, 1H), 3.35 (d, J=7.0 Hz, 2H), 2.89-2.77 (m, 2H), 2.30-1.99 (m, 4H), 1.88-1.47 (m, 7H); ESIMS m/z: [M+H]$^+$ 483.

EXAMPLE 73

6-Chloro-3-[(4,4-difluorocyclohexyl)methyl]-2-(1,1-difluoroethyl)-N-(2-oxaspiro[3.3]heptan-6-yl)imidazo[1,2-a]pyridine-7-carboxamide (Compound 147)

Compound 147 (21.3 mg, yield 86%) was obtained in the same manner as in Step 9 of Example 1, using 6-chloro-3-[(4,4-difluorocyclohexyl)methyl]-2-(1,1-difluoroethyl)imidazo[1,2-a]pyridine-7-carboxylic acid obtained in Step 8 of Example 5 and 2-oxaspiro[3.3]heptan-6-amine.

$^1$H NMR (300 MHz, CDCl$_3$, δ): 7.99 (s, 1H), 7.91 (s, 1H), 6.24 (d, J=7.0 Hz, 1H), 4.78 (s, 2H), 4.66 (s, 2H), 4.47-4.32 (m, 1H), 3.01 (d, J=7.0 Hz, 2H), 2.90-2.77 (m, 2H), 2.25-2.00 (m, 7H), 1.80-1.44 (m, 7H); ESIMS m/z: [M+H]$^+$ 488.

EXAMPLE 74

2-tert-Butyl-6-chloro-3-[(4,4-difluorocyclohexyl)methyl]-N-(2-oxaspiro[3.3]heptane-6-yl)imidazo[1,2-a]pyridine-7-carboxamide (Compound 148)

Step 1

3-(4,4-Difluorocyclohexyl)propionic acid (3.84 g, quantitative) was obtained in the same manner as in Step 8 of Example 1, using ethyl 3-(4,4-difluorocyclohexyl)propionate obtained in Step 2 of Example 1.

$^1$H NMR (270 MHz, CDCl$_3$, δ): 2.39 (t, J=7.7 Hz, 2H), 2.18-2.01 (m, 2H), 1.85-1.21 (m, 9H).

Step 2

3-(4,4-Difluorocyclohexyl)propionic acid obtained in Step 1 (330 mg, 1.72 mmol) was dissolved in thionyl chloride (3.0 mL), and the mixture was stirred under reflux with heating for 4 hours. The solvent in the reaction mixture was evaporated under reduced pressure. The residue was dissolved in THF (3.3 mL) under ice-cooled condition, copper(I) chloride(8.5 mg, 0.086 mmol) and tert-butylmagnesium chloride (2 mol/L solution in THF) (1.03 mL, 2.06 mmol) were added thereto, and the mixture was stirred at room temperature for 30 minutes. Under ice-cooled condition, a saturated aqueous ammonium chloride solution was added to the reaction mixture, and the mixture was extracted with ethyl acetate. The organic layer was washed with saturated brine and dried over anhydrous magnesium sulfate, and the solvent was evaporated under reduced pressure. The residue was dissolved in ethanol (4.0 mL), tetra-n-butylammonium tribromide (910 mg, 1.89 mmol) was added thereto, and the mixture was stirred under reflux with heating for 2 hours. Under ice-cooled condition, a saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=97/3 to 90/10), whereby 2-bromo-1-(4,4-difluorocyclohexyl)-4,4-dimethylpentan-3-one (433 mg, yield 81%) was obtained.

$^1$H NMR (270 MHz, CDCl$_3$, δ): 4.71-4.68 (m, 1H), 2.15-1.16 (m, 11H), 1.23 (d, J=5.6 Hz, 9H).

Step 3

2-tert-Butyl-6-chloro-3-[(4,4-difluorocyclohexyl)methyl]imidazo[1,2-a]pyridine-7-carbonitrile (161 mg, yield 9%) was obtained in the same manner as in Step 5 of Example 1, using 2-bromo-1-[(4,4-difluorocyclohexyl)methyl]-4,4-dimethylpentan-3-one obtained in Step 2 and 2-amino-5-chloro-4-cyanopyridine obtained in Step 1 of Example 5.

$^1$H NMR (300 MHz, CDCl$_3$, δ): 7.97 (s, 2H), 3.00 (d, J=7.3 Hz, 2H), 2.20-2.09 (m, 2H), 1.81-1.16 (m, 16H).

Step 4

2-tert-Butyl-6-chloro-3-[(4,4-difluorocyclohexyl)methyl]imidazo[1,2-a]pyridine-7-carboxylic acid (139 mg, yield 88%) was obtained in the same manner as in Step 8 of Example 1, using 2-tert-butyl-6-chloro-3-[(4,4-difluorocyclohexyl)methyl]imidazo[1,2-a]pyridine-7-carbonitrile obtained in Step 3.

$^1$H NMR (300 MHz, DMSO-d$_6$, δ): 8.66 (s, 1H), 7.96 (s, 1H), 3.06 (d, J=7.3 Hz, 2H), 2.06-1.19 (m, 18H); ESIMS m/z: [M+H]$^+$ 385, 387.

Step 5

Compound 148 (19.5 mg, yield 78%) was obtained in the same manner as in Step 9 of Example 1, using 2-tert-butyl-6-chloro-3-[(4,4-difluorocyclohexyl)methyl]imidazo[1,2-a]pyridine-7-carboxylic acid obtained in Step 4 and 2-oxaspiro[3.3]heptan-6-amine.

$^1$H NMR (300 MHz, CDCl$_3$, δ): 7.90 (s, 1H), 7.90 (s, 1H), 6.24 (d, J=6.8 Hz, 1H), 4.77 (s, 2H), 4.65 (s, 2H), 4.45-4.32 (m, 1H), 2.98 (d, J=7.3 Hz, 2H), 2.87-2.76 (m, 2H), 2.20-2.03 (m, 4H), 1.82-1.54 (m, 7H), 1.46 (s, 9H); ESIMS m/z: [M+H]$^+$ 480.

EXAMPLE 75

5-Cyano-3-[(4,4-difluorocyclohexyl)methyl]-N-[3-(2-oxopyrrolidin-1-yl)propyl]-2-(trifluoromethyl)imidazo[1,2-a]pyridine-7-carboxamide (Compound 149) Compound 149 (31.5 mg, yield 80%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and 1-(3-aminopropyl)pyrrolidin-2-one.

$^1$H NMR (300 MHz, CDCl$_3$, δ): 8.54 (d, J=1.8 Hz, 1H), 8.53 (br t, J=5.5 Hz, 1H), 8.16 (d, J=1.8 Hz, 1H), 3.48-3.41 (m, 6H), 3.35 (d, J=7.0 Hz, 2H), 2.49 (t, J=8.1 Hz, 2H), 2.10 (td, J=15.2, 7.7 Hz, 4H), 1.72-1.57 (m, 9H); ESIMS m/z: [M+H]$^+$ 512.

EXAMPLE 76

Ethyl 2-{3-[(4,4-difluorocyclohexyl)methyl]-5-methyl-2-(trifluoromethyl)imidazo[1,2-a]pyridin-7-yl}oxazole-5-carboxylate (Compound 153)

Step 1
3-[(4,4-Difluorocyclohexyl)methyl]-5-methyl-2-(trifluoromethyl)imidazo[1,2-a]pyridine-7-carboxamide (489 mg, yield 95%) was obtained in the same manner as in Step 9 of Example 1, using 3-[(4,4-difluorocyclohexyl)methyl]-5-methyl-2-(trifluoromethyl)imidazo[1,2-a]pyridine-7-carboxylic acid obtained in Step 2 of Example 32 and ammonium chloride.

$^1$H NMR (300 MHz, CDCl$_3$, δ): 7.87-7.86 (m, 1H), 7.18-7.17 (m, 1H), 3.22 (d, J=6.2 Hz, 2H), 2.89 (s, 3H), 2.10 (br s, 2H), 1.64-1.48 (m, 9H).

Step 2
3-[(4,4-Difluorocyclohexyl)methyl]-5-methyl-2-(trifluoromethyl)imidazo[1,2-a]pyridine-7-carboxamide obtained in Step 1 (500 mg, 1.33 mmol) was dissolved in THF (10 mL), sodium hydrogen carbonate (560 mg, 6.66 mmol) and ethyl bromopyruvate (0.931 mL, 6.66 mmol) were added thereto, and the mixture was stirred under reflux with heating overnight. Ethyl bromopyruvate (0.503 mL, 4.00 mmol) was further added to the reaction mixture, and the mixture was stirred under reflux with heating overnight. A saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=80/20 to 50/50), whereby ethyl 3-{3-[(4,4-difluorocyclohexyl)methyl]-5-methyl-2-(trifluoromethyl)imidazo[1,2-a]pyridine-7-carboxamide}-2-oxopropionate (783 mg, yield quantitative) was obtained.

$^1$H NMR (300 MHz, CDCl$_3$, δ): 8.14 (s, 1H), 7.27 (m, 2H), 4.85 (d, J=10.3 Hz, 1H), 4.45 (d, J=10.3 Hz, 1H), 4.36-4.32 (m, 2H), 3.22 (d, J=6.8 Hz, 2H), 2.87 (s, 3H), 2.10 (s, 2H), 1.67-1.25 (m, 10H).

Step 3
Ethyl 3-{3-[(4,4-difluorocyclohexyl)methyl]-5-methyl-2-(trifluoromethyl)imidazo[1,2-a]pyridine-7-carboxamide}-2-oxopropionate obtained in Step 2 (30.0 mg, 0.0610 mmol) was dissolved in xylene (0.5 mL), ammonium trifluoroacetate (161 mg, 1.23 mmol) was added thereto, and the mixture was stirred at 150° C. for 10 minutes using microwave chemical synthesis apparatus (CEM Discover). The reaction mixture was filtrated through Presep (registered trademark; diatomite, granular type M, 4.5 g/25 mL), and the solvent was evaporated under reduced pressure. The residue was purified by silica gel column chromatography (heptane/ethyl acetate=80/20 to 50/50), whereby Compound 153 (3.50 mg, yield 12%) was obtained.

$^1$H NMR (300 MHz, CDCl$_3$, δ): 8.32 (s, 1H), 8.19-8.16 (m, 1H), 7.50-7.47 (m, 1H), 4.45 (q, J=7.1 Hz, 2H), 3.23 (d, J=6.2 Hz, 2H), 2.91 (s, 3H), 2.25-2.11 (m, 3H), 1.69-1.26 (m, 9H); ESIMS m/z: [M+H]+ 472.

EXAMPLE 77

5-Cyano-3-[(4,4-difluorocyclohexyl)methyl]-N-[2-(dimethylamino)-2-methylpropyl]-2-(trifluoromethyl)imidazo[1,2-a]pyridine-7-carboxamide (Compound 156)

Step 1
N-(2-Amino-2-methylpropyl)-5-cyano-3-[(4,4-difluorocyclohexyl)methyl]-2-(trifluoromethyl)imidazo[1,2-a]pyridine-7-carboxamide (33.5 mg, 71%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and 2-methylpropane-1,2-diamine.

$^1$H NMR (400 MHz, CD$_3$OD, δ): 8.46 (d, J=1.7 Hz, 1H), 8.21 (d, J=1.7 Hz, 1H), 3.39-3.36 (m, 4H), 2.02-2.00 (m, 2H), 1.85-1.78 (m, 2H), 1.72-1.61 (m, 1H), 1.50-1.41 (m, 2H), 1.34-1.23 (m, 2H), 1.17 (s, 6H).

Step 2
N-(2-Amino-2-methylpropyl)-5-cyano-3-[(4,4-difluorocyclohexyl)methyl]-2-(trifluoromethyl)imidazo[1,2-a]pyridine-7-carboxamide obtained in Step 1 (32.0 mg, 0.0700 mmol) was dissolved in a mixed solvent of dichloromethane (1.0 mL) and methanol (1.0 mL), 37% aqueous formaldehyde (0.0520 mL, 0.700 mmol) and sodium triacetoxyborohydride (74.0 mg, 0.0350 mmol) were added thereto, and the mixture was stirred at room temperature for 45 minutes. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=100/0 to 90/10), whereby Compound 156 (26.4 mg, yield 78%) was obtained. 1H NMR (300 MHz, CDCl$_3$, δ): 8.28 (d, J=1.5 Hz, 1H), 8.12 (d, J=1.5 Hz, 1H), 7.39 (s, 1H), 3.37-3.35 (m, 4H), 2.25 (s, 6H), 2.12 (s, 2H), 1.70-1.55 (m, 7H), 1.09 (s, 6H); ESIMS m/z: [M+H]+ 486.

EXAMPLE 78

3-(5-Cyano-3-[(4,4-difluorocyclohexyl)methyl]-2-(trifluoromethyl)imidazo[1,2-a]pyridine-7-carboxamide)-2,2-dimethylpropyl formate (Compound 157)

Compound 155 (10.0 mg, 0.021 mmol) was dissolved in DMF, triethylamine (0.004 ml, 0.032 mmol) and p-toluenesulfonyl chloride (4.84 mg, 0.025 mmol) were added thereto at 0° C., and the mixture was stirred at room temperature overnight. p-Toluenesulfonyl chloride (4.84 mg, 0.025 mmol) was added to the reaction mixture at room temperature, and the mixture was stirred overnight. A saturated aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=99/1 to 97/3), whereby Compound 157 (8.10 mg, yield 76%) was obtained.

$^1$H NMR (300 MHz, CDCl$_3$, δ): 8.30 (d, J=1.8 Hz, 1H), 8.20 (s, 1H), 8.11 (d, J=1.5 Hz, 1H), 7.17 (t, J=6.2 Hz, 1H), 4.06 (s, 2H), 3.36-3.34 (m, 4H), 2.16-2.09 (m, 2H), 1.62 (m, 7H), 1.03 (s, 6H); ESIMS m/z: [M+H]$^+$ 501.

EXAMPLE 79

3-[(4,4-Difluorocyclohexyl)methyl]-2-(1,1-difluoroethyl)-5-formyl-N-(tetrahydro-2H-pyran-4-yl)imidazo[1,2-a]pyridine-7-carboxamide (Compound 158)

Step 1

3-[(4,4-Difluorocyclohexyl)methyl]-2-(1,1-difluoroethyl)-5-methyl-N-(tetrahydro-2H-pyran-4-yl)imidazo[1,2-a]pyridine-7-carboxamide (44.4 mg, yield 45%) was obtained in the same manner as in Step 9 of Example 1, using 3-[(4,4-difluorocyclohexyl)methyl]-2-(1,1-difluoroethyl)-5-methylimidazo[1,2-a]pyridine-7-carboxylic acid obtained in Step 2 of Example 67 and 4-aminotetrahydropyran hydrochloride.

$^1$H NMR (300 MHz, CDCl$_3$, δ): 7.77 (d, J=1.8 Hz, 1H), 7.06 (d, J=1.8 Hz, 1H), 6.05 (d, J=8.1 Hz, 1H), 4.26-4.12 (m, 1H), 4.06-3.96 (m, 2H), 3.61-3.48 (m, 2H), 3.26 (d, J=6.2 Hz, 2H), 2.88 (s, 3H), 2.15 (t, J=18.9 Hz, 3H), 2.11-1.96 (m, 4H), 1.72-1.39 (m, 9H); ESIMS m/z: [M+H]$^+$ 456.

Step 2

Compound 158 (41.3 mg, yield 65%) was obtained in the same manner as in Step 4 of Example 32, using 3-[(4,4-difluorocyclohexyl)methyl]-2-(1,1-difluoroethyl)-5-methyl-N-(tetrahydro-2H-pyran-4-yl)imidazo[1,2-a]pyridine-7-carboxamide obtained in Step 1.

$^1$H NMR (300 MHz, CDCl$_3$, δ): 10.01 (s, 1H), 8.22 (d, J=1.8 Hz, 1H), 8.11 (d, J=1.8 Hz, 1H), 6.17 (d, J=8.1 Hz, 1H), 4.30-4.17 (m, 1H), 4.06-3.98 (m, 2H), 3.61-3.51 (m, 2H), 3.45 (d, J=2.6 Hz, 2H), 2.18 (t, J=18.9 Hz, 3H), 2.08-1.93 (m, 4H), 1.71-1.28 (m, 9H); ESIMS m/z: [M+H]$^+$ 470.

EXAMPLE 80

5-Cyano-3-[(4,4-difluorocyclohexyl)methyl]-2-(1,1-difluoroethyl)-N-(tetrahydro-2H-pyran-4-yl)imidazo[1,2-a]pyridine-7-carboxamide (Compound 159)

Compound 158 (18.0 mg, 0.038 mmol) was dissolved in NMP (0.5 mL), hydroxyamine hydrochloride (3.2 mg, 0.046 mmol) was added thereto, and the mixture was stirred at 120° C. for 1 hour. Acetic anhydride (3.6 μL, 0.038 mmol) was added to the reaction mixture, and the mixture was stirred at 120° C. for 1 hour. After cooling the reaction mixture to room temperature, an aqueous sodium hydrogen carbonate solution was added thereto, and the mixture was extracted with ethyl acetate. The organic layer was washed with saturated brine and dried over anhydrous sodium sulfate, and the solvent was evaporated under reduced pressure. The residue was purified by silica gel column chromatography (chloroform/methanol=98/2 to 95/5) and then purified by preparative thin-layer chromatography (ethyl acetate), whereby Compound 159 (8.0 mg, yield 45%) was obtained.

$^1$H NMR (300 MHz, CDCl$_3$, δ): 8.17 (d, J=1.8 Hz, 1H), 7.98 (d, J=1.8 Hz, 1H), 6.09 (d, J=7.3 Hz, 1H), 4.28-4.17 (m, 1H), 4.07-3.99 (m, 2H), 3.61-3.49 (m, 2H), 3.40 (d, J=7.0 Hz, 2H), 2.21-1.95 (m, 7H), 1.92-1.45 (m, 9H); ESIMS m/z: [M+H]$^+$ 467.

EXAMPLE 81

Ethyl 1-{5-cyano-3-[(4,4-difluorocyclohexyl)methyl]-2-(trifluoromethyl)imidazo[1,2-a]pyridine-7-carboxamide}cyclopropanecarboxylate (Compound 161)

Compound 161 (23.8 mg, yield 62%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and ethyl 1-aminocyclopropanecarboxylate hydrochloride.

$^1$H NMR (300 MHz, CDCl$_3$, δ): 8.23 (d, J=1.8 Hz, 1H), 8.05 (d, J=1.8 Hz, 1H), 6.84 (s, 1H), 4.18 (q, J=7.2 Hz, 2H), 3.36 (d, J=7.0 Hz, 2H), 2.17-2.12 (m, 2H), 1.81-1.77 (m, 3H), 1.72 (dd, J=8.1, 4.8 Hz, 2H), 1.58 (m, 4H), 1.34 (dd, J=8.2, 4.9 Hz, 2H), 1.24 (t, J=7.1 Hz, 3H); ESIMS m/z: [M+H]$^+$ 499.

EXAMPLE 82

5-Cyano-3-[(4,4-difluorocyclohexyl)methyl]-N-(1-hydroxy-2-methylpropan-2-yl)methyl]-2-(trifluoromethyl)imidazo[1,2-a]pyridine-7-carboxamide (Compound 162)

Compound 162 (36.5 mg, yield 75%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and 2-amino-2-methylpropan-1-ol.

$^1$H NMR (300 MHz, CDCl$_3$, δ): 8.23 (d, J=1.5 Hz, 1H), 8.03 (d, J=1.8 Hz, 1H), 6.52 (s, 1H), 3.71 (s, 2H), 3.35 (d, J=7.0 Hz, 2H), 2.14-2.06 (m, 2H), 1.80-1.51 (m, 7H), 1.46 (s, 6H); ESIMS m/z: [M+H]$^+$ 459.

EXAMPLE 83

3-(2-Phenoxypropan-2-yl)-N-phenyl-2-(trifluoromethyl)imidazo[1,2-a]pyridine-7-carboxamide (Compound 163)

Step 1

2-Amino-4-cyanopyridine (1.00 g, 8.39 mmol) was dissolved in ethanol (5.0 mL), ethyl 2-chloro-4,4,4-trifluoroacetoacetate (2.52 g, 9.23 mmol) was added thereto, and the mixture was stirred under reflux with heating overnight. A saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=80/20), and then reslurried in tert-butyl methyl ether, whereby ethyl 7-cyano-2-(trifluoromethyl)imidazo[1,2-a]pyridine-3-carboxylate (1.11 g, yield 47%) was obtained.

$^1$H NMR (300 MHz, CDCl$_3$, δ): 9.55 (dd, J=7.1, 0.9 Hz, 1H), 8.20 (dd, J=1.1, 0.9 Hz, 1H), 7.30 (dd, J=7.3, 1.1 Hz, 1H), 4.51 (q, J=7.1 Hz, 2H), 1.45 (t, J=7.1 Hz, 3H); ESIMS m/z: [M+H]$^+$ 284.

Step 2

Ethyl 7-cyano-2-(trifluoromethyl)imidazo[1,2-a]pyridine-3-carboxylate obtained in Step 1 (1.00 g, 3.53 mmol) was dissolved in THF (20 mL), methylmagnesium bromide (14.3 mL, 14.1 mmol, 0.99 mol/L solution in THF) was added thereto at −78° C., and the mixture was stirred at room temperature for 2 hours. A saturated aqueous ammonium chloride solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (hexane/ethyl acetate=70/30), whereby 3-(2-hydroxypropan-2-yl)-2-(trifluoromethyl)imidazo[1,2-a]pyridine-7-carbonitrile (251 mg, yield 26%) was obtained.

$^{1}$H NMR (300 MHz, CDCl$_3$, δ): 9.17 (d, J=6.8 Hz, 1H), 8.06 (s, 1H), 7.00 (d, J=6.8 Hz, 1H), 1.85 (s, 6H); ESIMS m/z: [M+H]$^+$ 270.

Step 3

3-(2-Hydroxypropan-2-yl)-2-(trifluoromethyl)imidazo[1,2-a]pyridine-7-carbonitrile obtained in Step 2 (70.0 mg, 0.260 mmol) was dissolved in THF (1.0 mL), phenol (29.0 mg, 0.312 mmol), triphenylphosphine oxide (82.0 mg, 0.312 mmol), and diethyl azodicarboxylate (0.142 mL, 0.312 mmol, 2.2 mol/L solution in toluene) were added thereto, and the mixture was stirred under reflux with heating for 3 hours. After cooling the reaction mixture to room temperature, the solvent was evaporated under reduced pressure. The resulting residue was purified by silica gel column chromatography (heptane/ethyl acetate=80/20), whereby 3-(2-phenoxypropan-2-yl)-2-(trifluoromethyl)imidazo[1,2-a]pyridine-7-carbonitrile (23.6 mg, yield 26%) was obtained.

$^{1}$H NMR (300 MHz, CDCl$_3$, δ): 9.04 (dd, J=7.5, 0.9 Hz, 1H), 8.10 (t, J=0.9 Hz, 1H), 7.16-7.05 (m, 2H), 7.01-6.88 (m, 2H), 6.60-6.52 (m, 2H), 1.93 (s, 6H); ESIMS m/z: [M+H]$^+$ 346.

Step 4

3-(2-Phenoxypropan-2-yl)-2-(trifluoromethyl)imidazo[1,2-a]pyridine-7-carboxylic acid (14.2 mg, yield 59%) was obtained in the same manner as in Step 8 of Example 1, using 3-(2-phenoxypropan-2-yl)-2-(trifluoromethyl)imidazo[1,2-a]pyridine-7-carbonitrile obtained in Step 3. ESIMS m/z: [M+H]$^+$ 365.

Step 5

Compound 163 (6.8 mg, yield 68%) was obtained in the same manner as in Step 9 of Example 1, using 3-(2-phenoxypropan-2-yl)-2-(trifluoromethyl)imidazo[1,2-a]pyridine-7-carboxylic acid obtained in Step 4 and aniline.

$^{1}$H NMR (300 MHz, CDCl$_3$, δ): 9.01 (d, J=7.7 Hz, 1H), 8.14 (d, J=1.1 Hz, 1H), 7.79 (br s, 1H), 7.64-7.58 (m, 2H), 7.42-7.33 (m, 3H), 7.22-7.16 (m, 1H), 7.15-7.07 (m, 2H), 6.97-6.90 (m, 1H), 6.63-6.57 (m, 2H), 1.95 (s, 6H); ESIMS m/z: [M+H]$^+$ 440.

EXAMPLE 84

5-Cyano-3-[(4,4-difluorocyclohexyl)methyl]-2-(1,1-difluoroethyl)-N-(2-methoxy-2-methylpropyl)imidazo[1,2-a]pyridine-7-carboxamide (Compound 164)

Step 1

Ethyl 3-[(4,4-difluorocyclohexyl)methyl]-2-(1,1-difluoroethyl)-5-(hydroxymethyl)imidazo[1,2-a]pyridine-7-carboxylate (0.186 g, yield 72%) was obtained in the same manner as in Step 4 of Example 32, using ethyl 3-[(4,4-difluorocyclohexyl)methyl]-2-(1,1-difluoroethyl)-5-methylimidazo[1,2-a]pyridine-7-carboxylate obtained in Step 1 of Example 67.

$^{1}$H NMR (300 MHz, CDCl$_3$, δ): 8.34 (d, J=1.8 Hz, 1H), 7.46 (d, J=1.8 Hz, 1H), 5.01 (d, J=6.6 Hz, 2H), 4.41 (q, J=7.1 Hz, 2H), 3.33 (d, J=5.9 Hz, 2H), 2.17 (t, J=18.9 Hz, 3H), 2.08-1.93 (m, 3H), 1.77-1.45 (m, 6H), 1.41 (t, J=7.1 Hz, 3H); ESIMS m/z: [M+H]$^+$ 417.

Step 2

Ethyl 3-[(4,4-difluorocyclohexyl)methyl]-2-(1,1-difluoroethyl)-5-formylimidazo[1,2-a]pyridine-7-carboxylate (0.178 g, yield 99%) was obtained in the same manner as in Step 2 of Example 14, using ethyl 3-[(4,4-difluorocyclohexyl)methyl]-2-(1,1-difluoroethyl)-5-(hydroxymethyl)imidazo[1,2-a]pyridine-7-carboxylate obtained in Step 1.

$^{1}$H NMR (300 MHz, CDCl$_3$, δ): 9.99 (s, 1H), 8.63 (d, J=1.8 Hz, 1H), 8.20 (d, J=1.8 Hz, 1H), 4.47 (q, J=7.2 Hz, 2H), 3.46 (br s, 2H), 2.20 (t, J=18.9 Hz, 3H), 2.07-1.92 (m, 3H), 1.47-1.29 (m, 6H), 1.44 (t, J=7.2 Hz, 3H); ESIMS m/z: [M+H]$^+$ 415.

Step 3

Ethyl 5-cyano-3-[(4,4-difluorocyclohexyl)methyl]-2-(1,1-difluoroethyl)imidazo[1,2-a]pyridine-7-carboxylate (0.168 g, quantitative) was obtained in the same manner as in Example 80, using ethyl 3-[(4,4-difluorocyclohexyl)methyl]-2-(1,1-difluoroethyl)-5-formylimidazo[1,2-a]pyridine-7-carboxylate obtained in Step 2.

$^{1}$H NMR (300 MHz, CDCl$_3$, δ): 8.58 (d, J=1.8 Hz, 1H), 8.07 (d, J=1.8 Hz, 1H), 4.45 (q, J=7.2 Hz, 2H), 3.42 (d, J=7.3 Hz, 2H), 2.16 (t, J=18.9 Hz, 3H), 2.16-2.02 (m, 3H), 1.89-1.47 (m, 6H), 1.43 (t, J=7.2 Hz, 3H); ESIMS m/z: [M+H]$^+$ 412.

Step 4

5-Cyano-3-[(4,4-difluorocyclohexyl)methyl]-2-(1,1-difluoroethyl)imidazo[1,2-a]pyridine-7-carboxylic acid (0.123 g, yield 83%) was obtained in the same manner as in Step 8 of Example 1, using ethyl 5-cyano-3-[(4,4-difluorocyclohexyl)methyl]-2-(1,1-difluoroethyl)imidazo[1,2-a]pyridine-7-carboxylate obtained in Step 3.

ESIMS m/z: [M+H]$^+$ 384.

Step 5

Compound 164 (18.9 mg, yield 39%) was obtained in the same manner as in Step 9 of Example 1, using 5-cyano-3-[(4,4-difluorocyclohexyl)methyl]-2-(1,1-difluoroethyl)imidazo[1,2-a]pyridine-7-carboxylic acid obtained in Step 4 and 2-methoxy-2-methylpropan-1-amine.

$^{1}$H NMR (300 MHz, CDCl$_3$, δ): 8.20 (d, J=1.8 Hz, 1H), 8.02 (d, J=1.8 Hz, 1H), 6.59 (brt, J=5.5 Hz, 1H), 3.49 (d, J=5.5 Hz, 2H), 3.41 (d, J=7.3 Hz, 2H), 3.24 (s, 3H), 2.15 (t, J=18.7 Hz, 3H), 2.15-1.49 (m, 9H), 1.23 (s, 6H); ESIMS m/z: [M+H]$^+$ 469.

EXAMPLE 85

Methyl 1-{5-cyano-3-[(4,4-difluorocyclohexyl)methyl]-2-(1,1-difluoroethyl)imidazo[1,2-a]pyridine-7-carboxamide}cyclopropanecarboxylate (Compound 165)

Step 1

Ethyl 1-{3-[(4,4-difluorocyclohexyl)methyl]-2-(1,1-difluoroethyl)-5-methylimidazo[1,2-a]pyridine-7-carboxamide}cyclopropanecarboxylate (77.3 mg, yield 99%) was obtained in the same manner as in Step 9 of Example 1, using 3-[(4,4-difluorocyclohexyl)methyl]-2-(1,1-difluoroethyl)-5-methylimidazo[1,2-a]pyridine-7-carboxylic acid obtained in Step 2 of Example 67 and ethyl 1-aminocyclopropanecarboxylate hydrochloride.

$^1$H NMR (300 MHz, CDCl$_3$, δ): 7.79 (s, 1H), 7.06 (s, 1H), 6.65 (s, 1H), 4.17 (q, J=7.1 Hz, 2H), 3.26 (d, J=6.2 Hz, 2H), 2.86 (s, 3H), 2.25-1.99 (m, 5H), 1.77-1.21 (m, 14H); ESIMS m/z: [M+H]$^+$ 484.

Step 2

Ethyl 1-{3-[(4,4-difluorocyclohexyl)methyl]-2-(1,1-difluoroethyl)-5-(hydroxymethyl)imidazo[1,2-a]pyridine-7-carboxamide}cyclopropanecarboxylate (45.2 mg, yield 63%) was obtained in the same manner as in Step 4 of Example 32, using ethyl 1-{3-[(4,4-difluorocyclohexyl)methyl]-2-(1,1-difluoroethyl)-5-methylimidazo[1,2-a]pyridine-7-carboxamide}cyclopropanecarboxylate obtained in Step 1.

$^1$H NMR (300 MHz, CDCl$_3$, δ): 7.73 (s, 1H), 7.47 (s, 1H), 7.30 (s, 1H), 4.91 (d, J=6.6 Hz, 2H), 4.22 (q, J=7.1 Hz, 3H), 3.31 (d, J=5.5 Hz, 2H), 3.15 (t, J=6.6 Hz, 1H), 2.21-1.99 (m, 5H), 1.75-1.47 (m, 6H), 1.35-1.22 (m, 7H); ESIMS m/z: [M+H]$^+$ 500.

Step 3

Ethyl 1-{3-[(4,4-difluorocyclohexyl)methyl]-2-(1,1-difluoroethyl)-5-formylimidazo[1,2-a]pyridine-7-carboxamide}cyclopropanecarboxylate (38.2 mg, yield 96%) was obtained in the same manner as in Step 2 of Example 14, using ethyl 1-{3-[(4,4-difluorocyclohexyl)methyl]-2-(1,1-difluoroethyl)-5-(hydroxymethyl)imidazo[1,2-a]pyridine-7-carboxamide}cyclopropanecarboxylate obtained in Step 2.

$^1$H NMR (300 MHz, CDCl$_3$, δ): 9.99 (s, 1H), 8.23 (d, J=1.8 Hz, 1H), 8.12 (d, J=1.8 Hz, 1H), 6.82 (s, 1H), 4.19 (q, J=7.1 Hz, 2H), 3.46 (br s, 2H), 2.18 (t, J=18.9 Hz, 3H), 2.08-1.95 (br m, 2H), 1.89-1.19 (m, 14H); ESIMS m/z: [M+H]$^+$ 498.

Step 4

Ethyl 1-{5-cyano-3-[(4,4-difluorocyclohexyl)methyl]-2-(1,1-difluoroethyl)imidazo[1,2-a]pyridine-7-carboxamide}cyclopropanecarboxylate (29.9 mg, yield 97%) was obtained in the same manner as in Example 80, using ethyl 1-{3-[(4,4-difluorocyclohexyl)methyl]-2-(1,1-difluoroethyl)-5-formylimidazo[1,2-a]pyridine-7-carboxamide}cyclopropanecarboxylate obtained in Step 3.

$^1$H NMR (300 MHz, CDCl$_3$, δ): 8.23 (d, J=2.0 Hz, 1H), 7.99 (d, J=2.0 Hz, 1H), 7.00 (s, 1H), 4.17 (q, J=6.8 Hz, 2H), 3.39 (d, J=6.8 Hz, 2H), 2.21-2.02 (m, 6H), 1.85-1.46 (m, 6H), 1.33-1.22 (m, 7H); ESIMS m/z: [M+H]$^+$ 495.

Step 5

1-{5-Cyano-3-[(4,4-difluorocyclohexyl)methyl]-2-(1,1-difluoroethyl)imidazo[1,2-a]pyridine-7-carboxamide}cyclopropanecarboxylic acid (29.9 mg, yield 97%) was obtained in the same manner as in Step 1 of Example 21, using ethyl 1-{5-cyano-3-[(4,4-difluorocyclohexyl)methyl]-2-(1,1-difluoroethyl)imidazo[1,2-a]pyridine-7-carboxamide}cyclopropanecarboxylate obtained in Step 4.

ESIMS m/z: [M+H]$^+$ 467.

Step 6

Compound 165 (2.1 mg, yield 51%) was obtained in the same manner as in Step 9 of Example 1, using 1-{5-cyano-3-[(4,4-difluorocyclohexyl)methyl]-2-(1,1-difluoroethyl)imidazo[1,2-a]pyridine-7-carboxamide}cyclopropanecarboxylic acid obtained in Step 5 and methanol.

$^1$H NMR (300 MHz, CDCl$_3$, δ): 8.20 (d, J=1.8 Hz, 1H), 7.99 (d, J=1.8 Hz, 1H), 6.79 (s, 1H), 3.72 (s, 3H), 3.40 (d, J=7.3 Hz, 2H), 2.25-2.02 (m, 6H), 1.84-1.43 (m, 6H), 1.36-1.19 (m, 4H); ESIMS m/z: [M+H]$^+$ 481.

EXAMPLE 86

3-[(4,4-Difluorocyclohexyl)methyl]-5,8-dimethyl-N-(tetrahydro-2H-pyran-4-yl)-2-(trifluoromethyl)imidazo[1,2-a]pyridine-7-carboxamide (Compound 166)

Step 1

Compound 133 (150 mg, 0.306 mmol) was dissolved in DMSO (4 mL), dodecanethiol (0.367 mL, 15.3 mmol) and potassium tert-butoxide (172 mg, 1.53 mmol) were added thereto, and the mixture was stirred at 100° C. for 10 minutes. A saturated aqueous ammonium chloride solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5), whereby 3-[(4,4-difluorocyclohexyl)methyl]-8-hydroxy-5-methyl-N-(tetrahydro-2H-pyran-4-yl)-2-(trifluoromethyl)imidazo[1,2-a]pyridine-7-carboxamide (61.0 mg, yield 42%) was obtained.

$^1$H NMR (300 MHz, CDCl$_3$, δ): 8.59 (s, 1H), 7.21 (s, 1H), 4.14-4.00 (m, 2H), 3.94-3.86 (m, 2H), 3.51-3.36 (m, 2H), 3.13 (d, J=6.2 Hz, 2H), 2.76 (s, 3H), 2.10-1.15 (m, 13H); ESIMS m/z: [M+H]$^+$ 476.

Step 2

3-[(4,4-Difluorocyclohexyl)methyl]-8-hydroxy-5-methyl-N-(tetrahydro-2H-pyran-4-yl)-2-(trifluoromethyl)imidazo[1,2-a]pyridine-7-carboxamide obtained in Step 1 (55.0 mg, 0.116 mmol) was dissolved in dichloromethane (1 mL). Under ice-cooled condition, pyridine (0.022 mL, 0.278 mmol) and trifluoromethanesulfonic anhydride (0.023 mL, 0.139 mmol) were added thereto, and the mixture was stirred at room temperature for 2 hours. The reaction mixture was filtrated through Presep (registered trademark; diatomite, granular type M, 4.5 g/25 mL), and the solvent was evaporated under reduced pressure. The residue was purified by silica gel column chromatography (chloroform/methanol=95/5), whereby 3-[(4,4-difluorocyclohexyl)methyl]-5-methyl-7-(tetrahydro-2H-pyran-4-ylcarbamoyl)-2-(trifluoromethyl)imidazo[1,2-a]pyridin-8-yl trifluoromethanesulfonate (50.4 mg, yield 72%) was obtained.

ESIMS m/z: [M+H]$^-$ 606.

Step 3

3-[(4,4-Difluorocyclohexyl)methyl]-5-methyl-7-(tetrahydro-2H-pyran-4-ylcarbamoyl)-2-(trifluoromethyl)imidazo[1,2-a]pyridin-8-yl trifluoromethanesulfonate obtained in Step 2 (25.0 mg, 0.041 mmol) was dissolved in 1,4-dioxane (0.5 mL), trimethylboroxine (0.012 mL, 0.082 mmol), tetrakistriphenylphosphine palladium (4.76 mg, 0.004 mmol), and sodium carbonate (17.0 mg, 0.123 mmol) were added thereto, and the mixture was stirred under reflux with heating for 1 hour. An aqueous sodium hydrogen carbonate solution was added to the reaction mixture, the mixture was filtrated through Presep (registered trademark; diatomite, granular type M, 4.5 g/25 mL), and the solvent was evaporated under reduced pressure. The residue was purified by silica gel column chromatography (chloroform/methanol=95/5), whereby Compound 166 (12.1 mg, yield 62%) was obtained.

$^1$H NMR (300 MHz, CDCl$_3$, δ): 6.67 (s, 1H), 5.70 (d, J=7.7 Hz, 1H), 4.29-4.18 (m, 1H), 4.08-3.94 (m, 2H), 3.63-3.46 (m, 2H), 3.19 (d, J=6.2 Hz, 2H), 2.80 (s, 3H), 2.69 (s, 3H), 2.21-1.95 (m, 5H), 1.78-1.36 (m, 8H); ESIMS m/z: [M+H]+ 474.

EXAMPLE 87

3-[(4,4-Difluorocyclohexyl)methyl]-5,6-dimethyl-N-(tetrahydro-2H-pyran-4-yl)-2-(trifluoromethyl)imidazo[1,2-a]pyridine-7-carboxamide (Compound 167)

Compound 167 (23.1 mg, yield 52%) was obtained in the same manner as in Step 3 of Example 86, using 3-(4,4-difluorocyclohexylmethyl)-6-iodo-5-methyl-N-phenyl-2-trifluoromethylimidazo[1,2-a]pyridine-7-carboxamide obtained by a method described in WO2012/105594.

$^1$H NMR (300 MHz, CDCl$_3$, δ): 7.52 (s, 1H), 5.90 (d, J=7.7 Hz, 1H), 4.25-4.15 (m, 1H), 4.07-3.96 (m, 2H), 3.60-3.47 (m, 2H), 3.21 (d, J=5.9 Hz, 2H), 2.77 (s, 3H), 2.38 (s, 3H), 2.18-2.02 (m, 5H), 1.66-1.39 (m, 8H); ESIMS m/z: [M+H]+ 474.

EXAMPLE 88

6-Chloro-5-cyano-3-[(4,4-difluorocyclohexyl)methyl]-Netrahydro-2H-pyran-4-yl)-2-(trifluoromethyl)imidazo[1,2-a]pyridine-7-carboxamide (Compound 168)

Step 1

Ethyl 6-chloro-3-[(4,4-difluorocyclohexyl)methyl]-5-(hydroxymethyl)-2-(trifluoromethyl)imidazo[1,2-a]pyridine-7-carboxylate (124 mg, 67%) was obtained in the same manner as in Step 4 of Example 32, using ethyl 6-chloro-3-(4,4-difluorocyclohexylmethyl)-5-methyl-2-(trifluoromethyl)imidazo[1,2-a]pyridine-7-carboxylate obtained by a method described in WO2012/105594.

$^1$H NMR (300 MHz, CDCl$_3$, δ): 8.14 (s, 1H), 5.27 (d, J=7.0 Hz, 2H), 4.43 (q, J=7.1 Hz, 2H), 3.30 (d, J=6.2 Hz, 2H), 2.24-2.03 (m, 3H), 1.78-1.45 (m, 7H), 1.41 (t, J=7.1 Hz, 3H); ESIMS m/z: [M+H]+ 455.

Step 2

Ethyl 6-chloro-3-[(4,4-difluorocyclohexyl)methyl]-5-formyl-2-(trifluoromethyl)imidazo[1,2-a]pyridine-7-carboxylate (193 mg, yield 92%) was obtained in the same manner as in Step 2 of Example 14, using ethyl 6-chloro-3-[(4,4-difluorocyclohexyl)methyl]-5-(hydroxymethyl)-2-(trifluoromethyl)imidazo[1,2-a]pyridine-7-carboxylate obtained in Step 1.

$^1$H NMR (300 MHz, CDCl$_3$, δ): 10.58 (s, 1H), 8.46 (s, 1H), 4.48 (q, J=7.1 Hz, 2H), 3.05 (d, J=7.0 Hz, 2H), 2.07-1.94 (m, 2H), 1.67-1.25 (m, 7H), 1.44 (t, J=7.1 Hz, 3H); ESIMS m/z: [M+H]+ 453.

Step 3

Ethyl 6-chloro-5-cyano-3-[(4,4-difluorocyclohexyl)methyl]-2-(trifluoromethyl)imidazo[1,2-a]pyridine-7-carboxylate (174 mg, yield 92%) was obtained in the same manner as in Example 80, using ethyl 6-chloro-3-[(4,4-difluorocyclohexyl)methyl]-5-formyl-2-(trifluoromethyl)imidazo[1,2-a]pyridine-7-carboxylate obtained in Step 2.

$^1$H NMR (300 MHz, CDCl$_3$, δ): 8.48 (s, 1H), 4.47 (q, J=7.1 Hz, 2H), 3.37 (d, J=7.0 Hz, 2H), 2.16-1.49 (m, 9H), 1.43 (t, J=7.1 Hz, 3H); ESIMS m/z: [M+H]+ 450.

Step 4

6-Chloro-5-cyano-3-[(4,4-difluorocyclohexyl)methyl]-2-(trifluoromethyl)imidazo[1,2-a]pyridine-7-carboxylic acid (153 mg, yield 94%) was obtained in the same manner as in Step 2 of Example 21, using ethyl 6-chloro-5-cyano-3-[(4,4-difluorocyclohexyl)methyl]-2-(trifluoromethyl)imidazo[1,2-a]pyridine-7-carboxylate obtained in Step 3.

$^1$H NMR (300 MHz, DMSO-d$_6$, δ): 8.53 (s, 1H), 3.24 (d, J 7.3 Hz, 2H), 2.17-1.26 (m, 9H); ESIMS m/z: [M+H]+ 422.

Step 5

Compound 168 (55.5 mg, yield 77%) was obtained in the same manner as in Step 9 of Example 1, using 6-chloro-5-cyano-3-[(4,4-difluorocyclohexyl)methyl]-2-(trifluoromethyl)imidazo[1,2-a]pyridine-7-carboxylic acid obtained in Step 4.

$^1$H NMR (300 MHz, CDCl$_3$, δ): 8.10 (s, 1H), 5.95 (d, J=8.8 Hz, 1H), 4.30-4.16 (m, 1H), 4.08-3.99 (m, 2H), 3.60-3.51 (m, 2H), 3.35 (d, J=7.0 Hz, 2H), 2.22-1.42 (m, 13H); ESIMS m/z: [M+H]+ 505.

EXAMPLE 89

5-Cyano-N-(3,3-difluorocyclobutyl)-3-[(4,4-difluorocyclohexyl)methyl]-2-isopropylimidazo[1,2-a]pyridine-7-carboxamide (Compound 170)

Step 1

Ethyl 3-[(4,4-difluorocyclohexyl)methyl]-2-isopropyl-5-(hydroxymethyl)imidazo[1,2-a]pyridine-7-carboxylate (532 mg, yield 46%) was obtained in the same manner as in Step 4 of Example 32, using ethyl 3-[(4,4-difluorocyclohexyl)methyl]-2-isopropyl-5-methylimidazo[1,2-a]pyridine-7-carboxylate obtained in Step 4 of Example 71.

$^1$H NMR (300 MHz, CDCl$_3$, δ): 8.32 (d, J=1.5 Hz, 1H), 7.35 (d, J=1.5 Hz, 1H), 4.94 (d, J=6.6 Hz, 2H), 4.38 (q, J=7.1 Hz, 2H), 3.21-3.05 (m, 3H), 2.15-1.43 (m, 10H), 1.39 (t, J=7.1 Hz, 3H), 1.36 (d, J=6.6 Hz, 6H); ESIMS m/z: [M+H]+ 395.

Step 2

Ethyl 3-[(4,4-difluorocyclohexyl)methyl]-5-formyl-2-isopropylimidazo[1,2-a]pyridine-7-carboxylate (509 mg, yield 96%) was obtained in the same manner as in Step 2 of Example 14, using ethyl 3-[(4,4-difluorocyclohexyl)methyl]-2-isopropyl-5-(hydroxymethyl)imidazo[1,2-a]pyridine-7-carboxylate obtained in Step 1.

$^1$H NMR (300 MHz, CDCl$_3$, δ): 9.92 (s, 1H), 8.60 (d, J=1.8 Hz, 1H), 8.13 (d, J=1.8 Hz, 1H), 4.44 (q, J=7.1 Hz, 2H), 3.26 (d, J=5.9 Hz, 2H), 3.20 (ses, J=7.0 Hz, 1H), 2.07-1.93 (m, 2H), 1.53-1.24 (m, 16H); ESIMS m/z: [M+H]+ 393.

Step 3

Ethyl 5-cyano-3-[(4,4-difluorocyclohexyl)methyl]-2-isopropylimidazo[1,2-a]pyridine-7-carboxylate (466 mg, yield 94%) was obtained in the same manner as in Example 80, using ethyl 3-[(4,4-difluorocyclohexyl)methyl]-5-formyl-2-isopropylimidazo[1,2-a]pyridine-7-carboxylate obtained in Step 2.

$^1$H NMR (300 MHz, CDCl$_3$, δ): 8.54 (d, J=1.5 Hz, 1H), 7.98 (d, J=1.5 Hz, 1H), 4.42 (q, J=7.1 Hz, 2H), 3.17 (d, J=7.0 Hz, 2H), 3.15 (ses, J=6.6 Hz, 1H), 2.26-1.99 (m, 2H), 1.89-1.31 (m, 16H); ESIMS m/z: [M+H]+ 390.

Step 4

5-Cyano-3-[(4,4-difluorocyclohexyl)methyl]-2-isopropylimidazo[1,2-a]pyridine-7-carboxylic acid (311 mg, yield 99%) was obtained in the same manner as in Step 8 of Example 1, using ethyl 5-cyano-3-[(4,4-difluorocyclohexyl)methyl]-2-isopropylimidazo[1,2-a]pyridine-7-carboxylate obtained in Step 3.

$^1$H NMR (300 MHz, DMSO-d$_6$, δ): 8.31 (d, J=1.5 Hz, 1H), 8.00 (d, J=1.5 Hz, 1H), 3.23-3.13 (m, 3H), 2.12-1.31 (m, 9H), 1.27 (d, J=7.0 Hz, 6H); ESIMS m/z: [M+H]+ 362.

Step 5

Compound 170 (32.1 mg, yield 86%) was obtained in the same manner as in Step 9 of Example 1, using 5-cyano-3-[(4,4-difluorocyclohexyl)methyl]-2-isopropylimidazo[1,2-a]pyridine-7-carboxylic acid obtained in Step 4, 3,3-difluorocyclobutanamine hydrochloride, and triethylamine.

$^1$H NMR (300 MHz, CDCl$_3$, δ): 8.13 (d, J=1.8 Hz, 1H), 7.86 (d, J=1.8 Hz, 1H), 6.35 (d, J=5.9 Hz, 1H), 4.54-4.40 (m, 1H), 3.23-3.05 (m, 5H), 2.67-2.48 (m, 2H), 2.24-2.01 (m, 2H), 1.93-1.27 (m, 7H), 1.35 (d, J=7.0 Hz, 6H); ESIMS m/z: [M+H]$^+$ 451.

EXAMPLE 90

5-Cyano-3-[(4,4-difluorocyclohexyl)methyl]-2-isopropyl-N-(2,2,2-trifluoroethyl)imidazo[1,2-a]pyridine-7-carboxamide (Compound 171)

Compound 171 (28.2 mg, yield 77%) was obtained in the same manner as in Step 9 of Example 1, using 5-cyano-3-[(4,4-difluorocyclohexyl)methyl]-2-isopropylimidazo[1,2-a]pyridine-7-carboxylic acid obtained in Step 4 of Example 89 and 2,2,2-trifluoroethanamine.

$^1$H NMR (300 MHz, CDCl$_3$, δ): 8.17 (d, J=1.8 Hz, 1H), 7.90 (d, J=1.8 Hz, 1H), 6.36 (brt, J=6.3 Hz, 1H), 4.24-4.08 (m, 2H), 3.22-3.08 (m, 3H), 2.21-2.04 (m, 2H), 1.92-1.40 (m, 7H), 1.36 (d, J=6.6 Hz, 6H); ESIMS m/z: [M+H]$^+$ 443.

EXAMPLE 91

5-Chloro-N-[2-(3,3-difluoroazetidin-1-yl)-2-oxoethyl]-3-[(4,4-difluorocyclohexyl)methyl]-2-(trifluoromethyl)imidazo[1,2-a]pyridine-7-carboxamide (Compound 172)

Compound 172 (58.2 mg, yield 83%) was obtained in the same manner as in Step 9 of Example 1, using 2-{5-chloro-3-[(4,4-difluorocyclohexyl)methyl]-2-(trifluoromethyl)imidazo[1,2-a]pyridine-7-carboxamide}acetic acid obtained in Step 1 of Example 64, 3,3-difluoroazetidine hydrochloride, and triethylamine.

$^1$H NMR (300 MHz, CDCl$_3$, δ): 8.03 (d, J=1.8 Hz, 1H), 7.42 (d, J=1.5 Hz, 1H), 7.15 (br s, 1H), 4.56 (t, J=11.2 Hz, 2H), 4.45 (t, J=11.9 Hz, 2H), 4.11 (d, J=4.4 Hz, 2H), 3.35 (d, J=7.0 Hz, 2H), 2.11 (t, J=19.1 Hz, 2H), 1.84-1.40 (m, 7H); ESIMS m/z: [M+H]$^+$ 529.

EXAMPLE 92

6-Chloro-5-cyano-3-[(4,4-difluorocyclohexyl)methyl]-N-(2-methoxy-2-methylpropyl)-2-(trifluoromethyl)imidazo[1,2-a]pyridine-7-carboxamide (Compound 173)

Compound 173 (34.9 mg, yield 73%) was obtained in the same manner as in Step 9 of Example 1, using 6-chloro-5-cyano-3-[(4,4-difluorocyclohexyl)methyl]-2-(trifluoromethyl)imidazo[1,2-a]pyridine-7-carboxylic acid obtained in Step 4 of Example 88 and 2-methoxy-2-methylpropan-1-amine.

$^1$H NMR (300 MHz, CDCl$_3$, δ): 8.11 (s, 1H), 6.42 (t, J=5.5 Hz, 1H), 3.50 (d, J=5.5 Hz, 2H), 3.35 (d, J=7.0 Hz, 2H), 3.21 (s, 3H), 2.20-2.04 (m, 2H), 1.89-1.37 (m, 7H), 1.25 (s, 6H); ESIMS m/z: [M+H]$^+$ 507.

EXAMPLE 93

5-Chloro-3-[(4,4-difluorocyclohexyl)methyl]-N-{[1-(hydroxymethyl)cyclopropyl]methyl}-2-(trifluoromethyl)imidazo[1,2-a]pyridine-7-carboxamide (Compound 174)

Compound 174 (76.1 mg, yield 90%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 1 of Example 42 and [1-(aminomethyl)cyclopropyl]methanol.

$^1$H NMR (300 MHz, CDCl$_3$, δ): 7.92 (d, J=1.5 Hz, 1H), 7.48 (d, J=1.8 Hz, 1H), 3.58 (d, J=5.1 Hz, 2H), 3.49 (d, J=5.5 Hz, 2H), 3.35 (d, J=6.6 Hz, 2H), 2.32 (t, J=4.8 Hz, 1H), 2.12-2.09 (m, 2H), 1.68-1.51 (m, 7H), 0.60-0.56 (m, 4H); ESIMS m/z: [M+H]$^+$ 480.

EXAMPLE 94

5-Chloro-N-(1-cyanocyclopropyl)-3-[(4,4-difluorocyclohexyl)methyl]-2-(trifluoromethyl)imidazo[1,2-a]pyridine-7-carboxamide (Compound 175)

Compound 175 (9.10 mg, yield 26%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 1 of Example 42, 1-aminocyclopropanecarbonitrile hydrochloride, and triethylamine.

$^1$H NMR (300 MHz, CDCl$_3$, δ): 7.86 (d, J=1.5 Hz, 1H), 7.48 (d, J=1.5 Hz, 1H), 6.94 (br s, 1H), 3.35 (d, J=7.0 Hz, 2H), 2.12-2.09 (m, 2H), 1.74-1.46 (m, 11H); ESIMS m/z: [M+H]$^+$ 461.

EXAMPLE 95

5-Chloro-N-[(1-cyanocyclopropyl)methyl]-3-[(4,4-difluorocyclohexyl)methyl]-2-(trifluoromethyl)imidazo[1,2-a]pyridine-7-carboxamide (Compound 176)

Step 1

Compound 174 (60.0 mg, 0.125 mmol) was dissolved in dichloromethane (1.0 mL), Dess-Martin Periodinane (159 mg, 0.375 mmol) was added thereto, and the mixture was stirred at room temperature overnight. A saturated aqueous sodium hydrogen carbonate solution and an aqueous sodium thiosulfate solution were added to the reaction mixture, the mixture was filtrated through Presep (registered trademark; diatomite, granular type M, 4.5 g/25 mL), and the solvent was evaporated under reduced pressure. The residue was purified by silica gel column chromatography (heptane/ethyl acetate=50/50 to 0/100), whereby 5-chloro-3-[(4,4-difluorocyclohexyl)methyl]-N-[(1-formylcyclopropyl)methyl]-2-(trifluoromethyl)imidazo[1,2-a]pyridine-7-carboxamide (58.6 mg, yield 98%) was obtained.

$^1$H NMR (300 MHz, CDCl$_3$, δ): 8.61 (s, 1H), 7.93 (d, J=1.5 Hz, 1H), 7.39 (d, J=1.5 Hz, 1H), 7.01 (br s, 1H), 3.66 (d, J=6.2 Hz, 2H), 3.35 (d, J=7.3 Hz, 2H), 2.13-2.09 (m, 2H), 1.70-1.26 (m, 11H); ESIMS m/z: [M+H]$^+$ 478.

Step 2

5-Chloro-3-[(4,4-difluorocyclohexyl)methyl]-N-[(1-formylcyclopropyl)methyl]-2-(trifluoromethyl)imidazo[1, 2-a]pyridine-7-carboxamide obtained in Step 1 (58.6 mg, 0.123 mmol) was dissolved in NMP (1.5 mL), hydroxylamine hydrochloride (10.2 mg, 0.147 mmol) was added thereto, and the mixture was stirred at 120° C. for 1 hour. Acetic anhydride (0.12 mL, 1.23 mmol) was added to the reaction mixture, and the mixture was stirred at 120° C. for 1 hour. After cooling the reaction mixture to room temperature, saturated aqueous sodium hydrogen carbonate was added thereto, the mixture was filtrated through Presep (registered trademark; diatomite, granular type M, 4.5 g/25 mL), and the solvent was evaporated under reduced pressure. The residue was purified by silica gel column chromatography (heptane/ethyl acetate=80/20 to 50/50), whereby Compound 176 (25.6 mg, yield 44%) was obtained.

$^1$H-NMR (CDCl$_3$) δ: 8.03 (d, J=1.4 Hz, 1H), 7.48 (d, J 1.8 Hz, 1H), 7.18 (t, J=5.9 Hz, 1H), 3.57 (d, J=6.3 Hz, 2H), 3.35 (d, J=6.8 Hz, 2H), 2.13-2.10 (m, 2H), 1.84-1.19 (m, 7H), 1.35 (dd, J=7.5, 5.2 Hz, 2H), 1.21 (dd, J=7.2, 4.5 Hz, 2H); ESIMS m/z: [M+H]$^+$ 475.

EXAMPLE 96

5-Cyano-3-[(4,4-difluorocyclohexyl)methyl]-N-(2,2-difluoropropyl)-2-isopropylimidazo[1,2-a]pyridine-7-carboxamide (Compound 177)

Compound 177 (10.5 mg, yield 87%) was obtained in the same manner as in Step 9 of Example 1, using 5-cyano-3-[(4,4-difluorocyclohexyl)methyl]-2-isopropylimidazo[1,2-a]pyridine-7-carboxylic acid obtained in Step 4 of Example 89 and 2,2-difluoropropan-1-amine hydrochloride.

$^1$H NMR (300 MHz, CDCl$_3$, δ): 8.19 (d, J=1.8 Hz, 1H), 7.91 (d, J=1.8 Hz, 1H), 6.48 (br s, 1H), 3.89 (td, J=13.7, 6.2 Hz, 2H), 3.24-3.07 (m, 3H), 2.17-2.01 (m, 2H), 1.88-1.38 (m, 10H), 1.36 (d, J=7.0 Hz, 6H); ESIMS m/z: [M+H]$^+$ 439.

EXAMPLE 97

N-[(1R,2S,4S)-7-Oxabicyclo[2.2.1]heptan-2-yl]-5-cyano-3-[(4,4-difluorocyclohexyl)methyl]-2-(trifluoromethyl)imidazo[1,2-a]pyridine-7-carboxamide (Compound 178)

Compound 178 (21.1 mg, yield 42%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and (1R,2S,4S)-7-oxabicyclo[2.2.1]heptan-2-amine.

$^1$H NMR (400 MHz, CDCl$_3$, δ): 8.24 (d, J=2.0 Hz, 1H), 8.04-8.02 (m, 1H), 6.52 (d, J=7.8 Hz, 1H), 4.71 (t, J=4.9 Hz, 1H), 4.48 (d, J=5.9 Hz, 1H), 4.31 (td, J=7.8, 2.9 Hz, 1H), 3.35 (d, J=6.8 Hz, 2H), 2.16-2.02 (m, 3H), 1.81-1.25 (m, 12H); ESIMS m/z: [M+H]$^+$ 483.

EXAMPLE 98

N-[(1R,2S,4S)-7-Oxabicyclo[2.2.1]heptan-2-yl]-3-[(4,4-difluorocyclohexyl)methyl]-2-(1,1-difluoroethyl)-5-formylimidazo[1,2-a]pyridine-7-carboxamide (Compound 179)

Step 1

N-[(1R,2S,4S)-7-Oxabicyclo[2.2.1]heptan-2-yl]-3-[(4,4-difluorocyclohexyl)methyl]-2-(1,1-difluoroethyl)-5-methylimidazo[1,2-a]pyridine-7-carboxamide (119 mg, yield 95%) was obtained in the same manner as in Step 9 of Example 1, using 3-[(4,4-difluorocyclohexyl)methyl]-2-(1,1-difluoroethyl)-5-methylimidazo[1,2-a]pyridine-7-carboxylic acid obtained in Step 2 of Example 67 and (1R,2S,4S)-7-oxabicyclo[2.2.1]heptan-2-amine.

$^1$H NMR (300 MHz, CDCl$_3$, δ): 7.80 (s, 1H), 7.00 (s, 1H), 6.25 (d, J=7.3 Hz, 1H), 4.71-4.65 (m, 1H), 4.47-4.42 (m, 1H), 4.34-4.24 (m, 1H), 3.26 (d, J=6.6 Hz, 2H), 2.87 (s, 3H), 2.26-2.02 (m, 6H), 1.85-1.34 (m, 12H); ESIMS m/z: [M+H]$^+$ 468.

Step 2

N-[(1R,2S,4S)-7-Oxabicyclo[2.2.1]heptan-2-yl]-3-[(4,4-difluorocyclohexyl)methyl]-2-(1,1-difluoroethyl)-5-(hydroxymethyl)imidazo[1,2-a]pyridine-7-carboxamide (60.1 mg, yield 53%) was obtained in the same manner as in Step of Example 32, using N-[(1R,2S,4S)-7-oxabicyclo[2.2.1]heptan-2-yl]-3-[(4,4-difluorocyclohexyl)methyl]-2-(1,1-difluoroethyl)-5-methylimidazo[1,2-a]pyridine-7-carboxamide obtained in Step 1.

$^1$H NMR (300 MHz, CDCl$_3$, δ): 7.87 (s, 1H), 7.29 (s, 1H), 6.30 (d, J=7.3 Hz, 1H), 4.98 (d, J=6.2 Hz, 2H), 4.73-4.63 (m, 1H), 4.47-4.40 (m, 1H), 4.31-4.21 (m, 1H), 3.31 (d, J=6.6 Hz, 2H), 2.31-1.98 (m, 8H), 1.78-1.46 (m, 10H); ESIMS m/z: [M+H]$^+$ 484.

Step 3

Compound 179 (46.1 mg, yield 77%) was obtained in the same manner as in Step 2 of Example 14, using N-[(1R,2S,4S)-7-oxabicyclo[2.2.1]heptan-2-yl]-3-[(4,4-difluorocyclohexyl)methyl]-2-(1,1-difluoroethyl)-5-(hydroxymethyl)imidazo[1,2-a]pyridine-7-carboxamide obtained in Step 2.

$^1$H NMR (300 MHz, CDCl$_3$, δ): 10.00 (s, 1H), 8.24 (d, J=1.8 Hz, 1H), 8.08 (d, J=1.8 Hz, 1H), 6.40 (d, J=8.4 Hz, 1H), 4.77-4.65 (m, 1H), 4.54-4.45 (m, 1H), 4.38-4.26 (m, 1H), 3.45 (br s, 2H), 2.32-1.21 (m, 18H); ESIMS m/z: [M+H]$^+$ 482.

EXAMPLE 99

N-[(1R,2S,4S)-7-Oxabicyclo[2.2.1]heptan-2-yl]-5-cyano-3-[(4,4-difluorocyclohexyl)methyl]-2-isopropylimidazo[1,2-a]pyridine-7-carboxamide (Compound 180)

Compound 180 (4.0 mg, yield 32%) was obtained in the same manner as in Step 9 of Example 1, using 5-cyano-3-[(4,4-difluorocyclohexyl)methyl]-2-isopropylimidazo[1,2-a]pyridine-7-carboxylic acid obtained in Step 4 of Example 89 and (1R,2S,4S)-7-oxabicyclo[2.2.1]heptan-2-amine.

$^1$H NMR (300 MHz, CDCl$_3$, δ): 8.15 (d, J=1.8 Hz, 1H), 7.86 (d, J=1.8 Hz, 1H), 6.39 (d, J=8.4 Hz, 1H), 4.71-4.64 (m, 1H), 4.48-4.42 (m, 1H), 4.35-4.26 (m, 1H), 3.18-3.08 (m, 3H), 2.22-2.04 (m, 3H), 1.91-1.40 (m, 12H), 1.35 (d, J=7.0 Hz, 6H); ESIMS m/z: [M+H]$^+$ 457.

EXAMPLE 100

5-Cyano-3-[(4,4-difluorocyclohexyl)methyl]-6-methyl-N-(tetrahydro-2H-pyran-4-yl)-2-(trifluoromethyl)imidazo[1,2-a]pyridine-7-carboxamide (Compound 181)

Compound (4.0 mg, yield 83%) was obtained in the same manner as in Step 3 of Example 86, using Compound 168.

$^1$H NMR (300 MHz, CDCl$_3$, δ): 7.88 (s, 1H), 5.84 (d, J=8.1 Hz, 1H), 4.28-4.13 (m, 1H), 4.07-3.99 (m, 2H), 3.60-3.47 (m, 2H), 3.35 (d, J=6.6 Hz, 2H), 2.72 (s, 3H), 2.20-1.26 (m, 13H); ESIMS m/z: [M+H]$^+$ 485.

EXAMPLE 101

5-Cyano-3-[(4,4-difluorocyclohexyl)methyl]-N-[3-(dimethylamino)-2,2-dimethylpropyl]-2-(trifluoromethyl)imidazo[1,2-a]pyridine-7-carboxamide (Compound 182)

Compound 182 (11.5 mg, yield 45%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and N,N,2,2-tetramethyl-1,3-propanediamine.

$^1$H NMR (400 MHz, CDCl$_3$, δ): 10.08 (s, 1H), 8.13-8.09 (m, 2H), 3.40 (d, J=3.9 Hz, 2H), 3.36 (d, J=6.8 Hz, 2H), 2.42 (d, J=7.8 Hz, 8H), 2.12 (s, 2H), 1.83-1.48 (m, 7H), 1.02 (s, 6H); ESIMS m/z: [M+H]$^+$ 500.

EXAMPLE 102

N-[(1R,2S,4S)-7-Oxabicyclo[2.2.1]heptan-2-yl]-5-cyano-3-[(4,4-difluorocyclohexyl)methyl]-2-(1,1-difluoroethyl)imidazo[1,2-a]pyridine-7-carboxamide (Compound 183)

Compound 183 (27.3 mg, yield 62%) was obtained in the same manner as in Example 80, using Compound 179.

$^1$H NMR (300 MHz, CDCl$_3$, δ): 8.17 (d, J=1.8 Hz, 1H), 7.95 (d, J=1.8 Hz, 1H), 6.35 (d, J=8.8 Hz, 1H), 4.73-4.67 (m, 1H), 4.49-4.44 (m, 1H), 4.37-4.26 (m, 1H), 3.40 (d, J=7.0 Hz, 2H), 2.25-2.04 (m, 6H), 1.88-1.42 (m, 12H); ESIMS m/z: [M+H]$^+$ 479.

EXAMPLE 103

5-Cyano-3-[(4,4-difluorocyclohexyl)methyl]-2-(1,1-difluoroethyl)-N-(2-methoxy-2-methylpropyl)-6-methylimidazo[1,2-a]pyridine-7-carboxamide (Compound 184)

Step 1

1-Bromobutane-2,3-dione (5.53 g, 33.5 mmol) was dissolved in ethanol (30 mL), ethyl 6-amino-3-chloro-2-methylisonicotinate obtained by a method described in WO2012/105594 (6.00 g, 28.0 mmol) was added thereto, and the mixture was stirred under reflux with heating overnight. A saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (chloroform/methanol=95/5), whereby ethyl 2-acetyl-6-chloro-5-methylimidazo[1,2-a]pyridine-7-carboxylate (6.39 g, yield 81%) was obtained.

$^1$H NMR (300 MHz, CDCl$_3$, δ): 8.12 (s, 1H), 8.09 (s, 1H), 4.44 (q, J=7.2 Hz, 2H), 2.78 (s, 3H), 2.73 (s, 3H), 1.42 (t, J=7.2 Hz, 3H); ESIMS m/z: [M+H]$^+$ 281.

Step 2

Ethyl 2-acetyl-6-chloro-5-methylimidazo[1,2-a]pyridine-7-carboxylate obtained in Step 1 (6.30 g, 22.4 mmol) was dissolved in dichloromethane (100 mL), Deoxo-Fluor™ (50 mL, 271 mmol) was added thereto, and the mixture was stirred at room temperature for 3 days. Under ice-cooled condition, a saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=50/50), whereby ethyl 6-chloro-2-(1,1-difluoroethyl)-5-methylimidazo[1,2-a]pyridine-7-carboxylate (3.40 g, yield 50%) was obtained.

$^1$H NMR (300 MHz, CDCl$_3$, δ): 8.05 (s, 1H), 7.75 (s, 1H), 4.43 (q, J=7.2 Hz, 2H), 2.78 (s, 3H), 2.10 (t, J=18.5 Hz, 3H), 1.41 (t, J=7.2 Hz, 3H); ESIMS m/z: [M+H]$^+$ 303.

Step 3

Iodine (1.71 g, 6.74 mmol) was dissolved in dichloromethane (34 mL), pyridine (1.09 mL, 13.5 mmol) and [bis(trifluoroacetoxy)iodo]benzene (2.90 g, 6.74 mmol) were added thereto, and the mixture was stirred at room temperature for 20 minutes. Ethyl 6-chloro-2-(1,1-difluoroethyl)-5-methylimidazo[1,2-a]pyridine-7-carboxylate obtained in Step 2 (3.40 g, 11.2 mmol) was added to the reaction mixture, and the mixture was stirred at room temperature for 1 hour. A saturated aqueous sodium hydrogen carbonate solution and an aqueous sodium thiosulfate solution were added to the reaction mixture, the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=80/20), whereby ethyl 6-chloro-2-(1,1-difluoroethyl)-3-iodo-5-methylimidazo[1,2-a]pyridine-7-carboxylate (4.66 g, yield 97%) was obtained.

$^1$H NMR (300 MHz, CDCl$_3$, δ): 7.97 (s, 1H), 4.41 (q, J=7.2 Hz, 2H), 3.40 (s, 3H), 2.14 (t, J=18.5 Hz, 3H), 1.40 (t, J=7.2 Hz, 3H); ESIMS m/z: [M+H]$^+$ 429.

Step 4

Ethyl 6-chloro-3-[(4,4-difluorocyclohexyl)(hydroxy)methyl]-2-(1,1-difluoroethyl)-5-methylimidazo[1,2-a]pyridine-7-carboxylate (1.60 g, yield 44%) was obtained in the same manner as in Step 3 of Example 4, using ethyl 6-chloro-2-(1,1-difluoroethyl)-3-iodo-5-methylimidazo[1,2-a]pyridine-7-carboxylate obtained in Step 3.

$^1$H NMR (300 MHz, CDCl$_3$, δ): 7.99 (s, 1H), 5.36 (dd, J=10.0, 6.3 Hz, 1H), 4.43 (q, J=7.1 Hz, 3H), 3.15 (s, 3H), 2.52-2.37 (m, 2H), 2.27-1.47 (m, 10H), 1.41 (t, J=7.1 Hz, 3H); ESIMS m/z: [M+H]$^+$ 451.

Step 5

Ethyl 6-chloro-3-[(4,4-difluorocyclohexyl)(hydroxy)methyl]-2-(1,1-difluoroethyl)-5-methylimidazo[1,2-a]pyridine-7-carboxylate obtained in Step 4 (1.60 g, 3.55 mmol) was dissolved in trifluoroacetic acid (13.7 mL, 177 mmol), triethylsilane (5.67 mL, 35.5 mmol) was added thereto, and the mixture was stirred at 50° C. for 4 hours. After the excess amount of starting material reagent contained in the reaction mixture was evaporated under reduced pressure, ethyl acetate was added to the residue, then a saturated aqueous sodium hydrogen carbonate solution was added thereto, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=80/20), whereby ethyl 6-chloro-3-[(4,4-difluorocyclohexyl)methyl]-2-(1,1-difluoroethyl)-5-methylimidazo[1,2-a]pyridine-7-carboxylate (0.561 g, yield 36%) was obtained.

$^1$H NMR (300 MHz, CDCl$_3$, δ): 7.98 (s, 1H), 4.41 (q, J=6.8 Hz, 2H), 3.29 (d, J=6.8 Hz, 2H), 2.97 (s, 3H), 2.23-2.01 (m, 6H), 1.70-1.33 (m, 9H); ESIMS m/z: [M+H]$^+$ 435.

Step 6

Ethyl 6-chloro-3-[(4,4-difluorocyclohexyl)methyl]-2-(1,1-difluoroethyl)-5-methylimidazo[1,2-a]pyridine-7-carboxylate obtained in Step 5 (0.561 g, 1.29 mmol) was dissolved in chlorobenzene (6.0 mL), N-bromosuccinimide (0.241 g, 1.26 mmol) and azobisisobutyronitrile (0.021 g, 0.129 mmol) were added thereto, and the mixture was stirred at 100° C. for 1 hour. A saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=80/20), whereby ethyl 5-bromomethyl-6-chloro-3-[(4,4-difluorocyclohexyl)methyl]-2-(1,1-difluoroethyl)imidazo[1,2-a]pyridine-7-carboxylate (0.487 g, yield 74%) was obtained.

$^1$H NMR (300 MHz, CDCl$_3$, δ): 8.17 (s, 1H), 5.12 (br s, 2H), 4.43 (q, J=7.2 Hz, 2H), 3.40 (br s, 2H), 2.27-2.03 (m, 6H), 1.85-1.49 (m, 6H), 1.41 (t, J=7.2 Hz, 3H); ESIMS m/z: [M+H]$^+$ 513, 515.

Step 7

Molecular sieves 4A (0.020 g, 0.740 mmol) was suspended in acetonitrile (11 mL), ethyl 5-bromomethyl-6-chloro-3-[(4,4-difluorocyclohexyl)methyl]-2-(1,1-difluoroethyl)imidazo[1,2-a]pyridine-7-carboxylate obtained in Step 6 (0.38 g, 0.740 mmol) and N-methylmorpholine N-oxide (0.173 g, 1.48 mmol) were added thereto, and the mixture was stirred at room temperature for 4 hours. A saturated aqueous sodium hydrogen carbonate solution was added to the reaction mixture, and the mixture was extracted with ethyl acetate. The organic layer was washed with saturated brine and dried over anhydrous magnesium sulfate, and the solvent was evaporated under reduced pressure. The residue was purified by silica gel column chromatography (heptane/ethyl acetate=80/20), whereby ethyl 6-chloro-3-[(4,4-difluorocyclohexyl)methyl]-2-(1,1-difluoroethyl)-5-formylimidazo[1,2-a]pyridine-7-carboxylate (0.21 g, yield 63%) was obtained.

$^1$H NMR (300 MHz, CDCl$_3$, δ): 10.58 (s, 1H), 8.44 (s, 1H), 4.46 (q, J=7.2 Hz, 2H), 3.12 (d, J=6.8 Hz, 2H), 2.18 (t, J=18.5 Hz, 3H), 2.08-1.93 (m, 2H), 1.61-1.48 (m, 3H), 1.44 (t, J=6.8 Hz, 3H), 1.35-1.27 (m, 4H); ESIMS m/z: [M+H]$^+$ 449.

Step 8

A crude product of ethyl 6-chloro-5-cyano-3-[(4,4-difluorocyclohexyl)methyl]-2-(1,1-difluoroethyl)imidazo[1,2-a]pyridine-7-carboxylate (0.21 g) was obtained in the same manner as in Example 80, using ethyl 6-chloro-3-[(4,4-difluorocyclohexyl)methyl]-2-(1,1-difluoroethyl)-5-formylimidazo[1,2-a]pyridine-7-carboxylate obtained in Step 7. ESIMS m/z: [M+H]$^+$ 446.

Step 9

Ethyl 5-cyano-3-[(4,4-difluorocyclohexyl)methyl]-2-(1,1-difluoroethyl)-6-methylimidazo[1,2-a]pyridine-7-carboxylate (0.13 g, yield 65%) was obtained in the same manner as in Step 3 of Example 86, using the crude product of ethyl 6-chloro-5-cyano-3-[(4,4-difluorocyclohexyl)methyl]-2-(1,1-difluoroethyl)imidazo[1,2-a]pyridine-7-carboxylate obtained in Step 8. ESIMS m/z: [M+H]$^+$ 426.

Step 10

5-Cyano-3-[(4,4-difluorocyclohexyl)methyl]-2-(1,1-difluoroethyl)-6-methylimidazo[1,2-a]pyridine-7-carboxylic acid (86.4 mg, 71%) was obtained in the same manner as in Step 1 of Example 21, using ethyl 5-cyano-3-[(4,4-difluorocyclohexyl)methyl]-2-(1,1-difluoroethyl)-6-methylimidazo[1,2-a]pyridine-7-carboxylate obtained in Step 9. ESIMS m/z: [M+H]$^+$ 398.

Step 11

Compound 184 (24.8 mg, yield 68%) was obtained in the same manner as in Step 8 of Example 1, using 5-cyano-3-[(4,4-difluorocyclohexyl)methyl]-2-(1,1-difluoroethyl)-6-methylimidazo[1,2-a]pyridine-7-carboxylic acid obtained in Step 10 and 2-methoxy-2-methylpropan-1-amine.

$^1$H NMR (300 MHz, CDCl$_3$, δ): 7.89 (s, 1H), 6.28 (t, J=4.9 Hz, 1H), 3.47 (d, J=4.9 Hz, 2H), 3.40 (d, J=7.8 Hz, 2H), 3.20 (s, 3H), 2.72 (s, 3H), 2.23-2.04 (m, 5H), 1.93-1.42 (m, 7H), 1.24 (s, 6H); ESIMS m/z: [M+H]$^+$ 483.

EXAMPLE 104

5-Cyano-3-[(4,4-difluorocyclohexyl)methyl]-2-(1,1-difluoroethyl)-6-methyl-N-(tetrahydro-2H-pyran-4-yl)imidazo[1,2-a]pyridine-7-carboxamide (Compound 185)

Compound 185 (7.8 mg, yield 27%) was obtained in the same manner as in Step 9 of Example 1, using 5-cyano-3-[(4,4-difluorocyclohexyl)methyl]-2-(1,1-difluoroethyl)-6-methylimidazo[1,2-a]pyridine-7-carboxylic acid obtained in Step 10 of Example 103, tetrahydro-2H-pyran-4-amine hydrochloride, and potassium carbonate.

$^1$H NMR (300 MHz, CDCl$_3$, δ): 7.85 (s, 1H), 5.80 (d, J=8.1 Hz, 1H), 4.26-4.14 (m, 1H), 4.07-3.94 (m, 2H), 3.59-3.47 (m, 2H), 3.40 (d, J=7.0 Hz, 2H), 2.71 (s, 3H), 2.19-2.01 (m, 8H), 1.84-1.42 (m, 8H); ESIMS m/z: [M+H]$^+$ 481.

EXAMPLE 105

5-Cyano-3-[(4,4-difluorocyclohexyl)methyl]-N-(2-methoxy-d$_3$-2-methylpropyl)-2-(trifluoromethyl)imidazo[1,2-a]pyridine-7-carboxamide (Compound 186)

Step 1

Methyl 2-methoxy-d$_3$-2-methylpropanoate (3.50 g, quantitative) was obtained in the same manner as in Step 1 of Example 11, using methyl 2-hydroxy-2-methylpropanoate and iodomethane-d$_3$.

$^1$H NMR (300 MHz, CDCl$_3$, δ): 3.76 (s, 3H), 1.43 (s, 6H).

Step 2

2-Methoxy-d$_3$-2-methylpropan-1-ol (0.825 g, 30%) was obtained in the same manner as in Example 16, using methyl 2-methoxy-d$_3$-2-methylpropanoate obtained in Step 1.

$^1$H NMR (300 MHz, CDCl$_3$, δ): 3.43 (d, J=6.3 Hz, 2H), 1.92 (t, J=6.3 Hz, 1H), 1.16 (s, 6H).

Step 3

2-Methoxy-d$_3$-2-methylpropan-1-ol obtained in Step 2 (0.710 g, 6.63 mmol) was dissolved in toluene (7 mL), phthalimide (10.7 g, 7.29 mmol), triphenylphosphine oxide (2.09 g, 7.95 mmol), and diethyl azodicarboxylate (4.52 mL, 9.94 mmol, 2.2 mol/L solution in toluene) were added thereto, and the mixture was stirred at 50° C. for 1 hour. After cooling the reaction mixture to room temperature, the solvent was evaporated under reduced pressure. The resulting residue was purified by silica gel column chromatography (heptane/ethyl acetate=70/30), whereby 2-(2-methoxy-d$_3$-2-methylpropyl)isoindole-1,3-dione (0.701 g, yield 45%) was obtained.

$^1$H NMR (300 MHz, CDCl$_3$, δ): 7.86-7.83 (m, 2H), 7.73-7.70 (m, 2H), 3.73 (s, 2H), 1.23 (s, 6H).

Step 4

2-(2-Methoxy-d$_3$-2-methylpropyl)isoindole-1,3-dione obtained in Step 3 (0.801 g, 3.39 mmol) was suspended in ethanol (8 mL), hydrazine monohydrate (0.198 mL, 4.07 mmol) was added thereto, and the mixture was stirred under reflux with heating for 1 hour. The reaction mixture was cooled to 0° C., heptane was added thereto, and the precipitate was removed by filtration. Under ice-cooled condition, hydrochloric acid (1.87 mL, 3.73 mmol, 2 mol/L solution in ethanol) was added to the filtrate, and the precipitated impurities were removed by filtration. The solvent in the filtrate was evaporated under reduced pressure. The resulting residue was reslurried in tert-butyl methyl ether, whereby 2-methoxy-d$_3$-2-methylpropan-1-amine hydrochloride (0.396 g, yield 82%) was obtained.

$^1$H NMR (300 MHz, DMSO-d$_6$, δ): 7.96 (br s, 3H), 2.81 (q, J 5.9 Hz, 2H), 1.16 (s, 6H).

Step 5

Compound 186 (11.9 mg, yield 49%) was obtained in the same manner as in Step 9 of Example 1, using 2-methoxy-d$_3$-2-methylpropan-1-amine hydrochloride obtained in Step 4, 5-cyano-3-[(4,4-difluorocyclohexyl)methyl]-2-(trifluoromethyl)imidazo[1,2-a]pyridine-7-carboxylic acid obtained in Step 3 of Example 37, and potassium carbonate.

$^1$H NMR (300 MHz, CDCl$_3$, δ): 8.24 (d, J=2.0 Hz, 1H), 8.07 (d, J=2.0 Hz, 1H), 6.61 (t, J=4.9 Hz, 1H), 3.49 (d, J=4.9 Hz, 2H), 3.36 (d, J=6.8 Hz, 2H), 2.23-2.06 (m, 2H), 1.95-1.40 (m, 7H), 1.23 (s, 6H); ESIMS m/z: [M+H]$^+$ 476.

EXAMPLE 106

(S)-5-Cyano-3-[(4,4-difluorocyclohexyl)methyl]-N-[1-(dimethylamino)-1-oxopropan-2-yl]-2-(trifluoromethyl)imidazo[1,2-a]pyridine-7-carboxamide (Compound 187)

Step 1 tert-Butyl (S)-[1-(dimethylamino)-1-oxopropan-2-yl]carbamate (97.0 mg, yield 85%) was obtained in the same manner as in Step 9 of Example 1, using (S)-2-[(tert-butoxycarbonyl)amino]propanoic acid and dimethylamine.

$^1$H NMR (400 MHz, CDCl$_3$, δ): 5.50 (d, J=6.8 Hz, 1H), 4.63 (qd, J=6.8, 6.8 Hz, 1H), 3.06 (s, 3H), 2.97 (s, 3H), 1.44 (s, 9H), 1.30 (d, J=6.8 Hz, 3H).

Step 2

To tert-butyl (S)-[1-(dimethylamino)-1-oxopropan-2-yl]carbamate obtained in Step 1 (97.0 mg, 0.448 mmol), 4 mol/L hydrochloric acid 1,4-dioxane solution (1 mL) was added thereto, and the mixture was stirred at room temperature overnight. The solvent in the reaction mixture was evaporated under reduced pressure, whereby a crude product of (S)-2-amino-N,N-dimethylpropanamide hydrochloride (76.6 mg) was obtained.

$^1$H NMR (400 MHz, DMSO-d$_6$, δ): 8.15 (s, 2H), 4.34-4.28 (m, 1H), 3.01 (s, 3H), 2.88 (s, 3H), 1.30 (d, J=6.8 Hz, 3H).

Step 3

Compound 187 (14.2 mg, yield 57%) was obtained in the same manner as in Step 9 of Example 1, using the crude product of (S)-2-amino-N,N-dimethylpropanamide hydrochloride obtained in Step 2 and 5-cyano-3-[(4,4-difluorocyclohexyl)methyl]-2-(trifluoromethyl)imidazo[1,2-a]pyridine-7-carboxylic acid obtained in Step 3 of Example 37.

$^1$H NMR (400 MHz, CDCl$_3$, δ): 8.35-8.33 (m, 1H), 8.02 (d, J=2.0 Hz, 1H), 7.62 (d, J=6.8 Hz, 1H), 5.08-5.00 (m, 1H), 3.36 (d, J=6.8 Hz, 2H), 3.13 (s, 3H), 3.04 (s, 3H), 2.12 (s, 2H), 1.73-1.60 (m, 7H), 1.47 (d, J=6.8 Hz, 3H); ESIMS m/z: [M+H]$^+$ 486.

EXAMPLE 107

5-Cyano-3-[(4,4-difluorocyclohexyl)methyl]-N-[2-methyl-2-(methylsulfonyl)propyl]-2-(trifluoromethyl)imidazo[1,2-a]pyridine-7-carboxamide (Compound 189)

Step 1

5-Cyano-3-[(4,4-difluorocyclohexyl)methyl]-N-[2-methyl-2-(methylthio)propyl]-2-(trifluoromethyl)imidazo[1,2-a]pyridine-7-carboxamide (30.3 mg, yield 80%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example and 2-methyl-2-(methylthio)propan-1-amine (Enamine, catalog No. EN300-95952).

$^1$H NMR (300 MHz, CDCl$_3$, δ): 8.28 (d, J=1.8 Hz, 1H), 8.08 (d, J=1.8 Hz, 1H), 6.80 (br s, 1H), 3.47 (d, J=5.5 Hz, 2H), 3.37 (d, J=6.6 Hz, 2H), 2.17-2.07 (m, 2H), 2.03 (s, 3H), 1.85-1.45 (m, 7H), 1.33 (s, 6H); ESIMS m/z: [M+H]$^+$ 489.

Step 2

5-Cyano-3-[(4,4-difluorocyclohexyl)methyl]-N-[2-methyl-2-(methylthio)propyl]-2-(trifluoromethyl)imidazo[1,2-a]pyridine-7-carboxamide obtained in Step 1 (19.5 mg, 0.0400 mmol) was dissolved in dichloromethane (1 mL), meta-chloroperbenzoic acid (17.0 mg, 0.100 mmol) was added thereto, and the mixture was stirred at room temperature for 30 minutes. A saturated aqueous sodium hydrogen carbonate was added to the reaction mixture, and the mixture was extracted with dichloromethane. The organic layer was washed with saturated brine and dried over anhydrous magnesium sulfate, and the solvent was evaporated under reduced pressure. The residue was purified by preparative thin-layer chromatography (chloroform/methanol=9/1), whereby Compound 189 (13.4 mg, yield 65%) was obtained.

$^1$H NMR (400 MHz, CDCl$_3$, δ): 8.32-8.29 (m, 1H), 8.03 (d, J=2.0 Hz, 1H), 7.41 (br s, 1H), 3.90 (d, J=5.9 Hz, 2H), 3.36 (d, J=6.8 Hz, 2H), 2.91 (s, 3H), 2.12 (s, 2H), 1.75-1.56 (m, 13H); ESIMS m/z: [M+H]$^+$ 521.

EXAMPLE 108

5-Cyano-3-[(4,4-difluorocyclohexyl)methyl]-2-(1,1-difluoroethyl)-N-(2-methoxy-d$_3$-2-methylpropyl)-6-methylimidazo[1,2-a]pyridine-7-carboxamide (Compound 190)

Compound 190 (23.7 mg, yield 97%) was obtained in the same manner as in Step 9 of Example 1, using 5-cyano-3-[(4,4-difluorocyclohexyl)methyl]-2-(1,1-difluoroethyl)-6-methylimidazo[1,2-a]pyridine-7-carboxylic acid obtained in Step 10 of Example 103, 2-methoxy-d$_3$-2-methylpropan-1-amine hydrochloride obtained in Step 4 of Example 105, and potassium carbonate.

$^1$H NMR (300 MHz, CDCl$_3$, δ): 7.89 (s, 1H), 6.30 (t, J=5.9 Hz, 1H), 3.47 (d, J=5.9 Hz, 2H), 3.40 (d, J=6.8 Hz, 2H), 2.72 (s, 3H), 2.23-2.04 (m, 5H), 1.94-1.42 (m, 7H), 1.24 (s, 6H); ESIMS m/z: [M+H]$^+$ 486.

EXAMPLE 109

5,6-Dichloro-3-[(4,4-difluorocyclohexyl)methyl]-Netrahydro-2H-pyran-4-yl)-2-(trifluoromethyl)imidazo[1,2-a]pyridine-7-carboxamide (Compound 193)

Step 1

Methyl 5-amino-6-chloro-3-[(4,4-difluorocyclohexyl)methyl]-2-(trifluoromethyl)imidazo[1,2-a]pyridine-7-carboxylate (0.352 g, 0.826 mmol) was obtained in the same manner as in Step 1 of Example 5, using methyl 5-amino-3-[(4,4-difluorocyclohexyl)methyl]-2-(trifluoromethyl)imidazo[1,2-a]pyridine-7-carboxylate obtained in Step 4 of Example 25.

$^1$H NMR (300 MHz, CDCl$_3$, δ): 7.71 (s, 1H), 5.06 (br s, 2H), 3.96 (s, 3H), 3.21 (d, J=7.0 Hz, 2H), 2.16-1.41 (m, 9H); ESIMS m/z: [M+H]$^+$ 426.

Step 2

Methyl 5,6-dichloro-3-[(4,4-difluorocyclohexyl)methyl]-2-(trifluoromethyl)imidazo[1,2-a]pyridine-7-carboxylate (0.126 g, yield 34%) was obtained in the same manner as in Step 1 of Example 37, using methyl 5-amino-6-chloro-3-[(4,4-difluorocyclohexyl)methyl]-2-(trifluoromethyl)imidazo[1,2-a]pyridine-7-carboxylate obtained in Step 1.

$^1$H NMR (300 MHz, CDCl$_3$, δ): 8.12 (s, 1H), 3.99 (s, 3H), 3.36 (d, J=6.2 Hz, 2H), 2.22-1.35 (m, 9H).; ESIMS m/z: [M+H]$^+$ 445.

Step 3

5,6-Dichloro-3-[(4,4-difluorocyclohexyl)methyl]-2-(trifluoromethyl)imidazo[1,2-a]pyridine-7-carboxylic acid (0.106 g, yield 91%) was obtained in the same manner as in Step 9 of Example 1, using methyl 5,6-dichloro-3-[(4,4-difluorocyclohexyl)methyl]-2-(trifluoromethyl)imidazo[1,2-a]pyridine-7-carboxylate obtained in Step 2.

$^1$H NMR (300 MHz, CDCl$_3$, δ): 8.31 (s, 1H), 3.37 (d, J=6.6 Hz, 2H), 2.16-1.26 (m, 9H); ESIMS m/z: [M+H]$^+$ 431.

Step 4

Compound 193 (6.4 mg, yield 27%) was obtained in the same manner as in Step 9 of Example 1, using 5,6-dichloro-3-[(4,4-difluorocyclohexyl)methyl]-2-(trifluoromethyl)imidazo[1,2-a]pyridine-7-carboxylic acid obtained in Step 3, tetrahydro-2H-pyran-4-amine hydrochloride, and potassium carbonate.

$^1$H NMR (300 MHz, CDCl$_3$, δ): 7.76 (s, 1H), 5.93 (d, J=7.8 Hz, 1H), 4.27-4.18 (m, 1H), 4.08-3.96 (m, 2H), 3.59-3.48 (m, 2H), 3.34 (d, J=6.8 Hz, 2H), 2.17-1.24 (m, 13H); ESIMS m/z: [M+H]$^+$ 514.

EXAMPLE 110

5-Cyano-3-[(4,4-difluorocyclohexyl)methyl]-2-(1,1-difluoroethyl)-N-(2-methoxy-d$_3$-2-methylpropyl)imidazo[1,2-a]pyridine-7-carboxamide (Compound 194)

Step 1

3-[(4,4-Difluorocyclohexyl)methyl]-2-(1,1-difluoroethyl)-N-(2-methoxy-d$_3$-2-methylpropyl)-5-methylimidazo[1,2-a]pyridine-7-carboxamide (140 mg, yield 87%) was obtained in the same manner as in Step 9 of Example 1, using 3-[(4,4-difluorocyclohexyl)methyl]-2-(1,1-difluoroethyl)-5-methylimidazo[1,2-a]pyridine-7-carboxylic acid obtained in Step 2 of Example 67, 2-methoxy-d$_3$-2-methylpropan-1-amine hydrochloride obtained in Step 4 of Example 105, and potassium carbonate. ESIMS m/z: [M+H]$^+$ 461.

Step 2

3-[(4,4-Difluorocyclohexyl)methyl]-2-(1,1-difluoroethyl)-N-(2-methoxy-d$_3$-2-methylpropyl)-5-(hydroxymethyl)imidazo[1,2-a]pyridine-7-carboxamide (59.4 mg, yield 41%) was obtained in the same manner as in Step 4 of Example 32, using 3-[(4,4-difluorocyclohexyl)methyl]-2-(1,1-difluoroethyl)-N-(2-methoxy-d$_3$-2-methylpropyl)-5-methylimidazo[1,2-a]pyridine-7-carboxamide obtained in Step 1.

$^1$H NMR (300 MHz, CDCl$_3$, δ): 7.90 (d, J=1.8 Hz, 1H), 7.37 (d, J=1.8 Hz, 1H), 6.58 (t, J=5.5 Hz, 1H), 4.99 (s, 2H), 3.45 (d, J=5.5 Hz, 2H), 3.33 (d, J=5.9 Hz, 2H), 2.26-2.01 (m, 5H), 1.76-1.44 (m, 7H), 1.21 (s, 6H); ESIMS m/z: [M+H]$^+$ 477.

Step 3

3-[(4,4-Difluorocyclohexyl)methyl]-2-(1,1-difluoroethyl)-5-formyl-N-(2-methoxy-d$_3$-2-methylpropyl)imidazo[1,2-a]pyridine-7-carboxamide (54 mg, yield 99%) was obtained in the same manner as in Step 2 of Example 14, using 3-[(4,4-difluorocyclohexyl)methyl]-2-(1,1-difluoroethyl)-N-(2-methoxy-d$_3$-2-methylpropyl)-5-(hydroxymethyl)imidazo[1,2-a]pyridine-7-carboxamide obtained in Step 2.

ESIMS m/z: [M+H]$^+$ 475.

Step 4

Compound 194 (44 mg, yield 82%) was obtained in the same manner as in Example 80, using 3-[(4,4-difluorocyclohexyl)methyl]-2-(1,1-difluoroethyl)-5-formyl-N-(2-methoxy-d$_3$-2-methylpropyl)imidazo[1,2-a]pyridine-7-carboxamide obtained in Step 3.

$^1$H NMR (300 MHz, CDCl$_3$, δ): 8.20 (d, J=2.0 Hz, 1H), 8.02 (d, J=2.0 Hz, 1H), 6.59 (t, J=5.9 Hz, 1H), 3.49 (d, J=5.9 Hz, 2H), 3.41 (d, J=6.8 Hz, 2H), 2.23-2.02 (m, 5H), 1.92-1.44 (m, 7H), 1.23 (s, 6H); ESIMS m/z: [M+H]$^+$ 472.

EXAMPLE 111

5-Chloro-3-[(4,4-difluorocyclohexyl)methyl]-6-methyl-N-(tetrahydro-2H-pyran-4-yl)-2-(trifluoromethyl)imidazo[1,2-a]pyridine-7-carboxamide (Compound 195)

Step 1

Methyl 6-amino-2-chloro-3-iodoisonicotinate (0.412 g, yield 75%) was obtained in the same manner as in Step 2 of Example 4, using methyl 6-amino-2-chloroisonicotinate.

$^1$H NMR (300 MHz, CDCl$_3$, δ): 6.54 (s, 1H), 4.71 (s, 2H), 3.94 (s, 3H); ESIMS m/z: [M+H]$^+$ 313.

Step 2

Methyl 6-amino-2-chloro-3-methylisonicotinate (0.329 g, yield 45%) was obtained in the same manner as in Step 3 of Example 86, using methyl 6-amino-2-chloro-3-iodoisonicotinate obtained in Step 1.

$^1$H NMR (300 MHz, CDCl$_3$, δ): 6.75 (s, 1H), 4.50 (s, 2H), 3.90 (s, 3H), 2.40 (s, 3H); ESIMS m/z: [M+H]$^+$ 201.

Step 3

Methyl 5-chloro-3-[(4,4-difluorocyclohexyl)methyl]-6-methyl-2-(trifluoromethyl)imidazo[1,2-a]pyridine-7-carboxylate (195 mg, yield 54%) was obtained in the same manner as in Step 5 of Example 1, using methyl 6-amino-2-chloro-3-methylisonicotinate obtained in Step 2 and 3-bromo-4-(4,4-difluorocyclohexyl)-1,1,1-trifluorobutan-2-one obtained in Step 3 of Example 25.

$^1$H NMR (300 MHz, CDCl$_3$, δ): 8.17 (s, 1H), 3.95 (s, 3H), 3.36 (d, J=7.0 Hz, 2H), 2.63 (s, 3H), 2.17-1.43 (m, 9H); ESIMS m/z: [M+H]$^+$ 425.

Step 4

5-Chloro-3-[(4,4-difluorocyclohexyl)methyl]-6-methyl-2-(trifluoromethyl)imidazo[1,2-a]pyridine-7-carboxylic acid (182 mg, yield 86%) was obtained in the same manner as in Step 8 of Example 1, using methyl 5-chloro-3-[(4,4-difluorocyclohexyl)methyl]-6-methyl-2-(trifluoromethyl)imidazo[1,2-a]pyridine-7-carboxylate obtained in Step 3.

$^1$H NMR (300 MHz, CDCl$_3$, δ): 8.37 (s, 1H), 3.38 (d, J=7.5 Hz, 2H), 2.69 (s, 3H), 2.19-1.28 (m, 9H); ESIMS m/z: [M+H]$^+$ 411.

Step 5

Compound 195 (6.6 mg, yield 18%) was obtained in the same manner as in Step 9 of Example 1, using 5-chloro-3-[(4,4-difluorocyclohexyl)methyl]-6-methyl-2-(trifluoromethyl)imidazo[1,2-a]pyridine-7-carboxylic acid obtained in Step 4, tetrahydro-2H-pyran-4-amine hydrochloride, and potassium carbonate.

$^1$H NMR (300 MHz, CDCl$_3$, δ): 7.59 (s, 1H), 5.96 (d, J=7.8 Hz, 1H), 4.25-4.12 (m, 1H), 4.07-3.95 (m, 2H), 3.60-3.50 (m, 2H), 3.34 (d, J=6.8 Hz, 2H), 2.47 (s, 3H), 2.20-2.02 (m, 4H), 1.84-1.37 (m, 9H); ESIMS m/z: [M+H]$^+$ 494.

EXAMPLE 112

N-[(1R,5S,6r)-3-Oxabicyclo[3.1.0]hexan-6-yl]-5-chloro-3-[(4,4-difluorocyclohexyl)methyl]-2-(trifluoromethyl)imidazo[1,2-a]pyridine-7-carboxamide (Compound 196)

Compound 196 (8.1 mg, yield 34%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 3 of Example 26 and 3-oxobicyclo[3.1.0]hexan-6-amine (Ark Pharm, Inc., catalog No. AK-31516).

$^1$H NMR (300 MHz, CDCl$_3$, δ): 7.82 (d, J=2.0 Hz, 1H), 7.42 (d, J=2.0 Hz, 1H), 6.26 (br s, 1H), 4.11-4.04 (m, 2H), 3.81-3.75 (m, 2H), 3.35 (d, J=6.8 Hz, 2H), 2.78-2.74 (m, 1H), 2.10-1.25 (m, 11H); ESIMS m/z: [M+H]$^+$ 478.

EXAMPLE 113

5-Chloro-3-[(4,4-difluorocyclohexyl)methyl]-N-[2-methyl-2-(methylsulfonyl)propyl]-2-(trifluoromethyl)imidazo[1,2-a]pyridine-7-carboxamide (Compound 197)

Step 1

5-Chloro-3-[(4,4-difluorocyclohexyl)methyl]-N-[2-methyl-2-(methylthio)propyl]-2-(trifluoromethyl)imidazo[1,2-a]pyridine-7-carboxamide (28.0 mg, yield 74%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 1 of Example and 2-methyl-2-(methylthio)propan-1-amine (Enamine, catalog No. EN300-95952).

$^1$H NMR (400 MHz, CDCl$_3$, δ): 7.97 (d, J=1.7 Hz, 1H), 7.48 (d, J=1.7 Hz, 1H), 6.75 (br s, 1H), 3.45 (d, J=5.5 Hz, 2H), 3.35 (d, J=7.0 Hz, 2H), 2.09 (s, 2H), 2.02 (s, 3H), 1.62-1.55 (m, 7H), 1.32 (s, 6H); ESIMS m/z: [M+H]$^+$ 498.

Step 2

Compound 197 (17.6 mg, yield 59%) was obtained in the same manner as in Step 2 of Example 107, using 5-chloro-3-[(4,4-difluorocyclohexyl)methyl]-N-[2-methyl-2-(methylthio)propyl]-2-(trifluoromethyl)imidazo[1,2-a]pyridine-7-carboxamide obtained in Step 1.

$^1$H NMR (300 MHz, CDCl$_3$, δ): 8.01 (d, J=1.8 Hz, 1H), 7.41 (d, J=1.8 Hz, 1H), 7.31 (br s, 1H), 3.88 (d, J=5.9 Hz, 2H), 3.35 (d, J=6.6 Hz, 2H), 2.90 (s, 3H), 2.09 (s, 2H), 1.73-1.51 (m, 7H), 1.49 (s, 6H); ESIMS m/z: [M+H]$^+$ 530.

EXAMPLE 114

N-tert-Butyl-5-cyano-3-[(4,4-difluorocyclohexyl)methyl]-2-(trifluoromethyl)imidazo[1,2-a]pyridine-7-carboxamide (Compound 198)

Compound 198 (16.8 mg, yield 49%) was obtained in the same manner as in Step 9 of Example 1, using 5-cyano-3-[(4,4-difluorocyclohexyl)methyl]-2-(trifluoromethyl)imidazo[1,2-a]pyridine-7-carboxylic acid obtained in Step 3 of Example 37 and tert-butylamine.

$^1$H NMR (300 MHz, CDCl$_3$, δ): 8.12 (d, J=1.5 Hz, 1H), 8.01 (d, J=1.5 Hz, 1H), 5.94 (s, 1H), 3.35 (d, J=7.0 Hz, 2H), 2.12 (s, 2H), 1.81-1.25 (m, 16H); ESIMS m/z: [M+H]$^+$ 443.

EXAMPLE 115

5-Cyano-3-[(4,4-difluorocyclohexyl)methyl]-Netrahydro-2H-pyran-4-carbonyl)-2-(trifluoromethyl)imidazo[1,2-a]pyridine-7-carboxamide (Compound 201)

3-[(4,4-Difluorocyclohexyl)methyl]-5-methyl-2-trifluoromethylimidazo[1,2-a]pyridine-7-carboxamide obtained by a method described in WO2012/105594 (0.060 g, 0.155 mmol) was dissolved in THF (2.0 mL), potassium tert-butoxide (0.086 g, 0.775 mmol) was added thereto at 0° C., and the mixture was stirred 0° C. for 5 minutes. Tetrahydro-2H-pyran-4-carbonyl chloride (0.069 g, 0.466 mmol) was added to the reaction mixture, and the mixture was stirred at room temperature for 16 hours. The solvent was evaporated under reduce pressure, ethyl acetate and water were added to the resulting residue, and the mixture was extracted with ethyl acetate. The organic layer was washed with saturated brine and dried over anhydrous sodium sulfate, and the solvent was evaporated under reduced pressure. The residue was purified by silica gel column chromatography (hexane/ethyl acetate=80/20), whereby Compound 210 (0.016 g, yield 20%) was obtained.

$^1$H NMR (300 MHz, CH$_3$OD, δ): 8.41 (d, J=1.6 Hz, 1H), 8.09 (d, J=1.6 Hz, 1H), 4.44 (s, 1H) 3.92-3.89 (m, 2H), 3.38-3.44 (m, 2H), 3.28 (d, J=7.2 Hz, 2H), 3.10-3.03 (m, 1H), 1.94-1.91 (m, 3H), 1.79-1.55 (m, 8H), 1.39-1.36 (m, 2H); ESIMS m/z: [M+H]$^+$ 499.

EXAMPLE 116

5-Cyano-N-(cyclopropanecarbonyl)-3-[(4,4-difluorocyclohexyl)methyl]-2-(trifluoromethyl)imidazo[1,2-a]pyridine-7-carboxamide (Compound 202)

Compound 202 (0.018 g, yield 9%) was obtained in the same manner as in Example 115, using 3-[(4,4-difluorocyclohexyl)methyl]-5-methyl-2-trifluoromethylimidazo[1,2-a]pyridine-7-carboxamide obtained by a method described in WO2012/105594 and cyclopropanecarbonyl chloride.

$^1$H NMR (400 MHz, CDCl$_3$): 8.80 (s, 1H), 8.37 (d, J=1.6 Hz, 1H), 8.04 (d, J=1.6 Hz, 1H), 3.38 (d, J=7.2 Hz, 2H), 2.80-2.74 (m, 1H), 2.20-2.10 (m, 2H), 1.86-1.60 (m, 5H), 1.49-1.40 (m, 2H), 1.29-1.25 (m, 2H), 1.15-1.10 (m, 2H); ESIMS m/z: [M+H]$^+$ 455.

EXAMPLE 117

5-Cyano-3-[(4,4-difluorocyclohexyl)methyl]-N-pivaloyl-2-(trifluoromethyl)imidazo[1,2-a]pyridine-7-carboxamide (Compound 203)

Compound 203 (0.017 g, yield 12%) was obtained in the same manner as in Example 115, using 3-[(4,4-difluorocyclohexyl)methyl]-5-methyl-2-trifluoromethylimidazo[1,2-a]pyridine-7-carboxamide obtained by a method described in WO2012/105594 and pivaloyl chloride.

$^1$H NMR (400 MHz, CDCl$_3$): 8.31 (s, 1H), 8.18 (d, J=1.2 Hz, 1H), 7.79 (d, J=1.2 Hz, 1H), 3.36 (d, J=6.8 Hz, 2H), 2.20-2.10 (m, 2H), 1.83-1.61 (m, 5H), 1.52-1.46 (m, 2H), 1.34 (s, 9H); ESIMS m/z: [M+H]$^+$ 471.

EXAMPLE 118

5,6-Dichloro-3-[(4,4-difluorocyclohexyl)methyl]-N-(2,2-dimethyltetrahydro-2H-pyran-4-yl)-2-(trifluoromethyl)imidazo[1,2-a]pyridine-7-carboxamide (Compound 205)

Compound 205 (11.9 mg, yield 95%) was obtained in the same manner as in Step 9 of Example 1, using 5,6-dichloro-3-[(4,4-difluorocyclohexyl)methyl]-2-(trifluoromethyl)imidazo[1,2-a]pyridine-7-carboxylic acid obtained in Step 3 of Example 109 and 2,2-dimethyltetrahydro-2H-pyran-4-amine.

$^1$H NMR (300 MHz, CDCl$_3$, δ): 7.74 (s, 1H), 5.82 (d, J=8.1 Hz, 1H), 4.44-4.30 (m, 1H), 3.87-3.73 (m, 2H), 3.34 (d, J=7.0 Hz, 2H), 2.17-1.95 (m, 4H), 1.86-1.36 (m, 9H), 1.32 (s, 3H), 1.28 (s, 3H); ESIMS m/z: [M+H]$^+$ 542.

EXAMPLE 119

3-Benzyl-5-methyl-N-(tetrahydro-2H-pyran-4-yl)-2-(trifluoromethyl)imidazo[1,2-a]pyridine-7-carboxamide (Compound 206)

Step 1

Ethyl 5-methyl-2-(trifluoromethyl)imidazo[1,2-a]pyridine-7-carboxylate (9.50 g, yield 50%) was obtained in the same manner as in Step 1 of Example 103, using methyl 2-amino-6-methylisonicotinate and 3-bromo-1,1,1-trifluoropropan-2-one.

$^1$H NMR (300 MHz, CDCl$_3$, δ): 8.37 (s, 1H), 7.88 (s, 1H), 7.36 (s, 1H) 4.43 (q, J=7.2 Hz, 2H), 2.69 (s, 3H), 1.43 (t, J=7.2 Hz, 3H); ESIMS m/z: [M+H]$^+$ 273.

Step 2

Ethyl 5-methyl-2-(trifluoromethyl)imidazo[1,2-a]pyridine-7-carboxylate obtained in Step 1 (4.50 g, 16.5 mmol) was dissolved in acetic acid (45 mL), N-iodosuccinimide (5.50 g, 24.7 mmol) was added thereto, and the mixture was stirred at room temperature for 5 hours. Acetic acid was evaporated under reduced pressure, a saturated aqueous sodium hydrogen carbonate solution was added thereto, and the mixture was extracted with ethyl acetate. The organic layer was washed with saturated brine and dried over anhydrous sodium sulfate, and the solvent was evaporated under reduced pressure, whereby a crude product of ethyl 3-iodo-5-methyl-2-(trifluoromethyl)imidazo[1,2-a]pyridine-7-carboxylate (4.40 g, yield 67%) was obtained.

$^1$H NMR (300 MHz, CDCl$_3$, δ): 8.30 (d, J=1.2 Hz, 1H), 7.22 (s, 1H), 4.41 (q, J=7.2 Hz, 2H), 3.29 (s, 3H), 1.41 (t, J=7.2 Hz, 3H); ESIMS m/z: [M+H]$^+$ 399.

Step 3

Ethyl 3-[hydroxy(phenyl)methyl]-5-methyl-2-(trifluoromethyl)imidazo[1,2-a]pyridine-7-carboxylate (0.200 g, yield 43%) was obtained in the same manner as in Step 3 of Example 4, using the crude product of ethyl 3-iodo-5-methyl-2-(trifluoromethyl)imidazo[1,2-a]pyridine-7-carboxylate obtained in Step 2 and benzaldehyde.

$^1$H NMR (400 MHz, CDCl$_3$, δ): 8.28 (s, 1H), 7.35-7.28 (m, 3H), 7.18-7.14 (m, 3H), 6.82 (d, J=4.8 Hz, 1H), 4.39 (q, J=7.2 Hz, 2H), 3.14 (d, J=4.8 Hz, 1H), 2.41 (s, 3H), 1.39 (t, J=7.2 Hz, 3H); ESIMS m/z: [M+H]$^+$ 379.

Step 4

Ethyl 3-benzyl-5-methyl-2-(trifluoromethyl)imidazo[1,2-a]pyridine-7-carboxylate (0.200 g, yield 52%) was obtained in the same manner as in Step 5 of Example 103, using ethyl 3-[hydroxy(phenyl)methyl]-5-methyl-2-(trifluoromethyl)imidazo[1,2-a]pyridine-7-carboxylate obtained in Step 3.

$^1$H NMR (400 MHz, CDCl$_3$, δ): 8.28 (s, 1H), 7.35-7.20 (m, 3H), 7.10 (s, 1H), 6.90 (d, J=7.2 Hz, 2H), 4.70 (s, 2H), 4.39 (q, J=7.2 Hz, 2H), 2.67 (s, 3H), 1.39 (t, J=7.2 Hz, 3H); ESIMS m/z: [M+H]$^+$ 363.

Step 5

3-Benzyl-5-methyl-2-(trifluoromethyl)imidazo[1,2-a]pyridine-7-carboxylic acid (0.150 g, yield 81%) was obtained in the same manner as in Step 8 of Example 1, using ethyl 3-benzyl-5-methyl-2-(trifluoromethyl)imidazo[1,2-a]pyridine-7-carboxylate obtained in Step 4.

$^1$H NMR (400 MHz, DMSO-d$_6$, δ): 13.38 (bs, 1H), 8.08 (s, 1H), 7.33-7.29 (m, 2H), 7.24-7.17 (m, 2H), 6.92 (d, J=7.2 Hz, 2H), 4.74 (s, 2H), 2.68 (s, 3H); ESIMS m/z: [M+H]$^+$ 335.

Step 6

Compound 206 (0.120 g, yield 69%) was obtained in the same manner as in Step 9 of Example 1, using 3-benzyl-5-methyl-2-(trifluoromethyl)imidazo[1,2-a]pyridine-7-carboxylic acid obtained in Step 5 and tetrahydro-2H-pyran-4-amine.

$^1$H NMR (400 MHz, CDCl$_3$, δ): 7.83 (s, 1H), 7.30-7.28 (m, 1H), 7.24-7.20 (m, 2H), 6.97 (s, 1H), 6.89 (d, J=7.2 Hz, 2H), 6.01 (d, J=7.6 Hz, 1H), 4.69 (s, 2H), 4.23-4.11 (m, 1H), 4.01-3.99 (m, 2H), 3.56-3.50 (m, 2H), 2.66 (s, 3H), 2.04-1.99 (m, 2H), 1.62-1.53 (m, 2H); ESIMS m/z: [M+H]$^+$ 418.

EXAMPLE 120

5-Methyl-3-(4-methylbenzyl)-N-(tetrahydro-2H-pyran-4-yl)-2-(trifluoromethyl)imidazo[1,2-a]pyridine-7-carboxamide (Compound 207)

Step 1

Ethyl 3-[hydroxy(p-tolyl)methyl]-5-methyl-2-(trifluoromethyl)imidazo[1,2-a]pyridine-7-carboxylate (0.500 g, yield 50%) was obtained in the same manner as in Step 3 of Example 4, using the crude product of ethyl 3-iodo-5-methyl-2-(trifluoromethyl)imidazo[1,2-a]pyridine-7-carboxylate obtained in Step 2 of Example 119 and 4-methylbenzaldehyde.

$^1$H NMR: $^1$H NMR (300 MHz, CDCl$_3$, δ): 8.26 (s, 1H), 7.14-7.12 (m, 3H), 7.03 (d, J=7.8 Hz, 2H), 6.78 (d, J=4.5 Hz, 1H), 4.39 (q, J=7.2 Hz, 2H), 3.22 (d, J=5.1 Hz, 1H), 2.43 (s, 3H), 2.33 (s, 3H), 1.39 (t, J=7.2 Hz, 3H).

Step 2

Ethyl 5-methyl-3-(4-methylbenzyl)-2-(trifluoromethyl)imidazo[1,2-a]pyridine-7-carboxylate (0.250 g, yield 52%) was obtained in the same manner as in Step 5 of Example 103, using ethyl 3-[hydroxy(p-tolyl)methyl]-5-methyl-2-(trifluoromethyl)imidazo[1,2-a]pyridine-7-carboxylate obtained in Step 1.

¹H NMR (300 MHz, CDCl₃, δ): 8.27 (s, 1H), 7.10-7.07 (m, 3H), 6.78 (d, J=8.1 Hz, 2H), 4.65 (s, 2H), 4.43-4.36 (m, 2H), 2.68 (s, 3H), 2.30 (s, 3H), 1.39 (t, J=7.2 Hz, 3H).

Step 3

5-Methyl-3-(4-methylbenzyl)-2-(trifluoromethyl)imidazo[1,2-a]pyridine-7-carboxylic acid (170 mg, yield 80%) was obtained in the same manner as in Step 8 of Example 1, using ethyl 5-methyl-3-(4-methylbenzyl)-2-(trifluoromethyl)imidazo[1,2-a]pyridine-7-carboxylate obtained in Step 2.

¹H NMR (300 MHz, DMSO-d₆, δ): 13.29 (bs, 1H), 8.07 (d, J=1.2 Hz, 1H), 7.16-7.10 (m, 3H), 6.79 (d, J=7.8 Hz, 2H), 4.68 (s, 2H), 2.68 (s, 3H), 2.24 (s, 3H); ESIMS m/z: [M+H]⁺ 349.

Step 4

Compound 207 (0.150 g, yield 81%) was obtained in the same manner as in Step 9 of Example 1, using 5-methyl-3-(4-methylbenzyl)-2-(trifluoromethyl)imidazo[1,2-a]pyridine-7-carboxylic acid obtained in Step 3 and tetrahydro-2H-pyran-4-amine.

¹H NMR (400 MHz, CDCl₃, δ): 7.82 (s, 1H), 7.08 (d, J=8.0 Hz, 2H), 6.96 (s, 1H), 6.76 (d, J=8.0 Hz, 2H), 6.06 (d, J=7.6 Hz, 1H), 4.64 (s, 2H), 4.64-4.11 (m, 1H), 4.01-3.98 (m, 2H), 3.56-3.50 (m, 2H), 2.67 (s, 3H), 2.30 (s, 3H), 2.04-1.99 (m, 2H), 1.63-1.53 (m, 2H); ESIMS m/z: [M+H]⁺ 432.

EXAMPLE 121

3-(4-Chlorobenzyl)-5-methyl-N-(tetrahydro-2H-pyran-4-yl)-2-(trifluoromethyl)imidazo[1,2-a]pyridine-7-carboxamide (Compound 208)

Step 1

Ethyl 3-[(4-chlorophenyl)(hydroxy)methyl]-5-methyl-2-(trifluoromethyl)imidazo[1,2-a]pyridine-7-carboxylate (0.380 g, yield 36%) was obtained in the same manner as in Step 3 of Example 4, using ethyl 3-iodo-5-methyl-2-(trifluoromethyl)imidazo[1,2-a]pyridine-7-carboxylate obtained in Step 2 of Example 119 and 4-chlorobenzaldehyde.

¹H NMR (400 MHz, CDCl₃, δ): 8.29 (s, 1H), 7.34-7.28 (m, 2H), 7.17 (s, 1H), 7.12 (d, J=8.0 Hz, 2H), 6.76 (d, J=4.8 Hz, 1H), 4.41 (q, J=6.8 Hz, 2H), 2.94 (d, J=6.8 Hz, 1H), 2.83 (s, 3H), 1.41 (t, J=7.2 Hz, 3H); ESIMS m/z: [M+H]⁺ 413, 415.

Step 2

Ethyl 3-(4-chlorobenzyl)-5-methyl-2-(trifluoromethyl)imidazo[1,2-a]pyridine-7-carboxylate (0.244 g, yield 70%) was obtained in the same manner as in Step 5 of Example 103, using ethyl 3-[(4-chlorophenyl)(hydroxy)methyl]-5-methyl-2-(trifluoromethyl)imidazo[1,2-a]pyridine-7-carboxylate obtained in Step 1.

¹H NMR (300 MHz, CDCl₃, δ): 8.28 (s, 1H), 7.31 (d, J=2.7 Hz, 1H), 7.28 (s, 1H), 7.13 (s, 1H), 6.84 (d, J=8.4 Hz, 2H), 4.67 (s, 2H), 4.40 (q, J=7.2 Hz, 2H), 2.66 (s, 3H), 1.40 (t, J=7.2 Hz, 3H); ESIMS m/z: [M+H]⁺ 397, 399.

Step 3

3-(4-Chlorobenzyl)-5-methyl-2-(trifluoromethyl)imidazo[1,2-a]pyridine-7-carboxylic acid (180 mg, yield 84%) was obtained in the same manner as in Step 8 of Example 1, using ethyl 3-(4-chlorobenzyl)-5-methyl-2-(trifluoromethyl)imidazo[1,2-a]pyridine-7-carboxylate obtained in Step 2.

¹H NMR (300 MHz, DMSO-d₆, δ): 13.29 (bs, 1H), 8.07 (d, J=1.2 Hz, 1H), 7.16-7.10 (m, 3H), 6.79 (d, J=7.8 Hz, 2H), 4.68 (s, 2H), 2.68 (s, 3H); ESIMS m/z: [M+H]⁺ 369, 371.

Step 4

Compound 208 (0.132 g, yield 62%) was obtained in the same manner as in Step 9 of Example 1, using 3-(4-chlorobenzyl)-5-methyl-2-(trifluoromethyl)imidazo[1,2-a]pyridine-7-carboxylic acid obtained in Step 3 and tetrahydro-2H-pyran-4-amine.

¹H NMR (400 MHz, CDCl₃, δ): 7.83 (s, 1H), 7.30-7.24 (m, 2H), 7.00 (s, 1H), 6.90-6.80 (m, 2H), 5.99 (d, J=7.6 Hz, 1H), 4.66 (s, 2H), 4.14-4.23 (m, 1H), 3.99-4.02 (m, 2H), 3.56-3.50 (m, 2H), 2.66 (s, 3H), 2.03-1.99 (m, 2H), 1.63-1.53 (m, 2H); ESIMS m/z: [M+H]⁺ 452, 454.

EXAMPLE 122

3-(4-Methoxybenzyl)-5-methyl-N-(tetrahydro-2H-pyran-4-yl)-2-(trifluoromethyl)imidazo[1,2-a]pyridine-7-carboxamide (Compound 209)

Step 1

Ethyl 3-[hydroxy(4-methoxyphenyl)methyl]-5-methyl-2-(trifluoromethyl)imidazo[1,2-a]pyridine-7-carboxylate (0.500 g, yield 50%) was obtained in the same manner as in Step 3 of Example 4, using ethyl 3-iodo-5-methyl-2-(trifluoromethyl)imidazo[1,2-a]pyridine-7-carboxylate obtained in Step 2 of Example 119 and 4-methoxybenzaldehyde.

¹H NMR (400 MHz, CDCl₃, δ): 8.26 (s, 1H), 7.14 (s, 1H), 7.06 (d, J=8.4 Hz, 2H), 6.85 (d, J=8.8 Hz, 2H), 6.77 (d, J=4.4 Hz, 1H), 4.39 (q, J=7.2 Hz, 2H), 3.79 (s, 3H), 3.22 (d, J=4.8 Hz, 1H), 2.49 (s, 3H), 1.39 (t, J=7.2 Hz, 3H); ESIMS m/z: [M+H]⁺ 409.

Step 2

Ethyl 3-(4-methoxybenzyl)-5-methyl-2-(trifluoromethyl)imidazo[1,2-a]pyridine-7-carboxylate (0.250 g, yield 49%) was obtained in the same manner as in Step 5 of Example 103, using ethyl 3-[hydroxy(4-methoxyphenyl)methyl]-5-methyl-2-(trifluoromethyl)imidazo[1,2-a]pyridine-7-carboxylate obtained in Step 1.

¹H NMR (400 MHz, CDCl₃, δ): 8.27 (s, 1H), 7.10 (s, 1H), 6.81 (s, 4H), 4.63 (s, 2H), 4.39 (q, J=7.2 Hz, 2H), 3.76 (s, 3H), 2.69 (s, 3H), 1.39 (t, J=7.2 Hz, 3H).

Step 3

3-(4-Methoxybenzyl)-5-methyl-2-(trifluoromethyl)imidazo[1,2-a]pyridine-7-carboxylic acid (200 mg, yield 94%) was obtained in the same manner as in Step 8 of Example 1, using ethyl 3-(4-methoxybenzyl)-5-methyl-2-(trifluoromethyl)imidazo[1,2-a]pyridine-7-carboxylate obtained in Step 2.

¹H NMR (400 MHz, DMSO-d₆, δ): 8.07 (d, J=0.8 Hz, 1H), 7.16 (s, 1H), 6.88-6.81 (m, 4H), 4.65 (s, 2H), 3.70 (s, 3H), 2.70 (s, 3H).

Step 4

Compound 209 (0.105 g, yield 86%) was obtained in the same manner as in Step 9 of Example 1, using 3-(4-methoxybenzyl)-5-methyl-2-(trifluoromethyl)imidazo[1,2-a]pyridine-7-carboxylic acid obtained in Step 3 and tetrahydro-2H-pyran-4-amine.

¹H NMR (400 MHz, CDCl₃, δ): 7.82 (s, 1H), 6.97 (s, 1H), 6.83-6.78 (m, 4H), 6.06 (d, J=7.6 Hz, 1H), 4.61 (s, 2H), 4.22-4.14 (m, 1H), 4.01-3.98 (m, 2H), 3.76 (s, 3H), 3.56-3.50 (m, 2H), 2.68 (s, 3H), 2.02-1.99 (m, 2H), 1.63-1.53 (m, 2H); ESIMS m/z: [M+H]⁺ 448.

EXAMPLE 123

3-(4-Chlorobenzyl)-5-cyano-N-(tetrahydro-2H-pyran-4-yl)-2-(trifluoromethyl)imidazo[1,2-a]pyridine-7-carboxamide (Compound 211)

Step 1

5-(Bromomethyl)-3-(4-chlorobenzyl)-N-(tetrahydro-2H-pyran-4-yl)-2-(trifluoromethyl)imidazo[1,2-a]pyridine-7- carboxamide (28.8 mg, yield 35%) was obtained in the same manner as in Step 6 of Example 103, using Compound 208.

$^1$H NMR (300 MHz, CDCl$_3$, δ): 8.00 (d, J=1.5 Hz, 1H), 7.37 (d, J=1.5 Hz, 1H), 7.30-7.25 (m, 2H), 6.91-6.85 (m, 2H), 6.03 (d, J=7.7 Hz, 1H), 4.86 (s, 2H), 4.50 (s, 2H), 4.26-4.14 (m, 1H), 4.06-3.97 (m, 2H), 3.59-3.49 (m, 2H), 2.09-1.96 (m, 2H), 1.71-1.58 (m, 2H); ESIMS m/z: [M+H]$^+$ 530, 532.

Step 2

3-(4-Chlorobenzyl)-5-formyl-N-(tetrahydro-2H-pyran-4-yl)-2-(trifluoromethyl)imidazo[1,2-a]pyridine-7-carboxamide (14.5 mg, yield 59%) was obtained in the same manner as in Step 7 of Example 103, using 5-(bromomethyl)-3-(4-chlorobenzyl)-N-(tetrahydro-2H-pyran-4-yl)-2-(trifluoromethyl)imidazo[1,2-a]pyridine-7-carboxamide obtained in Step 1.

$^1$H NMR (300 MHz, CDCl$_3$, δ): 9.68 (s, 1H), 8.28 (d, J=1.8 Hz, 1H), 7.93 (d, J=1.8 Hz, 1H), 7.19-7.12 (m, 2H), 6.74-6.66 (m, 2H), 6.06 (d, J=7.3 Hz, 1H), 4.71 (s, 2H), 4.09-3.97 (m, 2H), 3.62-3.49 (m, 3H), 2.07-1.97 (m, 2H), 1.67-1.57 (m, 2H); ESIMS m/z: [M+H]$^+$ 466, 468.

Step 3

Compound 211 (14.3 mg, yield 99%) was obtained in the same manner as in Example 80, using 3-(4-chlorobenzyl)-5-formyl-N-(tetrahydro-2H-pyran-4-yl)-2-(trifluoromethyl)imidazo[1,2-a]pyridine-7-carboxamide obtained in Step 2.

$^1$H NMR (300 MHz, CDCl$_3$, δ): 8.25 (d, J=1.8 Hz, 1H), 7.93 (d, J=1.8 Hz, 1H), 7.28-7.24 (m, 2H), 6.97-6.92 (m, 2H), 6.14 (d, J=7.3 Hz, 1H), 4.82 (s, 2H), 4.30-4.14 (m, 1H), 4.06-3.97 (m, 2H), 3.59-3.48 (m, 2H), 2.07-1.98 (m, 2H), 1.67-1.53 (m, 2H); ESIMS m/z: [M−H]$^−$ 461, 463.

EXAMPLE 124

3-(4-Fluorobenzyl)-5-methyl-N-(tetrahydro-2H-pyran-4-yl)-2-(trifluoromethyl)imidazo[1,2-a]pyridine-7-carboxamide (Compound 212)

Step 1

Ethyl 3-[(4-fluorophenyl)(hydroxy)methyl]-5-methyl-2-(trifluoromethyl)imidazo[1,2-a]pyridine-7-carboxylate (0.031 g, yield 16%) was obtained in the same manner as in Step 3 of Example 4, using the crude product of ethyl 3-iodo-5-methyl-2-(trifluoromethyl)imidazo[1,2-a]pyridine-7-carboxylate obtained in Step 2 of Example 119 and 4-fluorobenzaldehyde.

$^1$H NMR (300 MHz, CDCl$_3$, δ): 8.30 (s, 1H), 7.17-7.14 (m, 3H), 7.07-7.00 (m, 2H), 6.79 (d, J=4.4 Hz, 1H), 4.40 (q, J=7.1 Hz, 2H), 2.94 (t, J=5.1 Hz, 1H), 2.42 (s, 3H), 1.40 (t, J=7.1 Hz, 3H); ESIMS m/z: [M+H]$^+$ 397.

Step 2

Ethyl 3-(4-fluorobenzyl)-5-methyl-2-(trifluoromethyl)imidazo[1,2-a]pyridine-7-carboxylate (0.022 g, yield 76%) was obtained in the same manner as in Step 5 of Example 103, using ethyl 3-[(4-fluorophenyl)(hydroxy)methyl]-5-methyl-2-(trifluoromethyl)imidazo[1,2-a]pyridine-7-carboxylate obtained in Step 1.

$^1$H NMR (300 MHz, CDCl$_3$, δ): 8.28 (d, J=0.7 Hz, 1H), 7.13 (s, 1H), 7.00-6.97 (m, 2H), 6.89-6.86 (m, 2H), 4.67 (s, 2H), 4.40 (q, J=7.5 Hz, 2H), 2.68 (s, 3H), 0.98 (t, J=7.5 Hz, 3H); ESIMS m/z: [M+H]$^+$ 381.

Step 3

3-(4-Fluorobenzyl)-5-methyl-2-(trifluoromethyl)imidazo[1,2-a]pyridine-7-carboxylic acid (0.017 g, yield 88%) was obtained in the same manner as in Step 8 of Example 1, using ethyl 3-(4-fluorobenzyl)-5-methyl-2-(trifluoromethyl)imidazo[1,2-a]pyridine-7-carboxylate obtained in Step 2.

$^1$H NMR (300 MHz, CDCl$_3$, δ): 8.46 (s, 1H), 7.20-7.16 (m, 1H), 7.03-6.96 (m, 2H), 6.92-6.85 (m, 2H), 4.68 (s, 2H), 2.70 (s, 3H).

Step 4

Compound 212 (0.009 g, yield 41%) was obtained in the same manner as in Step 9 of Example 1, using 3-(4-fluorobenzyl)-5-methyl-2-(trifluoromethyl)imidazo[1,2-a]pyridine-7-carboxylic acid obtained in Step 3, tetrahydro-2H-pyran-4-amine hydrochloride, and triethylamine.

$^1$H NMR (300 MHz, CDCl$_3$, δ): 7.84 (s, 1H), 7.00-6.97 (m, 3H), 6.88-6.85 (m, 2H), 6.02 (d, J=8.4 Hz, 1H), 4.66 (s, 2H), 4.21-4.16 (m, 1H), 4.03-3.99 (m, 2H), 3.56-3.52 (m, 2H), 2.67 (s, 3H), 2.04-2.00 (m, 2H), 1.65-1.57 (m, 2H); ESIMS m/z: [M+H]$^+$ 436.

EXAMPLE 125

5,6-Dichloro-3-[(4,4-difluorocyclohexyl)methyl]-N-[2-methyl-2-(methylthio)propyl]-2-(trifluoromethyl)imidazo[1,2-a]pyridine-7-carboxamide (Compound 213)

Compound 213 (73.3 mg, yield 99%) was obtained in the same manner as in Step 9 of Example 1, using 5,6-dichloro-3-[(4,4-difluorocyclohexyl)methyl]-2-(trifluoromethyl)imidazo[1,2-a]pyridine-7-carboxylic acid obtained in Step 3 of Example 109 and 2-methyl-2-(methylthio)propan-1-amine.

$^1$H NMR (300 MHz, CDCl$_3$, δ): 7.83 (s, 1H), 6.50 (br t, J 5.3 Hz, 1H), 3.48 (d, J=5.5 Hz, 2H), 3.35 (d, J=6.6 Hz, 2H), 2.17-2.04 (m, 2H), 2.01 (s, 3H), 1.69-1.40 (m, 7H), 1.35 (s, 6H); ESIMS m/z: [M+H]$^+$ 532, 534.

EXAMPLE 126

3-(4-Chlorobenzyl)-2-(1,1-difluoroethyl)-5-methyl-N-(tetrahydro-2H-pyran-4-yl)imidazo[1,2-a]pyridine-7-carboxamide (Compound 214)

Step 1

Ethyl 2-acetyl-5-methylimidazo[1,2-a]pyridine-7-carboxylate (122 mg, yield 45%) was obtained in the same manner as in Step 1 of Example 103, using 1-bromobutane-2,3-dione and ethyl 2-amino-6-methylpyridine-4-carboxylate obtained by a method described in WO2008/009750.

$^1$H NMR (300 MHz, CDCl$_3$, δ): 8.35 (dd, J=0.7, 1.5 Hz, 1H), 8.14 (d, J=0.7 Hz, 1H), 7.32 (d, J=1.5 Hz, 1H), 4.42 (q, J=7.2 Hz, 2H), 2.76 (s, 3H), 2.67 (s, 3H), 1.42 (t, J=7.2 Hz, 3H); ESIMS m/z: [M+H]$^+$ 247.

Step 2

Ethyl 2-(1,1-difluoroethyl)-5-methylimidazo[1,2-a]pyridine-7-carboxylate (25.3 mg, yield 47%) was obtained in the same manner as in Step 2 of Example 103, using ethyl 2-acetyl-5-methylimidazo[1,2-a]pyridine-7-carboxylate obtained in Step 1.

$^1$H NMR (300 MHz, CDCl$_3$, δ): 8.30 (d, J=0.7 Hz, 1H), 7.76 (d, J=0.7 Hz, 1H), 7.30 (s, 1H), 4.41 (q, J=7.1 Hz, 2H), 2.66 (s, 3H), 2.13 (t, J=18.5 Hz, 3H), 1.42 (t, J=7.1 Hz, 3H); ESIMS m/z: [M+H]$^+$ 269.

Step 3

Ethyl 2-(1,1-difluoroethyl)-3-iodo-5-methylimidazo[1,2-a]pyridine-7-carboxylate (47.6 mg, yield 89%) was obtained in the same manner as in Step 3 of Example 103, using ethyl 2-(1,1-difluoroethyl)-5-methylimidazo[1,2-a]pyridine-7-carboxylate obtained in Step 2.

¹H NMR (300 MHz, CDCl₃, δ): 8.27 (s, 1H), 7.17 (s, 1H), 4.40 (q, J=7.1 Hz, 2H), 3.30 (s, 3H), 2.16 (t, J=18.7 Hz, 3H), 1.40 (t, J=7.1 Hz, 3H); ESIMS m/z: [M+H]⁺ 395.

Step 4

Ethyl 3-[(4-chlorophenyl)(hydroxy)methyl]-2-(1,1-difluoroethyl)-5-methylimidazo[1,2-a]pyridine-7-carboxylate (837 mg, yield 73%) was obtained in the same manner as in Step 3 of Example 4, using ethyl 2-(1,1-difluoroethyl)-3-iodo-5-methylimidazo[1,2-a]pyridine-7-carboxylate obtained in Step 3 and 4-chlorobenzaldehyde.

¹H NMR (300 MHz, CDCl₃, δ): 8.26 (d, J=1.1 Hz, 1H), 7.35-7.28 (m, 2H), 7.15-7.11 (m, 3H), 6.99 (d, J=5.1 Hz, 1H), 4.68 (d, J=5.9 Hz, 1H), 4.39 (q, J=7.1 Hz, 2H), 2.40 (s, 3H), 2.25 (t, J=19.2 Hz, 3H), 1.39 (t, J=7.1 Hz, 3H); ESIMS m/z: [M+H]⁺ 409, 411.

Step 5

Ethyl 3-(4-chlorobenzyl)-2-(1,1-difluoroethyl)-5-methylimidazo[1,2-a]pyridine-7-carboxylate (7.2 mg, yield 15%) was obtained in the same manner as in Step 4 of Example 4, using ethyl 3-[(4-chlorophenyl)(hydroxy)methyl]-2-(1,1-difluoroethyl)-5-methylimidazo[1,2-a]pyridine-7-carboxylate obtained in Step 4.

¹H NMR (300 MHz, CDCl₃, δ): 8.25 (d, J=1.1 Hz, 1H), 7.32-7.23 (m, 2H), 7.07 (s, 1H), 6.93-6.79 (m, 2H), 4.74 (s, 2H), 4.39 (q, J=7.2 Hz, 2H), 2.65 (s, 3H), 2.18 (t, J=19.1 Hz, 3H), 1.39 (t, J=7.2 Hz, 3H); ESIMS m/z: [M+H]⁺ 393, 395.

Step 6

3-(4-Chlorobenzyl)-2-(1,1-difluoroethyl)-5-methylimidazo[1,2-a]pyridine-7-carboxylic acid (92.0 mg, yield 99%) was obtained in the same manner as in Step 1 of Example 21, using ethyl 3-(4-chlorobenzyl)-2-(1,1-difluoroethyl)-5-methylimidazo[1,2-a]pyridine-7-carboxylate obtained in Step 5.

¹H NMR (300 MHz, CDCl₃, δ): 8.31 (s, 1H), 7.29-7.21 (m, 2H), 7.08 (s, 1H), 6.90-6.82 (m, 2H), 4.74 (s, 2H), 2.66 (s, 3H), 2.18 (t, J=18.7 Hz, 3H); ESIMS m/z: [M+H]⁺ 365, 367.

Step 7

Compound 126 (40 mg, yield 81%) was obtained in the same manner as in Step 9 of Example 1, using 3-(4-chlorobenzyl)-2-(1,1-difluoroethyl)-5-methylimidazo[1,2-a]pyridine-7-carboxylic acid obtained in Step 6, tetrahydro-2H-pyran-4-amine hydrochloride, and triethylamine.

¹H NMR (300 MHz, CDCl₃, δ): 7.81 (s, 1H), 7.31-7.20 (m, 2H), 6.95 (s, 1H), 6.85-6.83 (m, 2H), 6.06-5.91 (br m, 1H), 4.73 (s, 2H), 4.32-4.10 (m, 1H), 4.09-3.94 (m, 2H), 3.62-3.46 (m, 2H), 2.65 (s, 3H), 2.17 (t, J=18.9 Hz, 3H), 2.10-1.96 (m, 2H), 1.69-1.53 (m, 2H); ESIMS m/z: [M+H]⁺ 448, 450.

EXAMPLE 127

N-[(1R,2S,4S)-7-Oxabicyclo[2.2.1]heptan-2-yl]-3-(4-chlorobenzyl)-2-(1,1-difluoroethyl)-5-methylimidazo[1,2-a]pyridine-7-carboxamide (Compound 215)

Compound 215 (43.9 mg, yield 87%) was obtained in the same manner as in Step 9 of Example 1, using 3-(4-chlorobenzyl)-2-(1,1-difluoroethyl)-5-methylimidazo[1,2-a]pyridine-7-carboxylic acid obtained in Step 6 of Example 126 and (1R,2S,4S)-7-oxabicyclo[2.2.1]heptan-2-amine.

¹H NMR (300 MHz, CDCl₃, δ): 7.84 (d, J=1.5 Hz, 1H), 7.25-7.22 (m, 2H), 6.90 (br s, 1H), 6.86-6.82 (m, 2H), 6.26 (d, J=8.4 Hz, 1H), 4.72 (s, 2H), 4.70-4.64 (m, 1H), 4.46-4.42 (m, 1H), 4.33-4.24 (m, 1H), 2.64 (s, 3H), 2.17 (t, J=19.4 Hz, 3H), 1.78-1.43 (m, 6H); ESIMS m/z: [M+H]⁺ 460, 462.

EXAMPLE 128

5,6-Dichloro-3-[(4,4-difluorocyclohexyl)methyl]-N-[2-methyl-2-(methylsulfonyl)propyl]-2-(trifluoromethyl)imidazo[1,2-a]pyridine-7-carboxamide (Compound 216)

Compound 216 (57.5 mg, yield 83%) was obtained in the same manner as in Step 2 of Example 107, using Compound 213.

¹H NMR (300 MHz, CDCl₃, δ): 7.80 (s, 1H), 6.99 (t, J=5.7 Hz, 1H), 3.89 (d, J=5.9 Hz, 2H), 3.35 (d, J=6.6 Hz, 2H), 2.88 (s, 3H), 2.24-2.01 (m, 2H), 1.81-1.58 (m, 5H), 1.52 (s, 6H), 1.52-1.40 (m, 2H); ESIMS m/z: [M+H]⁺ 564, 566, 568.

EXAMPLE 129

N-tert-Butyl-3-[(4,4-difluorocyclohexyl)methyl]-5-methyl-2-(trifluoromethyl)imidazo[1,2-a]pyridine-7-carboxamide (Compound 217)

Compound 217 (27.9 mg, yield 61%) was obtained in the same manner as in Step 9 of Example 1, using 3-[(4,4-difluorocyclohexyl)methyl]-5-methyl-2-(trifluoromethyl)imidazo[1,2-a]pyridine-7-carboxylic acid obtained in Step 2 of Example 32 and tert-butylamine.

¹H NMR (300 MHz, CDCl₃, δ): 7.73 (d, J=1.8 Hz, 1H), 7.10 (s, 1H), 5.94 (s, 1H), 3.21 (d, J=6.2 Hz, 2H), 2.87 (s, 3H), 2.16-2.03 (m, 2H), 1.70-1.38 (m, 7H), 1.47 (s, 9H); ESIMS m/z: [M+H]⁺ 432.

EXAMPLE 130

N-tert-Butyl-3-[(4,4-difluorocyclohexyl)methyl]-2-(1,1-difluoroethyl)-5-methylimidazo[1,2-a]pyridine-7-carboxamide (Compound 218)

Compound 218 (31.0 mg, yield 68%) was obtained in the same manner as in Step 9 of Example 1, using 3-[(4,4-difluorocyclohexyl)methyl]-2-(1,1-difluoroethyl)-5-methylimidazo[1,2-a]pyridine-7-carboxylic acid obtained in Step 2 of Example 67 and tert-butylamine.

¹H NMR (300 MHz, CDCl₃, δ): 7.70 (d, J=1.8 Hz, 1H), 7.05 (s, 1H), 5.95 (s, 1H), 3.26 (d, J=6.2 Hz, 2H), 2.86 (s, 3H), 2.25-1.99 (m, 5H), 1.73-1.41 (m, 7H), 1.47 (s, 9H); ESIMS m/z: [M+H]⁺ 428.

EXAMPLE 131

N-tert-Butyl-3-[(4,4-difluorocyclohexyl)methyl]-2-isopropyl-5-methylimidazo[1,2-a]pyridine-7-carboxamide (Compound 219)

Compound 219 (5.2 mg, yield 45%) was obtained in the same manner as in Step 9 of Example 1, using 3-[(4,4-difluorocyclohexyl)methyl]-2-isopropyl-5-methylimidazo[1,2-a]pyridine-7-carboxylic acid obtained in Step 5 of Example 71 and tert-butylamine.

¹H NMR (300 MHz, CDCl₃, δ): 7.68 (s, 1H), 6.98 (s, 1H), 5.97 (s, 1H), 3.09-3.00 (m, 3H), 2.82 (s, 3H), 2.17-1.97 (m, 2H), 1.72-1.26 (m, 22H); ESIMS m/z: [M+H]⁺ 406.

EXAMPLE 132

N-tert-Butyl-5-chloro-3-[(4,4-difluorocyclohexyl)methyl]-2-(trifluoromethyl)imidazo[1,2-a]pyridine-7-carboxamide (Compound 220)

Compound 220 (20.4 mg, yield 45%) was obtained in the same manner as in Step 9 of Example 1, using 5-chloro-3-[(4,4-difluorocyclohexyl)methyl]-2-(trifluoromethyl)imidazo[1,2-a]pyridine-7-carboxylic acid obtained in Step 1 of Example 42 and tert-butylamine.

$^1$H NMR (300 MHz, CDCl$_3$, δ): 7.81 (d, J=1.5 Hz, 1H), 7.41 (d, J=1.5 Hz, 1H), 5.92 (s, 1H), 3.34 (d, J=7.3 Hz, 2H), 2.17-2.03 (m, 2H), 1.80-1.41 (m, 7H), 1.48 (s, 9H); ESIMS m/z: [M+H]$^+$ 452.

EXAMPLE 133

3-(4-Chlorobenzyl)-5-cyano-2-(1,1-difluoroethyl)-N-(tetrahydro-2H-pyran-4-yl)imidazo[1,2-a]pyridine-7-carboxamide (Compound 221)

Step 1

Ethyl 3-(4-chlorobenzyl)-2-(1,1-difluoroethyl)-5-(hydroxymethyl)imidazo[1,2-a]pyridine-7-carboxylate (109 mg, yield 40%) was obtained in the same manner as in Step of Example 2, using ethyl 3-(4-chlorobenzyl)-2-(1,1-difluoroethyl)-5-methylimidazo[1,2-a]pyridine-7-carboxylate obtained in Step 5 of Example 126.

$^1$H NMR (300 MHz, CDCl$_3$, δ): 8.39 (d, J=2.0 Hz, 1H), 7.38 (d, J=2.0 Hz, 1H), 7.25-7.21 (m, 2H), 6.90-6.86 (m, 2H), 4.85 (s, 2H), 4.67 (d, J=6.8 Hz, 2H), 4.41 (q, J=7.2 Hz, 2H), 2.20 (t, J=19.0 Hz, 3H), 1.40 (t, J=7.2 Hz, 3H); ESIMS m/z: [M+H]$^+$ 409, 411.

Step 2

Ethyl 3-(4-chlorobenzyl)-2-(1,1-difluoroethyl)-5-formylimidazo[1,2-a]pyridine-7-carboxylate (116 mg, yield 90%) was obtained in the same manner as in Step 2 of Example 14, using ethyl 3-(4-chlorobenzyl)-2-(1,1-difluoroethyl)-5-(hydroxymethyl)imidazo[1,2-a]pyridine-7-carboxylate obtained in Step 1.

$^1$H NMR (300 MHz, CDCl$_3$, δ): 9.68 (s, 1H), 8.65 (d, J=1.8 Hz, 1H), 8.01 (d, J=1.8 Hz, 1H), 7.18-7.11 (m, 2H), 6.76-6.68 (m, 2H), 4.78 (s, 2H), 4.44 (q, J=7.2 Hz, 2H), 2.26 (t, J=18.9 Hz, 3H), 1.42 (t, J=7.2 Hz, 3H); ESIMS m/z: [M+H]$^+$ 407, 409.

Step 3

Ethyl 3-(4-chlorobenzyl)-5-cyano-2-(1,1-difluoroethyl)imidazo[1,2-a]pyridine-7-carboxylate (113 mg, yield 99%) was obtained in the same manner as in Example 80, using ethyl 3-(4-chlorobenzyl)-2-(1,1-difluoroethyl)-5-formylimidazo[1,2-a]pyridine-7-carboxylate obtained in Step 2.

$^1$H NMR (300 MHz, CDCl$_3$, δ): 8.60 (d, J=1.8 Hz, 1H), 7.97 (d, J=1.8 Hz, 1H), 7.25-7.21 (m, 2H), 6.99-6.93 (m, 2H), 4.88 (s, 2H), 4.44 (q, J=7.1 Hz, 2H), 2.20 (t, J=18.9 Hz, 3H), 1.42 (t, J=7.1 Hz, 3H); ESIMS m/z: [M+H]$^+$ 404, 406.

Step 4

3-(4-Chlorobenzyl)-5-cyano-2-(1,1-difluoroethyl)imidazo[1,2-a]pyridine-7-carboxylic acid (96.3 mg, yield 94%) was obtained in the same manner as in Step 1 of Example 21, using ethyl 3-(4-chlorobenzyl)-5-cyano-2-(1,1-difluoroethyl)imidazo[1,2-a]pyridine-7-carboxylate obtained in Step 3.

$^1$H NMR (300 MHz, CDCl$_3$, δ): 8.70 (d, J=2.0 Hz, 1H), 8.00 (d, J=2.0 Hz, 1H), 7.29-7.22 (m, 2H), 7.02-6.94 (m, 2H), 4.90 (s, 2H), 2.21 (t, J=19.0 Hz, 3H); ESIMS m/z: [M+H]$^+$ 376, 378.

Step 5

Compound 221 (7.5 mg, yield 88%) was obtained in the same manner as in Step 9 of Example 1, using 3-(4-chlorobenzyl)-5-cyano-2-(1,1-difluoroethyl)imidazo[1,2-a]pyridine-7-carboxylic acid obtained in Step 4, tetrahydro-2H-pyran-4-amine hydrochloride, and triethylamine.

$^1$H NMR (300 MHz, CDCl$_3$, δ): 8.19 (d, J=1.8 Hz, 1H), 7.85 (d, J=1.8 Hz, 1H), 7.33-7.18 (m, 2H), 7.02-6.90 (m, 2H), 5.96 (d, J=5.5 Hz, 1H), 4.86 (s, 2H), 4.25-4.15 (m, 1H), 4.06-3.97 (m, 2H), 3.59-3.48 (m, 2H), 2.18 (t, J=17.2 Hz, 3H), 2.06-1.97 (m, 2H), 1.69-1.53 (m, 2H); ESIMS m/z: [M+H]$^+$ 459, 461.

EXAMPLE 134

N-[(1R,2S,4S)-7-Oxabicyclo[2.2.1]heptan-2-yl]-3-(4-chlorobenzyl)-5-cyano-2-(1,1-difluoroethyl)imidazo[1,2-a]pyridine-7-carboxamide (Compound 222)

Compound 222 (7.6 mg, yield 87%) was obtained in the same manner as in Step 9 of Example 1, using 3-(4-chlorobenzyl)-5-cyano-2-(1,1-difluoroethyl)imidazo[1,2-a]pyridine-7-carboxylic acid obtained in Step 4 of Example 133 and (1R,2S,4S)-7-oxabicyclo[2.2.1]heptan-2-amine.

$^1$H NMR (300 MHz, CDCl$_3$, δ): 8.25 (d, J=1.8 Hz, 1H), 7.86 (d, J=1.8 Hz, 1H), 7.34-7.18 (m, 2H), 7.05-6.90 (m, 2H), 6.59 (d, J=8.1 Hz, 1H), 4.86 (s, 2H), 4.72-4.66 (m, 1H), 4.47-4.43 (m, 1H), 4.37-4.26 (m, 1H), 2.17 (t, J=19.1 Hz, 3H), 1.84-1.44 (m, 6H); ESIMS m/z: [M+H]$^+$ 471, 473.

EXAMPLE 135

3-(4-Chlorobenzyl)-5-cyano-2-(1,1-difluoroethyl)-N-(2-methoxy-d$_3$-2-methylpropyl)imidazo[1,2-a]pyridine-7-carboxamide (Compound 223)

Compound 223 (3.5 mg, yield 41%) was obtained in the same manner as in Step 9 of Example 1, using 3-(4-chlorobenzyl)-5-cyano-2-(1,1-difluoroethyl)imidazo[1,2-a]pyridine-7-carboxylic acid obtained in Step 4 of Example 133, 2-methoxy-d$_3$-2-methylpropan-1-amine hydrochloride obtained in Step 4 of Example 105, and triethylamine.

$^1$H NMR (300 MHz, CDCl$_3$, δ): 8.25 (d, J=1.8 Hz, 1H), 7.91 (d, J=1.8 Hz, 1H), 7.29-7.20 (m, 2H), 7.01-6.92 (m, 2H), 6.60 (t, J=5.1 Hz, 1H), 4.87 (s, 2H), 3.48 (d, J=5.1 Hz, 2H), 2.19 (t, J=18.9 Hz, 3H), 1.22 (s, 6H); ESIMS m/z: [M+H]$^+$ 464, 466.

EXAMPLE 136

3-(4-Chlorobenzyl)-2-isopropyl-5-methyl-N-(tetrahydro-2H-pyran-4-yl)imidazo[1,2-a]pyridine-7-carboxamide (Compound 224)

Step 1

Ethyl 3-[(4-chlorophenyl)(hydroxy)methyl]-2-isopropyl-5-methylimidazo[1,2-a]pyridine-7-carboxylate (307 mg, yield 81%) was obtained in the same manner as in Step 3 of Example 4, using ethyl 3-iodo-5-methyl-2-(1-methylcyclopropyl)imidazo[1,2-a]pyridine-7-carboxylate obtained by a method described in WO2012/105594 and 4-chlorobenzaldehyde.

$^1$H NMR (300 MHz, CDCl$_3$, δ): 8.24 (s, 1H), 7.33-7.27 (m, 2H), 7.18-7.12 (m, 2H), 7.05 (s, 1H), 6.63 (d, J=4.0 Hz,

1H), 4.37 (q, J=7.2 Hz, 2H), 3.19-3.10 (m, 1H), 2.74 (d, J=4.0 Hz, 1H), 2.46 (s, 3H), 1.42-1.32 (m, 9H); ESIMS m/z: [M+H]+ 387, 389.

Step 2

Ethyl 3-(4-chlorobenzyl)-2-isopropyl-5-methylimidazo[1,2-a]pyridine-7-carboxylate (234 mg, yield 84%) was obtained in the same manner as in Step 4 of Example 4, using ethyl 3-[(4-chlorophenyl)(hydroxy)methyl]-2-isopropyl-5-methylimidazo[1,2-a]pyridine-7-carboxylate obtained in Step 1.

$^1$H NMR (300 MHz, CDCl$_3$, δ): 8.25 (s, 1H), 7.28-7.20 (m, 2H), 6.99 (s, 1H), 6.86-6.79 (m, 2H), 4.51 (s, 2H), 4.37 (q, J=7.1 Hz, 2H), 3.13-3.04 (m, 1H), 2.60 (s, 3H), 1.40-1.34 (m, 9H); ESIMS m/z: [M+H]+ 370, 372.

Step 3

3-(4-Chlorobenzyl)-2-isopropyl-5-methylimidazo[1,2-a]pyridine-7-carboxylic acid (66.0 mg, yield 89%) was obtained in the same manner as in Step 1 of Example 21, using ethyl 3-(4-chlorobenzyl)-2-isopropyl-5-methylimidazo[1,2-a]pyridine-7-carboxylate obtained in Step 2.

ESIMS m/z: [M+H]+ 343, 345.

Step 4

Compound 224 (36.9 mg, yield 74%) was obtained in the same manner as in Step 9 of Example 1, using 3-(4-chlorobenzyl)-2-isopropyl-5-methylimidazo[1,2-a]pyridine-7-carboxylic acid obtained in Step 3, tetrahydro-2H-pyran-4-amine hydrochloride, and triethylamine.

$^1$H NMR (300 MHz, CDCl$_3$, δ): 7.79 (d, J=1.8 Hz, 1H), 7.30-7.21 (m, 2H), 6.87 (s, 1H), 6.83-6.77 (m, 2H), 5.99 (d, J=7.3 Hz, 1H), 4.50 (s, 2H), 4.23-4.13 (m, 1H), 4.04-3.96 (m, 2H), 3.60-3.48 (m, 2H), 3.08 (sept, 1H), 2.60 (s, 3H), 2.07-1.98 (m, 2H), 1.60-1.48 (m, 2H), 1.34 (d, J=7.0 Hz, 6H); ESIMS m/z: [M+H]+ 426, 428.

EXAMPLE 137

N-tert-Butyl-5-cyano-3-[(4,4-difluorocyclohexyl)methyl]-2-(1,1-difluoroethyl)imidazo[1,2-a]pyridine-7-carboxamide (Compound 225)

Compound 225 (9.6 mg, yield 84%) was obtained in the same manner as in Step 9 of Example 1, using 3-[(4,4-difluorocyclohexyl)methyl]-2-(1,1-difluoroethyl)-5-methylimidazo[1,2-a]pyridine-7-carboxylic acid obtained in Step 2 of Example 67 and tert-butylamine.

$^1$H NMR (300 MHz, CDCl$_3$, δ): 8.09 (d, J=2.0 Hz, 1H), 7.96 (d, J=2.0 Hz, 1H), 5.94 (br s, 1H), 3.40 (d, J=7.8 Hz, 2H), 2.29-2.06 (m, 5H), 1.90-1.51 (m, 7H), 1.48 (s, 9H); ESIMS m/z: [M+H]+ 439.

EXAMPLE 138

N-tert-Butyl-5-cyano-3-[(4,4-difluorocyclohexyl)methyl]-2-isopropylimidazo[1,2-a]pyridine-7-carboxamide (Compound 226)

Compound 226 (8.0 mg, yield 99%) was obtained in the same manner as in Step 9 of Example 1, using 5-cyano-3-[(4,4-difluorocyclohexyl)methyl]-2-isopropylimidazo[1,2-a]pyridine-7-carboxylic acid obtained in Step 4 of Example 89 and tert-butylamine.

$^1$H NMR (300 MHz, CDCl$_3$, δ): 8.04 (d, J=2.0 Hz, 1H), 7.87 (s, 1H), 5.93 (s, 1H), 3.16-3.09 (m, 3H), 2.17-2.07 (m, 2H), 1.83-1.38 (m, 16H), 1.35 (d, J=7.1 Hz, 6H); ESIMS m/z: [M+H]+ 417.

EXAMPLE 139

N-tert-Butyl-5,6-dichloro-3-[(4,4-difluorocyclohexyl)methyl]-2-(trifluoromethyl)imidazo[1,2-a]pyridine-7-carboxamide (Compound 227)

Compound 227 (13.0 mg, yield 38%) was obtained in the same manner as in Step 9 of Example 1, using 5,6-dichloro-3-[(4,4-difluorocyclohexyl)methyl]-2-(trifluoromethyl)imidazo[1,2-a]pyridine-7-carboxylic acid obtained in Step 3 of Example 109 and tert-butylamine.

$^1$H NMR (300 MHz, CDCl$_3$, δ): 7.70 (s, 1H), 5.70 (br s, 1H), 3.33 (d, J=7.0 Hz, 2H), 2.21-2.06 (m, 2H), 1.91-1.40 (m, 7H), 1.49 (s, 9H); ESIMS m/z: [M+H]+ 486, 488.

EXAMPLE 140

The following compounds were synthesized, respectively, in accordance with Step 7 of Production Method 1, using a compound of the formula (I) in which R$^3$ has a carboxy group or a group having a carboxy group, and a corresponding amine.

N-(4,4-Difluorocyclohexyl)-3-[(4,4-difluorocyclohexyl)methyl]-2-(2-hydroxypropan-2-yl)-5-methylimidazo[1,2-a]pyridine-7-carboxamide (Compound 9); ESIMS m/z: [M+H]+ 484.

N-(3,3-Difluorocyclobutyl)-3-[(4,4-difluorocyclohexyl)methyl]-2-(2-hydroxypropan-2-yl)-5-methylimidazo[1,2-a]pyridine-7-carboxamide (Compound 10); ESIMS m/z: [M+H]+ 456.

6-Chloro-2-cyclopropyl-N-(4,4-difluorocyclohexyl)-3-[(4,4-difluorocyclohexyl)methyl]imidazo[1,2-a]pyridine-7-carboxamide (Compound 14); ESIMS m/z: [M+H]+ 486.

6-Chloro-N-(4,4-difluorocyclohexyl)-3-[(4,4-difluorocyclohexyl)methyl]-2-(1,1-difluoroethyl)imidazo[1,2-a]pyridine-7-carboxamide (Compound 15); ESIMS m/z: [M+H]+ 510.

6-Chloro-N-(cyclopropylmethyl)-3-[(4,4-difluorocyclohexyl)methyl]-2-(1,1-difluoroethyl)imidazo[1,2-a]pyridine-7-carboxamide (Compound 21); ESIMS m/z: [M+H]+ 446.

6-Chloro-N-cyclobutyl-3-[(4,4-difluorocyclohexyl)methyl]-2-(1,1-difluoroethyl)imidazo[1,2-a]pyridine-7-carboxamide (Compound 22); ESIMS m/z: [M+H]+ 446.

6-Chloro-3-[(4,4-difluorocyclohexyl)methyl]-2-(1,1-difluoroethyl)-N-(2,2-dimethyltetrahydro-2H-pyran-4-yl)imidazo[1,2-a]pyridine-7-carboxamide (Compound 23); ESIMS m/z: [M+H]+ 504.

6-Chloro-3-[(4,4-difluorocyclohexyl)methyl]-2-(1,1-difluoroethyl)-N-[(tetrahydrofuran-3-yl)methyl]imidazo[1,2-a]pyridine-7-carboxamide (Compound 24); ESIMS m/z: [M+H]+ 476.

6-Chloro-3-[(4,4-difluorocyclohexyl)methyl]-2-(1,1-difluoroethyl)-N-(4-hydroxycyclohexyl)imidazo[1,2-a]pyridine-7-carboxamide (Compound 25); ESIMS m/z: [M+H]+ 490.

6-Chloro-3-[(4,4-difluorocyclohexyl)methyl]-2-(1,1-difluoroethyl)-N-(2-hydroxy-2-methylpropyl)imidazo[1,2-a]pyridine-7-carboxamide (Compound 26); ESIMS m/z: [M+H]+ 464.

3-(N-Cyclohexylacetamide)-2-isopropyl-5-methyl-N-(tetrahydro-2H-pyran-4-yl)imidazo[1,2-a]pyridine-7-carboxamide (Compound 32); ESIMS m/z: [M+H]+ 441.

3-[2-Oxo-2-(piperidin-1-yl)acetyl]-N-phenyl-2-(trifluoromethyl)imidazo[1,2-a]pyridine-7-carboxamide (Compound 37); ESIMS m/z: [M+H]+ 445.

3-(2-Morpholino-2-oxoacetyl)-N-phenyl-2-(trifluoromethyl)imidazo[1,2-a]pyridine-7-carboxamide (Compound 38); ESIMS m/z: [M+H]⁺ 447.

N-(2-Aminophenyl)-5-cyano-3-[(4,4-difluorocyclohexyl)methyl]-2-(trifluoromethyl)imidazo[1,2-a]pyridine-7-carboxamide (Compound 52); ESIMS m/z: [M+H]⁺ 478.

5-Cyano-N-(cyclopropylmethyl)-3-[(4,4-difluorocyclohexyl)methyl]-2-(trifluoromethyl)imidazo[1,2-a]pyridine-7-carboxamide (Compound 53); ESIMS m/z: [M+H]⁺ 441.

5-Cyano-N-cyclobutyl-3-[(4,4-difluorocyclohexyl)methyl]-2-(trifluoromethyl)imidazo[1,2-a]pyridine-7-carboxamide (Compound 54); ESIMS m/z: [M+H]⁺ 441.

5-Cyano-3-[(4,4-difluorocyclohexyl)methyl]-N-[(1R,4R)-4-hydroxycyclohexyl]-2-(trifluoromethyl)imidazo[1,2-a]pyridine-7-carboxamide (Compound 56); ESIMS m/z: [M+H]⁺ 485.

5-Cyano-3-[(4,4-difluorocyclohexyl)methyl]-N-(2,2-dimethyltetrahydro-2H-pyran-4-yl)-2-(trifluoromethyl)imidazo[1,2-a]pyridine-7-carboxamide (Compound 57); ESIMS m/z: [M+H]⁺499.

5-Cyano-3-[(4,4-difluorocyclohexyl)methyl]-N-[4-(hydroxymethyl)tetrahydro-2H-pyran-4-yl]-2-(trifluoromethyl)imidazo[1,2-a]pyridine-7-carboxamide (Compound 58); ESIMS m/z: [M+H]⁺ 501.

N-[(1,4-Dioxan-2-yl)methyl]-5-cyano-3-[(4,4-difluorocyclohexyl)methyl]-2-(trifluoromethyl)imidazo[1,2-a]pyridine-7-carboxamide (Compound 59); ESIMS m/z: [M+H]⁺ 487.

5-Cyano-3-[(4,4-difluorocyclohexyl)methyl]-Nxetan-3-yl)-2-(trifluoromethyl)imidazo[1,2-a]pyridine-7-carboxamide (Compound 60); ESIMS m/z: [M+H]⁺ 443.

5-Cyano-3-[(4,4-difluorocyclohexyl)methyl]-N-[(4-hydroxytetrahydro-2H-pyran-4-yl)methyl]-2-(trifluoromethyl)imidazo[1,2-a]pyridine-7-carboxamide (Compound 61); ESIMS m/z: [M+H]⁺ 501.

5-Cyano-3-[(4,4-difluorocyclohexyl)methyl]-Netrahydrofuran-3-yl)-2-(trifluoromethyl)imidazo[1,2-a]pyridine-7-carboxamide (Compound 62); ESIMS m/z: [M+H]⁺ 457.

5-Cyano-3-[(4,4-difluorocyclohexyl)methyl]-N-[2-(tetrahydro-2H-pyran-4-yl)propan-2-yl]-2-(trifluoromethyl)imidazo[1,2-a]pyridine-7-carboxamide (Compound 63); ESIMS m/z: [M+H]⁺ 513.

5-Cyano-3-[(4,4-difluorocyclohexyl)methyl]-Netrahydro-2H-pyran-3-yl)-2-(trifluoromethyl)imidazo[1,2-a]pyridine-7-carboxamide (Compound 64); ESIMS m/z: [M+H]⁺ 471.

5-Cyano-3-[(4,4-difluorocyclohexyl)methyl]-Netrahydro-2H-pyran-4-yloxy)-2-(trifluoromethyl)imidazo[1,2-a]pyridine-7-carboxamide (Compound 65); ESIMS m/z: [M+H]⁺ 487.

5-Cyano-3-[(4,4-difluorocyclohexyl)methyl]-N-[1-(tetrahydro-2H-pyran-4-yl)cyclopropyl]-2-(trifluoromethyl)imidazo[1,2-a]pyridine-7-carboxamide (Compound 66); ESIMS m/z: [M+H]⁺ 511.

5-Cyano-3-[(4,4-difluorocyclohexyl)methyl]-N-(2-oxo-2-phenylethyl)-2-(trifluoromethyl)imidazo[1,2-a]pyridine-7-carboxamide (Compound 67); ESIMS m/z: [M+H]⁺ 505.

5-Cyano-3-[(4,4-difluorocyclohexyl)methyl]-N-(2-hydroxypropyl)-2-(trifluoromethyl)imidazo[1,2-a]pyridine-7-carboxamide (Compound 68); ESIMS m/z: [M+H]⁺ 445.

5-Cyano-3-[(4,4-difluorocyclohexyl)methyl]-N-[(1-hydroxycyclopropyl)methyl]-2-(trifluoromethyl)imidazo[1,2-a]pyridine-7-carboxamide (Compound 69); ESIMS m/z: [M+H]⁺ 457.

5-Cyano-3-[(4,4-difluorocyclohexyl)methyl]-N-(2-oxaspiro[3.5]nonan-7-yl)-2-(trifluoromethyl)imidazo[1,2-a]pyridine-7-carboxamide (Compound 70); ESIMS m/z: [M+H]⁺ 511.

3-[(4,4-Difluorocyclohexyl)methyl]-5-methyl-N-(oxepan-4-yl)-2-(trifluoromethyl)imidazo[1,2-a]pyridine-7-carboxamide (Compound 74); ESIMS m/z: [M+H]⁺ 474.

3-[(4,4-Difluorocyclohexyl)methyl]-5-methyl-N-[1-(tetrahydro-2H-pyran-4-yl)cyclopropyl]-2-(trifluoromethyl)imidazo[1,2-a]pyridine-7-carboxamide (Compound 75); ESIMS m/z: [M+H]⁺ 500.

5-Cyano-N-cyclopropyl-3-[(4,4-difluorocyclohexyl)methyl]-2-(trifluoromethyl)imidazo[1,2-a]pyridine-7-carboxamide (Compound 76); ESIMS m/z: [M+H]⁺ 427.

N-[3,3-Bis(hydroxymethyl)cyclobutyl]-3-[(4,4-difluorocyclohexyl)methyl]-5-methyl-2-(trifluoromethyl)imidazo[1,2-a]pyridine-7-carboxamide (Compound 80); ESIMS m/z: [M+H]⁺ 490.

5-Chloro-3-[(4,4-difluorocyclohexyl)methyl]-N-[2-(tetrahydro-2H-pyran-4-yl)propan-2-yl]-2-(trifluoromethyl)imidazo[1,2-a]pyridine-7-carboxamide (Compound 81); ESIMS m/z: [M+H]⁺ 522.

N-(2-Aminophenyl)-2-{3-[(4,4-difluorocyclohexyl)methyl]-5-methyl-2-(trifluoromethyl)imidazo[1,2-a]pyridin-7-yl}acetamide (Compound 85); ESIMS m/z: [M+H]⁺ 481.

5-Chloro-3-[(4,4-difluorocyclohexyl)methyl]-N-[(4-hydroxytetrahydro-2H-pyran-4-yl)methyl]-2-(trifluoromethyl)imidazo[1,2-a]pyridine-7-carboxamide (Compound 86); ESIMS m/z: [M+H]⁺ 510.

N-[3,3-Bis(hydroxymethyl)cyclobutyl]-5-chloro-3-[(4,4-difluorocyclohexyl)methyl]-2-(trifluoromethyl)imidazo[1,2-a]pyridine-7-carboxamide (Compound 95); ESIMS m/z: [M+H]⁺ 510.

5-Chloro-3-[(4,4-difluorocyclohexyl)methyl]-N-(2-morpholinoethyl)-2-(tribluoromethyl)imidazo[1,2-a]pyridine-7-carboxamide (Compound 96); ESIMS m/z: [M+H]⁺ 509.

5-Chloro-3-[(4,4-difluorocyclohexyl)methyl]-Nyridin-4-ylmethyl)-2-(trifluoromethyl)imidazo[1,2-a]pyridine-7-carboxamide (Compound 97); ESIMS m/z: [M+H]⁺ 487.

N-Benzyl-5-chloro-3-[(4,4-difluorocyclohexyl)methyl]-2-(trifluoromethyl)imidazo[1,2-a]pyridine-7-carboxamide (Compound 98); ESIMS m/z: [M+H]⁺ 486.

5-Chloro-3-[(4,4-difluorocyclohexyl)methyl]-N-[2-(piperidin-1-yl)ethyl]-2-(trifluoromethyl)imidazo[1,2-a]pyridine-7-carboxamide (Compound 99); ESIMS m/z: [M+H]⁺ 507.

N-[3-(1H-Imidazol-1-yl)propyl]-5-chloro-3-[(4,4-difluorocyclohexyl)methyl]-2-(trifluoromethyl)imidazo[1,2-a]pyridine-7-carboxamide (Compound 100); ESIMS m/z: [M+H]⁺ 504.

5-Chloro-3-[(4,4-difluorocyclohexyl)methyl]-N-(2-hydroxyethyl)-2-(trifluoromethyl)imidazo[1,2-a]pyridine-7-carboxamide (Compound 102); ESIMS m/z: [M+H]⁺ 440.

5-Chloro-3-[(4,4-difluorocyclohexyl)methyl]-N-(3-hydroxybenzyl)-2-(trifluoromethyl)imidazo[1,2-a]pyridine-7-carboxamide (Compound 103); ESIMS m/z: [M+H]⁺ 502.

N-[2-(1H-Imidazol-4-yl)ethyl]-5-chloro-3-[(4,4-difluorocyclohexyl)methyl]-2-(trifluoromethyl)imidazo[1,2-a]pyridine-7-carboxamide (Compound 104); ESIMS m/z: [M+H]⁺ 490.

5-Chloro-3-[(4,4-difluorocyclohexyl)methyl]-Nyridin-3-ylmethyl)-2-(trifluoromethyl)imidazo[1,2-a]pyridine-7-carboxamide (Compound 105); ESIMS m/z: [M+H]⁺ 487.

5-Chloro-3-[(4,4-difluorocyclohexyl)methyl]-Nyridin-2-ylmethyl)-2-(trifluoromethyl)imidazo[1,2-a]pyridine-7-carboxamide (Compound 106); ESIMS m/z: [M+H]+ 487.

5-Chloro-3-[(4,4-difluorocyclohexyl)methyl]-N-(1,3-dihydroxypropan-2-yl)-2-(trifluoromethyl)imidazo[1,2-a]pyridine-7-carboxamide (Compound 108); ESIMS m/z: [M+H]+ 470.

N-{2-[Bis(2-hydroxyethyl)amino]ethyl}-5-chloro-3-[(4,4-difluorocyclohexyl)methyl]-2-(trifluoromethyl)imidazo[1,2-a]pyridine-7-carboxamide (Compound 109); ESIMS m/z: [M+H]+ 527.

Ethyl 2-{5-chloro-3-[(4,4-difluorocyclohexyl)methyl]-2-(trifluoromethyl)imidazo[1,2-a]pyridine-7-carboxamide}acetate (Compound 110); ESIMS m/z: [M+H]+ 482.

N-(2-Acetamideethyl)-5-chloro-3-[(4,4-difluorocyclohexyl)methyl]-2-(trifluoromethyl)imidazo[1,2-a]pyridine-7-carboxamide (Compound 113); ESIMS m/z: [M+H]+ 481.

5-Chloro-3-[(4,4-difluorocyclohexyl)methyl]-N-[2-(dimethylamino)ethyl]-2-(trifluoromethyl)imidazo[1,2-a]pyridine-7-carboxamide (Compound 114); ESIMS m/z: [M+H]+ 467.

tert-Butyl 2-{5-chloro-3-[(4,4-difluorocyclohexyl)methyl]-2-(trifluoromethyl)imidazo[1,2-a]pyridine-7-carboxamide}ethylcarbamate (Compound 115); ESIMS m/z: [M+H]+ 539.

(E)-3-{3-[(4,4-Difluorocyclohexyl)methyl]-5-methyl-2-(trifluoromethyl)imidazo[1,2-a]pyridin-7-yl}-N-[(4-hydroxytetrahydro-2H-pyran-4-yl)methyl]acrylamide (Compound 116); ESIMS m/z: [M+H]+ 516.

(E)-3-{3-[(4,4-Difluorocyclohexyl)methyl]-5-methyl-2-(trifluoromethyl)imidazo[1,2-a]pyridin-7-yl}-N-(2-hydroxy-2-methylpropyl)acrylamide (Compound 117); ESIMS m/z: [M+H]+ 474.

(E)-3-{3-[(4,4-Difluorocyclohexyl)methyl]-5-methyl-2-(trifluoromethyl)imidazo[1,2-a]pyridin-7-yl}-N-(tetrahydro-2H-pyran-4-yloxy)acrylamide (Compound 118); ESIMS m/z: [M+H]+ 502.

(E)-3-{3-[(4,4-Difluorocyclohexyl)methyl]-5-methyl-2-(trifluoromethyl)imidazo[1,2-a]pyridin-7-yl}-N-(2,2-dimethyltetrahydro-2H-pyran-4-yl)acrylamide (Compound 119); ESIMS m/z: [M+H]+ 514.

Ethyl 2-{5-chloro-3-[(4,4-difluorocyclohexyl)methyl]-2-(trifluoromethyl)imidazo[1,2-a]pyridine-7-carboxamide}propanoate (Compound 123); ESIMS m/z: [M+H]+ 496.

5-Chloro-3-[(4,4-difluorocyclohexyl)methyl]-N-[(1-hydroxycyclopropyl)methyl]-2-(trifluoromethyl)imidazo[1,2-a]pyridine-7-carboxamide (Compound 125); ESIMS m/z: [M+H]+ 466.

6-Chloro-3-[(4,4-difluorocyclohexyl)methyl]-2-(1,1-difluoroethyl)-N-(2-oxaspiro[3.5]nonan-7-yl)imidazo[1,2-a]pyridine-7-carboxamide (Compound 127); ESIMS m/z: [M+H]+ 516.

5-Chloro-3-[(4,4-difluorocyclohexyl)methyl]-N-[2-oxo-2-(tetrahydrofuran-3-ylamino)ethyl]-2-(trifluoromethyl)imidazo[1,2-a]pyridine-7-carboxamide (Compound 131); ESIMS m/z: [M+H]+ 523.

5-Chloro-3-[(4,4-difluorocyclohexyl)methyl]-N-[2-(2,2-dimethyltetrahydro-2H-pyran-4-ylamino)-2-oxoethyl]-2-(trifluoromethyl)imidazo[1,2-a]pyridine-7-carboxamide (Compound 132); ESIMS m/z: [M+H]+ 565.

N-(2-Amino-2-methylpropyl)-5-cyano-3-[(4,4-difluorocyclohexyl)methyl]-2-(trifluoromethyl)imidazo[1,2-a]pyridine-7-carboxamide (Compound 134); ESIMS m/z: [M+H]+ 458.

5-Cyano-3-[(4,4-difluorocyclohexyl)methyl]-N-(3-methylisoxazol-5-yl)-2-(trifluoromethyl)imidazo[1,2-a]pyridine-7-carboxamide (Compound 138); ESIMS m/z: [M+H]+ 468.

Ethyl 2-{5-cyano-3-[(4,4-difluorocyclohexyl)methyl]-2-(trifluoromethyl)imidazo[1,2-a]pyridine-7-carboxamide}acetate (Compound 139); ESIMS m/z: [M+H]+ 473.

5-Cyano-3-[(4,4-difluorocyclohexyl)methyl]-N-(2-oxotetrahydrofuran-3-yl)-2-(trifluoromethyl)imidazo[1,2-a]pyridine-7-carboxamide (Compound 140); ESIMS m/z: [M+H]+ 471.

5-Chloro-N'-(cyclopropanecarbonyl)-3-[(4,4-difluorocyclohexyl)methyl]-2-(trifluoromethyl)imidazo[1,2-a]pyridine-7-carbohydrazide (Compound 142); ESIMS m/z: [M+H]+ 479.

5-Chloro-3-[(4,4-difluorocyclohexyl)methyl]-N'-[2-(tetrahydro-2H-pyran-4-yl)acetyl]-2-(trifluoromethyl)imidazo[1,2-a]pyridine-7-carbohydrazide (Compound 143); ESIMS m/z: [M+H]+ 537.

3-[(4,4-Difluorocyclohexyl)methyl]-7-(2-oxoxazolidine-3-carbonyl)-2-(trifluoromethyl)imidazo[1,2-a]pyridine-5-carbonitrile (Compound 150); ESIMS m/z: [M+H]+ 457.

5-Chloro-3-[(4,4-difluorocyclohexyl)methyl]-N-[2-oxo-2-(phenylamino)ethyl]-2-(trifluoromethyl)imidazo[1,2-a]pyridine-7-carboxamide (Compound 151); ESIMS m/z: [M+H]+ 529.

5-Chloro-3-[(4,4-difluorocyclohexyl)methyl]-N-[(3-methyl-1H-pyrazol-5-yl)methyl]-2-(trifluoromethyl)imidazo[1,2-a]pyridine-7-carboxamide (Compound 152); ESIMS m/z: [M+H]+ 490.

5-Chloro-3-[(4,4-difluorocyclohexyl)methyl]-N-[(5-methylisoxazol-3-yl)methyl]-2-(trifluoromethyl)imidazo[1,2-a]pyridine-7-carboxamide (Compound 154); ESIMS m/z: [M+H]+ 491.

5-Cyano-3-[(4,4-difluorocyclohexyl)methyl]-N-(3-hydroxy-2,2-dimethylpropyl)-2-(trifluoromethyl)imidazo[1,2-a]pyridine-7-carboxamide (Compound 155); ESIMS m/z: [M+H]+ 473.

5-Cyano-3-[(4,4-difluorocyclohexyl)methyl]-N-(3,3-dimethyl-2-oxobutyl)-2-(trifluoromethyl)imidazo[1,2-a]pyridine-7-carboxamide (Compound 160); ESIMS m/z: [M+H]+ 485.

5-Cyano-3-[(4,4-difluorocyclohexyl)methyl]-N-[(3S,4R)-quinuclidin-3-yl]-2-(trifluoromethyl)imidazo[1,2-a]pyridine-7-carboxamide (Compound 169); ESIMS m/z: [M+H]+ 496.

N-(1-Azabicyclo[2.2.1]heptan-4-yl)-5-cyano-3-[(4,4-difluorocyclohexyl)methyl]-2-(trifluoromethyl)imidazo[1,2-a]pyridine-7-carboxamide (Compound 188); ESIMS m/z: [M+H]+ 482.

N-(endo-7-Acetyl-7-azabicyclo[2.2.1]heptan-2-yl)-5-cyano-3-[(4,4-difluorocyclohexyl)methyl]-2-(trifluoromethyl)imidazo[1,2-a]pyridine-7-carboxamide (Compound 191); ESIMS m/z: [M+H]+ 524.

5-Cyano-N-(1,3-diazaadamantan-6-yl)-3-[(4,4-difluorocyclohexyl)methyl]-2-(trifluoromethyl)imidazo[1,2-a]pyridine-7-carboxamide (Compound 199); ESIMS m/z: [M+H]+ 523.

5-Cyano-3-((4,4-difluorocyclohexyl)methyl)-N-(6-methylpyrazin-2-yl)-2-(trifluoromethyl)imidazo[1,2-a]pyridine-7-carboxamide (Compound 200); ESIMS m/z: [M+H]+ 479.

N-(endo-8-Azabicyclo[3.2.1]octan-3-ylmethyl)-5-cyano-3-[(4,4-difluorocyclohexyl)methyl]-2-(trifluoromethyl)imidazo[1,2-a]pyridine-7-carboxamide hydrochloride (Compound 204); ESIMS m/z: [M+H]+ 510.

3-[(4,4-Difluorocyclohexyl)methyl]-7-[(1R,5S)-9-oxo-3-oxa-7-azabicyclo[3.3.1]nonane-7-carbonyl)-2-(trifluoromethyl)imidazo[1,2-a]pyridine-5-carbonitrile (Compound 210); ESIMS m/z: [M+H]⁻ 511.

EXAMPLE 141

The following compounds were synthesized based on Example 51.

(Z)-3-[(4,4-Difluorocyclohexyl)methyl]-5-methyl-7-[2-(pyridin-4-yl)vinyl]-2-(trifluoromethyl)imidazo[1,2-a]pyridine (Compound 92); ESIMS m/z: [M+H]⁺ 436.

(E)-3-[(4,4-Difluorocyclohexyl)methyl]-5-methyl-7-[2-(pyridin-4-yl)vinyl]-2-(trifluoromethyl)imidazo[1,2-a]pyridine (Compound 93); ESIMS m/z: [M+H]⁺ 436.

EXAMPLE 142

The following compounds were synthesized based on Example 32.

3-[(4,4-Difluorocyclohexyl)methyl]-2-(1,1-difluoroethyl)-5-(hydroxymethyl)-N-(2-methoxy-d₃-2-methylpropyl)imidazo[1,2-a]pyridine-7-carboxamide (Compound 192); ESIMS m/z: [M+H]⁺ 477.

EXAMPLE 143

Tablet (Compound 1)

A tablet of the composition below is prepared using an ordinary method. Compound 1 (40 g), lactose (286.8 g), and potato starch (60 g) are mixed, and a 10% aqueous solution of hydroxypropyl cellulose (120 g) is added thereto. The resulting mixture is kneaded using an ordinary method, and granulated and dried. The mixture is then pulverized to form tableting granules. These are mixed with magnesium stearate (1.2 g), and punched with a tableting machine (Kikusui; Model RT-15; 8-mm punch diameter) to obtain tablets (containing 20 mg of active ingredient per tablet).

TABLE 25

| Formulation | |
| --- | --- |
| Compound 1 | 20 mg |
| Lactose | 143.4 mg |
| Potato starch | 30 mg |
| Hydroxypropyl cellulose | 6 mg |
| Magnesium stearate | 0.6 mg |
| | 200 mg |

EXAMPLE 144

Injection (Compound 1)

An injection of the composition below is prepared using an ordinary method. Compound 1 (1 g) is added to distilled water for injection and mixed. After adjusting the pH to 7 by adding hydrochloric acid and a sodium hydroxide aqueous solution, distilled water for injection is added to make the total amount of 1,000 mL. The resulting mixture is aseptically charged into glass vials in a 2-mL portion each to obtain injections (containing 2 mg of active ingredient per vial).

TABLE 26

| Formulation | |
| --- | --- |
| Compound 34 | 2 mg |
| Hydrochloric acid | appropriate amount |
| Sodium hydroxide aqueous solution | appropriate amount |
| Distilled water for injection | appropriate amount |
| | 2.00 mL |

INDUSTRIAL APPLICABILITY

The ring-fused heterocyclic compound or a pharmaceutically acceptable salt thereof according to the present invention has a T-type calcium channel regulatory effect and is useful, for example, as a medicament for treating and/or preventing pruritus.

The present invention can provide a novel ring-fused heterocyclic compound or a pharmaceutically acceptable salt thereof which has a T-type calcium channel regulatory effect and is useful as a therapeutic and/or preventive agent for pruritus, and the like, and also provide a T-type calcium channel inhibitor and the like containing, as an active ingredient, the ring-fused heterocyclic compound or a pharmaceutically acceptable salt thereof.

The invention claimed is:

1. A ring-fused heterocyclic compound represented by the general formula (I) or a pharmaceutically acceptable salt thereof:

(I)

wherein $R^1$ represents lower alkyl optionally substituted with halogen;

$R^2$ represents lower alkyl optionally substituted with cycloalkyl optionally substituted with halogen, or with phenyl optionally substituted with halogen;

$R^3$ represents:

(1)

wherein n represents 0 or 1, $R^{3a}$ represents a hydrogen atom or optionally substituted lower alkyl, $R^{3b}$ and $R^{3c}$ may be the same or different, and each represents a hydrogen atom, optionally substituted lower alkyl, optionally substituted cycloalkyl, optionally substituted aryl, an optionally substituted aromatic heterocyclic group, an optionally substituted aliphatic heterocyclic group, —OR$^{3d}$ wherein R$^{3d}$ represents an optionally substituted aliphatic heterocyclic group, or —C(=O)R$^{3j}$ wherein R$^{3j}$ represents optionally substituted lower alkyl, optionally substituted cycloalkyl, or an optionally substituted aliphatic heterocyclic group, or R$^{3b}$ and R$^{3c}$ are combined together with the adjacent nitrogen atom thereto to form an optionally substituted nitrogen-containing heterocyclic group;

Q represents cyano,

W$^1$ represents C—R$^4$ wherein R$^4$ represents a hydrogen atom, and

W$^2$ represents C—R$^5$ wherein, R$^5$ represents a hydrogen atom, halogen, or lower alkyl.

2. The ring-fused heterocyclic compound or a pharmaceutically acceptable salt thereof according to claim 1, wherein R$^3$ is

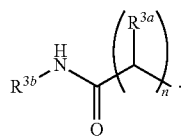

3. The ring-fused heterocyclic compound or a pharmaceutically acceptable salt thereof according to claim 1, wherein R$^3$ is

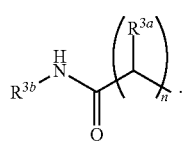

4. The ring-fused heterocyclic compound or a pharmaceutically acceptable salt thereof according to claim 3, wherein n is 0.

5. The ring-fused heterocyclic compound or a pharmaceutically acceptable salt thereof according to claim 4, wherein R$^{3b}$ is optionally substituted lower alkyl or an optionally substituted aliphatic heterocyclic group.

6. The ring-fused heterocyclic compound or a pharmaceutically acceptable salt thereof according to claim 1, wherein R$^1$ is lower alkyl optionally substituted with halogen.

7. The ring-fused heterocyclic compound or a pharmaceutically acceptable salt thereof according to claim 1, wherein R$^1$ is lower alkyl substituted with halogen.

8. The ring-fused heterocyclic compound or a pharmaceutically acceptable salt thereof according to claim 1, wherein R$^2$ is lower alkyl optionally substituted with cycloalkyl optionally substituted with halogen.

9. The ring-fused heterocyclic compound or a pharmaceutically acceptable salt thereof according to claim 1, wherein R$^2$ is cyclohexylmethyl optionally substituted with halogen.

10. The ring-fused heterocyclic compound or a pharmaceutically acceptable salt thereof according to claim 1, wherein R$^2$ is difluorocyclohexylmethyl.

11. The ring-fused heterocyclic compound or a pharmaceutically acceptable salt thereof according to claim 1, wherein W$^1$ is C—R$^4$.

12. The ring-fused heterocyclic compound or a pharmaceutically acceptable salt thereof according to claim 11, wherein R$^4$ is a hydrogen atom.

13. The ring-fused heterocyclic compound or a pharmaceutically acceptable salt thereof according to claim 1, wherein W$^2$ is C—R$^5$.

14. The ring-fused heterocyclic compound or a pharmaceutically acceptable salt thereof according to claim 13, wherein R$^5$ is a hydrogen atom.

15. The ring-fused heterocyclic compound or a pharmaceutically acceptable salt thereof according to claim 13, wherein R$^5$ is halogen.

16. The ring-fused heterocyclic compound or a pharmaceutically acceptable salt thereof according to claim 13, wherein R$^5$ is lower alkyl.

17. The ring-fused heterocyclic compound or a pharmaceutically acceptable salt thereof according to claim 1, wherein Q is cyano, W1 is C—R$^4$, and W$^2$ is C—R$^5$.

18. The ring-fused heterocyclic compound or a pharmaceutically acceptable salt thereof according to claim 17, wherein R$^1$ is lower alkyl optionally substituted with halogen.

19. The ring-fused heterocyclic compound or a pharmaceutically acceptable salt thereof according to claim 17, wherein R$^2$ is cyclohexylmethyl optionally substituted with halogen.

20. The ring-fused heterocyclic compound or a pharmaceutically acceptable salt thereof according to claim 17, wherein R$^4$ is a hydrogen atom.

21. The ring-fused heterocyclic compound or a pharmaceutically acceptable salt thereof according to claim 17, wherein R$^5$ is a hydrogen atom.

22. The ring-fused heterocyclic compound or a pharmaceutically acceptable salt thereof according to claim 17, wherein R$^5$ is halogen.

23. The ring-fused heterocyclic compound or a pharmaceutically acceptable salt thereof according to claim 17, wherein R$^5$ is lower alkyl.

24. A pharmaceutical composition, which comprises, as an active ingredient, the ring-fused heterocyclic compound or a pharmaceutically acceptable salt thereof according to claim 1.

25. A method for treating pruritus, which comprises a step of administering an effective amount of the ring-fused heterocyclic compound selected from the group consisting of:

6-Chloro-N-(4,4-difluorocyclohexyl)-3-[(4,4-difluorocyclohexyl)methyl]-2-(1,1-difluoroethyl)imidazo[1,2-a]pyridine-7-carboxamide, 5-Cyano-3-[4,4-difluorocyclohexyl)methyl]-N-(tetrahydro-2H-pyran-4-yl)-2-(trifluoromethyl)imidazo[1,2-a]pyridine-7-carboxamide, 5-Cyano-N-(cyclopropylmethyl)-3-[(4,4-difluorocyclohexyl)methyl]-2-(trifluoromethyl)imidazo[1,2-a]-pyridine-7-carboxamide, 5-Cyano-3-[(4,4-difluorocyclohexyl)methyl]-N-(2-methoxy-2-methylpropyl)-2-(trifluoromethyl)imidazo[1,2-a]pyridine-7-carboxamide, 5-Chloro-3-[(4,4-difluorocyclohexyl)methyl]-N-(2-oxaspiro[3,3]heptan-6-yl)-2-(trifluoromethyl)imidazo[1,2-a]pyridine-7-carboxamide, 5-Cyano-3-[(4,4-difluorocyclohexyl)methyl]-2-(1,1-difluoroethyl)-N-(2-methoxy-2-methylpropyl)imidazo[1,2-a]pyridine-7-carboxamide, 6-Chloro-5-cyano-3-[(4,4-difluorocyclohexyl)methyl]-N-(2-methoxy-2-methylpropyl)-2-(trifluoromethyl)imidazo[1,2-a]pyridine-7-carboxamide, 5-Chloro-N-[(1-cyanocyclopropyl)methyl]-3-[(4,4-difluorocyclohexyl)methyl]-2-(trifluoromethyl)imidazo[1,2-a]pyridine-7-carboxamide, N-[(1R,2S,4S)-7-Oxabicyclo[2,2,1]heptan-2-yl]-5-cyano-3-[(4,4-difluorocyclohexyl)methyl]-2-(trifluoromethyl)imidazo[1,2-a]pyridine-7-carboxamide, N-[(1R,2S,4S)-7-Oxabicyclo[2,2,1]heptan-2-yl]-5-cyano-3-[(4,4-difluorocyclohexyl)methyl]-2-isopropylimidazo[1,2-a]pyridine-7-carboxamide, 5-Cyano-3-[(4,4-difluorocyclohexyl)methyl]-6-methyl-N-(tetrahydro-2H-pyran-4-yl)-2-(trifluoromethyl)imidazo[1,2-a]pyridine-7-carboxamide, 5-Cyano-3-[(4,4-difluorocyclohexyl)methyl]-N-[3-(dimethylamino)-2,2-dimethylpropyl]-2-(trifluoromethyl)imidazo[1,2-a]pyridine-7-carboxamide, N-[(1R,2S,4S)-7-Oxabicyclo[2,2,1]heptan-2yl]-5-cyano-3-[(4,4-difluorocyclohexyl)methyl]-2-(1,1-difluoroethyl)imidazo[1,2-a]pyridine-7-carboxamide, 5-Cyano-3-[(4,4-difluorocyclohexyl)methyl]-2-(1,1-difluoroethyl)-N-(2-methoxy-2-methylpropyl)-6-methylimidazo[1,2-a]pyridine-7-carboxamide, 5-Cyano-3-[(4,4-difluorocyclohexyl)methyl]-2-(1,1-difluoroethyl)-6-methyl-N-tetrahydro-2H-pyran-4-yl)imidazo[1,2-a]pyridine-7-carboxamide, 5-Cyano-3-[(4,4-difluorocyclohexyl)methyl]-N-(2-methoxy-d3-2-methylpropyl)-2-(trifluoromethyl)imidazo[1,2-a]pyridine-7-carboxamide, 5-Cyano-3-[(4,4-difluorocyclohexyl)methyl]-N-[2-methyl-2-(methylsulfonyl)propyl]-2-(trifluoromethyl)imidazo[1,2-a]pyridine-7-carboxamide, 5-Cyano-3-[(4,4-difluorocyclohexyl)methyl]-2-(1,1-difluoroethyl)-N-(2-methoxy-d3-2-methylpropyl)-6-methylimidazo[1,2-a]pyridine-7-carboxamide, 5,6-Dichloro-3-[(4,4-difluorocyclohexyl)methyl]-N-(tetrahydro-2H-pyran-4-yl)-2-(trifluoromethyl)imidazo[1,2-a]pyridine-7-carboxamide, 5-Cyano-3-[(4,4-difluorocyclohexyl)methyl]-2-(1,1-difluoroethyl)-N-(2-methoxy-d3-2methylpropyl)imidazo[1,2-a]pyridine-7-carboxamide, 5-Chloro-3-[(4,4-difluorocyclohexyl)methyl]-N-[2-methyl-2-(methylsulfonyl)propyl]-2-(trifluoromethyl)imidazo[1,2-a]pyridine-7-carboxamide, and 3-(4-Chlorobenzyl)-5-methyl-N-(tetrahydro-2H-pyran-4-yl)-2-(trifluoromethyl)imidazo[1,2-a]pyridine-7-carboxamide, or a pharmaceutically acceptable salt thereof.

\* \* \* \* \*